(12) United States Patent
Szamosfalvi et al.

(10) Patent No.: US 8,945,036 B2
(45) Date of Patent: *Feb. 3, 2015

(54) SYSTEM AND METHOD FOR DELIVERY OF REGIONAL CITRATE ANTICOAGULATION TO EXTRACORPOREAL BLOOD CIRCUITS

(75) Inventors: Balazs Szamosfalvi, Bloomfield Hills, MI (US); Stanley Frinak, Farmington Hills, MI (US); Jerry Yee, Beverly Hills, MI (US)

(73) Assignee: Henry Ford Health System, Detroit, MI (US)

( * ) Notice: Subject to any disclaimer, the term of this patent is extended or adjusted under 35 U.S.C. 154(b) by 366 days.

This patent is subject to a terminal disclaimer.

(21) Appl. No.: 13/372,860

(22) Filed: Feb. 14, 2012

(65) Prior Publication Data

US 2012/0150090 A1 Jun. 14, 2012

Related U.S. Application Data

(60) Division of application No. 11/829,261, filed on Jul. 27, 2007, now Pat. No. 8,133,194, which is a continuation-in-part of application No. PCT/US2007/062589, filed on Feb. 22, 2007.

(Continued)

(51) Int. Cl.
*A61M 37/00* (2006.01)
*C02F 1/44* (2006.01)
(Continued)

(52) U.S. Cl.
CPC ........... *A61M 1/3672* (2013.01); *A61M 1/3455* (2013.01); *A61M 1/3675* (2013.01);
(Continued)

(58) Field of Classification Search
CPC .............. A61M 2230/207; A61M 2001/3434; A61M 2001/3403; A61M 1/34; A61M 1/342; A61M 1/3441
USPC ........ 210/645, 646, 739, 741; 604/4.01, 5.01, 604/5.04, 6.09, 6.11, 6.06, 6.07
See application file for complete search history.

(56) References Cited

U.S. PATENT DOCUMENTS

| 4,500,309 A | 2/1985 | Diederich et al. |
| 5,032,615 A | 7/1991 | Ward et al. |

(Continued)

FOREIGN PATENT DOCUMENTS

| EP | 0 678 301 | 10/1995 |
| JP | 05208048 | 8/1993 |

(Continued)

OTHER PUBLICATIONS

Supplementary European Search Report for Application No. 07757337.6 (PCT/US2007/062589) dated Jan. 5, 2012.

(Continued)

*Primary Examiner* — Leslie Deak
(74) *Attorney, Agent, or Firm* — Brooks Kushman P.C.

(57) ABSTRACT

The present invention includes a comprehensive replacement fluid system and method for the delivery of regional citrate anticoagulation (RCA) to extracorporeal blood circuits, wherein the system may include an online clearance monitor (OCM) and a circuit effluent online sensor system (OSS) for the continuous determination of patient plasma content of ultrafilterable solutes.

20 Claims, 65 Drawing Sheets

Related U.S. Application Data

(60) Provisional application No. 60/775,729, filed on Feb. 22, 2006, provisional application No. 60/775,728, filed on Feb. 22, 2006, provisional application No. 60/790,882, filed on Apr. 11, 2006, provisional application No. 60/791,055, filed on Apr. 11, 2006, provisional application No. 60/845,646, filed on Sep. 19, 2006.

(51) Int. Cl.
*A61M 1/36* (2006.01)
*A61M 1/34* (2006.01)

(52) U.S. Cl.
CPC ........... *A61M1/3406* (2013.01); *A61M 1/3434* (2014.02); *A61M 1/3609* (2014.02); *A61M 1/3413* (2013.01); *A61M 1/3653* (2013.01); *A61M 2205/3306* (2013.01); *A61M 2202/0486* (2013.01)
USPC ....... 604/6.07; 604/5.04; 604/6.06; 604/6.09; 604/6.11; 210/645; 210/739

(56) References Cited

U.S. PATENT DOCUMENTS

| | | | |
|---|---|---|---|
| 6,417,005 | B1 | 7/2002 | Barnard et al. |
| 6,627,177 | B2 | 9/2003 | Singaram et al. |
| 6,636,759 | B2 | 10/2003 | Robinson |
| 6,743,191 | B1 | 6/2004 | Chang |
| 6,821,441 | B2 | 11/2004 | Pedrini et al. |
| 6,911,007 | B2 | 6/2005 | Nier et al. |
| 7,174,198 | B2 | 2/2007 | Trofimov et al. |
| 7,186,420 | B2 | 3/2007 | Chang et al. |
| 7,209,773 | B2 | 4/2007 | Iuliano |
| 2002/0077579 | A1 | 6/2002 | Tobe |
| 2003/0232093 | A1 | 12/2003 | Faict et al. |
| 2004/0133145 | A1 | 7/2004 | Bene |
| 2004/0204634 | A1 | 10/2004 | Womble et al. |
| 2005/0020507 | A1 | 1/2005 | Zieske et al. |
| 2005/0131332 | A1 | 6/2005 | Kelly et al. |
| 2005/0236330 | A1 | 10/2005 | Nier et al. |
| 2005/0251086 | A1 | 11/2005 | Sternby |
| 2006/0041216 | A1 | 2/2006 | McLaughlin et al. |
| 2006/0052745 | A1 | 3/2006 | Van Antwerp et al. |
| 2006/0184084 | A1 | 8/2006 | Ware et al. |
| 2006/0240401 | A1 | 10/2006 | Clarke et al. |
| 2007/0062861 | A1 | 3/2007 | Lannoy |
| 2007/0066928 | A1 | 3/2007 | Lannoy |
| 2007/0110829 | A1 | 5/2007 | Tolwani et al. |
| 2007/0111245 | A1 | 5/2007 | Thadhani et al. |
| 2007/0134348 | A1 | 6/2007 | Chang et al. |
| 2007/0225675 | A1 | 9/2007 | Robinson et al. |
| 2009/0221948 | A1 | 9/2009 | Szamosfalvi et al. |

FOREIGN PATENT DOCUMENTS

| | | |
|---|---|---|
| JP | 2002248165 | 9/2002 |
| WO | WO 0249693 A2 | 6/2002 |
| WO | WO 0249694 | 6/2002 |
| WO | 2004069311 | 8/2004 |
| WO | WO 2005039671 | 5/2005 |
| WO | 2007101064 A2 | 9/2007 |

OTHER PUBLICATIONS

A.N. Thomas et al., Comparison of Lactate and Bicarbonate Buffered Haemofiltration Fluids: Use in Critically Ill Patients, Nephrol Dial Transplant (1997) 12: pp. 1212-12-17.

Christophe Ridel et al., Regional Citrate Anticoagulation During Hemodialysis, Blood Purif 23: 473-480, Nov. 10, 2005.

Theoharia Sideroudi et al., Non-Contact Detection of Ciprofloxacin in a Model Anterior Chamber Using Raman Spectroscopy, Journal of Biomedical Optics 12(3) 034005, May 8, 2007.

Justyna Kozik-Jaromin, Citrate Kinetics During Regional Citrate Anticoagulation in Extracorporeal Organ Replacement Therapy, 2005.

Marc Dorval et al., A Novel Citrate Anticoagulation Regimen for Continuous Venovenous Hemodiafiltration, Intensive Care Med (2003) 29: 1186-1189, May 22, 2003.

D. Parker et al., A pH-insensitive, ratiometric chemosensor for citrate using europium luminescence, Chemical Communications, (25) 3141-3143, May 20, 2005.

Per Kjellstrand et al., Degradation in Peritoneal Dialysis Fluids may be avoided by using low ph and High Glucose Concentration, Peritoneal Dialysis International, vol. 21, pp. 338-344, Jul.-Aug. 2001.

Martin Erixon et al., Take Care in How you Store your PD Fluids: Actual Temperature Determines the Balance Between Reactive and Non-Reactive GDPs, Peritoneal Dialysis International, vol. 25, pp. 583-590, Nov.-Dec. 2005.

Martin Erixon et al., How to Avoid Glucose Degradation Products in Peritoneal Dialysis Fluids, Peritoneal Dialysis International, vol. 26, pp. 490-497, Jul.-Aug. 2006.

Luciano A. Pedrini et al., On-Line Mixed Hemodiafiltration with a Feedback for Ultrafiltration Control: Effect on Middle-Molecule Removal, Kidney International, vol. 64, pp. 1505-1513, 2003.

International Preliminary Report on Patentability for PCT/IB2008/002146 dated Feb. 11, 2010.

International Search Report for PCT/IB08/02146, dated May 28, 2009.

Office Action for U.S. Appl. No. 12/280,450 dated Sep. 16, 2011.

International Search Report for International Application No. PCT/US07/62589 mailed Sep. 2, 2008.

European Patent Office, Extended Search Report for the corresponding European Patent Application No. 08789092.7 mailed Jul. 31, 2014.

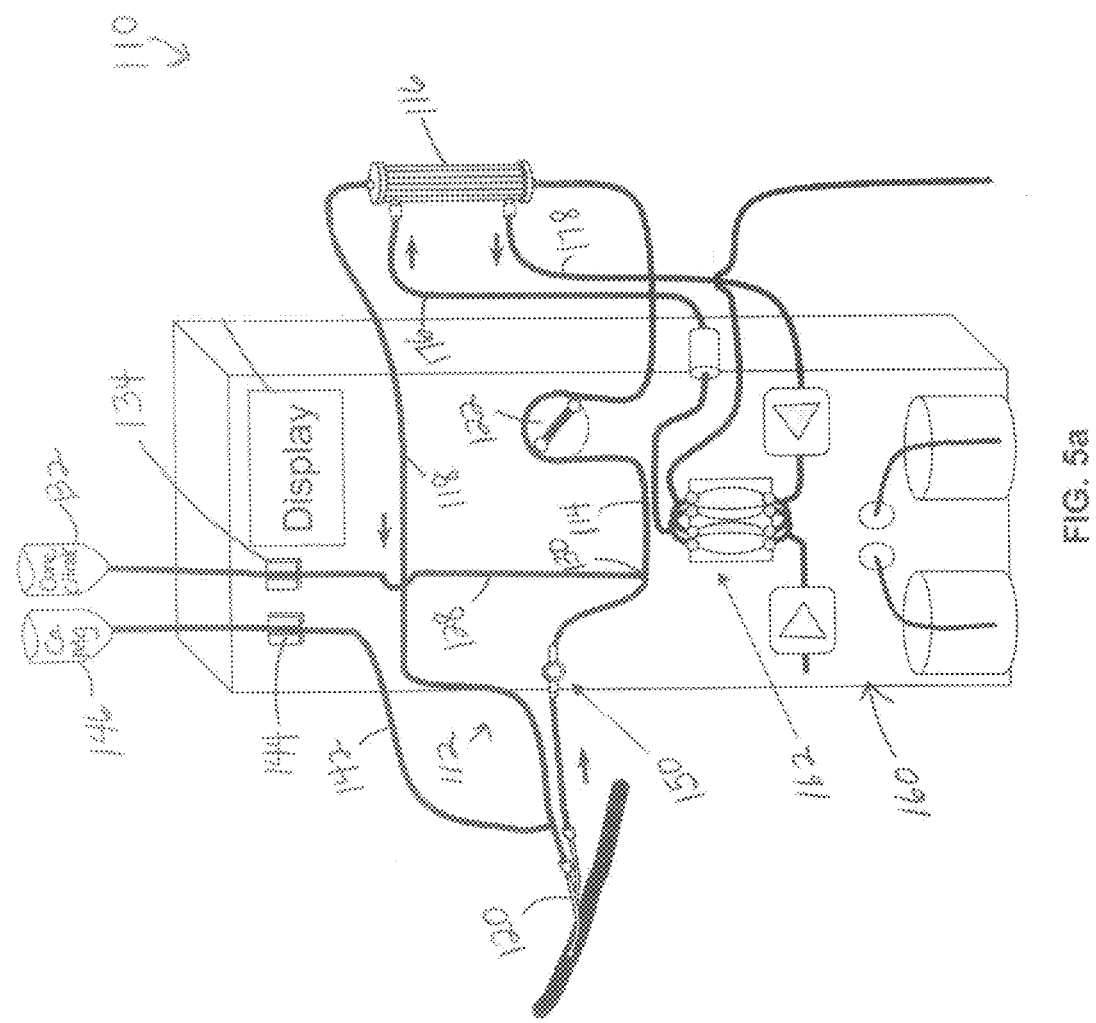

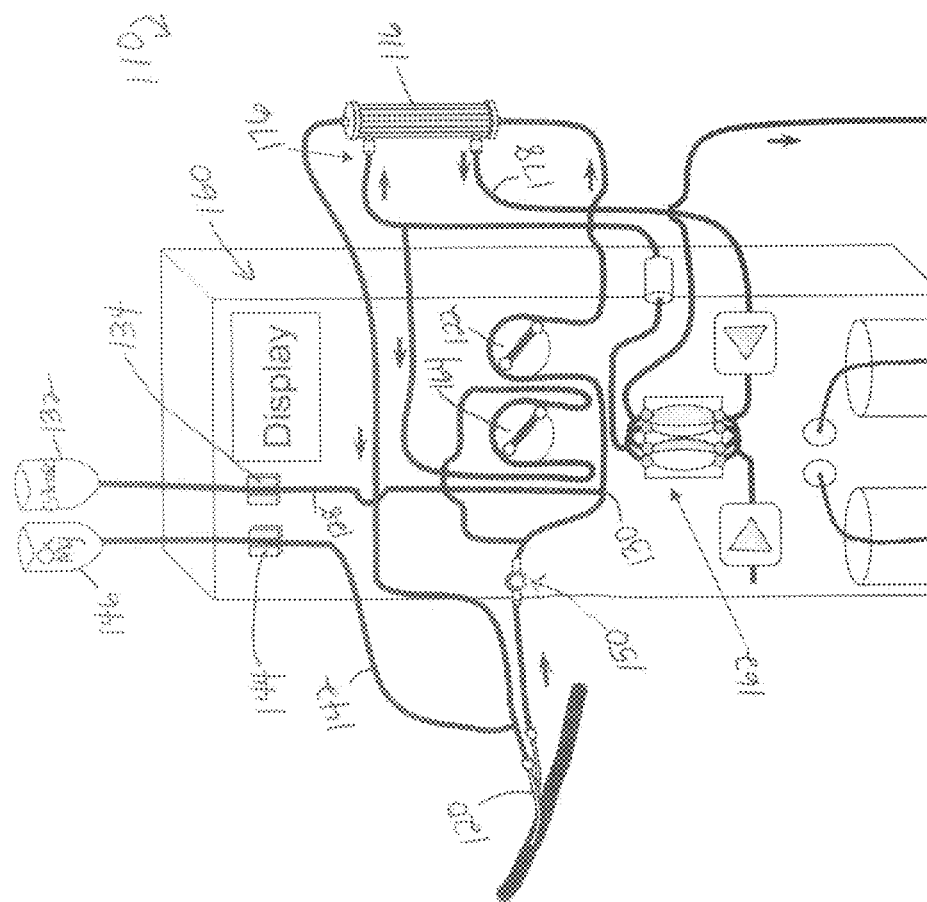

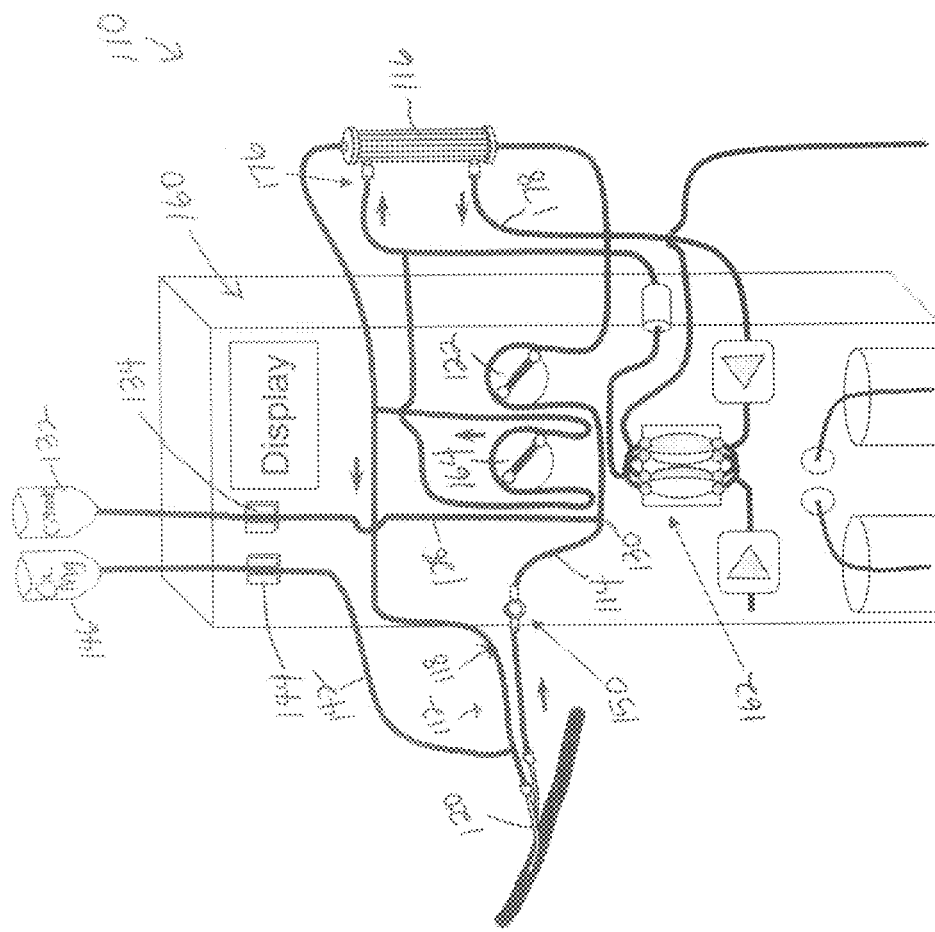

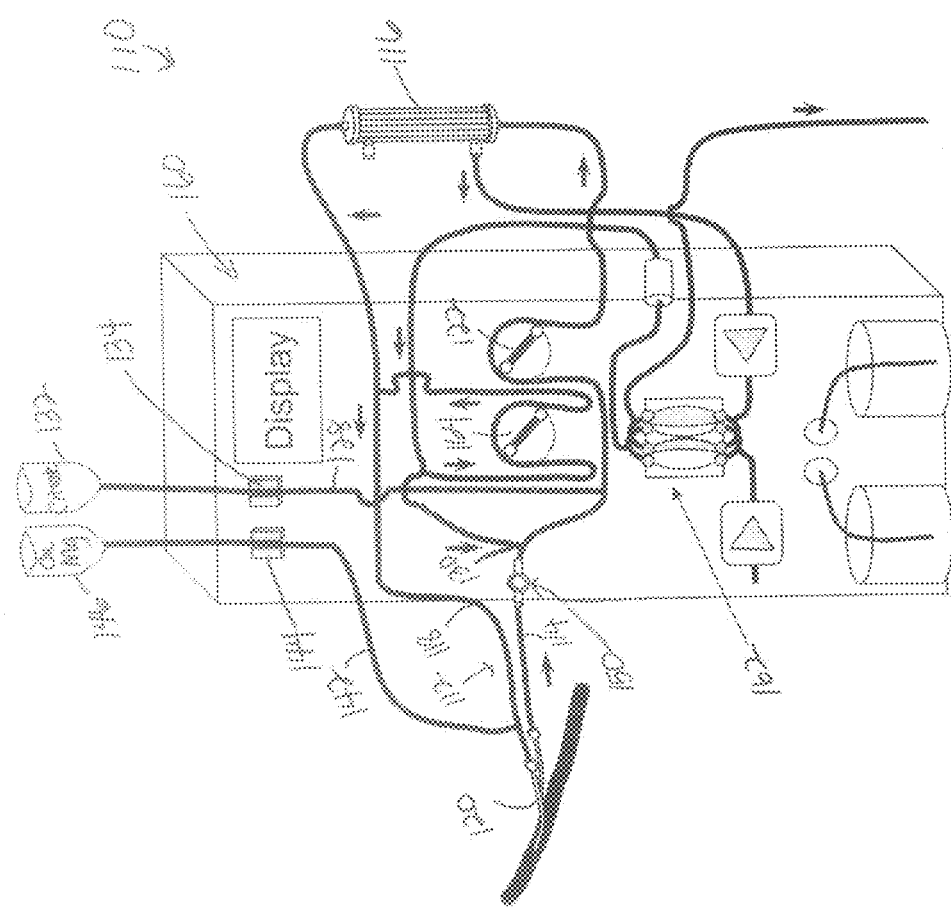

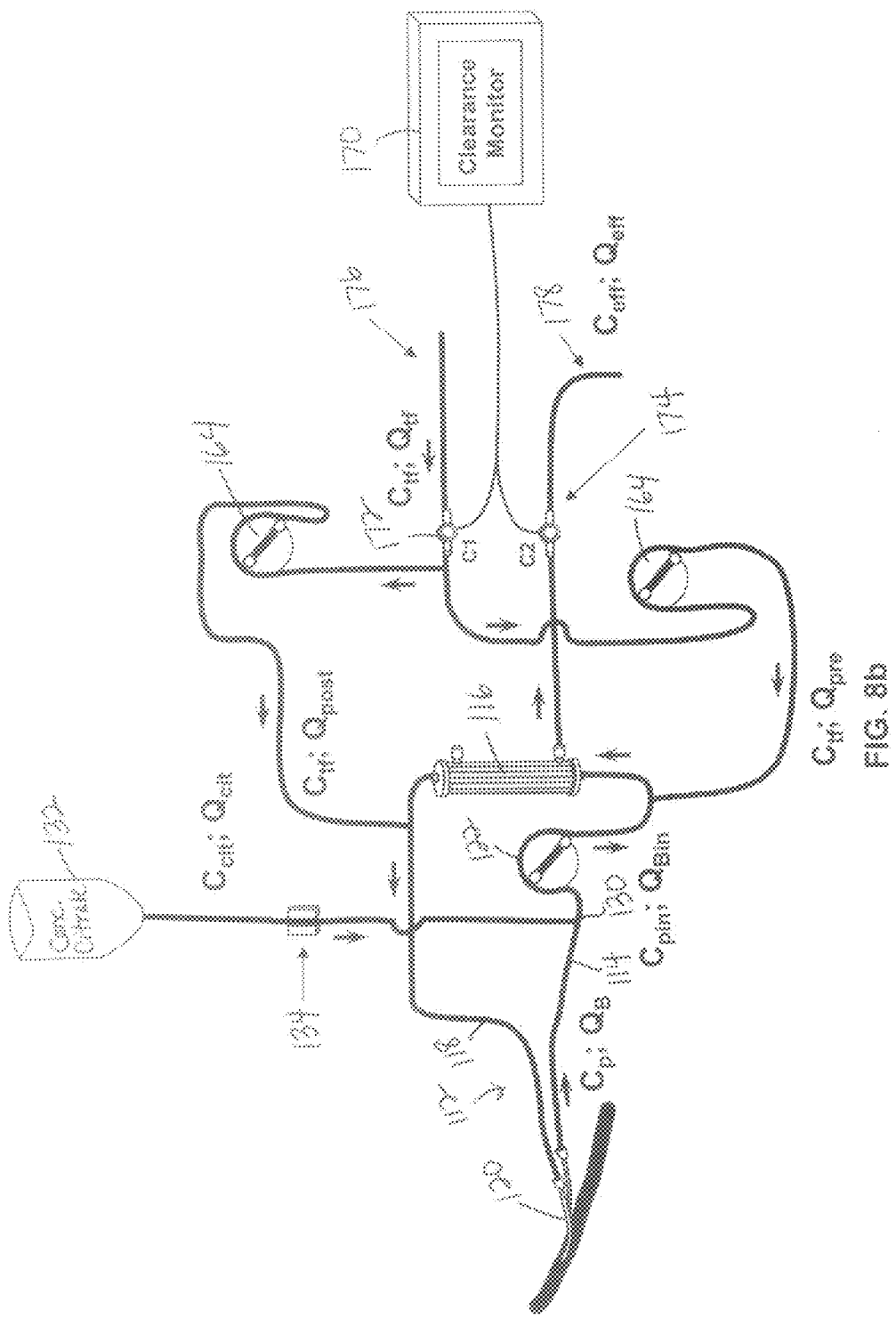

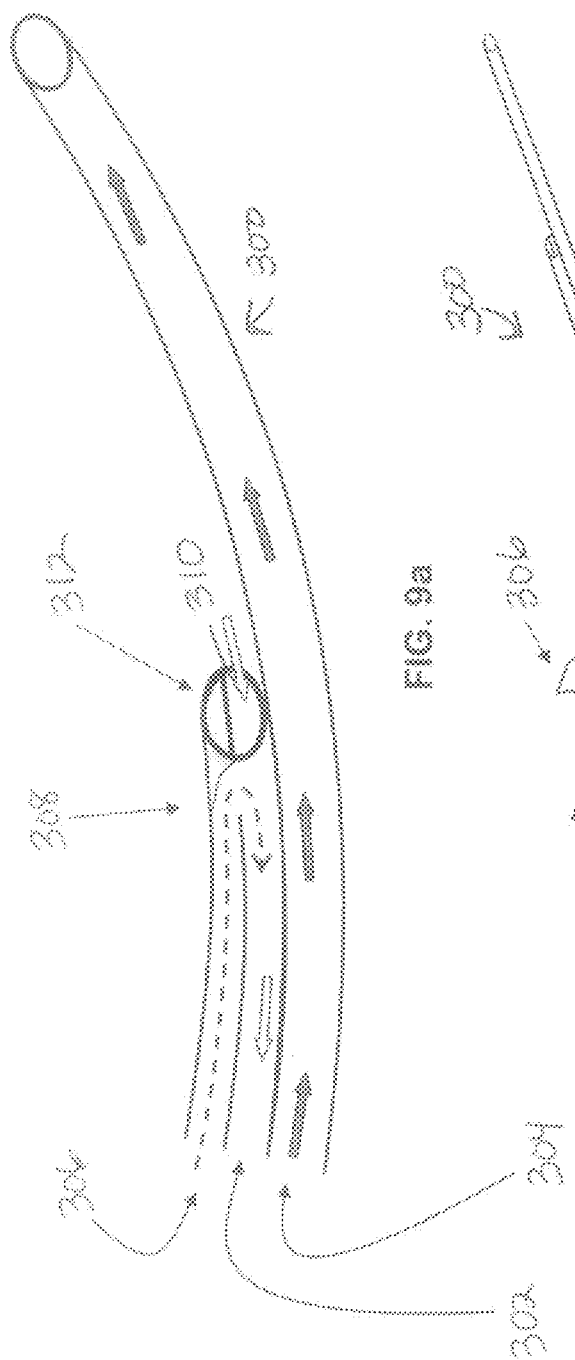
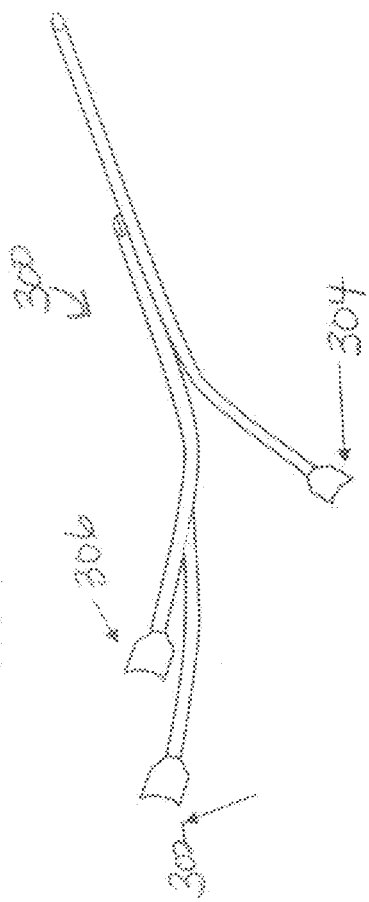
FIG. 9a
FIG. 9b

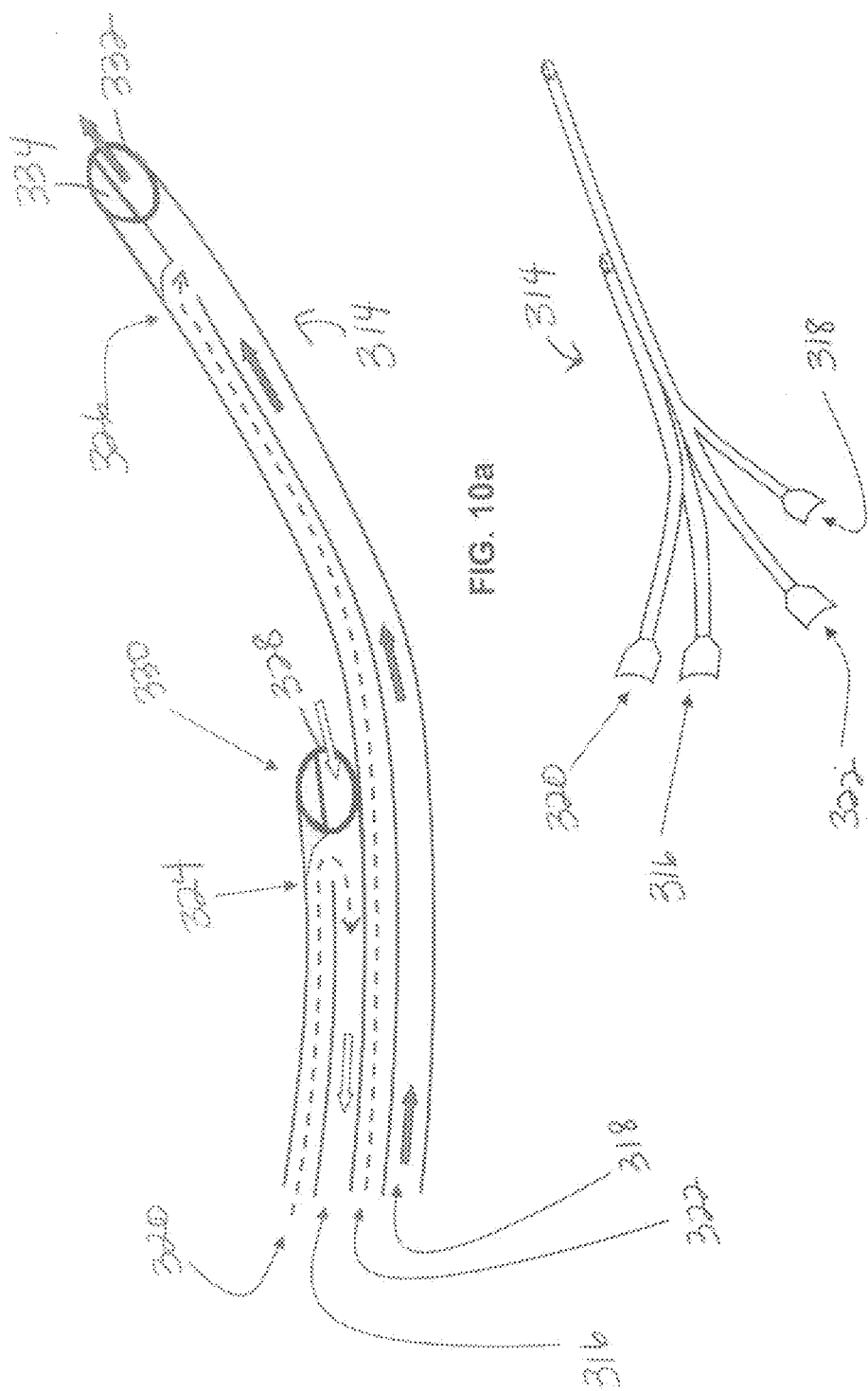

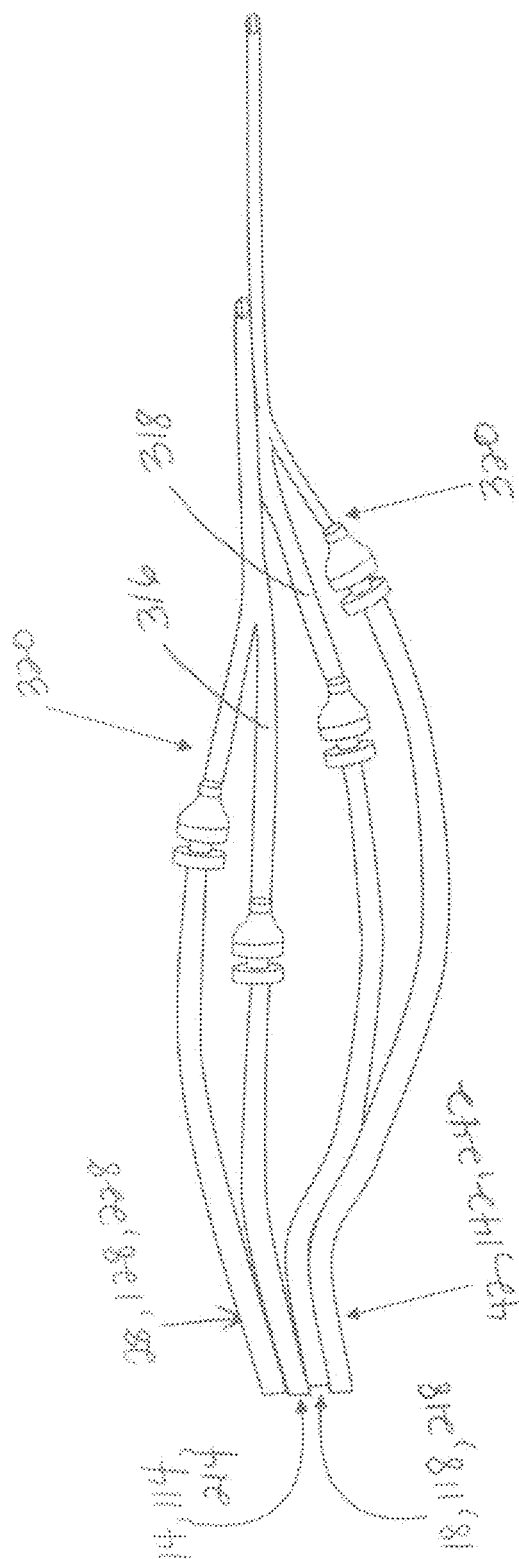

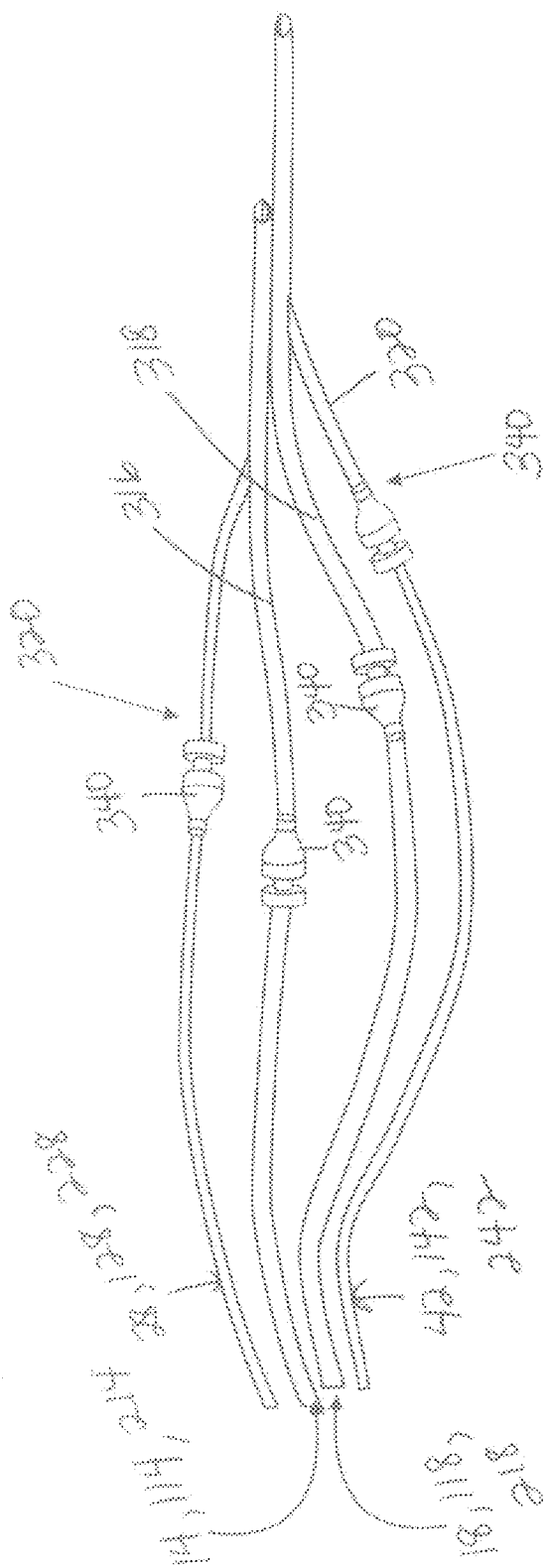

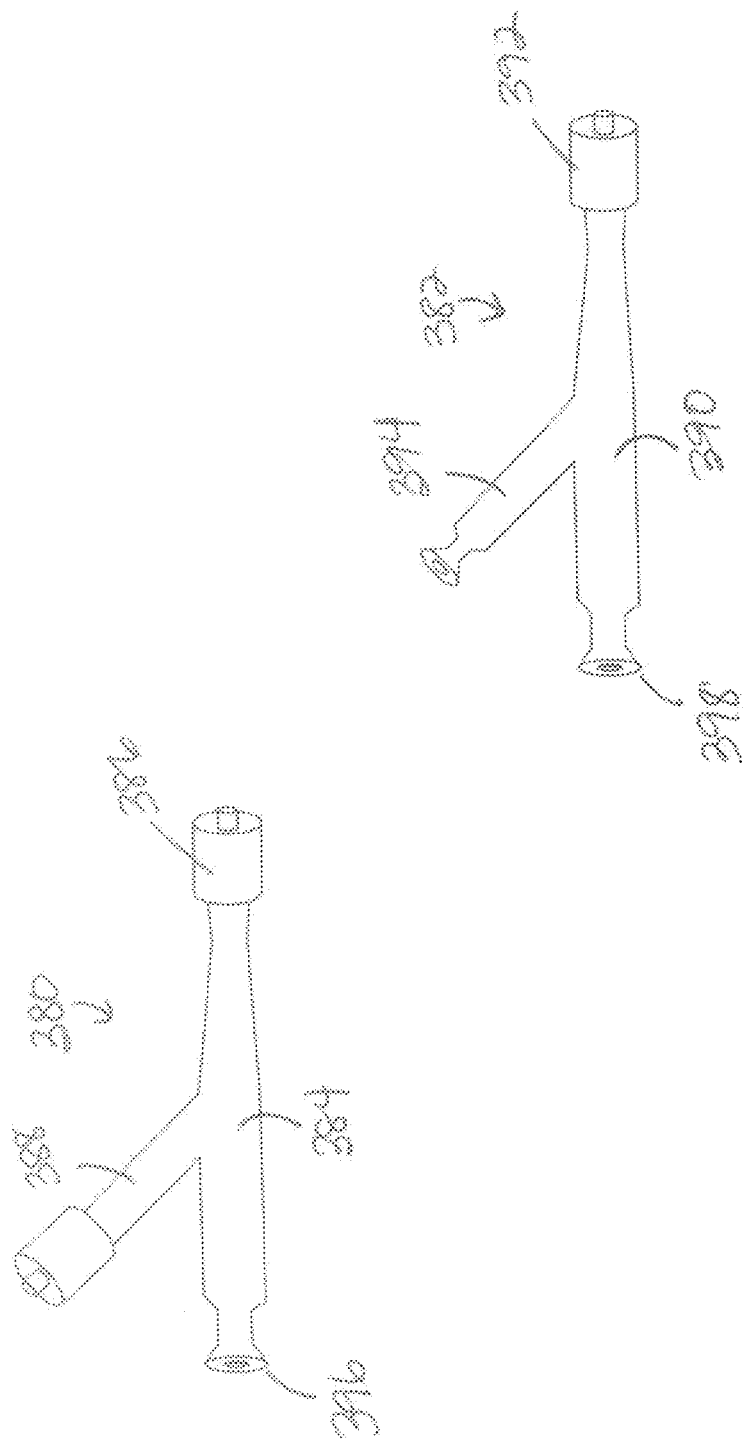

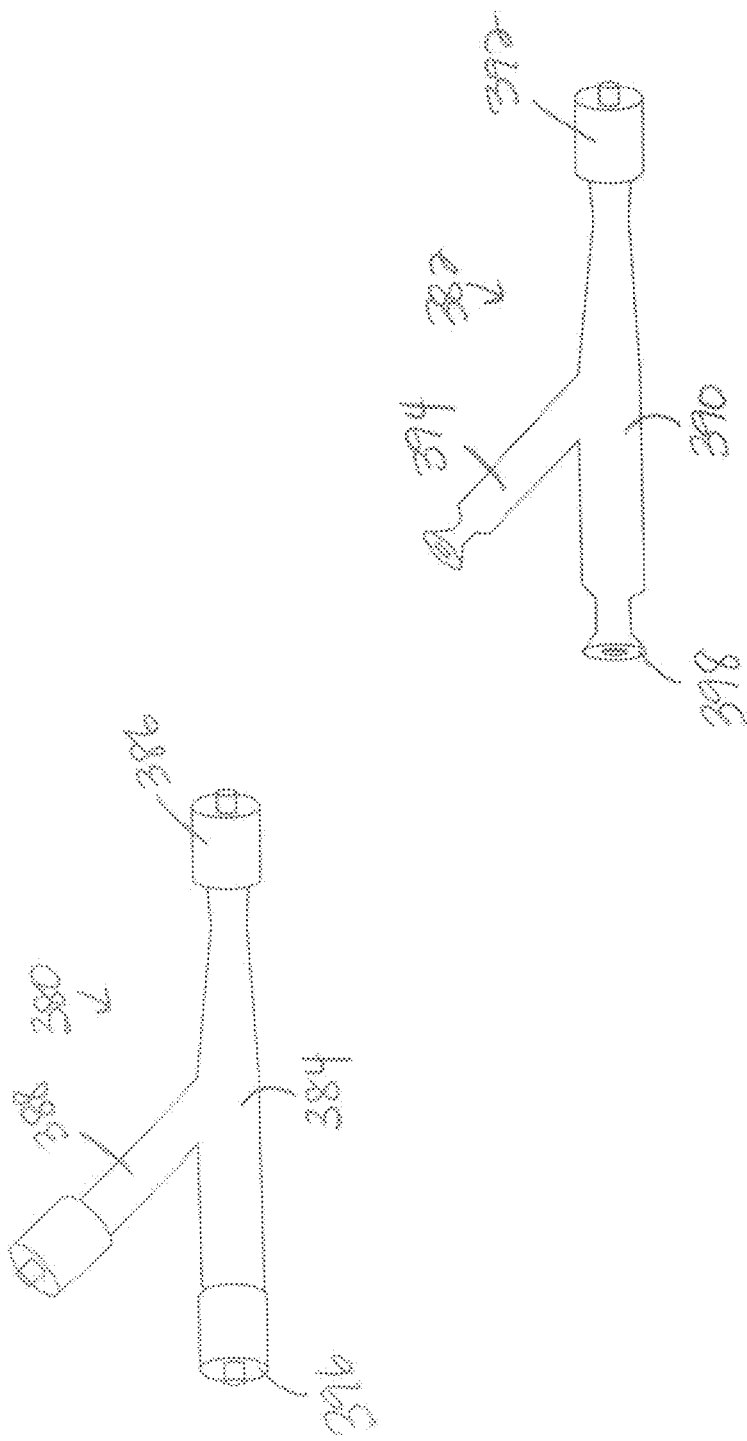

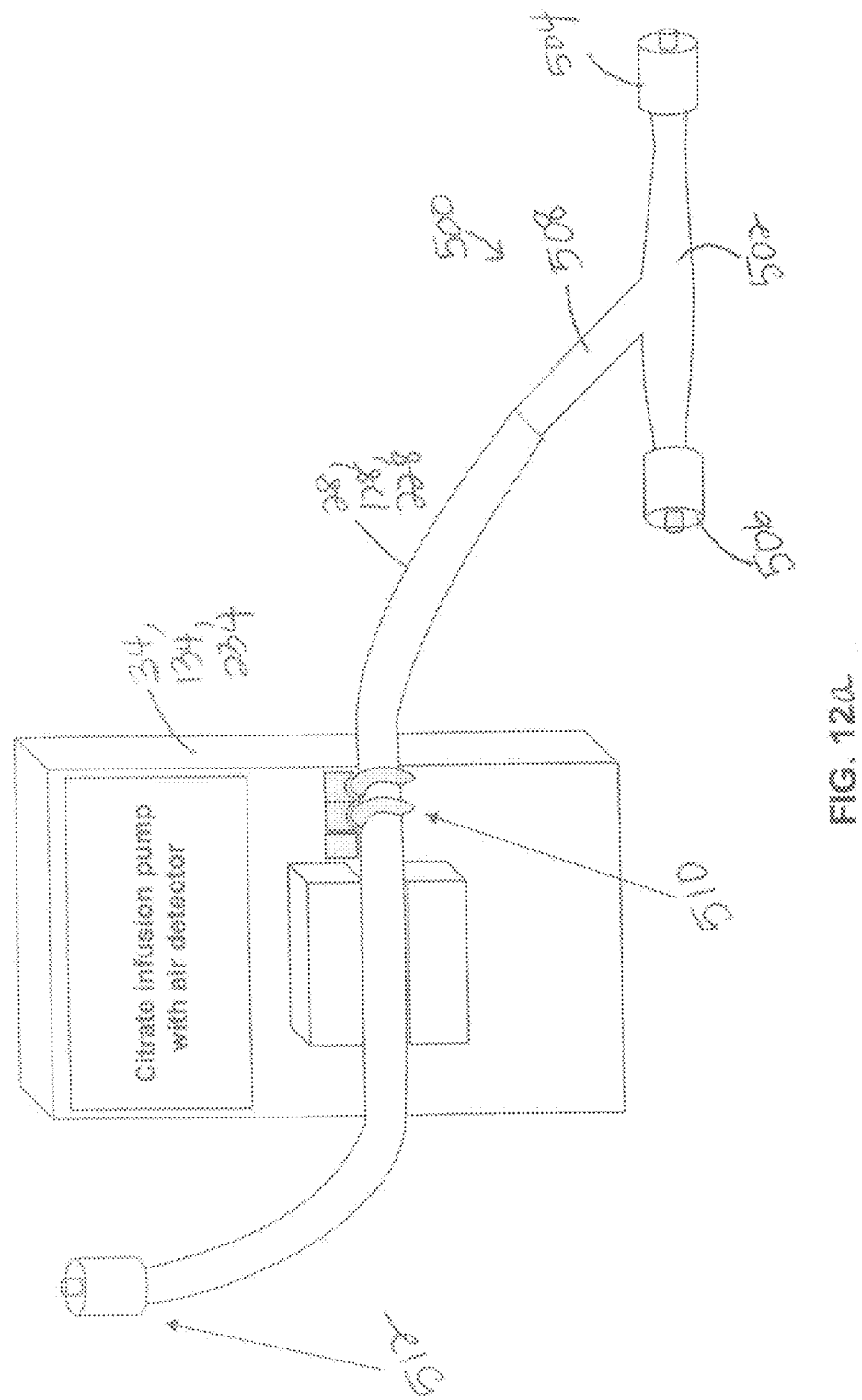

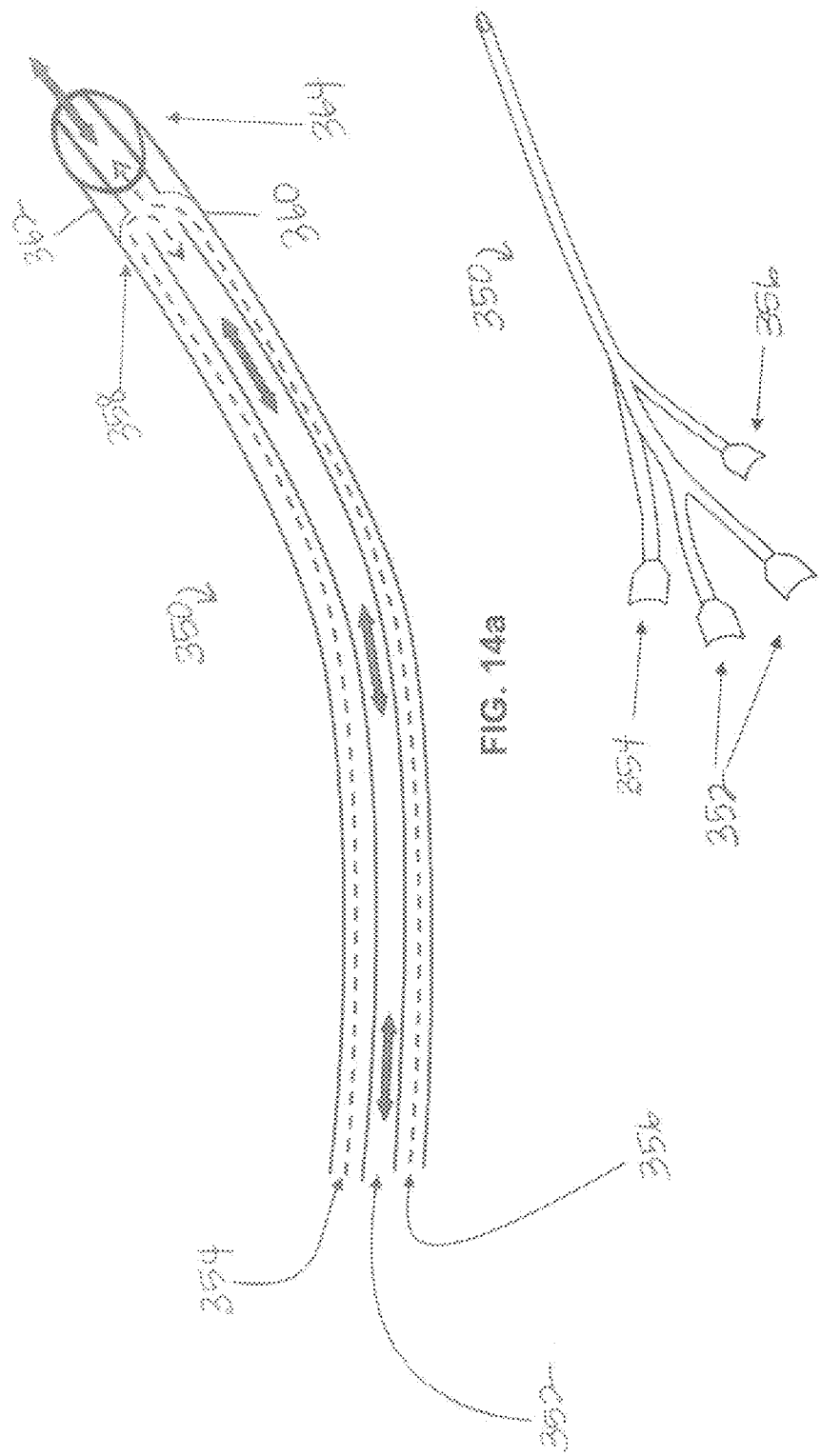

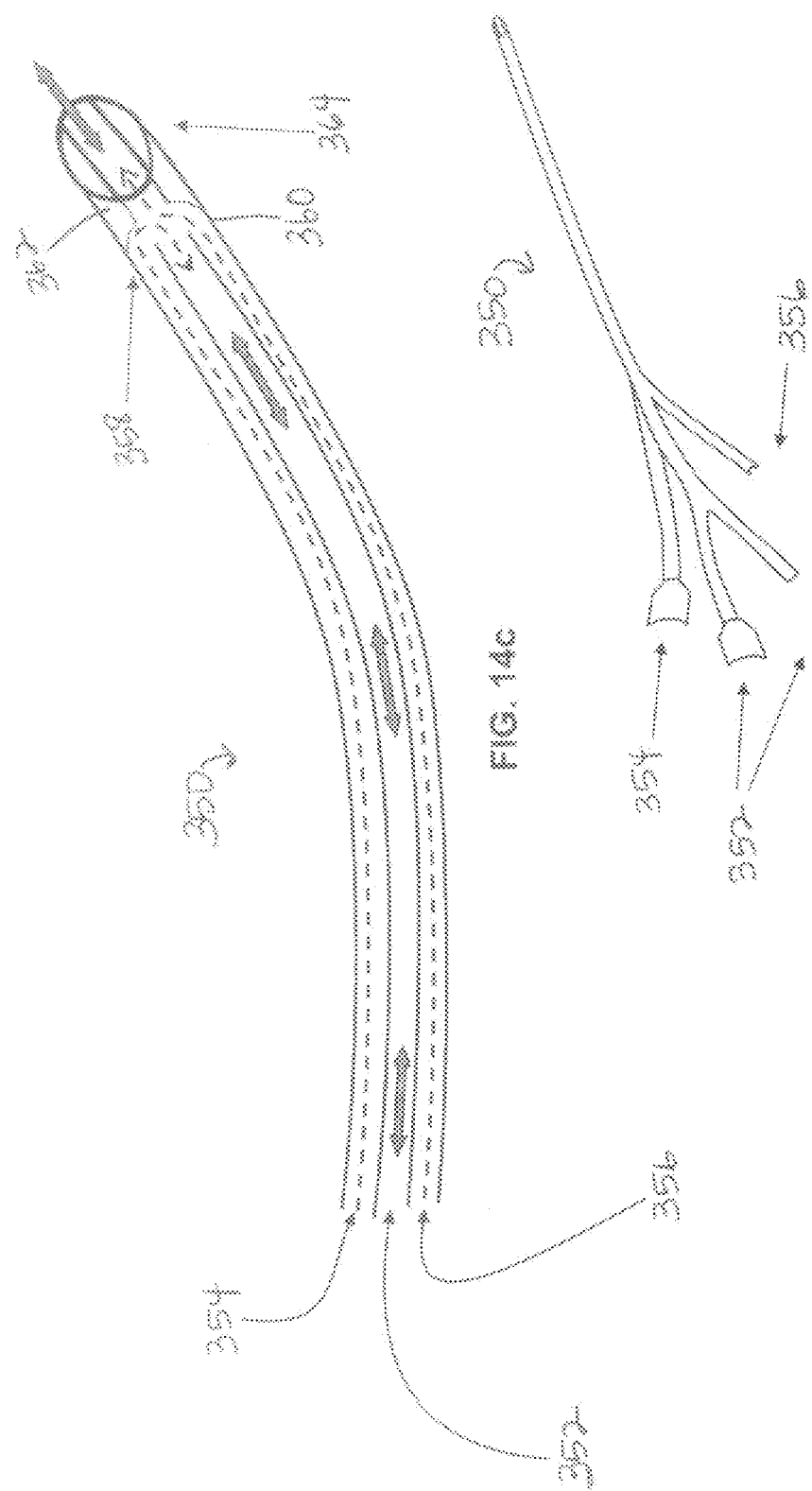

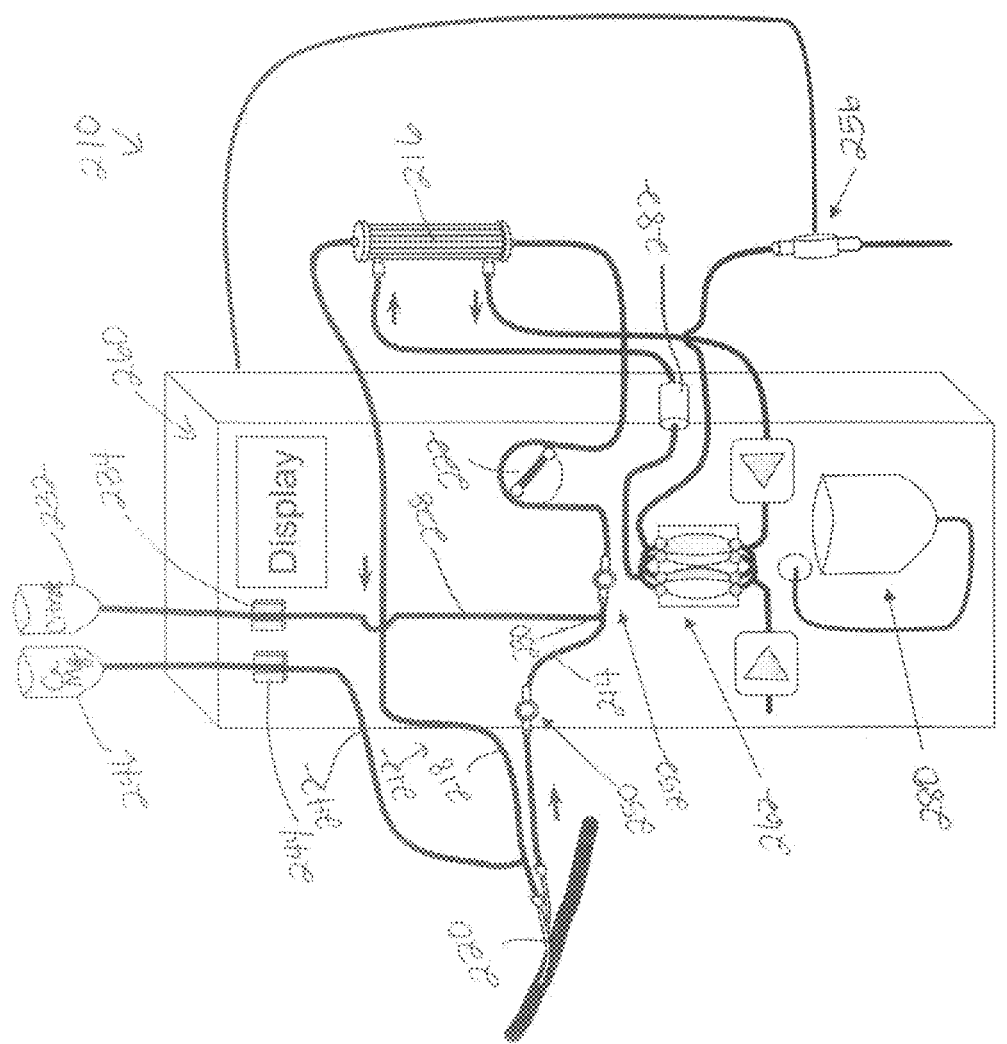

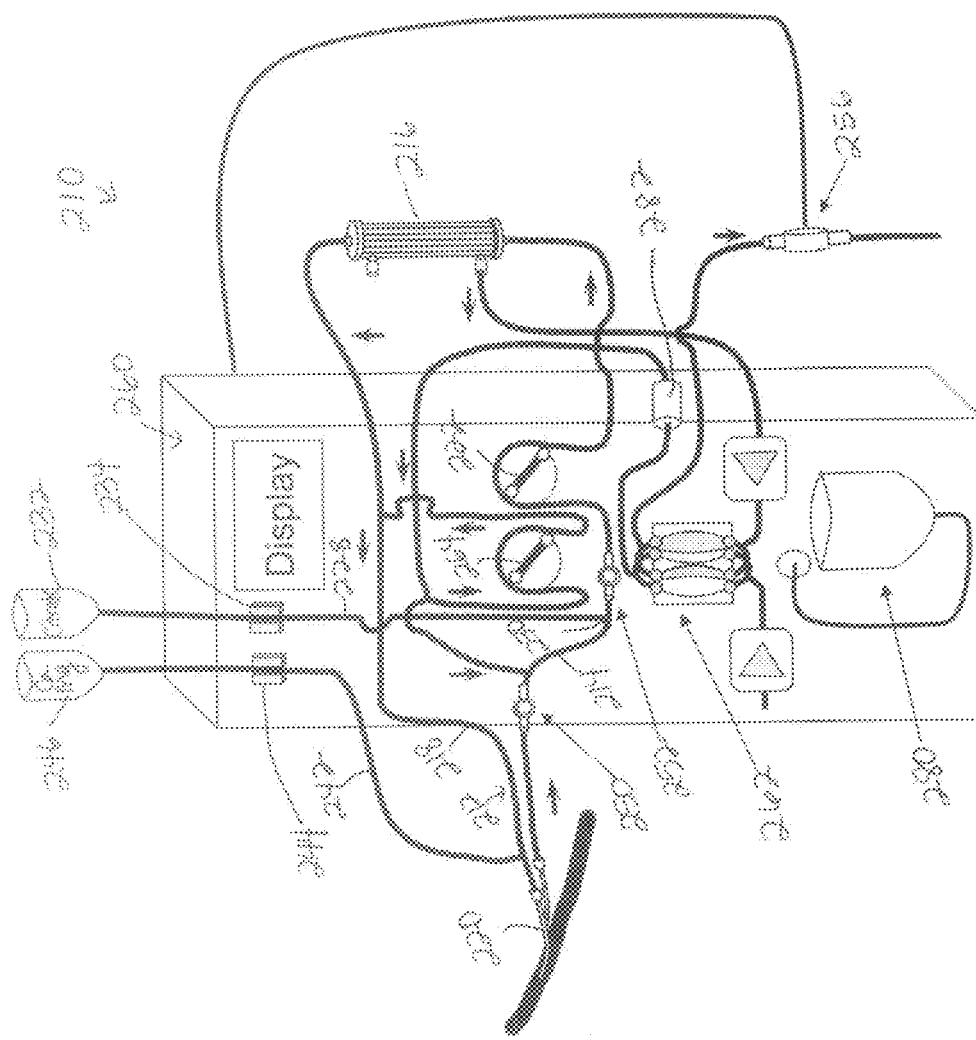

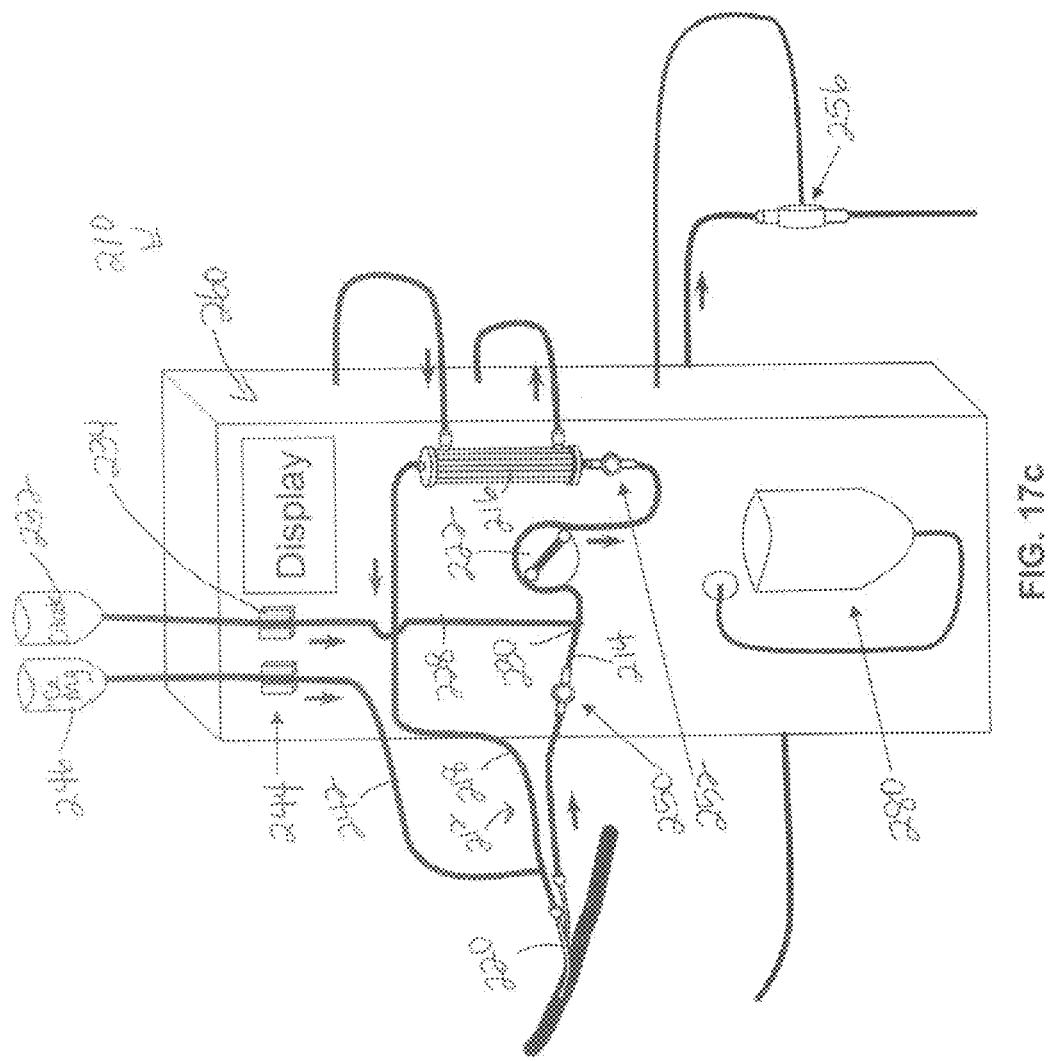

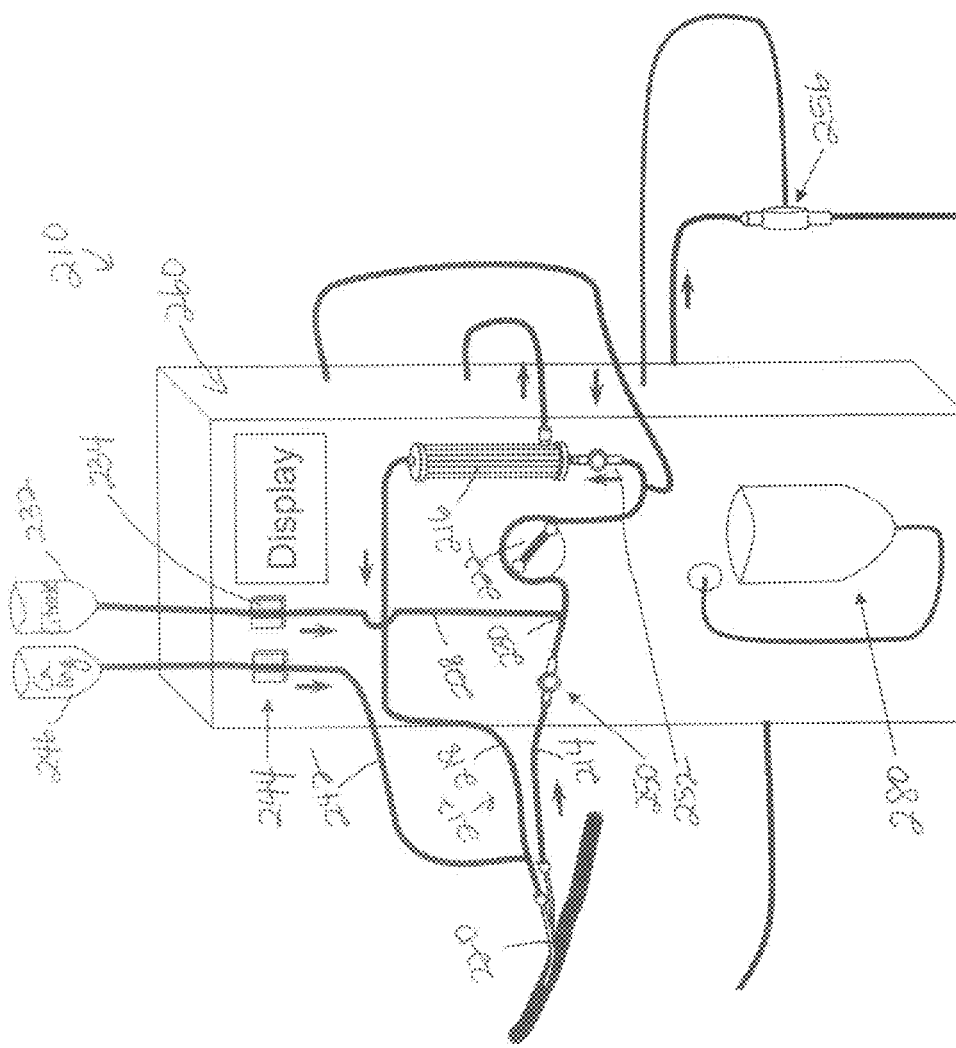

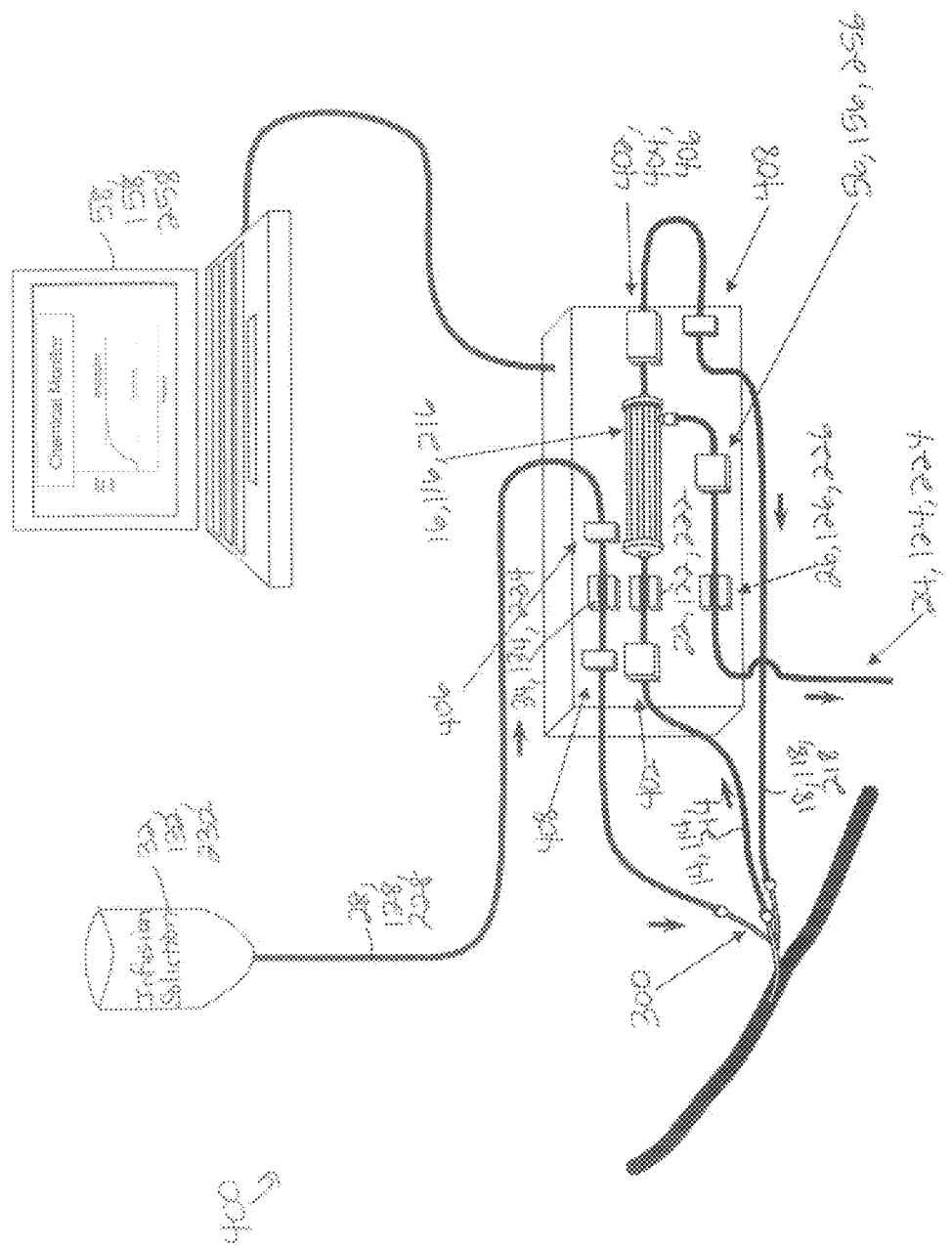

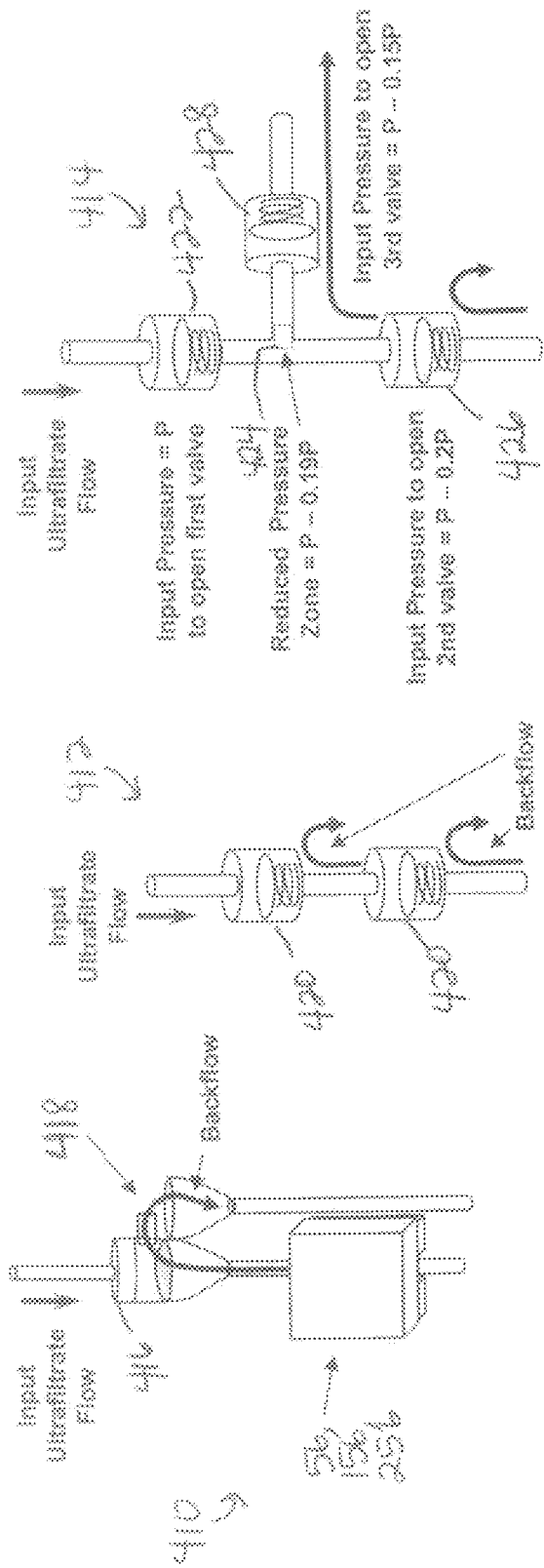

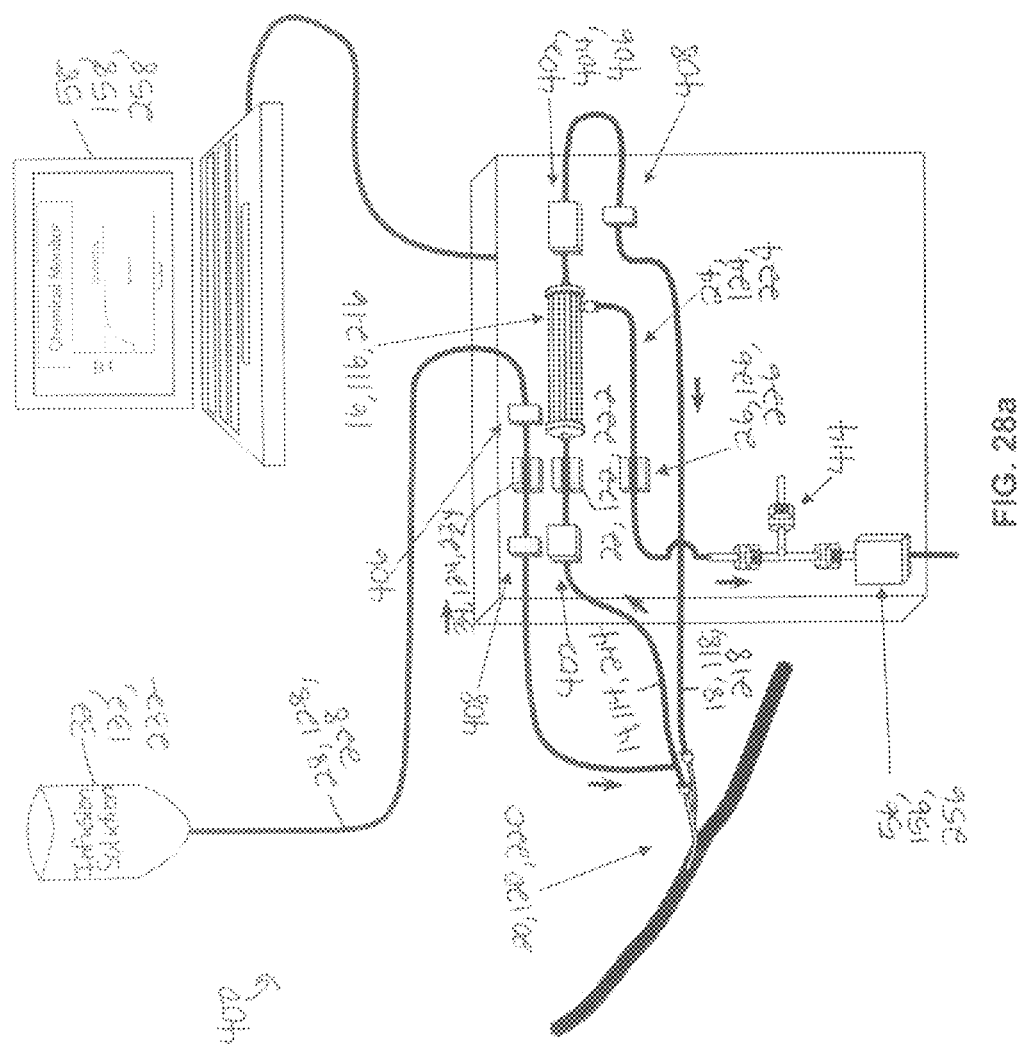

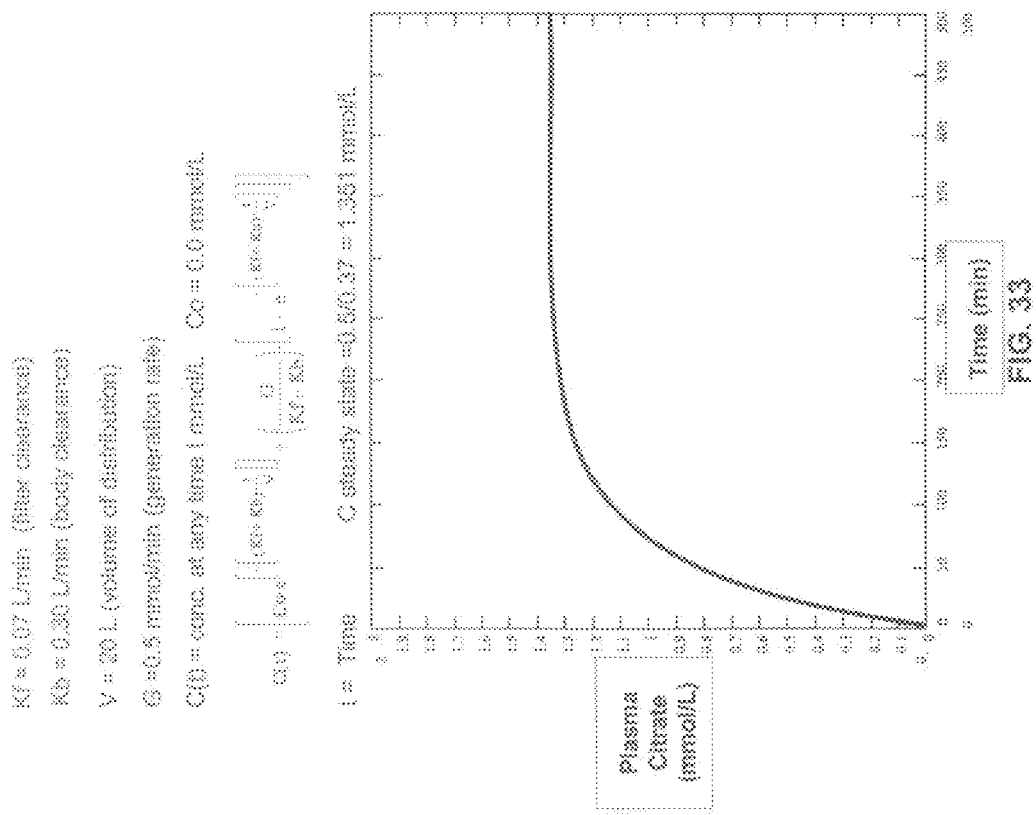

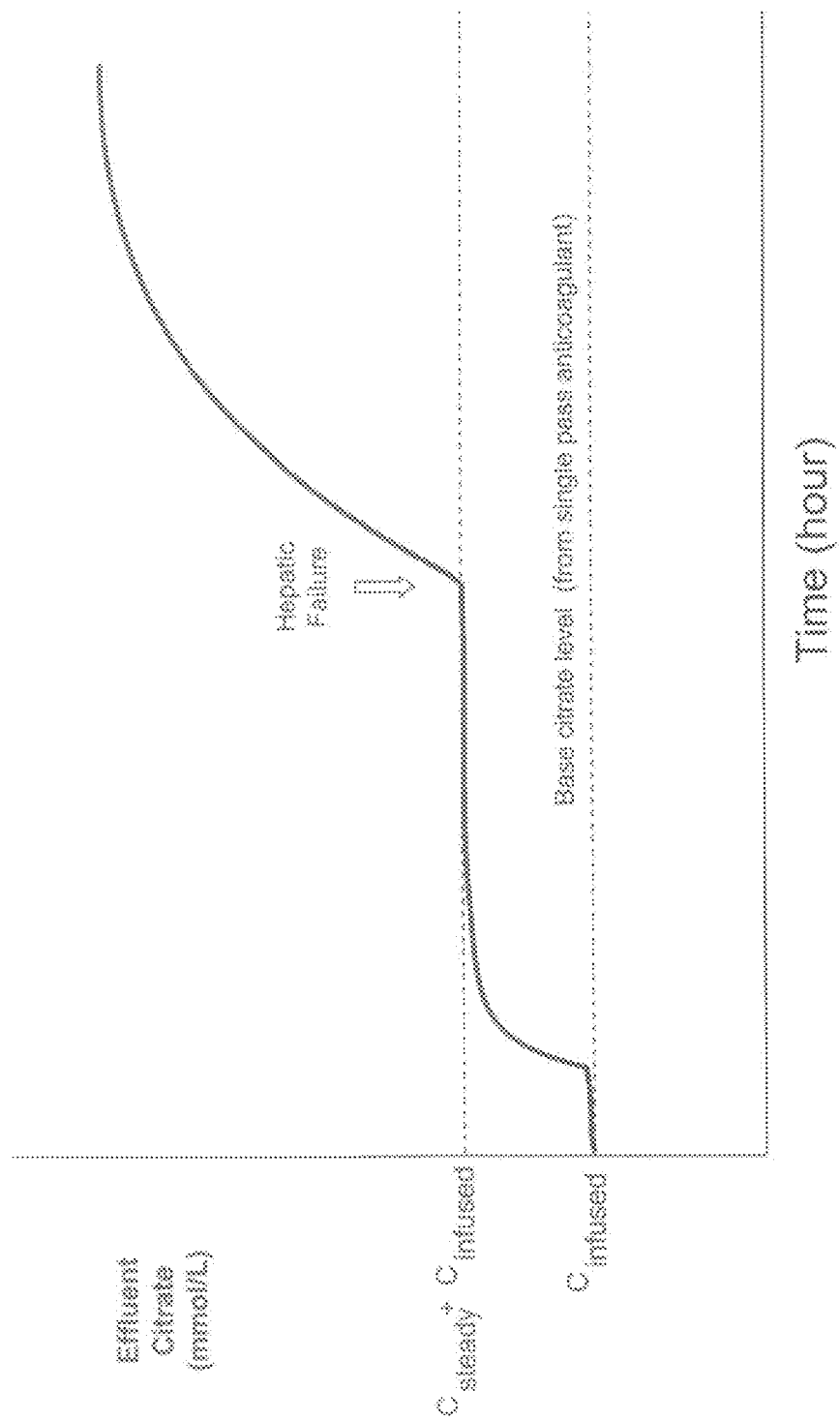

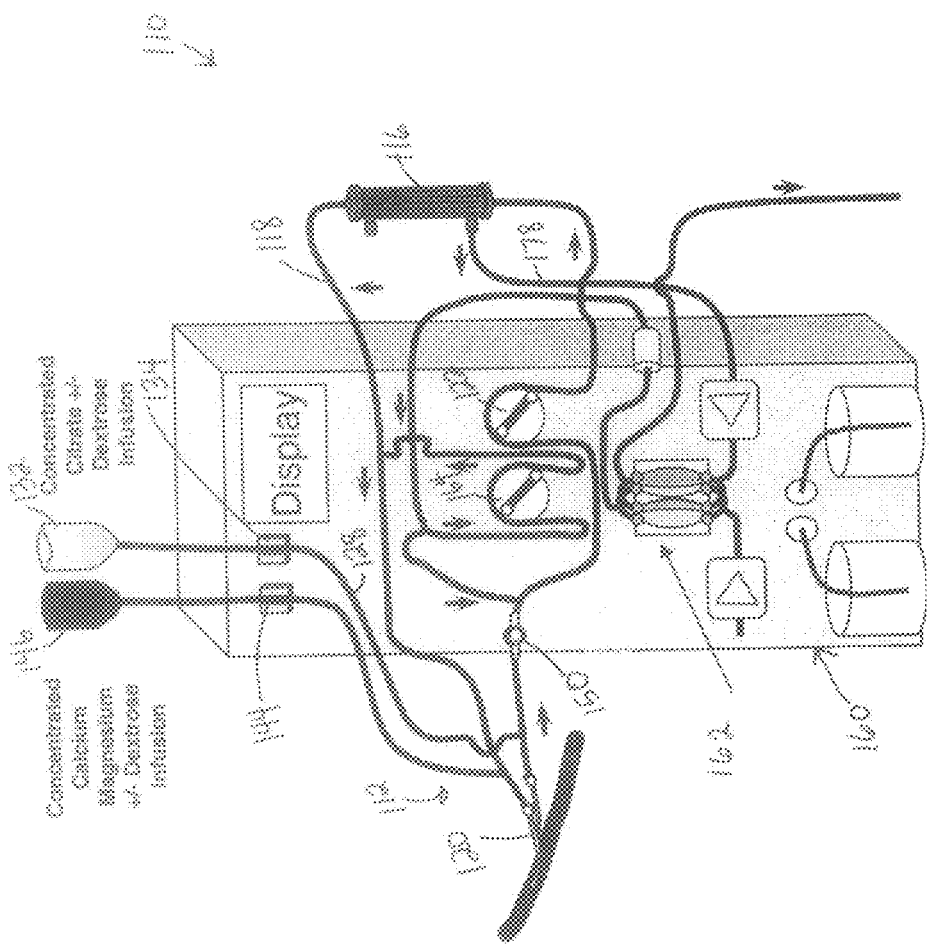

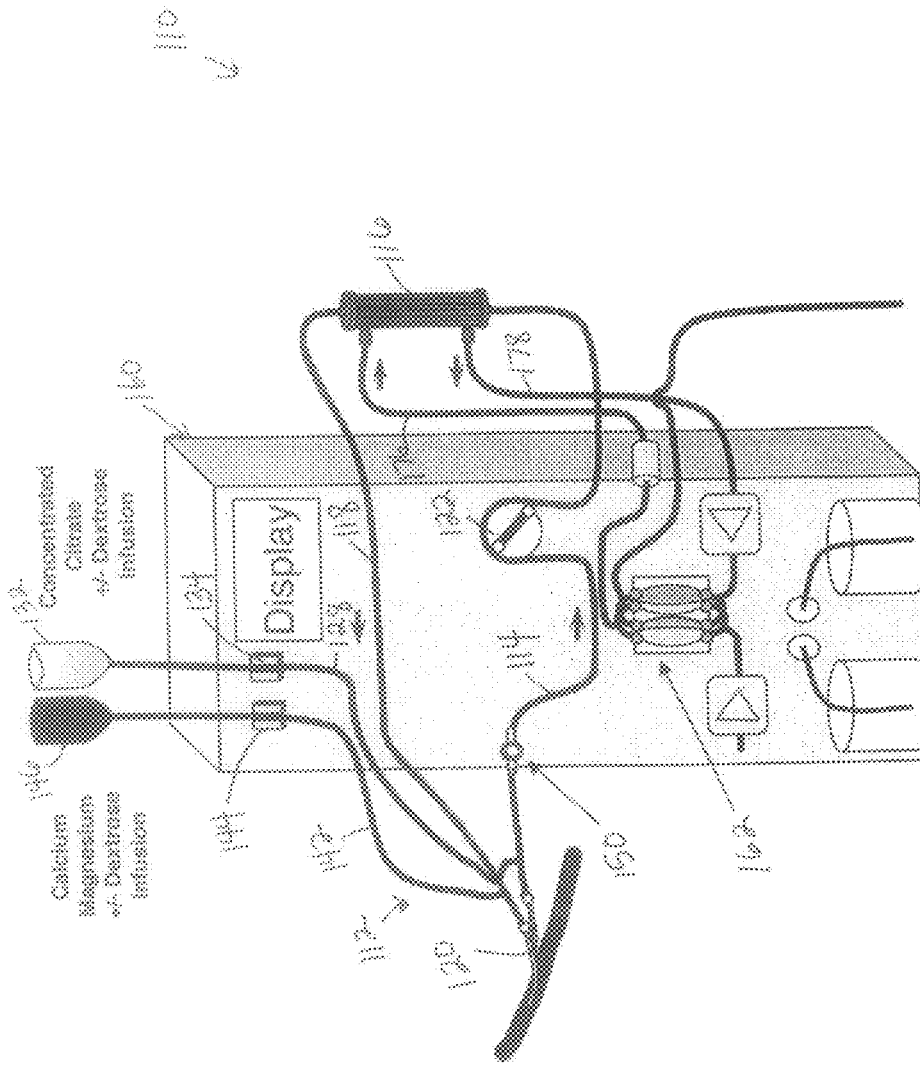

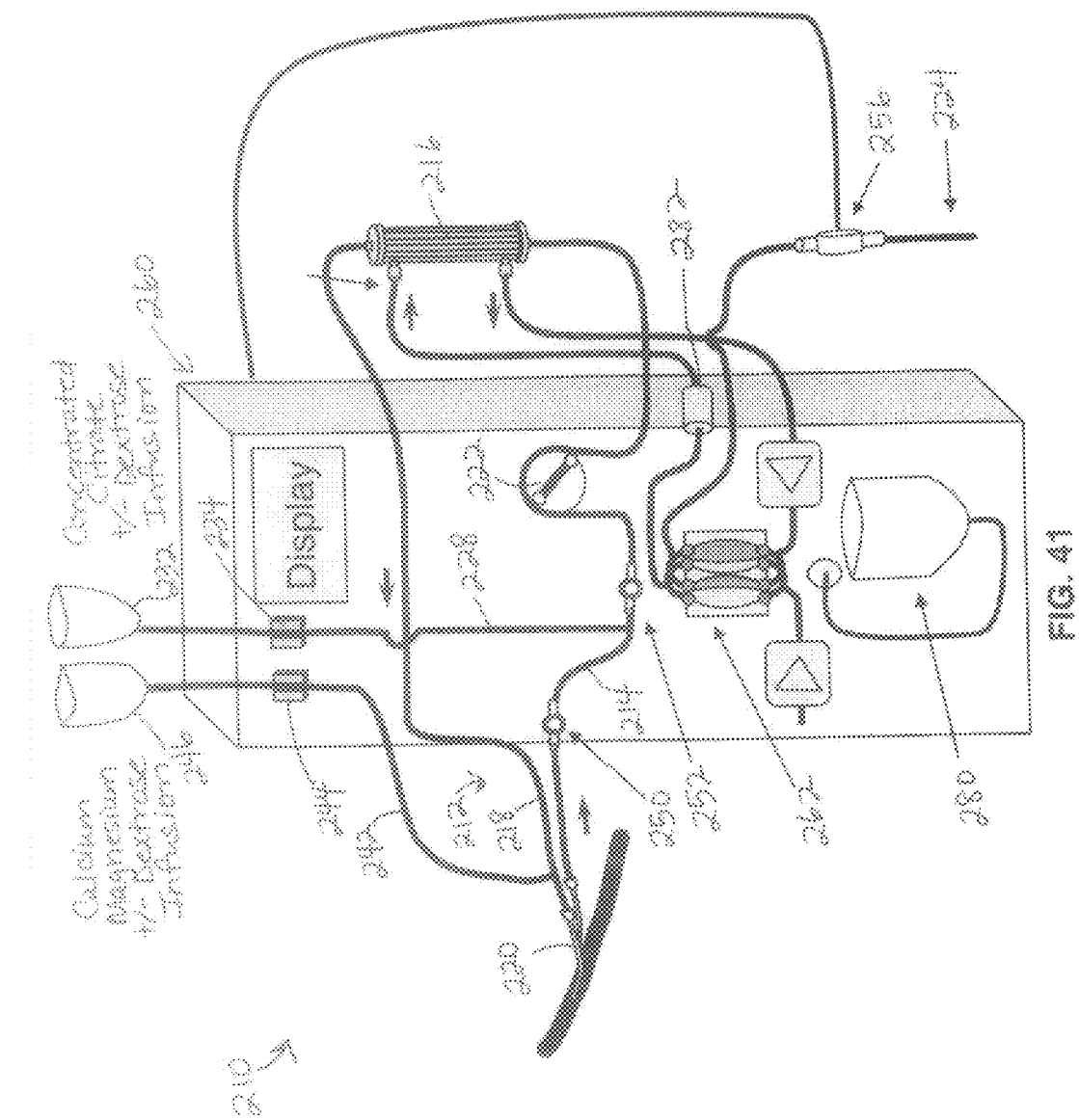

US 8,945,036 B2

SYSTEM AND METHOD FOR DELIVERY OF REGIONAL CITRATE ANTICOAGULATION TO EXTRACORPOREAL BLOOD CIRCUITS

CROSS-REFERENCE TO RELATED APPLICATIONS

This application is a division of U.S. application Ser. No. 11/829,261 filed Jul. 27, 2007, now U.S. Pat. No. 8,133,194 issued Mar. 13, 2012, which is a continuation-in-part of PCT/US07/062,589 filed Feb. 22, 2007 which, in turn, claims the benefit of U.S. provisional application Ser. No. 60/775,729 filed Feb. 22, 2006; U.S. provisional application Ser. No. 60/775,728 filed Feb. 22, 2006; U.S. provisional application Ser. No. 60/790,882 filed Apr. 11, 2006; U.S. provisional application Ser. No. 60/791,055 filed Apr. 11, 2006; and U.S. provisional application Ser. No. 60/845,646 filed Sep. 19, 2006, each of which is incorporated by reference herein.

BACKGROUND OF THE INVENTION

1. Field of the Invention

This invention relates to a system and method for the delivery of regional citrate anticoagulation (RCA) to extracorporeal blood circuits.

2. Background Art

Continuous renal replacement therapy (CRRT) is a form of extracorporeal blood treatment (EBT) that is performed in the intensive care unit (ICU) for patients with acute renal failure (ARF) or end-stage renal disease (ESRD), who are often hemodynamically unstable with multiple co-morbidities. In a specific form of CRRT, continuous veno-venous hemofiltration (CVVH) (FIG. 1), blood is pumped through a hemofilter and uremic toxin-laden plasma ultrafiltrate is discarded at a rate of 1-10 liters per hour (convective removal of solutes). An equal amount of sterile crystalloid solution (replacement fluid, CRRT fluid) with physiological electrolyte and base concentrations is simultaneously infused into the blood circuit either before the hemofilter (pre-dilution) or after the hemofilter (post-dilution) to avoid volume depletion and hemodynamic collapse. From a theoretical and physiological point of view, when run continuously for 24 hours per day, CVVH is the closest of all available renal replacement therapy (RRT) modalities today to replicating the function of the native kidneys. Most experts in the field believe that it should be the preferred treatment modality for unstable patients with renal failure. Nevertheless, 90% of RRT in the ICU is performed as intermittent hemodialysis (IHD), sustained low efficiency dialysis (SLED), or sometimes as continuous veno-venous hemo-diafiltration (CVVHDF). Common to all of these latter methods of RRT is that the removal of most solutes is predominantly by the process of diffusion from blood plasma through the membrane of the hemofilter into the dialysis fluid. Diffusion is less efficient in the removal of larger solutes than convection and therefore, from a theoretical standpoint, CVVH is a superior method of RRT.

The most important reason for the limited use of CVVH in the ICU is that anticoagulation is mandatory to prevent clotting of the extracorporeal circuit in 24-hour treatments. Systemic anticoagulation has an unacceptable rate of major bleeding complications and cannot be done safely. Similarly, extracorporeal blood treatments including plasmapheresis, plasma adsorption on specialized columns, blood banking procedures, lipid apheresis systems, plasma adsorption-based endotoxin removal, treatment with a bioartificial kidney device that contains live renal tubular cells, or with a liver replacement therapy circuit also require powerful regional anticoagulation. Regional citrate anticoagulation has emerged as a possible solution to the clinical problem of circuit clotting.

Citrate (or the quickly buffered citric acid) is present in the human plasma as the trivalent negative citrate anion. This ion chelates ionized calcium in the plasma resulting in a single negative Ca-citrate complex and in low free ionized calcium levels. Since the coagulation cascade requires free ionized calcium for optimal function, blood clotting in the extracorporeal blood circuit (EBC) can be completely prevented by an infusion of citrate into the arterial (incoming) limb of the EBC. When the blood is passed through the extracorporeal processing unit, the anticoagulant effect can be fully reversed by the local infusion of free ionized calcium into the venous (return) limb of the EBC. Therefore, theoretically, regional citrate anticoagulation can be both very powerful and fully reversible without systemic (intra-patient) bleeding tendencies.

Regional citrate anticoagulation has been performed for more than 20 years. Nevertheless, all currently described regional citrate anticoagulation methods are labor intensive and complex with the ICU nurse administering several potentially very dangerous IV infusions in the circuit and/or in central venous lines with frequent laboratory measurements and prescription adjustments. Physician errors in prescription and nursing errors in administration can quickly lead to major complications, and even to death. Due to its well-documented dangers, regional citrate anticoagulation has not gained wide use in clinical practice. The recognized dangers of RCA include hypernatremia; metabolic alkalosis; metabolic acidosis; hypocalcemia 1 (due to net calcium loss from the patient); hypocalcemia 2 (due to systemic citrate accumulation); rebound hypercalcemia (due to release of calcium from citrate after CVVH is stopped); hypophosphatemia; fluctuating levels of anticoagulation; nursing and physician errors; ionized hypomagnesemia; declining filter performance; trace metal depletion; access disconnection; wrong connection of citrate, calcium infusions, and/or of the blood circuit to the patient; and accidental disconnection of the citrate or calcium infusion.

BRIEF DESCRIPTION OF THE DRAWINGS

FIG. 5a illustrates a hemodialysis system which may be used for 24-hour sustained low efficiency dialysis (SLED) or 4-5 hour intermittent hemodialysis (IHD) with RCA according to the present invention;

FIG. 6a illustrates a hemodialysis system which may be used for continuous veno-venous hemodialysis with pre-dilution hemofiltration (CVVHDF or c-SLEDF) with RCA according to the present invention;

FIG. 7a illustrates a hemodialysis system which may be used for 4-5-hour post-dilution hemodiafiltration (intermittent post-HDF) with RCA according to the present invention;

FIG. 8a illustrates a hemodialysis system which may be used for simultaneous pre- and post-dilution continuous veno-venous hemofiltration (CVVH) or 4-6 hour intermittent high volume hemofiltration (HVHF) with RCA according to the present invention;

FIG. 8b illustrates a conductivity-based OCM according to the present invention for pre- and post-dilution CVVH or HVHF with online-generated replacement fluid and automated RCA;

FIGS. 9a and 9b illustrate a triple lumen venous catheter with an infusion pathway according to the present invention;

FIGS. 10a and 10b illustrate a quadruple lumen catheter with an infusion pathway according to the present invention;

FIG. 10c illustrates a quadruple lumen vascular access catheter according to another aspect of the present invention with connection lines of different lengths and colors;

FIG. 10d illustrates a quadruple lumen vascular access catheter according to another aspect of the present invention with the male and female line connectors reversed and of different colors;

FIG. 11a illustrates connectors according to the present invention used to attach standard dialysis blood lines (independent arterial and venous blood circuit ends) for dialysis using separate arterial and venous needles;

FIG. 11b illustrates connectors according to the present invention used to attach a citrate-dedicated dialysis blood tubing (different arterial and venous blood circuit ends) for dialysis using separate arterial and venous needles;

FIG. 12a illustrates an arterial infusion line connector according to the present invention which may be used to attach a citrate-dedicated dialysis arterial blood line using separate arterial and venous needles;

FIGS. 14a-14b illustrates a triple lumen vascular access catheter according to the present invention for use with single needle dialysis operational mode;

FIGS. 14c-14d illustrates a triple lumen vascular access catheter according to the present invention for use with single needle dialysis operational mode that accommodates citrate-dedicated blood tubing and medication infusion lines with different arterial and venous connectors;

FIG. 17a illustrates a hemodialysis system which may be used for 24-hour sustained low efficiency dialysis (SLED) or 4-5 hour intermittent hemodialysis (IHD) with RCA according to the present invention;

FIG. 17b illustrates a hemodialysis system which may be used for simultaneous pre- and post-dilution continuous veno-venous hemofiltration (CVVH) or 4-6 hour intermittent high volume hemofiltration (HVHF) with RCA according to the present invention;

FIG. 17c illustrates a hemodialysis system with sensors and online generation of fluid for continuous SLED with RCA according to the present invention;

FIG. 17d illustrates a hemodialysis system with sensors and online generation of fluid for pre-dilution CVVH with RCA according to the present invention;

FIG. 26 illustrates a hemofiltration circuit according to the present invention showing the location of the triple lumen venous catheter with an infusion port at the tip of the withdrawal lumen;

FIG. 27a illustrates an air gap backflow prevention device which may be used to isolate ultrafiltrate from the patient circuit according to the present invention;

FIG. 27b illustrates a backflow prevention device comprising a series of one way valves which may be used to isolate ultrafiltrate from the patient circuit according to the present invention;

FIG. 27c illustrates a reduced pressure zone backflow prevention device which may be used to isolate ultrafiltrate from the patient circuit according to the present invention;

FIG. 28a illustrates a hemofiltration circuit according to the present invention showing a possible location for a reduced pressure zone backflow prevention device;

FIG. 29c depicts a configuration according to the present invention for deriving the patient systemic citrate level $C_{Sys}$ by measuring the ultrafiltrate citrate concentration $C_{UF}$;

FIG. 33 is a graph depicting plasma citrate concentration in the patient during RCA in accordance with the present invention;

FIG. 34b is a graph depicting citrate concentration measured by a citrate sensor in the drain circuit of a dialysis machine utilizing RCA according to the present invention;

FIG. 39 depicts a system for pre- and post-veno-venous hemofiltration (CVVH) with RCA and online replacement fluid generation according to the present invention;

FIG. 40 depicts a system for sustained low efficiency dialysis (SLED) or intermittent dialysis (IHD) with RCA and online dialysis fluid generation according to the present invention; and FIG. 41 depicts a system for SLED or IHD with RCA with a single concentrate proportioning system according to one aspect of the present invention.

DETAILED DESCRIPTION OF THE INVENTION

Figure 1:
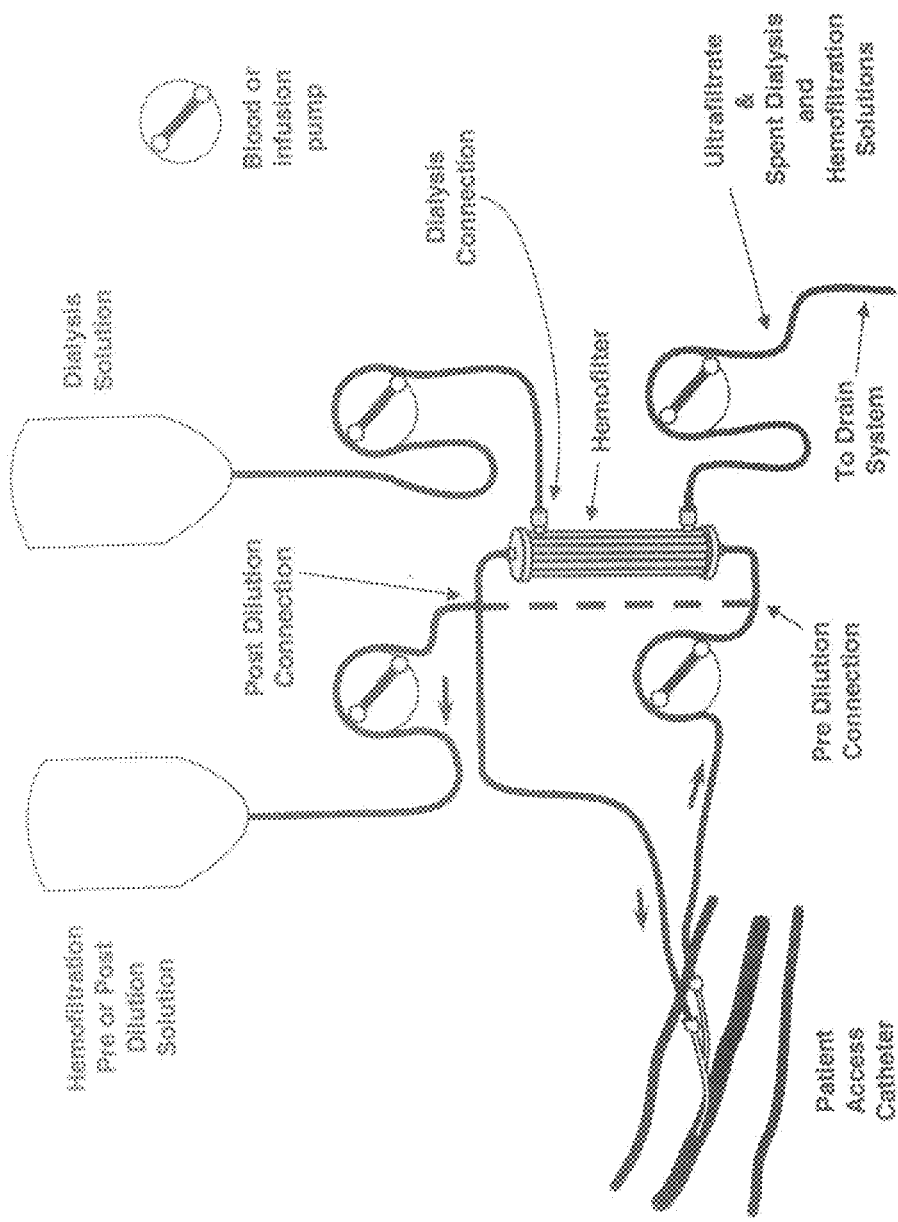
FIG. 1 illustrates a prior art system for continuous veno-venous hemofiltration (CVVH) or CVVH with dialysis (CVVHDF)

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention.

The present invention includes a comprehensive, two replacement fluid system and method for the delivery of regional citrate anticoagulation (RCA) to extracorporeal blood circuits, wherein the system may include an online clearance monitor (OCM) and a circuit effluent online sensor system (OSS) for the continuous determination of patient plasma content of ultrafilterable solutes. It is understood that components described for one system according to the present invention can be implemented within other systems according to the present invention as well.

The system and method according to the present invention is capable of delivering RCA to an extracorporeal system requiring anticoagulation. The system addresses the difficulties and risks to patients associated with extracorporeal anticoagulation methods and CRRT devices currently in use for continuous veno-venous hemofiltration (CVVH). The system may include a combination of various CRRT and dialysis machine hardware components, a software control module, and a sensor module to measure citrate or other solute levels online to ensure the maximum accuracy and safety of treatment prescriptions, and the use of replacement fluids designed to fully exploit the design of the system according to the present invention.

The system and method according to the present invention provide an automated approach to writing safe citrate prescriptions which utilizes the integration of IV pumps with a special citrate anticoagulation control program for the machine-controlled and, in some instances, fully automated delivery of citrate and calcium infusions for the safety of the RCA procedure. One important element of the procedure is the automated generation of citrate prescriptions by the machine which do not allow citrate accumulation in the patient, regardless of body metabolism of citrate. Prior art systems may include a dosing program which allows unlimited calcium and citrate accumulation in the patient's circulation as long as the systemic ionized calcium is normal. This can be very dangerous if the liver function suddenly improves, for instance, if renal replacement therapy (RRT) with citrate is provided before and during liver transplantation. In contrast, the system and method according to the present invention will not allow dangerous citrate accumulation (e.g., greater than about 2.7-4 mM) while keeping the systemic ionized calcium normal as long as the hemofilter (artificial kidney) is removing citrate at the prescribed rate. Another important element of the system presented herein is the integration of the safe prescriptions with the continuous, online monitoring of the hemofilter performance by a plurality of methods to ensure that citrate removal in the circuit remains stable and at the prescribed level. In some embodiments, the levels of all major electrolytes needed to define the ideal prescription may be discerned in the systemic plasma which, together with the flexible dosing of citrate, bicarbonate, sodium, potassium, phosphate, calcium, and magnesium, allows complete automation of the RRT procedure with citrate anticoagulation.

Prior art systems may rely on citrate metabolism predominantly or exclusively to deliver bicarbonate to the patient. Such systems do not provide fluids that deliver bicarbonate in sufficient amounts directly to the patient, and instead provide citrate as a bicarbonate precursor molecule. This is a major problem as patients with impaired metabolism of citrate may develop severe metabolic acidosis when such fluids are used. According to one aspect of the present invention, the system and method described herein use bicarbonate supplementation of the replacement fluid and the citrate anticoagulant infusion and do not allow this complication. The fluid designs according to the present invention provide for flexible direct delivery of bicarbonate as needed by the patient.

Unlike the present invention wherein magnesium may be removed from the replacement and dialysis fluids, prior art systems which do not remove magnesium from these fluids have a resulting suboptimal anticoagulant effect, preclude the manufacture of a single chamber bicarbonate-based replacement or dialysis fluid, and make phosphate supplementation at the point of manufacture difficult, if not impossible. In addition, the present invention may provide calcium infusions with different calcium to magnesium molar ratios to accommodate the individual patient. Prior art systems may provide potassium with the calcium replacement infusion. However, this is unnecessary from the perspective of providing RCA and incurs the risks of use of a potassium-free dialysis fluid. According to an aspect of the present invention, this problem may be avoided by providing potassium in the replacement or dialysis fluid.

Prior art systems may not include monitoring of the delivered plasma flow or filter performance online as in the system and method according to the present invention, wherein the integration of these technologies is important to automated citrate anticoagulation. In addition, CRRT in the intensive care unit (ICU) with RCA requires online filter performance monitoring at low flow rates not possible with prior art systems. The present invention may utilize online conductivity dialysance to monitor filter performance at blood flows down to as low as about 50 ml/min and dialysate flows down to as low as about 100 ml/min. Prior art systems may use ionic dialysance of whole blood to derive the calcium, magnesium, and potassium replacement infusion rate. This may be inaccurate and can lead to dangerous calcium dosing errors if the hemoglobin level of patients varies greatly as is the case in the ICU. The present invention provides methods to convert whole blood conductivity dialysance into citrate (and calcium) plasma dialysance and dose the calcium infusion accordingly. The present invention may monitor the filter clearance of various indicator substances (e.g., glucose, citrate, and inulin) by measuring the concentrations of these substances in the filter effluent during RRT. The present invention also may deliver some or all of these substances with the citrate anticoagulant solution and measure their level in the filter effluent while delivering an anticoagulant bolus as detailed herein with respect to online clearance monitoring.

The system and method according to the present invention allow for the manipulation of the conductivity, dextrose content, and/or other solute content of the citrate anticoagulant solutions, calcium replacement solutions, acid concentrates and, in general, any fluid used during RCA to make possible the identification and ensure the proper connection of these fluids through their effect on the filter effluent composition during the priming procedure and/or the treatment session. Unlike systems which monitor blood composition by inserting sensors directly into the blood circuit, raising safety concerns and potentially encountering bio-fouling of the sensors, the system and method according to the present invention avoids these concerns by instead monitoring the filter effluent. The present invention may employ methods for analyzing the complex mixture of calcium, magnesium, and citrate in the filter effluent. Non-reacting and non-depletable, chemical-optical sensors (optrodes) and/or Raman spectroscopy may be used to monitor the filter effluent composition. The present invention also provides corrections for the effects of access recirculation and the specific RCA prescription and fluids used on the composition of the filter effluent to derive the variable of interest, the patient blood solute level. The present invention further includes the full automation of access recirculation measurements with high accuracy even at low circuit blood flow rates by deploying one or more hematocrit sensors on the venous blood line in addition to one or more hematocrit sensors present on the arterial blood line.

Unlike the prior art, the present invention monitors filter effluent concentrations of substances and may integrate Raman spectroscopy with a dialysis machine that may be specifically designed to deliver RCA. The present invention can monitor the concentration of any filterable or dialyzable antibiotic in the filter effluent fluid. Monitoring of the blood concentrations of protein-bound, partially or completely non-dialyzable and non-filterable analytes can be accomplished by deploying a Raman sensor at some point on the blood circuit instead of the filter effluent line. In previous methods, measurement of urea has been targeted, a solute of limited interest during citrate anticoagulation. The present invention may include the measurement of the free citrate, the calcium-citrate complex, the magnesium-citrate complex, and possibly the calcium-phosphate and magnesium-phosphate complex in the filter effluent fluid as well as any clinically important solute including, but not limited to, dextrose, lactate, beta-hydroxy-butyrate, free phosphate species, and antibiotics most commonly including vancomycin, aminoglycoses, and all other filterable or dialyzable antibiotics in general. Still further, peptide composition may be monitored in the filter effluent fluid to follow the level of various cytokines in the patient and to follow the systemic inflammatory response syndrome Raman signature and organ-specific injury peptide patterns in the filter effluent. Systemic cystatin C, creatinine, and/or inulin levels may also be monitored. Para-amino-hippuric acid (PAH) and albumin levels in the blood plasma may be monitored directly by deploying the optical probe of the Raman device on the blood circuit.

The present invention may deploy a Raman optical probe (laser irradiation and scattered light collection elements) on the filter effluent line. This location allows any laser wavelength and energy to be deployed without safety concerns about effects on human tissue or blood cells, and the simplified sample matrix of the ultrafiltrate (when compared to whole blood) predictably improves the signal to noise ratio. Deploying the Raman optical probe on a continuous light transparent flow-through chamber may allow automated, frequent measurements without the need for a complex sampling apparatus. Bio-fouling may also be minimized as blood clotting cannot occur, allowing the use of surface-enhanced Raman scatter spectroscopy (SERS) in an intermittent sampling device or in a continuous flow-through chamber for increased sensitivity in detecting substances in low concentrations (e.g., antibiotics and various peptides). With Raman spectroscopy during dialysis, the same device without any hardware change can be used to detect a multitude of analytes by detecting Raman scatter light intensity at specific wavelengths and/or using a different exciting laser as selected by the operating software. An additional benefit is that specific analytes can also be detected in the blood circuit safely and in a sterile fashion by simply deploying a Raman optical probe on the blood line as long as the laser with the specific energy and wavelength is safe to use in that location.

Prior art systems may rely on pressure measurements to set the rate of the pre-dilution and post-dilution replacement fluid flows. This requires that potentially dangerous, high transmembrane pressures develop before a change in fluid flow rates is effected. The system and method according to the present invention instead may calculate the replacement fluid flow rates in advance to avoid excessive hemoconcentration in the hemofilter during ultrafiltration and thereby greatly reduce the risk of high transmembrane pressures developing. Trans-membrane pressure monitoring, a standard feature of renal replacement devices in current use, therefore may become a second line safety monitoring tool in the system according to the present invention.

The integration of the system according to the present invention with secondary extracorporeal blood processing systems is contemplated, wherein the safely anticoagulated blood from the system is passed through a secondary system including, but not limited to, blood banking devices, plasmapheresis devices, liver support circuits for protein-bound toxin removal, lipid apheresis devices, and endotoxin removal columns and devices before return to the system circuit and reversal of the anticoagulation with the calcium infusion. For implementations where the secondary extracorporeal blood processing may introduce undesirable water soluble, ultrafilterable and/or dialyzable solutes into the processed blood, one site of connecting the secondary blood circuit may be on the arterial blood line after the infusion of citrate but before the hemofilter of the primary circuit, so that the introduced undesirable substances could be subsequently largely removed by the artificial kidney of the primary circuit.

Multiple applications for the system and method according to the present invention exist including, but not limited to, short as well as extended duration renal replacement therapies both in a health care center and in the patient's home, indirect sensing of the patient's blood composition for various target solutes, kinetic monitoring of organ function, and providing safely anticoagulated blood for secondary blood processing units.

Figure 2:
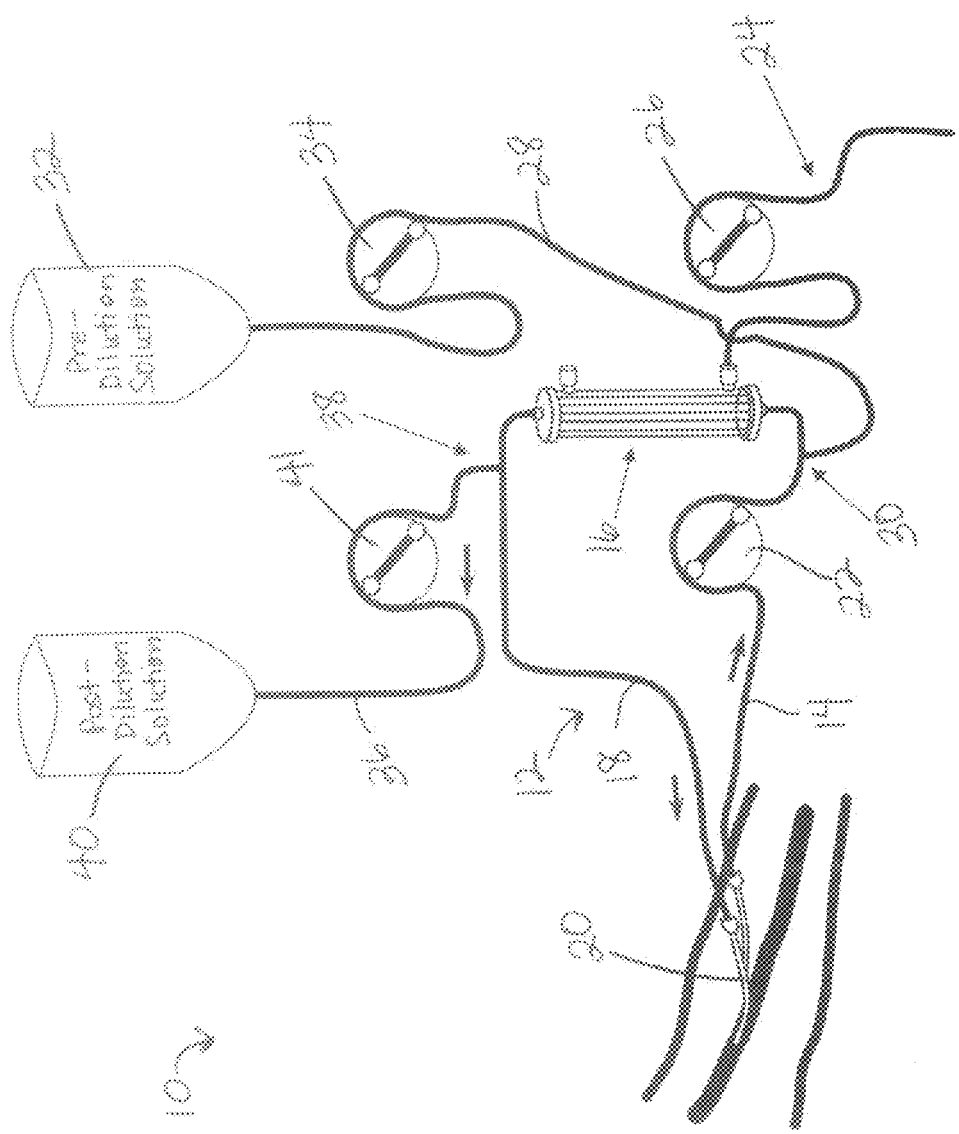
FIG. 2 illustrates a system according to the present invention for using citrate in the pre-dilution solution and infusion of a post-dilution solution to enhance removal of citrate in the hemofilter.

With reference first to FIG. 2, a system for CRRT according to the present invention is illustrated and designated generally by reference numeral 10. System 10 includes a CRRT circuit 12 including an arterial blood line 14, a hemofilter 16 in fluid communication with arterial blood line 14, and a venous blood line 18 in fluid communication with hemofilter 16. Arterial and venous blood lines 14, 18 are arranged to be connected to an access catheter 20 in order to withdraw blood from and return blood to a patient. A blood pump 22 is operably connected to arterial blood line 14 in order to facilitate movement of blood from access catheter 20 through CRRT circuit 12. According to one aspect of the present invention, blood pump 22 may be precise, with pumping speeds which may be adjustable in 5 ml/min or finer increments. An effluent line 24 is also in fluid communication with hemofilter 16 for carrying effluent fluid to a drain to be discarded. An ultrafiltration pump 26 may be operably connected to effluent line 24 to facilitate this process, wherein ultrafiltration pump 26 may be an overall ultrafiltration pump that may be non-volumetric in a scale-based system, or a net ultrafiltration pump which may be volumetric.

While CRRT circuit 12 is shown and described, it is understood that the system according to the present invention may comprise any extracorporeal circuit, either wholly or only partially outside the body. Furthermore, it is understood that "patient" as used herein is not limited to human beings, but may comprise other species as well.

With continuing reference to FIG. 2, system 10 further comprises a pre-filter infusion line 28 having a pre-dilution connection 30 to arterial blood line 14 upstream from hemofilter 16. Pre-filter infusion line 28 may supply a pre-dilution solution, such as a citrate-containing anticoagulation solution as described below, from a pre-filter source (e.g., bag 32). A pre-filter replacement fluid pump 34 may be operably connected to pre-filter infusion line 28 to facilitate infusion of the pre-dilution solution, wherein pre-filter pump 34 may be implemented as a volumetric pump. A non-volumetric pump may be acceptable with scale-based balancing. Hemofilter 16 may then be used to remove the citrate anticoagulant (and the bound calcium) from the blood before it is returned to the patient. System 10 may also include a post-filter infusion line 36 having a post-dilution connection 38 to venous blood line 18 downstream from hemofilter 16 for restoring the so processed anticoagulated blood to normal volume. Post-filter infusion line 36 may supply a post-dilution solution, such as an essentially calcium-free, bicarbonate solution as described below, from a post-filter source (e.g., bag 40). A post-filter replacement fluid pump 41 may be operably connected to post-filter infusion line 36 to facilitate infusion of the post-dilution solution, wherein post-filter pump 41 may be implemented as a volumetric pump, although a non-volumetric pump may be acceptable with scale-based balancing.

Figure 3:
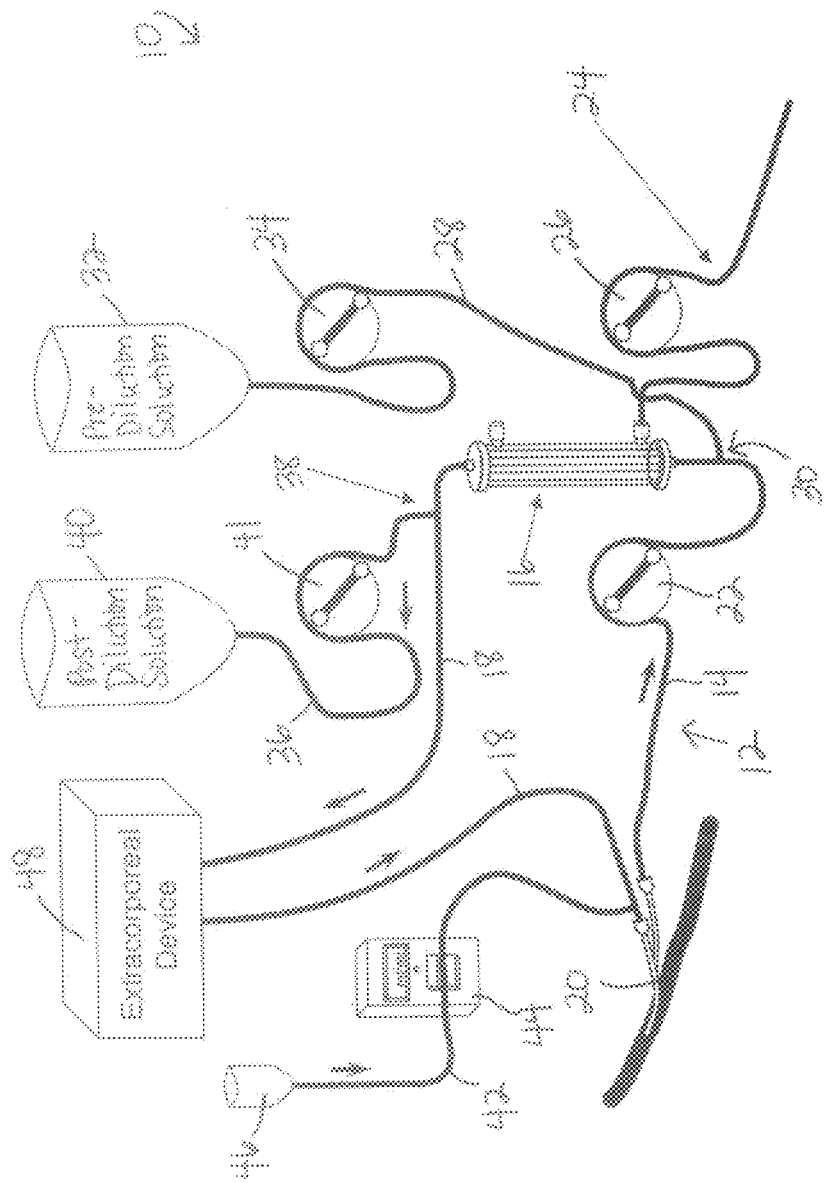
FIG. 3 illustrates use of a regional citrate anticoagulation (RCA) system according to the present invention to anticoagulate the extracorporeal circuit of applications other than CRRT.

In accordance with the present invention, an additional IV infusion line 42 and associated IV infusion pump 44 may be utilized for an IV solution infusion into venous blood line 18 downstream from post-dilution connection 38. In particular, IV infusion pump 44 may be used to administer a pre-mixed calcium and magnesium-containing infusion from an IV infusion source (e.g., bag 46) in coordination with the CVVH prescription (described below) and patient chemistry values. Patients will differ in their need for calcium supplementation to reverse the citrate anticoagulation as they will have different albumin and steady state citrate levels. There may also be differences in calcium release from or uptake into the bones. Finally, one may have to administer extra calcium and magnesium in the initial few-hour "loading" phase of RCA to saturate the expanding systemic citrate pool until the steady state is reached. As depicted in FIG. 3, the anticoagulated blood restored to normal volume with the post-filter replacement fluid infusion can be perfused into any secondary extracorporeal blood treatment (EBT) device 48.

Figure 4A:
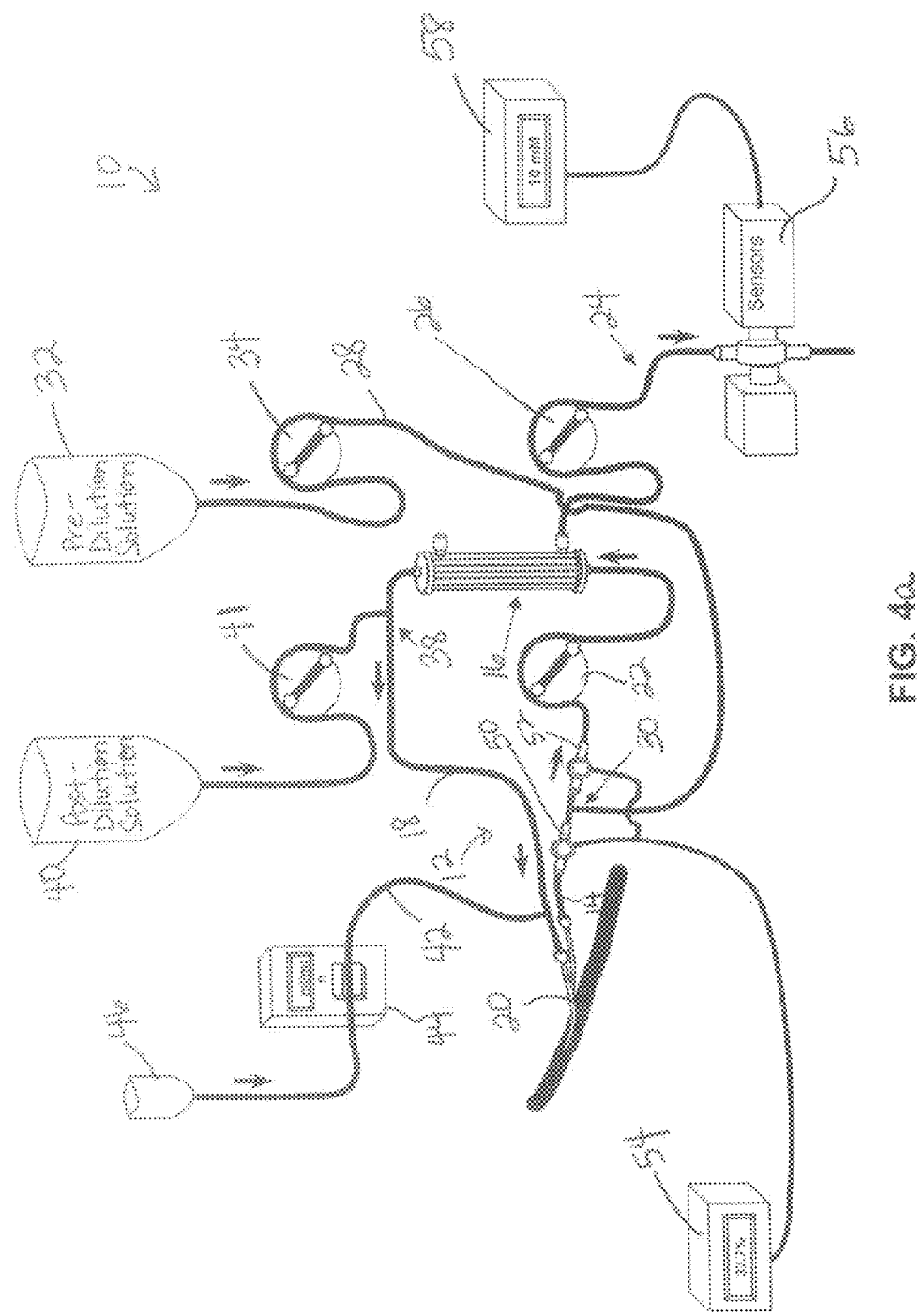
FIGS. 4a-4b illustrate a continuous renal replacement therapy (CRRT) circuit based on pre- and post-dilution hemofiltration with an integrated online sensor system (OSS) and hematocrit sensors according to the present invention.

FIG. 4a illustrates additional components which may be included in system 10 according to the present invention. System 10 may integrate online (e.g., optical) hematocrit sensors 50 and/or 52 operably connected to arterial blood line 14 to determine the dilution of the incoming blood and in communication with an associated display 54. Hematocrit sensors 50, 52 may be deployed in duplicate, one before (sensor 50) and one after (sensor 52) pre-dilution connection 30. First hematocrit sensor 50 may be used to determine arterial plasma flow in real time. Second hematocrit sensor 52 may allow for checking the reliability of the two sensors 50, 52 against each other when the pre-dilution fluid is not running. When the pre-dilution fluid is running at a known (machine settings and volumetric pump defined) rate, the readout from hematocrit sensors 50, 52 may allow for the determination of the degree of hemodilution with the pre-filter infusion, and thereby for the calculation of the delivered blood flow to the dialyzer 16. Online hematocrit sensors 50 and/or 52 allow minute-to-minute calculation of the plasma volume in the blood flowing into the dialyzer 16. This ensures the most accurate and possibly continuously-adjusted dosing of citrate-containing pre-filter fluid to achieve the target citrate to plasma flow ratio. Hematocrit sensors 50 and/or 52 can also be used to detect access recirculation. Finally, the readout from first hematocrit sensor 50 (before the pre-dilution infusion) allows for monitoring the patient's blood volume and will detect excessive net ultrafiltration leading to intravascular volume depletion with concomitant hemoconcentration in the patient before hemodynamic compromise could result. Doppler based fluid flow, hematocrit monitors, and volumetric fluid pumps may be used on arterial and venous blood lines 14, 18 as well as the replacement fluid lines 28, 36 and effluent fluid line 24 for maximal precision in ensuring that the set blood flow rate on blood pump 22 matches the actual blood flow delivered by the action of blood pump 22, and that all other fluid flows (pre-filter fluid flow, effluent flow, venous blood flow and net ultrafiltration amount) are all the same as defined by the machine settings.

Figure 4B:
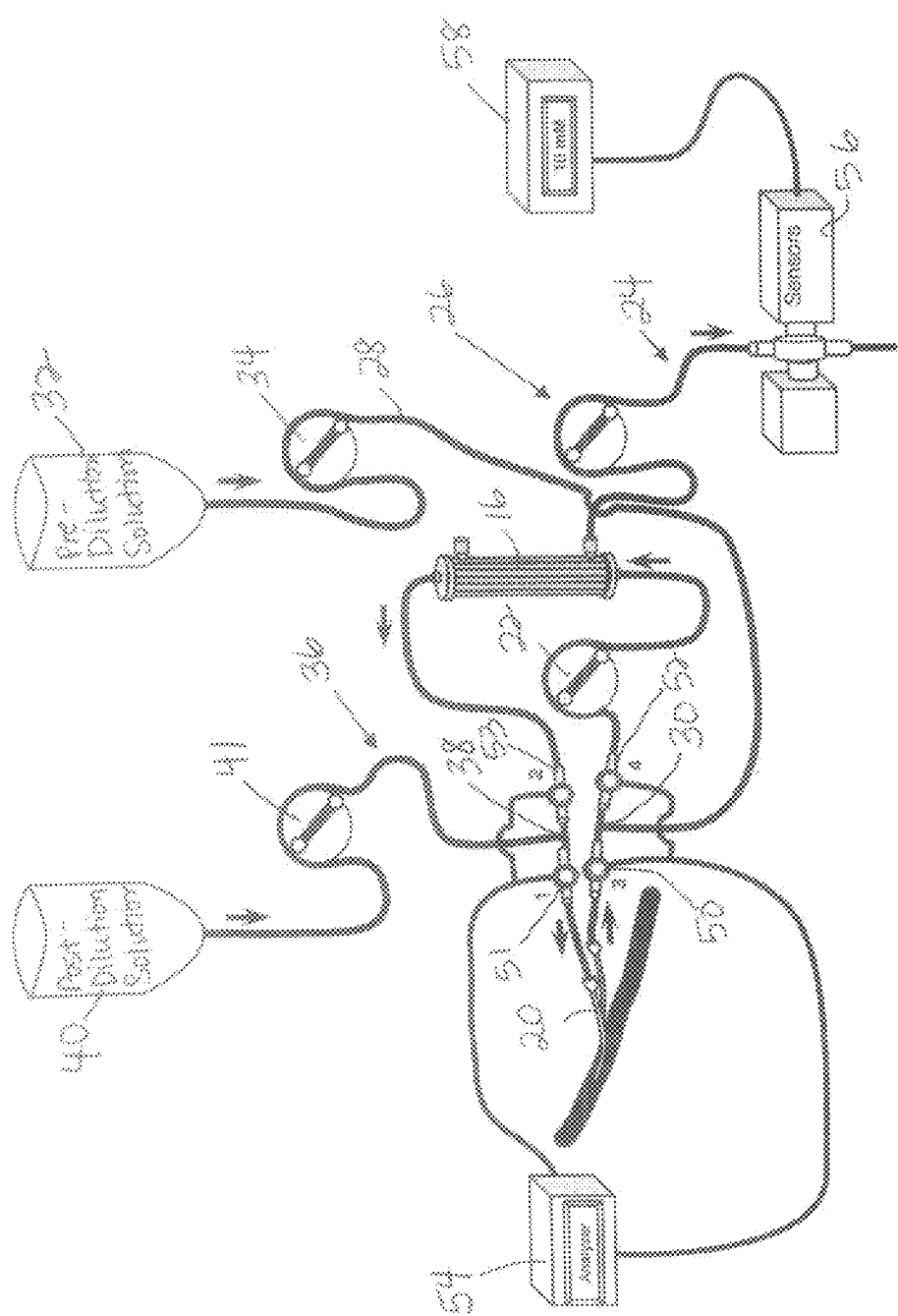
Figure 5B:
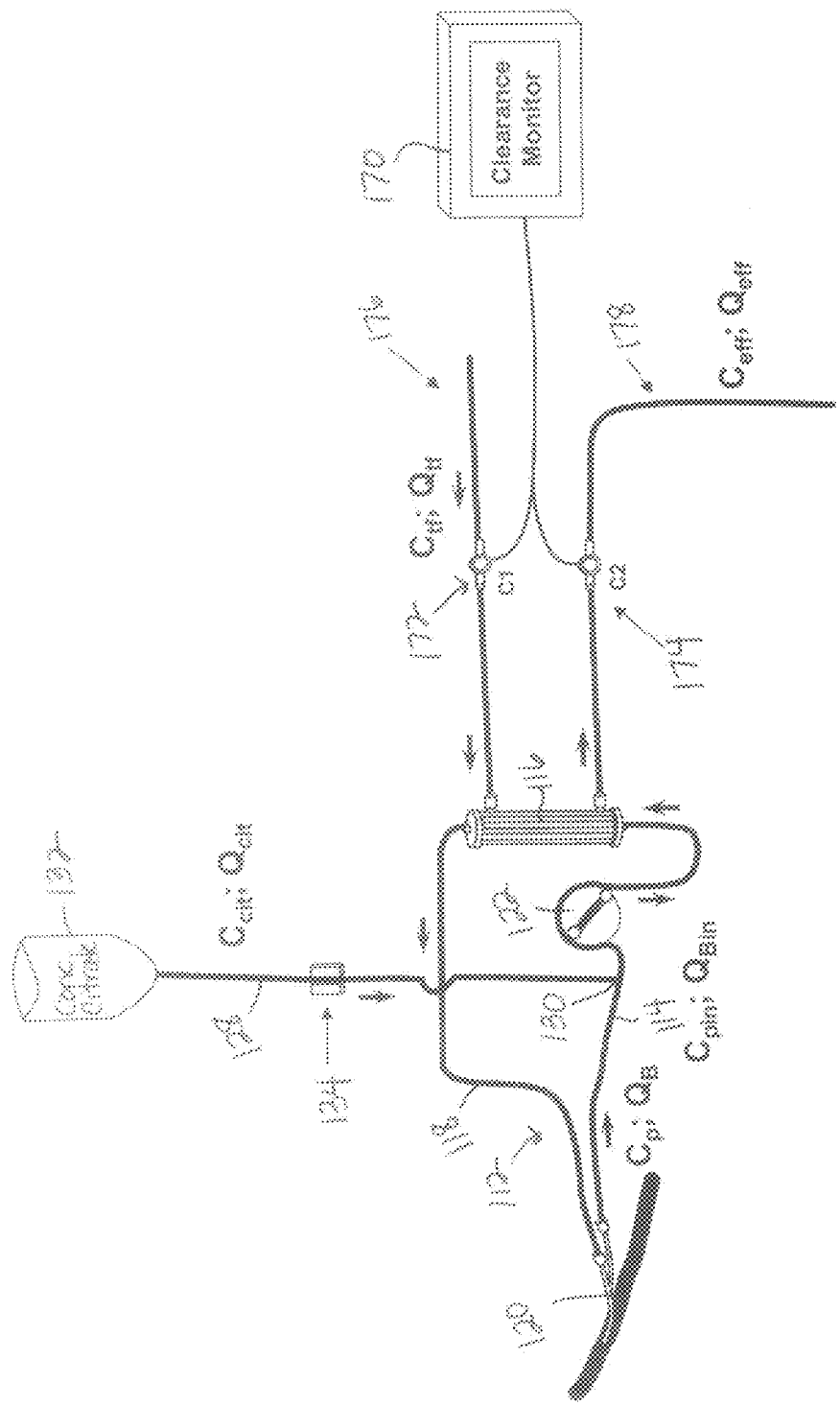
FIG. 5b illustrates a conductivity-based online clearance monitor (OCM) according to the present invention for 24-hour SLED or IHD with online-generated dialysis fluid and automated RCA.
Figure 6B:
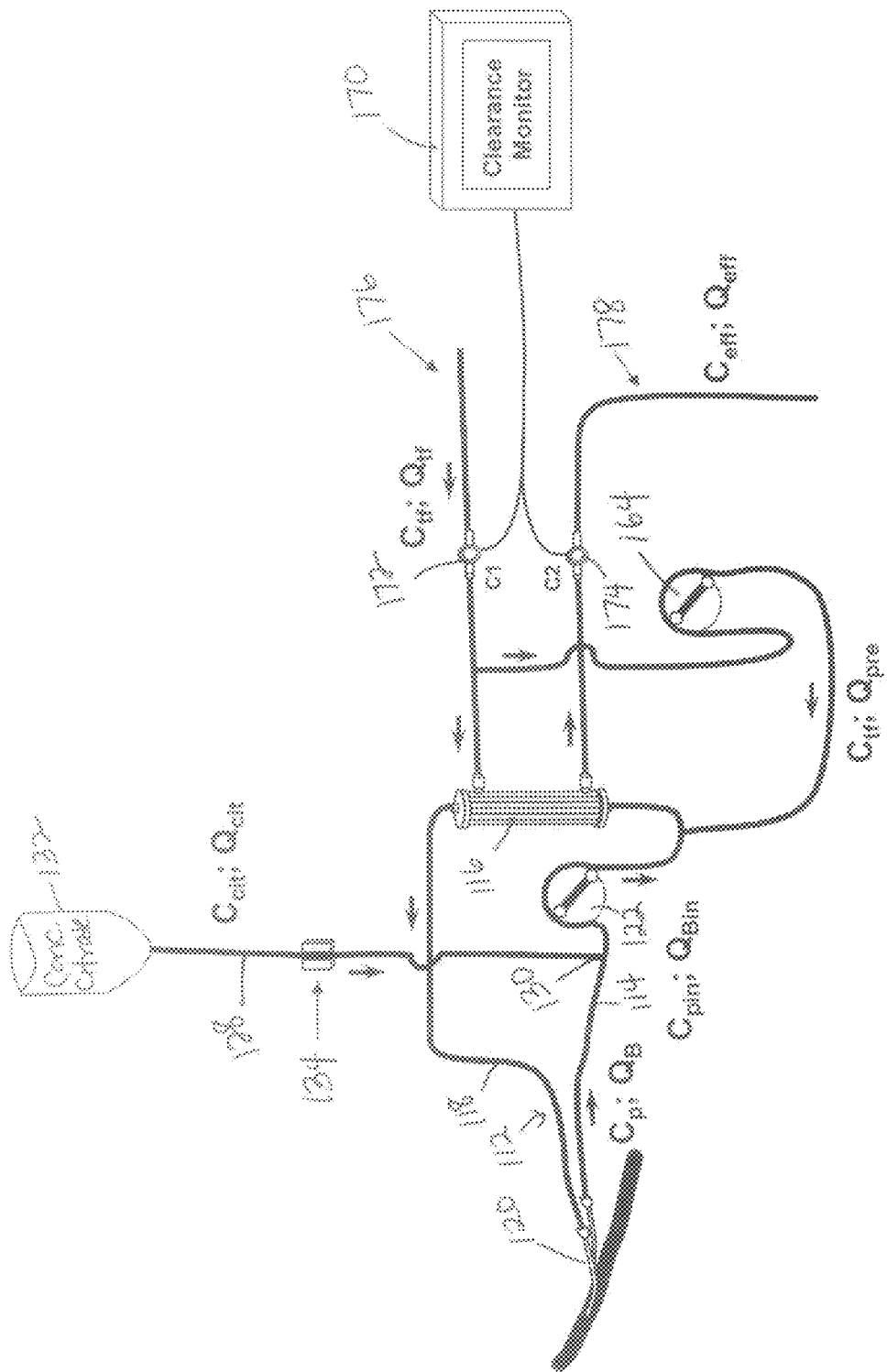
FIG. 6b illustrates a conductivity-based OCM according to the present invention for pre-dilution CVVHDF with online-generated therapy fluid and automated RCA.
Figure 7B:
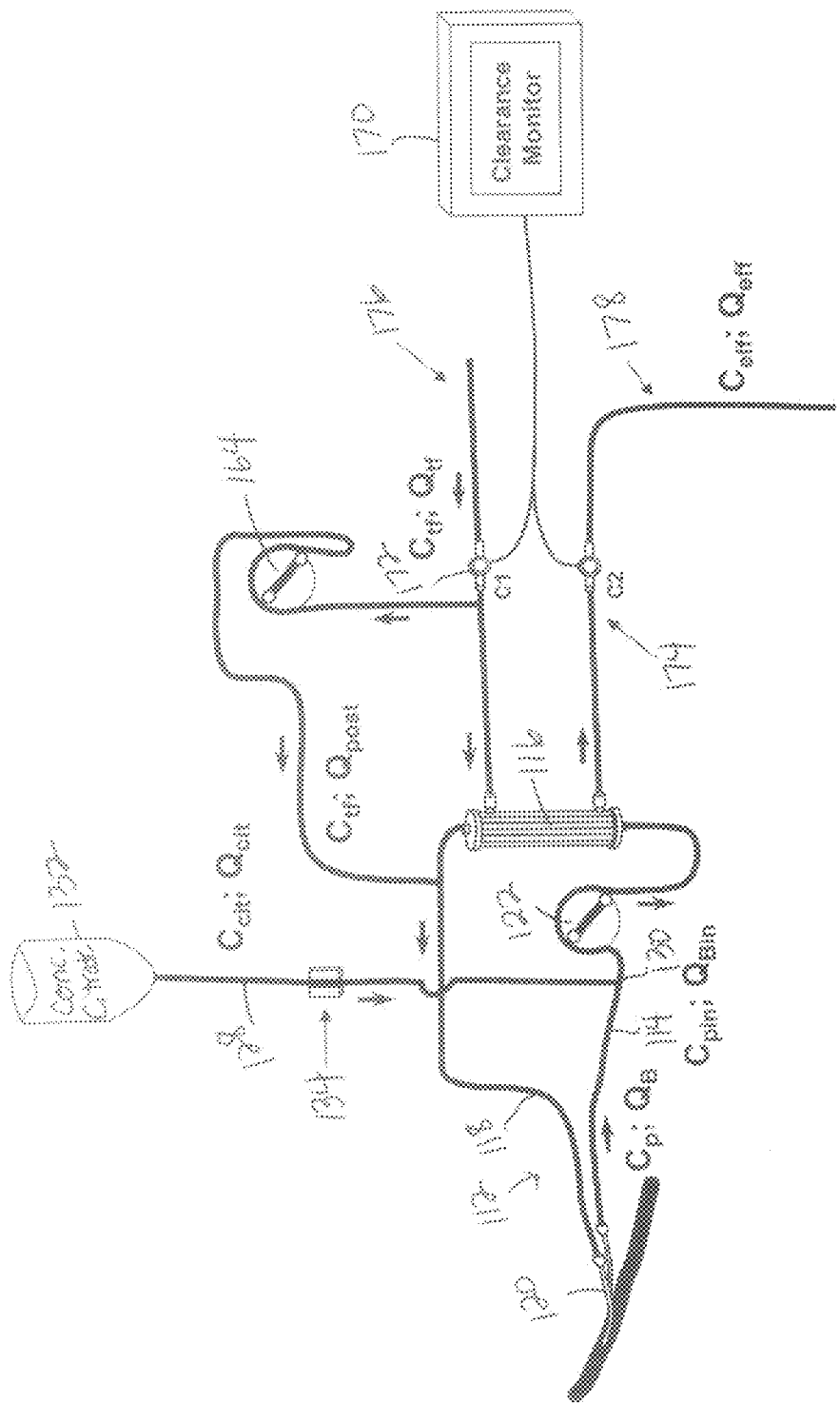
FIG. 7b illustrates a conductivity-based OCM according to the present invention for post-dilution hemodiafiltration (HDF) with online-generated therapy fluid and automated RCA.

As shown in FIG. 4b, a total of four hematocrit sensors 50, 51, 52, 53 may be used to determine the dilution of the blood hemoglobin in the arterial limb 14 as well as the venous limb 18 of the extracorporeal circuit 12. FIG. 4b depicts a comprehensive battery of four online hematocrit sensors 50-53 deployed in close physical proximity to each other, at strategic points of the extracorporeal blood circuit 12 for a single modular implementation integrated into system 10 according to the present invention. Such integration is fully possible and is contemplated in all other systems described herein. In addition to sensors 50, 52 described above, sensors 51, 53 may be deployed in duplicate, one before and one after the post-dilution connection 38. The venous limb hemoglobin concentration, which may be determined using sensor 51, may be temporarily increased by increased ultrafiltration on the hemofilter 16 with or without a simultaneous decrease in the rate of infusion of one or more of the crystalloid fluids used by the system. Conversely, the circuit venous limb hemoglobin concentration (sensor 51) can be temporarily decreased by faster infusion of one or more of the crystalloid fluids used by the system with or without a simultaneous decrease in ultrafiltration. The effect on the arterial limb hemoglobin concentration (sensor 50) of such programmed, intermittent, temporary changes in the venous limb hemoglobin concentration allow the precise, automated, intermittent calculation of access recirculation, R as apparent to those skilled in the art.

System 10 may further include an integrated online sensor system (OSS) comprising a solute sensor or sensor array 56 operably connected to effluent fluid line 24 for determining the solute concentration of the ultrafiltrate, and in communication with an associated display 58. In one embodiment, solute sensor 56 may comprise an online citrate sensor which may be used to eliminate the risk of undetected citrate accumulation and may double as an online delivered clearance and liver function monitor. Solute sensor 56 may also function as an online calcium and magnesium sensor. The current clinical practice of monitoring laboratory parameters every six hours to detect citrate accumulation is not applicable to the new treatment protocols with higher clearance goals and a concomitant more rapid citrate accumulation that would occur with a sudden decline in liver function. More frequent laboratory testing is clinically not practical. Solute sensor 56 according to the present invention allows for the derivation of the citrate, calcium and magnesium level in the patient's systemic plasma. Under such monitoring, RCA may be performed with complete safety. The post-filter fluid summary bicarbonate content could also be adjusted and the liver function monitored in real time through observing the metabolism of citrate. Solute sensor 56 may also serve as an online clearance module.

All of these elements may be coordinated and monitored by a control program, which may be utilized to determine the optimal ratio of pre- and post-dilution fluids and the fluid flow rates required to reach treatment goals while minimizing citrate load into the patient.

Disposable, sterile fluid circuits may be utilized according to the present invention. System 10 may work with, but is not limited to, blood flows in the range of 50-450 ml/min with flows optimally around the 75 to 200 ml/min range (for 24-hour CVVH versus high volume hemofiltration (HVHF) operational mode). This is a benefit, as even the least optimally performing catheter access will deliver such flows. According to one aspect of the present invention, hemofilter 16 may be removable from system 10, so that an appropriate size filter could be used for the prescribed blood flow and hourly ultrafiltration goals, and also so that elective filter changes could be performed every 24 hours because of predictable protein fouling even in the absence of clotting. More frequent filter changes may also be needed for the clinical application (e.g. cytokine removal).

Since only convective clearance may be used according to the present invention (no diffusive or dialytic component is required), the anticoagulation achieved remains uniform along the axis of hemofilter 16, promising superior results when compared with other protocols using CVVH with simultaneous dialysis (CVVHDF). The amount of middle molecular weight uremic toxin clearance including inflammatory cytokines will also be predictably greater than in any prior CRRT implementations. System 10 according to the present invention running on a CVVH machine or a dedicated device with the necessary pumps and controls may be used to safely provide citrate anticoagulation to any extracorporeal blood circuit, wherein the maximum operational blood flow may be, but is not limited to, 450 ml/minute.

The RCA system according to the present invention eliminates the risks associated with a separate concentrated citrate infusion for anticoagulation in CVVH and other extracorporeal circuits. Citrate removal by hemofilter 16 is important for safe operation of a CVVH system using citrate anticoagulation. If hemofiltration is stopped and blood continues to flow through the circuit 12 to prevent coagulation, the separate infusion of citrate has to be stopped immediately or the patient will receive an excess amount of citrate which could be life threatening. In RCA system 10, if for any reason hemofiltration stops and blood continues to flow through circuit 12 to prevent coagulation (e.g., replacement solution bags 32, 40 are empty), the delivery of citrate with the pre-dilution fluid and also the delivery of calcium with the post-dilution fluid are immediately aborted to protect the patient from an infusion of excess citrate and calcium.

The RCA system according to the present invention markedly reduces the need for health care personnel to monitor and adjust CRRT based on hemofiltration. The use of the post-filter fluid provides for enhanced clearance and variability in the treatment prescription with the varying potassium and alkali content depending on the fluid selected as described below. Finally, the RCA system according to the present invention greatly reduces the risk of citrate accumulation in the patient associated with RCA during hemofiltration or any other extracorporeal blood processing intervention. The specific dangers of RCA as addressed by the RCA system according to the present invention are explained below:

1) Hypernatremia: Only isonatric solutions may be used including the calcium solution. Clinically significant hypernatremia (or hyponatremia) due to the treatment cannot occur.

2) Metabolic alkalosis: The sum of bicarbonate and anions metabolizable to bicarbonate (in mEq) may be kept between 25-50 mEq bicarbonate equivalents per liter of replacement fluid. This is in keeping with fluid alkali content per liter prescribed in most CVVH protocols in the literature. Mild metabolic alkalosis with systemic plasma bicarbonate in the range of 25-30 is possible with high clearance goals but it is not likely to occur or be clinically highly relevant. Changing the ratio of the 25 and 50 bicarbonate bags on the scales (2:0, 1:1, 0:2) and/or supplementing any post-dilution fluid bag with up to 5 mEq/L $NaHCO_3$ (from standard IV push bicarbonate ampoules) will allow flexible adjustment of the overall post-dilution fluid bicarbonate content from 25 to 55 in about 5 mEq/L increments.

3) Metabolic acidosis: With the above flexibility in fluid alkali content, it could only develop if citrate were not metabolized. Even so, if the post-dilution fluid is bicarbonate based, life-threatening wash out of bicarbonate could not occur with prescriptions with >=50% citrate extraction. Citrate sensor 56 may detect the lack of liver metabolism of citrate and may alert the operator to change to a pair of replacement fluids and treatment settings specifically designed for anhepatic patients. The additional citric acid in the pre-filter fluid is not an effective acid from the standpoint of the patient, as the bicarbonates that it consumes are regenerated through the metabolism of the citrate anion in the liver without any net acid generation (analogous to the course diabetic ketoacidosis in a Type 1 diabetic ESRD patient). In the near anhepatic patient, bicarbonate lost through ultrafiltration will not be regenerated by citrate metabolism. However, even such patients can continue on RCA with CVVH, provided that the citrate extraction is >=60%, 50 bicarbonate post-dilution fluid is used, and the calcium homeostasis is adequately managed with a carefully selected (and higher) dose of the calcium and magnesium infusion.

4) Hypocalcemia 1 (due to net calcium loss from the patient): The ultrafiltrate total calcium and magnesium losses are easily calculable in the RCA system according to the present invention. Calcium and magnesium supplements needed in the form of the dedicated infusion regulated by the system may be calculated by a dosing program also taking into account any ongoing citrate accumulation predicted by kinetic modeling and measured by citrate sensor 56. The patient's systemic total and ionized calcium levels may be measured every 6 hours as well as calcium volume of distribution determined by anthropomorphic and citrate sensor data. Magnesium may be dosed to maintain a total plasma Ca:Mg=2:1 mM ratio (as ionized magnesium measurements are not routinely available and all chelators of calcium (albumin, citrate, etc) also chelate magnesium.

5) Hypocalcemia 2 (due to citrate accumulation): Citrate will be given in the pre-dilution fluid. This eliminates the risk of nursing errors with a separate citrate infusion. This protocol achieves equally or more efficient anti-coagulation than any previous protocol with 30-40% less net citrate load into the patient. Careful selection of the pre-filter fluid citrate content and keeping the citrate extraction >=50-66% will eliminate the risk of citrate accumulation beyond 3.75-5 mM. Finally, marked citrate accumulation due to lack of metabolism when it occurs, may also be detected accurately by citrate sensor 56 before the ionized calcium could drop by more than 0.25 mmol/L. This may be accomplished by analyzing the sensor-measured systemic plasma levels of citrate by a kinetic modeling program according to the present invention. The kinetic program analyzes the CVVH prescription (fluid compositions and flow rates as well as blood flow rate) and the sensor data when available. It also utilizes anthropomorphic data to predict the citrate volume of distribution in the patient. Finally the patient's citrate clearance in L/minute may be calculated and subsequently used to generate the expected citrate accumulation curve and guide calcium and magnesium replacement to saturate the retained citrate. In citrate non-metabolizers (patients with liver failure), RCA with CVVH will be either terminated or carefully continued with special consideration of the risk of rebound hypercalcemia at the cessation of RCA and metabolic acidosis from bicarbonate wash-out.

6) Rebound hypercalcemia (due to release of calcium from citrate after CVVH is stopped): The RCA prescription will ensure that systemic citrate levels stay <=3-5 mM corresponding to about maximum 0.6-1 mM chelated calcium that could be released after RCA is stopped in all patients who can metabolize citrate. Most patients will have 1 mM citrate and about 0.25 mM Ca chelated by citrate in the steady state. The RCA system and method according to the present invention may be designed to keep systemic ionized Ca levels around 1-1.25 and therefore the highest calcium level after RCA is stopped will be <=1.6-1.85 mM and most patients will rebound to <=1.5 mM Ca levels after treatment. If a patient with liver failure is treated with RCA for CVVH, the prescription may be modified so that the steady state citrate level does not exceed 4 mM and the ionized calcium will be maintained at 1.0. A 35 ml/kg/hour treatment goal may still be achieved for any patient size. Total magnesium will be kept at 50% of total calcium (mM/mM). This will require large doses of the additional calcium and magnesium infusions, as there will be more calcium and magnesium in the ultrafiltrate. If the liver function improves the values will gradually normalize with ongoing CVVH and a reduction in the calcium and magnesium infusion without rebound hypercalcemia. If the liver does not improve, rebound hypercalcemia will not occur as the citrate will not be metabolized. Finally, prior to a liver transplant, high volume hemofiltration without citrate anticoagulation can be rendered for a few hours to wash out all citrate and chelated extra calcium and magnesium before the new liver (with good metabolic function) is put in. This way even the anhepatic patient will be able to receive high dose RCA for CVVH.

7) Hypophosphatemia: Because of the lack of calcium or magnesium, the pre-filter and post-filter solutions both can also be supplemented with phosphate by the manufacturer without the risk of calcium- or magnesium-phosphate precipitation. The phosphate-containing fluids can be used even when the serum phosphorus is high as the large filtration goals will allow significant net phosphate removal. Conversely, the fluids may also serve to correct hypophosphatemia towards normal when needed.

8) Fluctuating levels of anticoagulation: The fixed composition of the pre-filter fluid and the blood plasma flow to pre-filter fluid ratio that is kept fixed during a treatment ensures predictable citrate levels and very effective anticoagulation in the circuit as well as a clearly defined hourly citrate load into the patient. Since only convective clearance is used, the concentrations of ionized calcium and citrate remain unchanged and uniform along the axis of hemofilter 16, quite different from other protocols using CVVHDF. The consideration of the patient's hemoglobin, and total plasma protein level allows for maximizing the post-dilution ultrafiltration without inducing excessive hemoconcentration.

9) Nursing and physician errors: These are near completely eliminated by the system and method according to the present invention, as the nurse's role is mainly to obtain blood samples for total and ionized calcium at specified intervals and notify nephrology of the results. The nurse may also make the needed changes to the mixed calcium and magnesium infusion based on the dosing program (may be provided as a web application or integrated into the RCA for CVVH system according to the present invention). Since the control program may write the entire prescription and continuously monitor the machine settings, physician errors are eliminated. Citrate sensor 56 may obviate the need for any laboratory monitoring.

10) Ionized hypomagnesemia: Since clinical monitoring of ionized magnesium is usually not possible, the protocol will aim to maintain a 2:1 mM/mM ratio between total plasma calcium and total plasma magnesium. To achieve this, the mM ratio of calcium and magnesium may be fixed at 2:1 in the regulated calcium/magnesium infusion. Such dosing ensures that total and ionized magnesium levels will be appropriate for the steady state plasma citrate levels.

11) Declining filter performance: Due to the purely convective nature of small solute removal, this is not expected to be a problem before transmembrane pressure alarms are generated. Elective filter changes every 24 hours may be recommended due to the predictable protein fouling of the filters even in the absence of clotting.

12) Trace metal depletion: Cationic trace metal supplementation may be provided with the calcium infusion to restore precise mass balance for these trace solutes. Should any trace metal be incompatible with chloride as an anion, it can be provided in a higher concentration in the pre-filter solution.

13) Access disconnection: Most patients treated will have catheter access with a low risk of accidental disconnection.

14) Wrong connection of citrate, calcium, or blood circuit to patient: These errors are prevented by the hardware and disposable tubing set design of the system as explained herein.

15) Disconnection of the citrate, post-filter or calcium infusion: This can be completely prevented by appropriate circuit tubing design (contiguous connection to the blood line, air in-line detection plus scale based monitoring).

The various solutions and fluids which may be utilized according to the system and method of the present invention explained above are now described. For any description of solutions and fluids herein, except where expressly indicated, all numerical quantities in this description indicating amounts of material or conditions of reaction and/or use are to be understood as modified by the word "about" in describing the broadest scope of the present invention. Practice within the numerical limits stated is generally preferred. Furthermore, the phrase "essentially free" is understood to mean that only trace amounts of a material, compound, or constituent may be present.

The description of a single material, compound or constituent or a group or class of materials, compounds or constituents as suitable for a given purpose in connection with the present invention implies that mixtures of any two or more single materials, compounds or constituents and/or groups or classes of materials, compounds or constituents are also suitable. Also, unless expressly stated to the contrary, percent, "parts of," and ratio values are by weight. Description of constituents in chemical terms refers to the constituents at the time of addition to any combination specified in the description, and does not necessarily preclude chemical interactions among constituents of the mixture once mixed.

The replacement solutions that may be used by the system according to the present invention include solutions which are referred to below as "CitrateEasy" and "BicarbEasy" solutions for CVVH and which may be provided in two formulations each, described in detail below. Using the system and method according to the present invention, the citrate solution may be introduced into extracorporeal circuit 12 before the blood enters hemofilter 16. The system and method of the present invention may utilize a combination of pre-dilution and post-dilution hemofiltration, wherein the pre-dilution solution may be CitrateEasy and the post-dilution fluid may be BicarbEasy.

CitrateEasy is a near isonatric (to physiologic human plasma) and isoalkalic (to other commercial CRRT fluids and in terms of metabolizable bicarbonate equivalent anions per liter) citrate anticoagulant-containing hemofiltration solution. BicarbEasy is a bicarbonate-based hemofiltration fluid that may be essentially calcium and magnesium free and contains phosphate. BicarbEasy may be manufactured in a single chamber bag 40, allowing for ease of use and significant cost savings in the process. The post-dilution ultrafiltration provides for maximal fractional extraction of the citrate load from extracorporeal circuit 12 and for maximal uremic clearance achieved for a given rate of extracorporeal circuit blood flow. Since CitrateEasy and BicarbEasy are essentially free of calcium and magnesium, phosphate can be added to both for physiologic phosphate balance. The composition of both the pre-filter and post-filter fluids and the control algorithm of the system and method according to the present invention allows for high blood flows and high per hour clearance rates to be accomplished with the special requirements of twelve hour daily CVVH and high volume hemofiltration (HVHF), without overloading the patient with citrate or inducing undue acid-base or electrolyte changes.

The use of the CitrateEasy fluid with the system of the present invention eliminates the need for and all the associated risks of a separate concentrated citrate infusion. Citrate removal by hemofilter 16 is important for safe operation of a CVVH system using citrate anticoagulation. The separate infusion of citrate in a traditional set-up will have to be stopped immediately when solute clearance is aborted or the patient will receive an excess amount of citrate which could be life threatening. In the system using CitrateEasy, if for any reason hemofiltration stops, the delivery of citrate with the pre-dilution fluid is immediately aborted.

Further, while calcium and magnesium are essentially completely eliminated from the replacement fluids, the net balance of these divalent cations in the CVVH circuit may be kept zero in the individual patient by careful and strictly machine-regulated and coordinated dosing of a combined calcium and magnesium supplement infusion. Nursing errors with the calcium and magnesium infusion may be eliminated by physically integrating this infusion pump 44 with system 10 for the delivery of additional mixed calcium and magnesium into venous blood line 18 of circuit 12, ensuring maintenance of physiologic ionized calcium and free magnesium levels in the patient. The system according to the present invention may monitor the rate settings of this pump 44 and may alert the operator if the value detected is unusual in the light of other treatment and patient parameters. Finally, the mandatory addition of phosphate to the pre-filter and post-filter replacement fluid by the manufacturer will eliminate the need for separate intravenous phosphate administration to prevent hypophosphatemia due to removal by CVVH. The pre-filter phosphate may yield a further (minor) Ca chelation and anticoagulation as well.

Pre-Filter CitrateEasy Fluids:

It is understood that the fluids may be provided in a 1×, 5×, 10×, 50×, or any other concentrated or diluted ratio of the fluid components described herein. In addition, citrate could be replaced by isocitrate or another non-toxic, metabolizable calcium chelator. Any such variations of the following fluids are fully contemplated.

|  | mmol/L | mEq/L |
| --- | --- | --- |
| Sodium ($Na^+$) | 135-150 | 135-150 |
| Potassium ($K^+$) | 0-4 | 0-4 |
| Citrate ($Cit^{3-}$) | 8-16.67 | 24-50 |
| Acid citrate ($CitH_3$) | 0-10 | 0-30 |
| Chloride ($Cl^-$) | 95-120 | 95-120 |
| Calcium ($Ca^{2+}$) | 0-4.0 | 0-8.0 |
| Magnesium ($Mg^{2+}$) | 0-2.0 | 0-4.0 |
| Dextrose | 5.5-11.0 | 5.5-11.0 |
| Phosphate | 0.0-5.0 | 0.0-5.0 |
| Inulin | 0-few mM | 0-few mM |
| PAH | 0-few mM | 0-few mM |
| Trace metals | Only if incompatible with the Ca infusion | |

Inulin and PAH may be introduced in their usual, fluoro-probe-, or biotin-labeled form here to allow online monitoring of glomerular filtration rate and renal tubular secretory function as described with reference to the online sensor system. In addition, the above solution may be provided consisting essentially of all components except for inulin, PAH, and trace metals.

Pre-Filter Solution 1: "CitrateEasy16Ca0K2/4P1"

This is a high citrate fluid with phosphorus added, wherein one preferred mode of operation is simultaneous pre- and post dilution CVVH. This solution may not be advised for patients with liver failure and inability to attain >=66% citrate extraction and/or preexisting severe metabolic acidosis. This solution works with BicarbEasy25/50Ca0K2/4P1.

|  | mmol/L | mEq/L |
| --- | --- | --- |
| Sodium ($Na^+$) | 140-145 | 140-145 |
| Potassium ($K^+$) | 2 or 4 | 2 or 4 |
| Citrate ($Cit^{3-}$) | 14 | 42 |
| Acid citrate | 2 | 6 |
| Chloride ($Cl^-$) | 105 or 107 | 105 or 107 |
| Calcium ($Ca^{2+}$) | 0 | 0 |
| Magnesium ($Mg^{2+}$) | 0 | 0 |
| Phosphoric acid ($H_3PO_4$) | 1.25 | 1.25 |
| Dextrose | 5.5 | 5.5 |

The removal of both calcium and magnesium is important to the maximal anticoagulant effect and for the safe addition of phosphate to the fluids. The addition of phosphate is possible as there are no divalent ions that could precipitate it. The addition of acid citrate in this ratio is also novel. Finally, the sodium is slightly higher than in most commercial replacement fluids.

The CitrateEasy16 fluid is the most likely to yield completely normal plasma electrolyte values with high volume treatments. The lack of calcium and magnesium and the acid citrate and basic citrate values in combination with phosphate make this a unique fluid. Adding additional solutes to published fluids at the point of use with multiple additives would likely be too cumbersome and error prone to be an alternative.

Pre-Filter Solution 1: "CitrateEasy16Ca0K2/4P4"

This is a variation for a pre- and post-dilution system without IV infusion pump 44. This is a high citrate fluid with more phosphorus added, wherein one preferred mode of operation is simultaneous pre- and post dilution CVVH. This solution may not be advised for patients with liver failure and inability to attain >=66% citrate extraction and/or preexisting severe metabolic acidosis. This solution works with BicarbEasy25/50Ca3.5/K2/4P0.

|  | mmol/L | mEq/L |
| --- | --- | --- |
| Sodium ($Na^+$) | 145 | 145 |
| Potassium ($K^+$) | 2 or 4 | 2 or 4 |
| Citrate ($Cit^{3-}$) | 15.0 | 45 |
| Acid citrate | 1 | 3 |
| Chloride ($Cl^-$) | 102 or 104 | 102 or 104 |
| Calcium ($Ca^{2+}$) | 0 | 0 |
| Magnesium ($Mg^{2+}$) | 0 | 0 |
| Phosphoric acid ($H_3PO_4$) | 4 | 4 |
| Dextrose | 5.5 | 5.5 |

The removal of both calcium and magnesium is important to the maximal anticoagulant effect and for the safe addition of phosphate to the fluids. More phosphate is added, as the post-filter fluid will have calcium and therefore cannot have phosphate. The acid citrate is reduced because of the phosphoric acid.

Pre-Filter Solution 1: "CitrateEasy16Ca2.5K2/4P1"

This is a variation for an isolated pre-dilution system without pump 44. The fluid has calcium added, wherein one preferred mode of operation is isolated pre-dilution CVVH. This solution may not be advised for patients with impaired liver function. The low 33% citrate extraction due to the absence of post-filtration may recommend the use of an online citrate sensor for safe treatments.

|  | mmol/L | mEq/L |
| --- | --- | --- |
| Sodium ($Na^+$) | 145 | 145 |
| Potassium ($K^+$) | 2 or 4 | 2 or 4 |
| Citrate ($Cit^{3-}$) | 14 | 42 |
| Acid citrate | 2 | 6 |
| Chloride ($Cl^-$) | 112.5 or 114.5 | 112.5 or 114.5 |
| Calcium ($Ca^{2+}$) | 2.5 | 5 |
| Magnesium ($Mg^{2+}$) | 1.25 | 2.5 |
| Phosphoric acid ($H_3PO_4$) | 1.25 | 1.25 |
| Dextrose | 5.5 | 5.5 |

The addition of both calcium and magnesium ensures mass balance for these ions. The anticoagulant effect may be reduced but still good due to the excess amount of citrate. Similarly, the very low ionized calcium levels and acidic pH in the fluid bags allows the safe addition of phosphate by the manufacturer as well.

Pre-Filter Solution 2: "CitrateEasy8Ca0P1"

This less acidic citrate fluid with phosphorus added can be used for patients with liver failure and an inability to attain >66% citrate extraction (indefinite use) and/or preexisting severe metabolic acidosis (initial use). This solution works with BicarbEasy25/50Ca0K2/4P1.

|  | mmol/L | mEq/L |
| --- | --- | --- |
| Sodium (Na$^+$) | 145 | 145 |
| Potassium (K$^+$) | 2 or 4 | 2 or 4 |
| Citrate (Cit$^{3-}$) | 7 | 21 |
| Acid citrate | 1 | 3 |
| Chloride (Cl$^-$) | 124.75 or 126.75 | 124.75 or 126.75 |
| Calcium (Ca$^{2+}$) | 0 | 0 |
| Magnesium (Mg$^{2+}$) | 0 | 0 |
| Phosphate (H$_2$PO$_4^-$) | 1.25 | 1.25 |
| Dextrose | 5.5 | 5.5 |

The safety of the phosphate-containing CVVH fluid is predicted based on inorganic fluid chemistry principles: sodium and potassium do not precipitate with phosphate. The addition of phosphate will eliminate hypophosphatemia, a relatively less acute but clinically still significant complication of CVVH seen particularly often when high clearance goals are targeted and achieved. Finally, CitrateEasy should come with at least two different potassium concentrations (2 and 4 mM) to allow flexibility in potassium mass balance handling.

Pre-Filter Solution 2: "CitrateEasy8Ca0K2/4P4"

This is a variation for a pre- and post-dilution system without pump 44. This less acidic citrate fluid with more phosphate added can be used for patients with liver failure and an inability to attain >66% citrate extraction (indefinite use) and/or preexisting severe metabolic acidosis (initial use). This solution works with BicarbEasy25/50Ca3.5K2/4P0.

|  | mmol/L | mEq/L |
| --- | --- | --- |
| Sodium (Na$^+$) | 145 | 145 |
| Potassium (K$^+$) | 2 or 4 | 2 or 4 |
| Citrate (Cit$^{3-}$) | 7 | 21 |
| Acid citrate | 1 | 3 |
| Chloride (Cl$^-$) | 120 or 122 | 120 or 122 |
| Calcium (Ca$^{2+}$) | 0 | 0 |
| Magnesium (Mg$^{2+}$) | 0 | 0 |
| Phosphate (H$_2$PO$_4^-$) | 4 | 4 |
| Dextrose | 5.5 | 5.5 |

The safety of the phosphate-containing CVVH fluid is predicted based on inorganic fluid chemistry principles: sodium and potassium do not precipitate with phosphate. The addition of more phosphate will eliminate hypophosphatemia, even with a calcium-containing, and therefore phosphate-free, post-filter bicarbonate fluid. The overall acid content of the fluid is nearly unchanged.

Post-Filter BicarbEasy Fluids:

It is understood that the fluids may be provided in a 1×, 5×, 10×, 50×, or any other concentrated or diluted ratio of the fluid components described herein.

|  | mmol/L | mEq/L |
| --- | --- | --- |
| Sodium (Na$^+$) | 135-150 | 135-150 |
| Potassium (K$^+$) | 0-4 | 0-4 |
| Bicarbonate | 20-60 | 20-60 |
| Chloride (Cl$^-$) | 85-120 | 85-120 |
| Calcium (Ca$^{2+}$) | 0-4 | 0-8 |
| Magnesium (Mg$^{2+}$) | 0-2.0 | 0-4.0 |
| Phosphate (PO$_4^{3-}$) | 0-5 | 0-15 |
| Dextrose | 5.5-11.0 | 5.5-11.0 |

Post-Filter Solution 3 and 4 (BicarbEasy25Ca0K2/4P1 and BicarbEasy50Ca0K2/4P1):

BicarbEasy25 and BicarbEasy50 are designed to complement the CitrateEasy16 and CitrateEasy8 fluids, and they are provided with variable potassium content. BicarbEasy50 with CitrateEasy8 may be advised for patients who have severe preexisting metabolic acidosis and/or liver failure. These patients will have systemic bicarbonate levels around 15 or less, and for them the use of the CitrateEasy16 fluid could possibly lead to dangerous circuit acidification to pH near 6.0 or less. The amount of bicarbonate in the BicarbEasy50 solution is much more than in the BicarbEasy25 fluid and will provide more bicarbonate through the CVVH circuit when the patient has liver failure, and thus will correct metabolic acidosis faster in other patients who can metabolize citrate.

The addition of phosphate may be mandatory by the manufacturer and safe as divalent cations (magnesium and calcium) have been essentially removed from the fluids. The phosphate may be provided as a pH-adjusted mix of the tri-basic and di-basic salt in the BicarbEasy solutions to avoid CO$_2$ gas generation when mixed with bicarbonate in a single bag, or simply as the tri-basic salt. In the latter case, upon entering the blood, some additional bicarbonate generation (about 2.5 mEq per liter of post-filter fluid) will occur as the phosphate picks up hydrogen ions from carbonic acid dissolved in the plasma. Finally, BicarbEasy should come with at least two different potassium concentrations (2 and 4 mM) to allow flexibility in potassium mass balance handling. A major advantage is that the BicarbEasy25/50Ca0 fluids can be manufactured in a single compartment sterile bag 40 as opposed to current bicarbonate formulations that have to separate the bicarbonate in a dedicated second compartment because of the risk of Ca-carbonate and Mg-carbonate precipitation.

Post-Filter Solution 3: "BicarbEasy25Ca0K2/4P1"

May be preferred in combination with CitrateEasy16Ca0K2/4P1 for patients with no evidence of liver failure or severe preexisting metabolic acidosis.

|  | mmol/L | mEq/L |
| --- | --- | --- |
| Sodium (Na$^+$) | 140 | 140 |
| Potassium (K$^+$) | 2 or 4 | 2 or 4 |
| Bicarbonate | 25 | 25 |
| Chloride (Cl$^-$) | 113.25 or 115.25 | 113.25 or 115.25 |
| Calcium (Ca$^{2+}$) | 0 | 0 |
| Magnesium (Mg$^{2+}$) | 0 | 0 |
| Phosphate (PO$_4^{3-}$) | 1.25 | about 3.75 |
| Dextrose | 5.5 | 5.5 |

The removal of calcium and magnesium and the addition of tri-basic phosphate provides a novel solution according to the present invention. The phosphate may also be pH-adjusted between the tri-basic and di-basic salt form to be compatible with the bicarbonate in the fluid without CO$_2$ generation. The exact bicarbonate concentration will depend on the clinical protocol. Higher treatment goals allow (and require) the use of lower bicarbonate concentrations in the post-filter fluid as long as citrate metabolism is not impaired, to avoid metabolic alkalosis.

Post-Filter Solution 3: "BicarbEasy25Ca3.5K2/4P0"

This is a variation for a pre-post-dilution system without pump 44, which may be preferred in combination with CitrateEasy16Ca0K2/4P4 for patients with no evidence of liver failure or severe preexisting metabolic acidosis.

|  | mmol/L | mEq/L |
|---|---|---|
| Sodium (Na$^+$) | 140 | 140 |
| Potassium (K$^+$) | 2 or 4 | 2 or 4 |
| Bicarbonate | 29 | 29 |
| Chloride (Cl$^-$) | 128.5 or 130.5 | 128.5 or 130.5 |
| Calcium (Ca$^{2+}$) | 3.5 | 7 |
| Magnesium (Mg$^{2+}$) | 1.75 | 3.5 |
| Phosphate (PO$_4^{3-}$) | 0 | 0 |
| Lactic acid with Ca | 4 | 4 |
| Dextrose | 5.5 | 5.5 |

The addition of a very high calcium and magnesium is a novel solution according to the present invention. The phosphate is removed, and the bicarbonate should be separated from the calcium, magnesium and lactic acid, such as in a traditional two-chamber bag. The exact bicarbonate concentration will depend on the clinical protocol. Higher treatment goals allow (and require) the use of lower bicarbonate concentrations in the post-filter fluid as long as citrate metabolism is not impaired, to avoid metabolic alkalosis. The lactic acid may be added to ensure an acid pH after the mixing of the contents at the point of use, to lessen the risk of carbonate precipitation. The bicarbonate content is before mixing with the lactic acid; after mixing it will be 25.

Post-Filter Solution 4: "BicarbEasy50Ca0K2/4P1"

This solution may be preferred in combination with CitrateEasy8Ca0K2/4P1 for patients with liver failure or until severe metabolic acidosis is corrected.

|  | mmol/L | mEq/L |
|---|---|---|
| Sodium (Na$^+$) | 140 | 140 |
| Potassium (K$^+$) | 2 or 4 | 2 or 4 |
| Bicarbonate | 50 | 50 |
| Chloride (Cl$^-$) | 88.25 or 90.25 | 88.25 or 90.25 |
| Calcium (Ca$^{2+}$) | 0 | 0 |
| Magnesium (Mg$^{2+}$) | 0 | 0 |
| Phosphate (PO$_4^{3-}$) | 1.25 | about 3.75 |
| Dextrose | 5.5 | 5.5 |

The removal of calcium and magnesium and the addition of a phosphate is a novel solution according to the present invention. Most importantly, the bicarbonate is very high to compensate for the bicarbonate lost in the ultrafiltrate through the circuit and for the lack of liver conversion of citrate into bicarbonate in a liver failure patient. The phosphate may be pH adjusted between the tri-basic and di-basic salt form to be compatible with the bicarbonate in the fluid without $CO_2$ generation and to avoid carbonate formation.

Post-Filter Solution 4: "BicarbEasy50Ca3.5K2/4P0"

This is a variation for a pre- and post-dilution system without pump 44, which may be preferred in combination with CitrateEasy8Ca0K2/4P4 for patients with evidence of liver failure or severe preexisting metabolic acidosis.

|  | mmol/L | mEq/L |
|---|---|---|
| Sodium (Na$^+$) | 140 | 140 |
| Potassium (K$^+$) | 2 or 4 | 2 or 4 |
| Bicarbonate | 54 | 54 |
| Chloride (C$^-$) | 98.5 or 100.5 | 98.5 or 100.5 |
| Calcium (Ca$^{2+}$) | 3.5 | 7 |
| Magnesium (Mg$^{2+}$) | 1.75 | 3.5 |
| Phosphate (PO$_4^{3-}$) | 0 | 0 |
| Lactic acid with Ca | 4 | 4 |
| Dextrose | 5.5 | 5.5 |

The addition of a very high calcium and magnesium is a novel solution according to the present invention. The phosphate is removed, and the bicarbonate should be separated from the calcium, magnesium and lactic acid, such as in a traditional two-chamber bag. The high bicarbonate concentration may be needed in the absence of citrate metabolism. The lactic acid is added to ensure an acid pH after the mixing of the contents at the point of use, to lessen the risk of carbonate precipitation. The bicarbonate content is before mixing with the lactic acid; after mixing it will be 50.

Solution 5:

Concentrated calcium and magnesium chloride infusion (0.5×, 1×, 2×, 4×, 20× or other concentrated or diluted formulations) with a 2:1 to 4:1 (preferred 2.5:1) Ca:Mg molar ratio.

|  | mmol/L | mEq/L |
|---|---|---|
| Calcium | 50 | 100 |
| Magnesium | 25 | 50 |
| Sodium | 150 | 150 |
| Chloride | 300 | 300 |

Trace metals may be added in a molar ratio to calcium that is the same as in the ultrafiltrate during CVVH with RCA at a time point when the systemic blood plasma has normal trace metal and total calcium content. This fluid may be infused into venous blood line 18 of circuit 12 as close to the venous port of access catheter 20 as possible. A dedicated IV infusion pump 44 integrated into the system according to the present invention may drive the fluid flow. The amount infused may be set by the operator and monitored for safety by a calcium dosing program to ensure full coordination with the patient's chemistry values that are updated regularly, the patient's estimated volume of distribution for calcium, as well as the RCA for CVVH prescription parameters and citrate sensor data. A typical prescription will result in a flow rate of 100-140 ml/hour with the above fluid composition. This allows for precise pumping and 10% dosing steps with the PBP pump in use on one commercial device (e.g., Prismaflex). It is expected that the rate of the infusion will be steady and unchanged after the first few hours of treatment with the system of the present invention and no significant changes to the calcium infusion rate will be needed.

Finally a circuit priming solution may also be utilized for calibration of the OSS according to the present invention:

|  | mmol/L | mEq/L |
|---|---|---|
| Sodium (Na$^+$) | 130-150 | 130-150 |
| Citrate (Cit$^{3-}$) | 1-20 | 3-60 |
| Chloride (Cl$^-$) | 100-140 | 100-140 |
| Calcium (Ca$^{2+}$) | 0.5-10 | 1-20 |
| Magnesium (Mg$^{2+}$) | 0.25-5 | 0.5-10 |

According to one non-limiting aspect of the present invention, a preferred composition may be:

|  | mmol/L | mEq/L |
|---|---|---|
| Sodium (Na$^+$) | 140 | 140 |
| Citrate (Cit$^{3-}$) | 7 | 21 |
| Chloride (Cl$^-$) | 124.1 | 124.1 |
| Calcium (Ca$^{2+}$) | 1.7 | 3.4 |
| Magnesium (Mg$^{2+}$) | 0.85 | 1.7 |

This solution may be used to prime the circuit at the start of the procedure and will allow the OSS to test the accurate functioning of the safety sensors 56 for citrate, calcium and magnesium.

The rationale behind the CitrateEasy and BicarbEasy fluid designs according to the present invention is explained below. First, the sodium content may be 140-145 mEq/L, whereas all commercial fluids use a 140 sodium solution. It is of note that patients treated with such fluids often stay or become hyponatremic to around 136 serum values. The explanation may be that the strength of the Gibbs-Donnan effect is slightly different when the same fluid is infused pre-filter or post-filter (the negatively charged proteins are diluted in the pre-filter infusion mode). The solutions according to the present invention may use the industry standard sodium of 140 for the post-filter fluid and 145 for the pre-filter fluid. The additional 5 mM sodium above usual fluid sodium content may result in serum sodium levels around 140-142 in most patients.

The potassium content may be 2.0-4.0 mEq/L. Manipulation of potassium mass balance may be achieved by selecting 2.0 or 4.0 K CitrateEasy and BicarbEasy fluids. Two bags of each fluid may be hung and used at any given time. The ratio of 2 and 4 K bags therefore can change from 0:4 to 4:0. This will make the overall K content of the summary replacement fluids adjustable in 0.5 mEq increments, satisfactory for all K mass balance purposes. Finally, when only pre-dilution hemofiltration is performed, the pre-dilution CitrateEasy fluids will have at least a 2.0 and 4.0 K formulation with phosphate.

The pre-filter fluid may have an alkali equivalent content of 20 and 40 mEq/L. Current hemofiltration fluids usually contain 40-47 mEq/L lactate (1/1 bicarbonate equivalent) or 13.3-14 mmol/L or 40-42 mEq/L trisodium-citrate (3/1 bicarbonate equivalent). Even with high clearances achieved with such high alkali equivalent containing fluids in some protocols, serum bicarbonate stabilizes around 24-28 values and severe alkalosis does not occur. The exact explanation is unclear, but may be explained by the unstable patient losing bicarbonate through body metabolism as well as ultrafiltration of bicarbonate and the metabolizable anions citrate and lactate, the sum of which could easily equal 30-40 mEq/L. Whatever the mechanism, it seems prudent to design the fluid to deliver at least 40 mEq net bicarbonate equivalent citrate per liter in patients who can metabolize citrate. The net alkali content for the pre-filter fluids may be fine-tuned with clinical data between 35 and 45 mEq/L. These calculations do not apply to the CitrateEasy8 fluids which are designed assuming impaired citrate metabolism and rely on the high bicarbonate BicarbEasy50 fluids for alkali mass balance. Variable ratio of similar CitrateEasy 8 and 16 bags (2:0, 1:1 and 0:2) can also be used for citrate dosing flexibility.

The citrate and acid citrate combined content may be mEq/L (24 or 48): The total citrate content will be 8-16 mmol, while the net alkali equivalent citrate will be only 7-14 mmol or 21-42 mEq, and the acid citrate content will be 3-8 mEq Due to the different pKas of the three carboxyl groups on the citrate molecule, the mixture of the above will yield about equal amounts of citrateNa$_3$ and citrateNa$_2$H. Since the ratio of the salt and acid form is near 1/1, the fluid pH will be around the pKa3=6.3. This will have the added benefit of being protective from bacterial growth in the fluid. When the fluid reaches the patient's blood, the citrateHNa$_2$ will react with the bicarbonate in the blood to generate citrateNa$_3$ and H$_2$O plus CO$_2$. Assuming a mixing ratio of 2 liters of plasma to 1 liter of pre-filter fluid and ignoring RBC buffering, the new bicarbonate will be (67% of systemic serum values after dilution)−3. For example, if systemic bicarbonate is 24, the circuit bicarbonate after the pre-filter fluid infusion will be 13. However, there will also be a 14 mEq/L added alkali equivalent citrate in the fluid for a total alkali content of at least 27. The generated CO$_2$ will also contribute to the acidification of the circuit and will ultimately be eliminated through the circuit and by pulmonary gas exchange. The amount of CO$_2$ added to the patient's blood is not clinically significant based on calculations as well as the outcomes of clinical trials of CVVH using concentrated acid citrate dextrose as anticoagulant (ACD-A, Baxter). However, the circuit acidification with the high local citrate levels will ensure that nearly all calcium in the plasma will be removed from albumin and other proteins and will be freely ultrafilterable. This will make calcium mass balance calculations in the CVVH circuit very reliable. Bicarbonate levels will be restored by citrate metabolism in the patient as well as by the alkalinizing effects of the post-dilution step where citrate will be exchanged for bicarbonate. The circuit acidification may possibly further interfere with blood clotting.

CRRT fluid calcium and magnesium has essentially zero content. The massive amount of citrate in the pre-filter fluid strips calcium and magnesium from albumin. Total ultrafilterable calcium will be nearly equal to total calcium in circuit blood due to this "stripping" of calcium from albumin by citrate as well as with significant acidification of the circuit with the pre-filter fluid. The cumulative ultrafilterable calcium content is predicted at 0.25 mM/mM citrate (in systemic blood), 0.2 mM/g stripped from albumin, and 1.25 mM targeted systemic ionized calcium for a total filterable calcium of 1.5-3.0 mmol/liter filtrate after adjusting for the pre-dilution effect, depending on citrate accumulation, albumin level and systemic ionized calcium. Individual patients who may markedly differ in their serum albumin and citrate and therefore total plasma calcium levels cannot be kept in ideal balance without a dedicated Ca and Mg infusion. Therefore, the present invention replaces all of these losses with a dedicated calcium and magnesium infusion which may be strictly coordinated with the operation of the machine. This allows for both pre-filter and post-filter CRRT fluids with physiological phosphate concentrations, the ratio of which can be varied freely, in good agreement with the physiologic and symmetric fluid concepts according to the pre-post dilution method of the present invention. The lack of calcium and magnesium allows for single-chamber bicarbonate-based fluid formulation, a major manufacturing advantage over currently existing formulations.

Calcium and magnesium replacement may include trace metals. This is coordinated strictly with calcium dosing by using a single mixed infusion of these two cations (and possibly trace metals that are also chelated by citrate) to account for the filtered losses of calcium, magnesium and trace metals through the CVVH circuit.

Dextrose content may be 5.5 mmol/L. To match the physiologic plasma glucose concentration, as CVVH is not meant to be a form of nutrition. Recent publications on the improved clinical outcomes with strict glycemic control in the ICU may also warrant the use of hemofiltration fluid with physiologic glucose content, lower than what was used in the past. The impact of potentially substantial glucose removal from the diabetic patient with suboptimal blood sugar control and high clearance goal CVVH will need to be recognized by the ICU team and proper blood sugar control will need to be maintained.

Phosphate may be about 1.25 mmol/L. The absence of calcium and magnesium allows the mixing of phosphate in all CRRT fluid bags without the risk of Ca$_3$(PO$_4$)$_2$ or Mg$_3$(PO$_4$)$_2$ precipitation. The addition of phosphate to a commercial single chamber bicarbonate based CRRT fluid is also a reality for the first time and represents a major improvement over currently available bicarbonate based solutions. Hypophosphatemia or hyperphosphatemia cannot occur with these fluid designs. Finally, pre-filter phosphate itself may act as an additional anticoagulant by also chelating calcium to a minor degree.

Citrate content may be 8 or 16 mmol/L and bicarbonate content may be 25 or 50 mmol/L. The scales of a Prismaflex machine, for example, can hold 2 fluid bags each or a total of 10 liters per scale. Flexibility in citrate dosing (when the plasma flow to pre-filter fluid flow ratio is kept constant at 2:1) may be achieved by varying the ratio of the 8- and 16-mmol citrate bags from 0:2 to 1:1 to 2:0. Flexibility in bicarbonate dosing may be achieved by varying the ratio of the 25- and 50-mmol bicarbonate bags from 0:2 to 1:1 to 2:0. Also, the post-filter fluids can be supplemented with half ampoule (25 mEq) bicarbonate per bag if needed for further flexibility.

For reference, pKa values for acids relevant to RCA at 25 C are as follows:

Citrate1: 3.13
Citrate2: 4.76
Citrate3: 6.40
Carbonic acid 1: 6.37
Carbonic acid 2: 10.33
Phosphoric acid1: 2.12
Phosphoric acid2: 7.2
Phosphoric acid3: 12.67

The present invention includes a control program for determining the optimal ultrafiltration, pre- and post dilution fluid, and blood flow rates required to reach treatment goals while minimizing citrate load into the patient. The control program also estimates supplemental calcium and magnesium infusion rates and can monitor the settings of integrated single calcium plus magnesium infusion pump 44 for added safety. The control program can also calculate bicarbonate balance using either citrate sensor 56 or clinical laboratory data to inform clinical care decisions on replacement fluid selection for the patient. This control program may be incorporated into the software of the system used for delivering the fluids according to the present invention. The control program simplifies the use of the system and allows for exact calculation of the prescribed treatment variables including blood flow, pre-filter fluid flow and post-filter fluid flow, net ultrafiltration, as well as rate of calcium and magnesium supplement infusion.

The physician may select the duration of the treatment, the hourly treatment goal, and indicate the presence of severe liver dysfunction and or acidosis. The systemic hemoglobin and albumin concentration may also be needed. The control program may then calculate the most effective, safe the prescription that can be delivered without dangerous citrate accumulation in the systemic plasma of the patient. All patients (including those with liver failure) can safely reach the 35 ml/kg/hr treatment goal for 24-hour CVVH. The clearance goal is expressed corrected for the degree of pre-dilution. Unique kinetic modeling modules and citrate sensor 56 may be provided to predict citrate accumulation, bicarbonate wash-out or accumulation, and the development of hypo- or hypercalcemia with any particular prescription before these complications could occur providing a chance for the operator (or the automated dosing program) to make corrective changes to the treatment parameters.

Principles of the Control Algorithm Include:

1) Operational mode of simultaneous pre- and post-dilution CVVH with two different fluids to maximize single pass citrate extraction on hemofilter 16. The novel addition of a maximal amount of ultrafiltration possible for a given blood flow with simultaneous post-dilution (citrate-free) fluid replacement allows enhancing the fractional removal of the citrate load to 50-75% in a single pass through hemofilter 16. This means that the twice as high pre-filter fluid rates can be reached by use of the system and method according to the present invention with the same obligatory citrate load into the patient as with prior RCA protocols. The ultrafiltration may be further doubled by the post-dilution step. The summary effect is a 3 to 4-fold increase in uremic clearance for the same citrate load. In clinical practice, this will allow the treatment of almost all patients to the most aggressive pre-dilution adjusted clearance goal of 35 ml/kg/hr with markedly enhanced safety.

2) Sufficient plasma total calcium to citrate ratio must be achieved for effective anticoagulation. The total Ca (mM) to citrate (mM) ratio will range between 2 to 4 in extracorporeal circuit 12. Part of the citrate may be provided as acid citrate in the pre-filter fluid (to further enhance anti-coagulation through acidification of thrombin and other coagulation cascade proteins). The plasma flow may be monitored online with a hematocrit and blood flow sensor module 50, 52. This will allow the calculation of the delivered calcium load into circuit 12 and will define the necessary anticoagulant infusion rate. Both calcium and citrate do not distribute into the RBC volume.

3) The prescription should eliminate the possibility of citrate accumulation even in the complete absence of liver metabolism (liver failure). This may be achieved by keeping the citrate single pass plasma extraction above 66% when the CitrateEasy16 fluids are used in a 2:1 plasma to fluid ratio and above 50% when the CitrateEasy8 fluids are used in a 2:1 plasma to fluid ratio. This will limit the systemic plasma citrate to 3.75-5 mM or less, regardless of liver function.

4) The target plasma total calcium level should be defined (usually 2-2.5 mmol/L, depending on the serum albumin concentration and the achieved citrate extraction ratio) by the operator. This will have an indirect impact on the systemic plasma ionized Ca content in steady state. The systemic citrate level will have a modest impact, even in ICU patients with liver failure, because citrate accumulation beyond 3-5 mM levels cannot occur when filter performance is maintained at the specified fluid flow rates.

5) Providing prescriptions and therapy fluid compositions that allow exact mass balance calculations for citrate, calcium and magnesium, sodium and bicarbonate (and trace metal minerals).

6) Varying the ratio of the different pre-filter fluid bags and post-filter fluid bags for greater flexibility in citrate and bicarbonate dosing.

In the following description, a glossary of the abbreviations used is as follows:

Csys: calculated steady state systemic plasma citrate concentration in a patient with zero citrate metabolism (liver failure; worst case scenario in RCA)

E: apparent circuit post-anticoagulant infusion arterial plasma citrate to therapy fluid citrate concentration difference reduction ratio during a single filter pass ("plasma citrate extraction ratio")

DCit: apparent citrate plasma dialysance when expressed for QP)

QB: the total blood flow here

QP: The arterial blood plasma flow (effective blood water flow for citrate)

Cinf: The increase in the arterial plasma citrate concentration as a result of the pre-filter replacement fluid infusion with the pre-dilution effect removed Hgb: hemoglobin concentration in the arterial blood
C8, C16Cit: citrate concentration (mM) in the citrate pre-filter fluid
B25, B50: bicarbonate concentration (mM) in the post-filter fluid
Quf: net ultrafiltration negative fluid balance goal
QCa/Mg: calcium plus magnesium infusion rate
Qpre: pre-filter citrate based replacement fluid flow rate
Qpost: post-filter bicarbonate based replacement fluid flow rate
DCit: the calculated citrate dialysance (DCit* when expressed for the adjusted QBCit during calculations and DCit when expressed for the unadjusted QP)
f: correction factor to obtain the ultrafilterable fraction of Ca from total plasma Ca
S: sieving coefficient; SCond; SCit)

The control algorithm according to the present invention may include, but is not limited to, the following flow steps:
1) Start machine in pre- and post-CVVH mode.
2) a) Machine advises filter, tubing, citrate pre-filter, bicarbonate post-filter and calcium solutions.
   b) Confirm all disposables are as advised by the machine
   c) Connect tubing to dialyzer (if not pre-connected) and fluid bags.
   d) Load tubing onto infusion pumps.
   e) Prime system with priming solution.
   f) Test system integrity (current machine protocol).
3) RCA priming checks: performed with the circuit arterial and venous ends connected in recirculation mode.
   a) Confirm accuracy of the OSS by filtering the circuit priming solution (a standard for Ca, Mg and citrate).
   b) Alarm: the values returned by the OSS are not accurate, confirm correct priming solution, check OSS.
   c) Confirm citrate replacement fluid loading onto pre-dilution pump 34 by turning on the pump 34 and measuring the increase in citrate concentration in the drain circuit 24 of the hemofilter 16 (if OSS available).
   d) Alarm: it is not the citrate infusion solution that is loaded onto the citrate pump 34 based on effluent citrate changes.
   e) Confirm calcium infusion loading onto the calcium pump 44 by turning on the calcium pump 44 and measuring the increase in calcium and magnesium in the drain circuit 24 of the hemofilter 16 (if OSS available).
   f) Alarm: it is not the calcium infusion solution that is loaded onto the $Ca^{2+}$-pump 44 based on effluent calcium changes.
4) Input Patient Information.
   a) Sex, height, age, weight (if Watson volume and $V_E$ calculations are desired; minimum data is weight).
   b) Minimum laboratory data is hemoglobin, serum albumin, and serum bicarbonate concentration.
5) Treatment Information advised by software based on prior selections.
   a) Input: Dialyzer type (determines expected KoACit, SCit).
   b) Input: Maximum hemoconcentration allowed in the circuit (may define as 60%).
   c) Input: Daily maximum replacement fluid amount (may be about 80-100 liters).
   d) Input: Total pre-dilution adjusted plasma clearance goal for CVVH (may be about 40+ liters).
   e) Input: Total net ultrafiltration desired per treatment (or over 24 hours).
   f) Input: Set CRRT machine alarm parameters.
   g) Input: Estimated liver plasma citrate clearance: normal 0.5, poor 0.25, none 0 (all L/min)
   h) Input: Type of calcium solution (ICU versus OPD, likely uniform).
   i) Input: Maximum citrate level in systemic blood allowed (may be about 4.0 mM).
6) Connect the patient.
7) Safety checks after initial patient connection in CVVH mode.
   a) Start treatment, confirm citrate is infusing in the arterial limb 14 by watching the effluent citrate level (if available).
   b) Measure access recirculation with online hemodilution technique (if available).
8) Display Confirmation Alarms.
   a) Alarm if more than 10-15% recirculation is detected. The treatment will still be safe, but less effective for uremic clearance.
   b) Measure Hgb concentration with the online sensor (alarm if more than 20% different from initially provided value).
   c) Alarm if citrate-containing pre-dilution fluid is not on arterial limb 14 of circuit 12.
9) Analyze input data.
   a) Determine highest post-filtration flow possible as % of QB with set hemoconcentration limit.
   b) If plasma fraction of blood is <=0.66, then Program Qpost for the above maximum post-filtration, minus (QCa/Mg+Quf) for maximum citrate clearance with a given QB and total Qtf. Otherwise, maximum post-filtration is 50% of QP.
   c) The Qpre is always 50% of QP (QP:Qpre=2:1).
   d) For citrate single pass fractional extraction, E is (Qpre+Qpost+QCa/Mg+Quf)/(Qpre+QP).
   e) The pre-dilution bag C16:C8 ratio is: If E=0.66 2:0, if between 0.66-0.6 1:1, if 0.60-0.50 0:2.
   f) If E>=0.5 cannot be achieved with CVVH because of limited postUF, use of SLED or CVVHDF may be advised.
   g) The post-dilution bag B25:B50 ratio is: Initially 1:1, adjust 2:0 (usual), or 0:2 (liver failure).
   h) Aim for 10 liters of pre-dilution fluid use every 6 hours so that bag changes are predictable.
10) Determine prescription and machine settings.
    a) Display QB, Qpre and Qpost, Quf, QCa/Mg.
    b) Display expected maximum Csys (<=4 mM citrate).
    c) Display expected circuit Ca loss (mmol/hour) before replacement infusion (prescriptions can have uniform QP and DCit versus weight adjusted).
    d) Operator selects K content (2K and 4K bags of each fluid type, use ratio 2:0, 1:1, 0:2). The 2:0, 1:1, 0:2 ratios of different bags may be used for flexibility in K, citrate and bicarbonate dosing in a system where each scale can hold two 5 L bags at a time.
11) Calcium Dosing.
    a) ECit is essentially equal to ECa*f, where f is the correction for ultrafilterable fraction (f will be about 0.95 when 2:0, 0.9 when 1:1 and 0.8 when 0:2 ratio C16:C8 pre-dilution fluids are used. f may also have to be corrected for albumin levels and circuit pH.).
    b) Target systemic plasma total Ca (mM) is defined: Use Csys (0.25 mM Ca/1 mM citrate), systemic albumin (0.2 mM Ca/1 g/dL) and target systemic ionized Ca (target Cai=1.00 mM when systemic citrate is assumed to be equal to Csys=3).
    c) Circuit Ca loss in steady state is equal to QP (L/hour) *Target systemic total Ca(mM)*ECit*f.
    d) QCa/Mg is easily calculated from the circuit Ca loss and Ca concentration of the Ca infusion solution.
    e) At the start, the operator may have to give 1-4 amps of Ca-gluconate over 1-2 hours to bring the systemic ionized Ca close to 1.25-1.5.

f) Ca dosing may be completely automated with the OSS integrated into effluent line 24.

12) Continuous safety check.

a) Citrate solution is properly on citrate pump 34 and arterial limb 14 is arterial (expected constant step-up in effluent citrate from baseline) (with OSS). Alarm if citrate bag changed to calcium or saline or access connection reversed during operation based on effluent citrate and calcium monitoring with all the above IV fluids having different ingredients.

b) Input: Set access blood flow rate: current (QB) (Alarm: when QB is changed because of access issues recalculate all pump speeds and fluid flows).

c) Input: Measured hemoglobin concentration (Alarm: when changed by more than 10% alert operator to possible bleeding or over-ultrafiltration; recalculate prescription, recommend CBC check, net ultrafiltration target revision).

13) 6 Hourly safety check: input data.

a) Input: measured venous blood gas (VBG) and ionized Ca on the arterial limb before citrate or on the venous limb 18 of the blood circuit 12 after the Ca infusion (Systemic arterial blood gas (ABG) or VBG with ionized Ca also acceptable).

b) Systemic total and ionized Ca if indicated only.

c) Hemoglobin every 12 hours (or online with sensor).

d) Albumin once daily or if receiving albumin/plasma products.

e) Hourly net UF goal if changed.

f) Test OSS with zero QB and with filtering the standard priming solution.

14) Recalculation of the prescription.

a) Re-calculate: maximum post-filtration, maximum ECit, bicarbonate flux then adjust.

b) Pre-filter fluid C16:C8 ratio.

c) Post-filter fluid B25:B50 ratio.

d) Supplement either B25 or B50 with ½ amp NaHCO3 per 5 L bag if needed.

e) Adjust rate of QCa/Mg infusion.

f) Adjust QB (to adjust QP) and Qpre to use about 10 L/6 hours pre-filter fluid (keep QP:Qpre 2:1).

15) Other alarms.

a) Change filter electively every 24-48 hours to prevent protein fouling even in the absence of clotting.

b) Change entire circuit every 72 hours.

c) Replace OSS sensors as needed regularly.

System 10 according to the present invention may contain an OSS for measuring calcium, magnesium and citrate in the ultrafiltrate. As explained herein, the calcium, magnesium and citrate values measured from the ultrafiltrate by the OSS can be used to back-calculate the values in the patient's plasma. As also explained, the kinetic curve of systemic plasma citrate concentration can be used to derive the exact value of the liver clearance of citrate as well as the volume of distribution of citrate, $V_E$. Using the above parameters, systemic citrate levels can be accurately predicted at any future T time point. The calcium pump 44 and citrate pump 34 as well as the entire prescription including the therapy fluid bicarbonate concentration (when flexible) can then be completely controlled by the machine software according to the present invention.

Filter performance can be monitored by online citrate clearance measurements. The direct citrate clearance measurements again enable complete precision in calcium and citrate dosing. Since calcium exits through hemofilter 16 almost entirely as Ca-citrate complex, the measured citrate dialysance will be nearly equal to the total calcium dialysance. The slightly lower Ca-dialysance will be due to the Gibbs-Donnan effect and the minimal albumin-bound Ca in circuit 12 (about 5-20% depending on the amount of citrate infused in the arterial limb 14 of the circuit 12, the acidity of the citrate infusion and the plasma albumin level).

In further accordance with the present invention, an RCA system is provided which may include an online clearance monitor (OCM) and can safely provide fully automated RCA with any online fluid generation-based modality of RRT currently in clinical use. This embodiment of the RCA system is designated generally by reference numeral 110 and is illustrated in FIGS. 5-8, wherein components similar to those described for system 10 are given like reference numerals except for the addition of a "1" prefix. System 110 is capable of simultaneous pre- and post-dilution hemofiltration for the greatest therapy fluid efficiency. The online fluid generation system of RCA system 110 may follow the traditional two-(acid and base) concentrate component design, thus allowing the greatest variability in the final sodium and bicarbonate concentration to best suit the needs of individual patients. Finally, system 110 also incorporates a dialysis machine module to measure conductivity of the fresh online therapy fluid as well as the filter effluent fluid. These measurements are obtained in conjunction with alterations of the citrate anticoagulant solution infusion rate and are analyzed using calculations markedly different from prior art. The method according to the present invention allows precise online clearance measurements even in CRRT operational modes which is not possible with the prior art, and thus allows the continuous monitoring of the filter performance (clearance). This, in turn, ensures the maintenance of the efficacy and safety of the treatment prescription.

RCA system 110 can safely provide therapy to critically ill patients even if they have acute liver failure with inability to metabolize citrate. The system design prevents citrate accumulation in the patient, while maintaining highly efficient anticoagulation of the extracorporeal circuit. System 110 can also provide fully regionally anticoagulated blood to any extracorporeal blood circuit, such as up to a maximum operational blood flow of 500 ml/minute. System 110 is thus suitable to accommodate the emerging hybrid therapies that combine uremic solute clearance with plasmapheresis or plasma adsorption by running the anticoagulated blood through specialized adsorption columns or plasma separation devices. Following citrate removal in the dialyzer, the anticoagulated blood could also be perfused through a bioartificial kidney device that contains live renal tubular cells or through a MARS liver replacement therapy circuit before the reversal of anticoagulation by the calcium infusion. RCA system 110 achieves these goals with minimal input from the operator and delivers the treatment without any need for intervention in all modes of operation. This will broaden the settings in which a 12 to 24-hour CRRT procedure can be performed and will likely increase its utilization. System 110 can also be used to provide highly effective and safe RCA for any modality of RRT including in-center intermittent hemodialysis or hemodiafiltration and home quotidian or nocturnal hemodialysis, making it applicable to the far greater market of outpatient RRT sessions where heparin anticoagulation is not preferred.

As will be described in greater detail below, system 110 according to the present invention also utilizes novel therapy fluid concentrates, a novel citrate anticoagulant and novel single premixed calcium plus magnesium infusions that have been designed to fully exploit the system's capabilities. A control algorithm is provided which derives a safe treatment prescription according to the treatment goals selected by the operator. Special access catheters and/or special circuit tubing connectors allow system 110 to provide RCA as soon as the blood enters the catheter tip (or the circuit tubing from the access needle). The single needle operational mode eliminates the concerns about access disconnection.

The following describes a comprehensive system and method according to the present invention for providing highly effective and completely safe RCA for a hemodialysis machine 160 designed for CRRT. With reference to FIGS. 5a, 6a, 7a, and 8a, system 110 includes a CRRT circuit 112 which includes arterial blood line 114, hemofilter 116, and venous blood line 118. System 110 includes a blood pump 122 which should ensure as accurate as possible agreement between the set and delivered blood flow. System 110 may also include volumetric balancing chambers 162 for coordinating total ultrafiltration and CRRT replacement fluid infusion volumes, obviating the need for the machine operator to rely on a scale-based system with frequent measurement and exchange of various fluid bags.

Volumetric balancing chambers 162 include a replacement fluid pump (e.g., volumetric) that diverts a portion of the online therapy fluid for pre- or post-dilution hemodiafiltration (FIG. 6a). Fluid removed by this pump subtracts from the total fresh therapy fluid delivered to the hemofilter 116. The action of the balancing chamber 162 ensures that all fresh therapy fluid delivered to the extracorporeal circuit as a pre-dilution replacement infusion, post-dilution replacement infusion, or dialysis fluid is precisely equal to the total circuit effluent minus a small portion of the effluent that is diverted before such balancing by the net ultrafiltration pump. This volumetric pump may infuse about 75% of the therapy fluid either as pre-dilution replacement fluid (simultaneous pre-post-dilution CVVH) or as dialysate in pre- or post-dilution hemodiafiltration. Finally, this pump may pump 100% of the therapy fluid as dialysis fluid in pure hemodialysis. Additional pump(s) 164 (e.g. volumetric) may be provided to divert a portion of the online therapy fluid for pre-dilution hemodiafiltration (FIG. 6a), post-dilution hemodiafiltration (FIG. 7a), or simultaneous pre- and post-dilution hemodiafiltration (FIG. 8a). Another volumetric pump may divert a small portion of the effluent fluid as net ultrafiltrate before the bulk of the effluent enters the volumetric balancing chamber. Still another optional pump is an additional blood pump that is only needed if the single-needle dialysis mode is used. The benefit of this operational mode is that the machine immediately detects accidental access disconnection. This is of great clinical value when a permanent access (fistula or graft) is used for CRRT in the ICU or for nocturnal hemodialysis in-center or at home.

System 110 according to the present invention may include a volumetric, precise IV infusion pump 134 for the infusion of concentrated citrate anticoagulant into the arterial limb 114 of the extracorporeal circuit 112. Pump 134 may operate in the 0.1-20 ml/min flow rate range and may be precise to ±3% of the prescribed rate. Also, for essentially continuous flow of the pumped liquid, the volume per single pumping cycle may be in the 0.05-0.2 ml/cycle range. In one implementation, this pump 134 may have a dedicated air detector controlling a line clamp (not shown). A volumetric, precise IV infusion pump 144 may be provided for the infusion of concentrated calcium and magnesium chloride into the venous limb 188 of the extracorporeal circuit 112 to restore calcium and magnesium mass balance. The same pump specifications would apply here as for the citrate pump 134. In one implementation, this pump 144 may also have a dedicated air detector controlling a line clamp (not shown). All of the above-described pumps may be operated and monitored for safety by a control algorithm built into the hemodialysis machine software program.

FIG. 5a depicts a system with pumps and fluid connections suitable for sustained low efficiency dialysis (SLED) or 4-5 hour intermittent hemodialysis (IHD). FIG. 6a depicts a system with pumps and fluid connections suitable for continuous veno-venous hemodialysis with pre-dilution ultrafiltration (CVVHDF). FIG. 7a depicts a system with pumps and fluid connections suitable for post-dilution hemodiafiltration (HDF). FIG. 8a depicts a system with pumps and fluid connections suitable for continuous simultaneous pre- and post-dilution veno-venous hemofiltration (CVVH) or 4-6 hour intermittent high volume hemofiltration (HVHF).

RCA system 110 may include a conductivity-based online clearance monitor (OCM) 170 that provides precise measurement of the delivered small solute clearance in any operational mode. FIGS. 5b, 6b, 7b, and 8b illustrate a conductivity-based OCM according to the present invention with online-generated dialysis fluid and automated RCA corresponding to the different treatment scenarios depicted in FIGS. 5a, 6a, 7a, and 8a, respectively, wherein all of the parameters are known or measured except $C_p$ and $C_{pin}$. OCM 170 according to the present invention may include conductivity sensors 172, 174 operably connected to line 176 carrying filtered sterile pyrogen-free online therapy fluid and line 178 carrying effluent fluid, respectively. Precise dosing of RRT based on conductivity dialysance will provide pharmacists with invaluable data for medication dosing and will aid clinical research in CRRT.

Automated self-check methods for proper circuit fluid connections according to the present invention may be provided to provide safety monitoring of the RRT circuit connections. At startup, before the patient is connected to the extracorporeal circuit 112, the machine 160 may automatically fill the blood circuit with priming solution and may remove air from all infusion lines as well. The machine 160 may then run a few-minute mock treatment session with the priming solution instead of blood recirculating in the blood circuit. During this time, loading of the calcium pump 144 and the citrate pump 134 with the appropriate infusion solution may be confirmed by giving a bolus from each pump and confirming the expected change in the filter effluent conductivity appropriate for the pumped medication infusion. This startup method will utilize the fact that the conductivity of the citrate anticoagulant and the calcium infusion is markedly different. During this startup period, the baseline filter conductivity dialysance may also be obtained with priming solution in the circuit and compared with the value expected for the filter and the prescription fluid flow rates. Significant differences may trigger a filter alarm. After the proper loading of the medication pumps is confirmed with the effluent conductivity method, the patient may be connected and the blood circuit tubing filled with blood.

The machine 160 may then give a small priming solution bolus in the blood circuit and check for access recirculation by looking for any hemodilution in the arterial limb 114 of the blood circuit using the online hematocrit sensor 150. If recirculation is detected, the machine 160 may prompt the operator to review the access connections and/or the access itself. After assessing for recirculation, the machine 160 may deliver a citrate bolus into the arterial limb of the blood circuit connected to the citrate pump 134 and may compare the imaged change in filter effluent fluid conductivity with what is expected. If the citrate pump 134 is infusing into the venous limb 118 due to wrong connection, the bolus will not be seen in the filter effluent and the machine 160 will halt the citrate infusion and alert the operator to the wrong connection. During this initial citrate bolus, the baseline filter conductivity dialysance may also be obtained, now with blood in the circuit, and compared with the expected value for the filter and the prescription fluid flow rates. Significant differences may trigger a filter alarm. Finally, if during a treatment interruption the patient is removed from the machine, and the blood circuit is subsequently wrongly reconnected leading to venous infusion of the citrate anticoagulant, the resultant marked change (drop) in the filter effluent conductivity may be immediately detected and may cause a machine alarm and cessation of the citrate infusion and RRT delivery until the connections are reviewed by the operator.

The RCA system 110 eliminates the risks associated with the nurses dosing a concentrated citrate and or calcium infusion for anticoagulation during a CRRT or other extracorporeal blood treatment procedure that uses RCA. Citrate removal by the hemofilter 116 is important for safe operation of a CRRT system using citrate anticoagulation. If solute removal is stopped and blood continues to flow through the extracorporeal circuit to prevent coagulation, the infusion of the anticoagulant solution has to be stopped immediately or the patient will receive an excess amount of citrate which could be life threatening. In RCA system 110, if for any reason solute removal stops and blood continues to flow through the extracorporeal circuit to prevent coagulation (for example: when the machine has a dialysate/replacement fluid conductivity alarm), the delivery of citrate as well as any calcium plus magnesium replacement infusion is immediately aborted to protect the patient from receiving an excessive amount of citrate and or calcium plus magnesium.

The automated RCA system 110 according to the present invention markedly reduces the need for health care personnel to monitor and adjust the CRRT. Significant modifications to the software running the hemodialysis machine 160 are necessary to provide online conductivity dialysance measurements during CRRT and support the various operational modes with RCA according to the present invention. The control program (described below) allows tailoring of the prescription to the specific treatment objectives and the individual patient's condition with scientific accuracy by defining only a few variables. Calcium infusion dosing is predictive and automated. Finally, the RCA system 110 eliminates the risk of citrate accumulation in the patient associated with RCA during hemofiltration or any other extracorporeal blood processing intervention, such as up to blood flow rates of 500 ml/min. This is expected to finally bring this treatment modality from highly specialized academic health care institutions to a broad group of patients and to allow the safe operation of the procedure by less experienced health care personnel in most (not-academic) health care settings.

The RCA system 110 eliminates the dangers of prior RCA protocols in CRRT as discussed below:
1) Hypernatremia: The coordinated and carefully calculated pre-filter infusion of the anticoagulant citrate and use of the online generated therapy fluid solution always ensures the adherence to an operator-selected final sodium concentration in the summary fluids that come into contact with the patients' blood in the range of 135 to 145 as well as attaining a selected (usually 140 mM) sodium concentration in the venous blood returning to the patient.
2) Metabolic alkalosis: The sum of bicarbonate and anions metabolizable to bicarbonate (in mEq) may be kept between 25-40 mEq bicarbonate equivalents per liter of summary therapy fluid. This is in keeping with fluid alkali content per liter prescribed in most high dose CRRT protocols in the literature. Since the therapy fluid bicarbonate concentration can be freely adjusted in the range of 25-40 mM, this complication will be eliminated or easily corrected.
3) Metabolic acidosis: The system does not depend on citrate metabolism to provide bicarbonate to the patient. The prescriptions will keep the systemic citrate level in a narrow range (0-3 mM) regardless of liver function. Therefore metabolic acidosis will not develop even in the patient with severe liver failure and no significant citrate metabolism and even anhepatic patients can continue on high dose CRRT with RCA system 110 without the need for separate bicarbonate supplementation.
4) Hypocalcemia 1 (due to net calcium loss from the patient): The ultrafiltrate total calcium and magnesium losses are precisely calculable in system 110 that measures conductivity dialysance directly and calculates Ca and Mg dialysance indirectly. The combined calcium plus magnesium infusion regulated by the machine 160 will be dosed by the control program also taking into account any initial citrate accumulation predicted by kinetic modeling. It is expected that the system 110 will be fully automated and that no changes to the infusion rate will be needed during therapy. Such predictive dosing will also enable the operator writing the CRRT prescription to specify or "dial in" the target systemic plasma total calcium level that corresponds to a target (normal) ionized calcium level in the given patient. Clinical prudence will likely mandate that the patient's systemic total and ionized calcium levels continue to be measured every 6 hours with adjustments made to the infusion as required (but such adjustments are not expected). Magnesium will be dosed to maintain a total plasma Ca:Mg=2:1 to 2:0.8 molar ratio (as ionized magnesium measurements are not routinely available and all calcium chelators (albumin, citrate etc also chelate magnesium).
5) Hypocalcemia 2 (due to citrate accumulation): Citrate will be given by a machine controlled IV pump 134. This eliminates the risk of nursing errors with a separate citrate infusion. The default mode of RCA system 110 provides for 75% or higher citrate extraction on the hemofilter 116 in a single pass during CRRT. This eliminates the possibility of marked systemic citrate accumulation even in the absence of liver metabolism. Appropriate calcium infusion dosing will prevent the initial mild hypocalcemia due to a limited systemic citrate buildup. This will be accomplished by using the estimated systemic plasma levels of citrate as predicted by a kinetic modeling program. The kinetic program analyzes the CRRT prescription (fluid compositions and flow rates as well as blood flow rate). It also utilizes anthropomorphic data to predict the citrate volume of distribution in the patient. Finally, for safety the patient's citrate clearance in L/minute will be estimated as zero, to generate the expected citrate accumulation curve and guide calcium and magnesium replacement to saturate the retained citrate in the first few hours of the treatment. In all patients, RCA system 110 will always be run in the safest mode with no possibility of citrate accumulation or significant metabolic acidosis.
6) Rebound hypercalcemia (due to release of calcium from citrate after CRRT with RCA is stopped): System 110 may not allow treatment prescriptions that could result in systemic citrate levels in excess of about 3 mmol/L. This will ensure that systemic citrate levels stay <=3 mM corresponding to about maximum 0.6 mM chelated calcium that could be released after RCA is stopped in all patients who can metabolize citrate. (Most patients will have 1 mM plasma citrate and about 0.25 mM Ca chelated by citrate in the steady state). The RCA protocol according to the present invention is designed to keep systemic ionized Ca levels around 1-1.25 and therefore the highest calcium level after RCA is stopped will be <=1.5-1.75 mM and most patients will rebound to 1.5 mM Ca levels after treatment.

7) Hypophosphatemia: In all operational modes except short outpatient dialysis or HVHF, the online generated pre-filter therapy fluid can be supplemented with physiologic amounts of phosphate by the manufacturer of the concentrate without the risk of calcium- or magnesium-phosphate precipitation. The phosphate-containing fluid can be used even when the serum phosphorus is high, as the large clearance goals will allow significant net phosphate removal while the hyperphosphatemia is present. Conversely, the pre-filter fluid will also serve to correct hypophosphatemia towards normal when needed.

8) Fluctuating levels of anticoagulation: The high citrate to calcium ratio maintained in the circuit 112 (and the marked pre-dilution in some operational modes) ensures predictable citrate levels and very effective anticoagulation in the circuit 112 as well as a clearly defined hourly citrate load into the patient.

9) Nursing errors: The RCA system 110 is designed so that the nurses or other operators only need to ensure timely supply of the fluids used by the system 110 and regular laboratory monitoring for total and ionized calcium as clinical prudence dictates. Therefore, nursing errors are near completely eliminated by the system design, as the nurse's role is mainly to obtain blood samples at specified intervals and notify the operating physician of the results as well as possibly manually enter/confirm treatment prescriptions as specified.

10) Rare: Ionized hypomagnesemia: Since clinical monitoring of ionized magnesium is usually not possible, the method according to the present invention may aim to maintain a 2:1 molar ratio between total plasma calcium and total plasma magnesium. To achieve this, the molar ratio of calcium and magnesium may be fixed at 2:1 in the RCA system-regulated calcium plus magnesium infusion as well as in some 1× therapy fluids (dialysate). Such dosing ensures that total and ionized magnesium levels will be appropriate for the steady state plasma citrate levels.

11) Declining filter performance: The novel conductivity-based online clearance monitor will detect this complication and alert the operator that the filter needs to be replaced. The optical hematocrit sensors 150 can detect access recirculation and can enable the correction of blood bolus-based clearance measurements as well as derived systemic citrate and calcium levels for this phenomenon.

12) Trace metal depletion: Cationic trace metal supplementation may be provided with the calcium infusion to restore precise mass balance for these trace solutes. Any trace metal incompatible with the calcium infusion can be provided in the citrate anticoagulant infusion in an adjusted concentration.

13) Access disconnection: Needle disconnection can be safely detected if a single needle operational mode is used in combination with the novel circuit tubing connector to access a permanent access for CRRT or daily nocturnal dialysis.

14) Wrong connection of citrate, calcium or acid concentrate or blood circuit to patient: These errors are prevented by the hardware design of the system 110 as well as through conductivity monitoring based safety checks.

15) Disconnection of the calcium and or citrate infusion: This can be completely prevented by appropriate circuit tubing design (non-disconnectable, physically continuous infusion to blood line connection). The disconnection of the citrate infusion can also be detected by monitoring the circuit effluent conductivity and or citrate concentration.

For use with RCA system 110, an anticoagulant citrate solution may be provided according to the present invention with 5.33:0.66 molar ratio of tri-sodium citrate and acid citrate and a total concentration in the 100 to 500 mmol/L range. At a plasma flow of 100 ml/min, a 150 mM solution will be infused around 240 ml/hour. The acid citrate content was reduced to increase the conductivity and allow safe (from the standpoint of circuit acidification) intermittent bolusing for online clearance measurements. The citrate concentration will be the highest allowed by the FDA that still allows precision in delivering exact amounts of sodium citrate boluses during the clearance measurements. If the solution according to the present invention is not available, a commercially available tri-sodium citrate can be used (139 mmol/L) at about 260 ml/min at 100 ml/min plasma flow. In one modification specifically contemplated herein, trace metal minerals that are incompatible with the calcium infusion may be added to the above citrate solutions in a concentration sufficient to restore circuit mass balance for the specific trace metal mineral. Finally, the concentration of the citrate solution may also be correlated with the calcium infusion to make sure these two fluids have markedly different conductivities.

In addition, the anticoagulant citrate solution may contain sodium chloride in the 0-4000 mmol/L concentration range to increase the conductivity of the solution. The fluid may contain NaCl at about 150 mM. This will increase the accuracy of the novel conductivity-based clearance monitor without requiring the use of highly concentrated sodium citrate solutions. The higher sodium and chloride content of the anticoagulant is easily compensated for by reducing the sodium and chloride content of the online dialysis and/or replacement fluid if needed. The addition of any concentrated electrolyte solution (including the other specific example of sodium bicarbonate in the 0-2000 mmol/L concentration range when only basic citrate anticoagulant is used) to the citrate anticoagulant solution to increase its conductivity for the purposes of online clearance monitoring through conductivity measurements and to identify the solution through its measured conductivity is fully contemplated in accordance with the present invention.

Novel acid concentrates may be designed according to the concentrate proportioning systems of the hemodialysis machine 160. The final 1× therapy fluid concentrations are defined for all operational modes (the 34× acid and base concentrate compositions follow from the 1× values as apparent to those skilled in the art). The acid concentrates in one implementation will have essentially zero Ca, Mg and citrate content and some will have (in the case of the CRRT concentrates) phosphate in them. The unique acid concentrates may be diluted and mixed with the standard bicarbonate concentrate. However, in a variation of all the unique CRRT acid concentrates, the phosphate will not be added to the acid concentrate but rather it will be in the base concentrate as an approximately 20:1 mixture of di- and mono-sodium phosphate salt to be pH compatible with the bicarbonate. The purely diffusive and convective operational modes in CRRT may perform well with a single fluid design. This acid concentrate design is presented for procedural simplicity and flexibility for all CRRT. The same single acid concentrate without phosphate is suitable for all intense, 4-5 hour outpatient HVHF, HDF or IHD operational modes.

A novel calcium plus magnesium chloride mixed infusion with a Ca:Mg molar ratio of 2:1 (range 4:1 to 2:1) and in one implementation a total Ca about 200 mmol/L and total Mg about 80 mmol/L is contemplated with the possible simultaneous use of a traditional, lower conductivity citrate anticoagulant. At a plasma flow of 100 ml/min, this will result in a 40-70 ml/hour calcium infusion rate. The dilution of the solution will be selected to ensure the precision of dosing (a reasonably concentrated solution will be used as allowed by the pumping precision of the IV pump). In another application, the solution will be more dilute with a total Ca about 50 mmol/L and total Mg 25 mmol/L with the possible simultaneous use of a high conductivity novel citrate anticoagulant. In one modification contemplated herein, trace metal minerals may be added to the above solutions with each specific trace metal having a specific predefined molar ratio to calcium (similar to the concept for magnesium). This molar ratio (for each specific trace metal species) will be the same as the molar ratio of total calcium to the total specific trace in the RRT circuit effluent during RCA. (This ratio, in turn, may be about the same as their respective total molar concentration ratio in human plasma during RCA.) The ratio for each trace metal will be refined based on results of clinical mass balance studies.

Finally, in one embodiment, all calcium replacement solutions may be supplemented with sodium chloride to a final concentration of 150 mmol/L for easier sodium mass balance calculations and also to modulate the final conductivity of the fluid. The addition of any concentrated electrolyte solution (including the specific example of sodium chloride in the 0-2000 mmol/L concentration range) to the calcium replacement solution for the purposes of easier mass balance calculations and to increase its conductivity to help identify the solution through its measured (directly, or indirectly through its effects on the filter effluent) conductivity is fully contemplated in accordance with the present invention.

The novel fluids which may be used by RCA system 110 according to the present invention are detailed below. Common to all 1× final dialysate compositions is the fact that they are generated by diluting and mixing an acid and a base concentrate. The shown separation of the components into the acid and base concentrates was chosen to best accommodate the online fluid generation system of the dialysis machine (Fresenius 2008) used for initial testing. However, all permutations of separations of the components of the final dialysates in all concentrated and diluted formulation including, but not limited to, a 0.25×-50× concentration range that by mixing would result in the same 1× online fluid are fully contemplated. Also, all concentrates can be provided as dry powders as well to be dissolved and diluted with water. For online therapy fluids, the complete 1× fluid, as well as the portion of the individual solute components coming from the acid concentrate are defined herein.

Citrate Anticoagulant Solutions for RCA System 110:

For all patients receiving CRRT (pre-post-dilution CVVH, pre-dilution 24-hour CVVHDF, or 24-hour SLEDD), the usually used anticoagulant solution is a 5.33:0.66 molar mixture of basic and acid citrate:

1. Acid Citrate Anticoagulant 1 for CRRT:

| Acid Citrate Anticoagulant 1 for CRRT: about 4% w/v total citrate; a mixture of basic and acid citrate in a 8:1 molar ratio | mmol/L | mEq/L |
| --- | --- | --- |
| Sodium chloride | 150 | 150 |
| Total Citrate | 150 | 450 |
| Trisodium (Basic) Citrate | 133.33 | 400 |
| Citric Acid | 16.67 | 50 |

The hypertonic sodium content makes online clearance measurements possible and more accurate with the novel method described earlier. The accuracy is greatest when the fluid sodium concentration is highest, limited by taking into account the precision of the sodium citrate pump 134. The conductivity increment of the anticoagulant over normal plasma is also significantly (150%) different from the calcium infusion to detect an accidental mix-up of the infusates. The acid component is included for its antibacterial effects during storage and also as it contributes to predictable circuit calcium-albumin dissociation as well as anticoagulation by a separate circuit acidification effect. This solution is around the 4% weight per volume concentration (w/v) limit for citrate recommended by the FDA for direct infusion.

2. Acid Citrate Anticoagulant 2 for Short, Intense IHD, HDF or Pre-Post HVHF:

| Acid Citrate Anticoagulant 2 for short, intense IHD, HDF or pre-post HVHF: about 4% w/v total citrate; a mixture of basic and acid citrate in a 2:1 molar ratio | mmol/L | mEq/L |
| --- | --- | --- |
| Sodium Chloride | 250 | 250 |
| Total Citrate | 150 | 450 |
| Trisodium (Basic) Citrate | 100 | 300 |
| Citric Acid | 50 | 150 |

These acid citrate anticoagulants are different from the prior art (e.g., the ACD-A Solution of Baxter) as they contain no dextrose and have a higher total citrate and sodium content. The acidity of the anticoagulant is very important and provides for further disruption of the coagulation cascade beyond the chelation of calcium. In solution 2, the proportion of the acid is increased as the total amount of citrate mixed with a liter of plasma is reduced in shorter, more intensive renal replacement therapy sessions. (The need for intense anticoagulation is less here as filter clotting only needs to be averted for 4-5 hours as opposed to days in CRRT). The sodium concentration is highest to allow precise online clearance measurements, and more importantly, to allow the use of a low sodium content in the special acid concentrates used for RCA, making it possible for the system to detect these concentrates through the lower conductivity of the final therapy fluid generated at standard dilution ratios with their use. This is important to avoid the accidental use of a low or zero calcium acid concentrate meant for RCA during an RRT session without RCA and the combination of moderately lower sodium acid concentrates and final dialysis fluids with higher sodium anticoagulant infusions is specifically contemplated according to the present invention.

The two anticoagulant fluids described above have identical total molar citrate content to eliminate the chance of a severe citrate dosing error if one solution is inadvertently used instead of the other and also have identical sodium (and conductivity) content to allow uniformity during the online clearance measurements. FDA recommendations on maximum citrate content of infusates may mandate the use of fluids with total citrate content limited to 4% w/v. However, this may not be necessary as these fluids are part of the extracorporeal circuit and are immediately diluted there. The strictly machine-controlled administration of these infusates ensures that no concentrated citrate can enter the patient's body. Anticoagulant solutions with basic to acid citrate ratio 2:1 to 8:1, and total millimolar citrate content 50 to 1000 mmol/L are contemplated according to the present invention, along with total citrate content around 4% w/v. Anticoagulant solutions with only basic citrate (50-1200 mmol/liter citrate) and additional sodium bicarbonate or sodium chloride either or both in the range of 0-2000 mmol/L to increase the conductivity are also contemplated. Finally, anticoagulant infusions with similar designs but the citrate molecules replaced by other chelators of calcium that are safe for human infusion in large amounts (for example isocitrate) are also fully contemplated in accordance with the present invention.

Novel Calcium Plus Magnesium Premixed Single Replacement Solution:

A concentrated calcium and magnesium chloride infusion having a 0.25×-4× continuous range diluted/concentrated formulations with a 2:1 (range 1:1 to 4:1) molar ratio of calcium and magnesium are provided according to the present invention. All other possible formulations with similar Ca and Mg content and with any anion accompanying these cations that can be used for human IV infusion are also fully contemplated including, but not limited to, lactate, acetate or gluconate.

1. CaCl2 and MgCl2 Infusion in the Venous Blood Circuit Limb Near the Access Catheter or Needle:

|  | mmol/L | mEq/L |
|---|---|---|
| A. CaCl2 and MgCl2 infusion in venous limb near catheter | | |
| Calcium | 50 | 100 |
| Magnesium | 25 | 50 |
| Sodium | 150 | 150 |
| Chloride | 300 | 300 |
| Trace metals | see text | see text |
| B. CaCl2 and MgCl2 infusion in venous limb near catheter | | |
| Calcium | 200 | 400 |
| Magnesium | 80 | 160 |
| Sodium | 150 | 150 |
| Chloride | 710 | 710 |
| Trace metals | see text | see text |

The above are the most likely formulations of the infusion and are based on the novel concept that under any operating conditions during RCA for CRRT, calcium and magnesium is lost from the extracorporeal circuit in the effluent fluid in a roughly 2:1 to 2:0.8 molar ratio (depending on the steady sate citrate level in the patient's plasma), corresponding to the molar ratio of these ions in human plasma under normal physiologic conditions (about 2.4:1) as altered by the accumulated modest systemic citrate levels. Therefore, the calcium plus magnesium infusion that restores the normal total calcium and magnesium content of blood in the venous limb of the circuit should also contain these ions in a 2:1 to 2:0:8 molar ratio. Such a solution may be important to the optimal performance of RCA with CRRT. With a plasma flow of about 100 ml/min and corresponding calcium and magnesium losses in the circuit, the above more dilute (A) fluid will provide convenient flow rates of 200-300 ml/hour. More dilute (A; such as for CRRT) and concentrated (B; such as for outpatient HD) forms of the above solution with calcium to magnesium molar ratio in the range of 1:1 to 4:1 are also contemplated.

Selection of the proper calcium content will be guided by the need for precise pumping (more dilute fluid preferred) and the need for limited volume to be infused and conductivity to be different from that of the citrate anticoagulant solutions. The idea to use online conductivity measurement of either the citrate and calcium infusion fluids directly (such as with a non-contact, sterile method) or the changes in filter effluent fluid conductivity in response to a presumed (if the infusion bags are connected appropriately) citrate anticoagulant and/or calcium infusion bolus to detect accidental mix-up of the citrate and calcium infusions is novel according to the present invention.

Trace Cationic Metal Element Supplementation with the Calcium Infusion:

In their cationic form, trace elements like chromium, copper, manganese, molybdenum, selenium, zinc and iron are chelated by citrate. It is expected that citrate will strip many or all of these trace metals from their carrier proteins in the plasma and will remove them from the patient's body through the extracorporeal circuit. Similar to the concept of proportional magnesium removal detailed above, it is expected that the removal of the trace metals will be proportional to the removal of calcium, according to their individual renal replacement therapy circuit effluent molar concentration ratios to the effluent calcium. Therefore, the present invention provides a calcium plus magnesium infusion that is supplemented by the cationic trace metals present in human plasma, in a fixed molar ratio to the calcium in the infusion as defined by their total calcium to total trace metal molar concentration ratios in the circuit effluent during RCA, plus or minus 100% range in the molar concentration ratio. The anion accompanying the $Ca^{2+}$, $Mg^{2+}$ and cationic trace metals will have to be compatible with all cations without precipitation and will have to be safe for IV infusion. The likely candidates include, but are not limited to, chloride, lactate, gluconate or acetate. All possible formulations with any suitable anion of this calcium plus magnesium and multiple trace element infusion that satisfies the above molar ratio requirements are fully contemplated in accordance with the present invention. In a separate approach, it is also possible to provide the trace element replacement with the citrate anticoagulant, the dialysis fluid or with the pre- or post-dilution replacement fluid infusion, therefore the present invention also contemplates supplementing these fluids with trace metal elements to restore mass balance for these metals during regional citrate anticoagulation.

Finally, all calcium replacement solutions may be supplemented with sodium chloride to a final concentration of 150 mmol/L for easier sodium mass balance calculations and also to modulate the final conductivity of the fluid. The addition of any concentrated electrolyte solution (including the specific example of sodium chloride in the 0-4000 mmol/L concentration range) to the calcium replacement solution for the purposes of easier mass balance calculations and to increase its conductivity to help identify the solution through its measured (directly, or indirectly through its effects on the filter effluent) conductivity is fully contemplated according to the present invention.

Bicarbonate with Phosphate for any Treatment Modality:

In one embodiment of the novel 1× dialysate formulations, all novel electrolyte features are provided by the unique composition of the acid concentrates. In this manner, the standard base (bicarbonate) concentrates currently in use with commercial dialysis machines can be used without alterations. However, in one possible embodiment, the phosphate could be provided as part of the base concentrate, to eliminate concerns about incompatibility with $Ca^{2+}$ and $Mg^{2+}$ ions in the acid concentrate.

1. Base Concentrate with Phosphate:

The most important design feature here is the need to provide the phosphate as a mixture of its disodium and monosodium salts in a ratio that results in the same buffered pH as the pH of a solution prepared by dissolving just sodium-bicarbonate in water. The target pH value is defined as pH=$(pKa1+pKa2)/2$, where pKa1 and pKa2 are the acid dissociation constants of carbonic acid at 25 C and the ionic strength of the concentrate (expected about 6.4 and 10.3 with the target pH around 8.4). The ratio of the sodium phosphate salts can be derived from the equation pH=pKa2+log(salt/acid), where pKa2 is now the second acid dissociation constant of phosphoric acid, about 7.1 at 25 C. Therefore, the ratio of the salt (disodium-phosphate) to acid (monosodium phosphate) will be about 20:1. The exact ratio may be different slightly (the pKas may be slightly different at the ionic strength of the concentrate) and can be easily determined experimentally. Such fluid design ensures that excessive $CO_2$ gas, or conversely $CO_3^{2-}$ ion generation does not occur in the bicarbonate/phosphate combined concentrate. The concentrate will be provided so that the 1× bicarbonate can vary between 20 to 40 mmol/L depending on the dilution. The phosphate will be 1.25 mmol when the bicarbonate is 30 and will vary from 0.8 to about 1.7 mmol/L with the dilution of the concentrate.

Base Concentrate with Phosphate:

| Base concentrate with phosphate contribution after mixing with the acid concentrate and water to 1X | 1X base fluid component mmol/L | 1Xbase fluid component mEq/L |
| --- | --- | --- |
| Sodium | 32.44 | 32.44 |
| HCO3— | 30 | 30 |
| H2PO4(−):HPO4(2−) in 1:20 ratio | 1.25 | *2.44 |

Base Concentrate without Phosphate:

| Base concentrate after mixing with the acid concentrate and water to 1X | 1X base fluid component mmol/L | 1Xbase fluid component mEq/L |
| --- | --- | --- |
| Sodium | 30 | 30 |
| HCO3— | 30 | 30 |

Acid Concentrates with Phosphate Dedicated to the Various Operational Modes:

The most important novel features are the low sodium, calcium and magnesium and the added citrate and phosphate content (where applicable). These fluids also assume the use of the sodium chloride supplemented citrate anticoagulant solutions. About 25%+/−range is also contemplated for all of these novel component concentrations. The 1× sodium concentration is approximate and will be clinically variable as allowed by the sodium-modeling program (standard feature of modern dialysis machines) to suit the individual patient and the selected treatment modality. The final 1× therapy fluids could also be theoretically provided as bagged sterile fluids and the compositions for such use are also contemplated herein.

Acid Concentrate with Phosphate Dedicated to Simultaneous Pre- and Post-Dilution CVVH:

| Replacement fluid acid concentrate with phosphate components after mixing with the base concentrate and water to 1X | 1X final fluid composition; mmol/L | 1X acid fluid component; mEq/L |
| --- | --- | --- |
| Sodium | 136 | 106 |
| Potassium | 4.0 | 4.0 |
| Chloride | 110 | 110 |
| Bicarbonate | 30 | 0 |
| Calcium | 0 | 0 |
| Magnesium | 0 | 0 |
| Phosphoric acid | 1.25 | 1.25 |
| Dextrose | 5.5 | 5.5 |

Acid Concentrate with Phosphate Dedicated to 12-24-Hour SLEDD: (Only if Near Complete Removal of Calcium and Citrate from the Circuit Blood is Found to be Clinically Detrimental)

| Dialysis fluid acid concentrate with phosphate components after mixing with the base concentrate and water to 1X | 1X final fluid composition; mmol/L | 1X acid fluid component; mEq/L |
| --- | --- | --- |
| Sodium | 139 | 111 |
| Potassium | 4.0 | 4.0 |
| Acid and basic citrate 1:2 | 0.9 | 2.7 |
| Chloride | 114.1 | 114.1 |
| Bicarbonate | 28 | 0 |
| Calcium | 0.3 | 0.6 |
| Magnesium | 0.15 | 0.3 |
| Phosphoric acid | 1.25 | 1.25 |
| Dextrose | 5.5 | 5.5 |

The calcium can range from 0.0 mM to 0.8 mM and magnesium from 0.0 mM to 0.4 mM (magnesium is about 40-50% of calcium usually). Acid citrate can vary from 0.0 mM to 1.5 mM and total citrate from 0.5 to 3.0 mM. All such variations of the above fluid are fully contemplated according to the present invention. All other ion concentrations can change by about +−10% and all such variations are also contemplated herein.

Single, Compromise Acid Concentrate with Phosphate for all Online CRRT:

| Therapy fluid acid concentrate with phosphate components after mixing with the base concentrate and water to 1X | 1X final fluid composition; mmol/L | 1X acid fluid component; mEq/L |
| --- | --- | --- |
| Sodium | 138 | 108 |
| Potassium | 4.0 | 4.0 |
| Chloride | 114 | 114 |
| Bicarbonate | 28 | 0 |
| Calcium | 0 | 0 |
| Magnesium | 0 | 0 |
| Phosphoric acid | 1.25 | 1.25 |
| Dextrose | 5.5 | 5.5 |

The calcium can range from 0.0 mM to 0.8 mM and magnesium from 0.0 mM to 0.4 mM (magnesium is about 40-50% of calcium usually). Acid citrate can vary from 0.0 mM to 1.5 mM and total citrate from 0.5 to 3.0 mM. All such variations of the above fluid are fully contemplated according to the present invention. All other ion concentrations can change by about +−10% and all such variations are also contemplated herein.

Single, Compromise Acid Concentrate without Phosphate for all Outpatient Intensive Blood Purification Therapies Including Pre- and Post-Dilution HVHF and Regular HD and Post Dilution HDF:

| Dialysis fluid acid concentrate components after mixing with the base concentrate and water to 1X | 1X final fluid composition; mmol/L | 1X acid fluid component; mEq/L |
| --- | --- | --- |
| Sodium | 136 | 99 |
| Potassium | 2.0 or 3.0 or 4.0 | 2.0 or 3.0 or 4.0 |
| Acetic acid | 3.0 | 3.0 |
| Chloride | 101 or 102 or 103 | 101 or 102 or 102 |
| Bicarbonate | 37 | 0 |

-continued

| Dialysis fluid acid concentrate components after mixing with the base concentrate and water to 1X | 1X final fluid composition; mmol/L | 1X acid fluid component; mEq/L |
|---|---|---|
| Calcium | 0.0 | 0.0 |
| Magnesium | 0.0 | 0.0 |
| Dextrose | 5.5 | 5.5 |

The greatest concern with high blood flows is systemic citrate accumulation. Therefore, there is no citrate in the above fluids and acetate is used for acidification (to prevent bacterial growth). The acetate content is comparable to standard acid concentrates in clinical use but could be reduced markedly at 1× dilution if desired for a nearly acetate free therapy fluid and such alterations are fully contemplated according to the present invention. At blood flows above 300 ml, current filter technology will limit the plasma citrate and calcium extraction to 60-80% in a single pass. In alternative embodiments, the calcium can range from 0.0 mM to 1.0 mM and magnesium from 0.0 mM to 0.5 mM (magnesium is about 40-50% of calcium usually). Acid citrate can vary from 0.0 mM to 1.5 mM and total citrate from 0.5 to 3.0 mM. All such variations of the above fluid are contemplated herein. All other ion concentrations can change by about +−10% and all such variations are also fully contemplated. Finally, potassium (K) concentration can be 2, 3, or 4 mM in any of the above 1× therapy fluids.

Specifically, the sodium at the standard 34× dilution may be targeted to about 130 mM by providing the low or zero calcium and magnesium acid concentrates with about 3-5% less electrolyte content (with preserving the above molar ratios) for safety monitoring purposes (particularly when hypertonic sodium is present in the modified citrate anticoagulant) and this method is provided according to the present invention. The final conductivity of the dialysate at usual dilution ratios then would be about 12.6, about 10% less than the usual 14.0 due to the lower sodium and absent calcium and magnesium, allowing the machine to detect through fresh dialysate conductivity monitoring (done routinely on all dialysis machines) that a calcium and magnesium free acid concentrate is being used. When the operator confirms the use of the special acid concentrate for RCA, the acid concentrate dilution ratio could be automatically adjusted to yield a final fluid with about 134-138 mM sodium as required by the treatment prescription. The only drawback to this method is that high sodium profiling may be mildly limited with the use of such acid concentrates.

The 1× fluid compositions are provided above. These values may still be slightly modified based on clinical experience. The machine will vary the dilution of the concentrates depending on the treatment prescription to best suit the individual patient. This will result in a range of concentrations of the electrolytes in the final ready to use online generated fluid.

When needed, the phosphate can be provided in the acid concentrate instead as well in an acid form to hinder bacterial growth. Phosphate may be omitted from the acid and base concentrates specifically designed for short, intense, 3-6-hour, 3-times-per-week therapy. When phosphoric acid is not used, acidity of the acid concentrate is ensured by the inclusion of citric acid or acetic acid. In the absence of calcium and magnesium, salt fouling of the fluid circuits is very unlikely and acidification mainly serves to prevent bacterial growth in the acid concentrate. The citrate and sodium content is correlated with the operational mode and the expected composition and rate of infusion of the anticoagulant solution. The lower sodium, calcium and magnesium content results in lower conductivity at standard dilution ratios, allowing the machine to detect the presence of the unusual acid concentrate for RCA, an important safety feature.

When a predominantly diffusive mode of blood purification is employed during CRRT, (pre-dilution HDF or SLED), calcium and magnesium may have to be present in the fresh therapy fluid (albeit at reduced concentrations), to avoid the complete decalcification of the blood that might have untoward physiologic consequences (this possible untoward effect is speculative as no clinical protocols to date have achieved such high fractional citrate and calcium extraction in the extracorporeal circuit and is in fact not expected to occur).

Concentrations shown are the contributions to the final 1× combined concentrate from Part 1 (Acid) and Part 2 (Base). Depending on the relative flow of fluids from the concentrate Part 1 and Part 2 (machine and online fluid generation system design dependent), the exact composition design of the Part 1 and Part 2 concentrates can naturally be defined exactly to yield the desired final diluted summary 1× product. Such calculations and final concentrate compositions are apparent to those skilled in the art from the usual practice of online fluid generation and from the target concentration ranges to be reached in the final 1× fluid as described above, and are contemplated according to the present invention.

The physical design of RCA system 110 and the fluid compositions (anticoagulant, calcium plus magnesium infusion, separate acid and base concentrates) according to the present invention allow for the independent and flexible selection of anticoagulation intensity (the amount of citrate infused into a liter of plasma), calcium and magnesium infusion rate, therapy fluid sodium and potassium concentration and therapy fluid bicarbonate concentration. Detailed knowledge of the movement of the key small solutes in the patient's body and in the extracorporeal circuit during RCA allows automatic, precise mass balance calculations for all solutes during the use of any treatment operational mode. This permits the selection of fluid flow rates and therapy fluid composition best suited for the individual prescription. The solute fluxes may be inferred from the prescription and fluid compositions as well as verified/adjusted based on the online clearance measurements.

Online hematocrit sensor 150 and OCM 170 provide for continuous safety monitoring of the performance of system 110. The OCM 170 allows for mathematical precision in clearance dosing, in calcium dosing, in predicting citrate accumulation and in calculating the diffusive versus convective component of the blood purification important for medication dosing and research purposes. The hematocrit sensor 150 may also detect access recirculation. Finally, subsequent measurement of online clearance with the anticoagulant infusion bolus based method and the traditional dialysate conductivity modeling based method, when correlated with the measured access recirculation, may allow the online monitoring of the patients cardiac output with clinically useful accuracy when a permanent (arterial) access is used.

The software control module according to the present invention may include elements to verify proper circuit tubing connections and may guide the selection of safe citrate prescriptions by the operator. As a safety measure, prescriptions that entail the possibility of citrate accumulation or other complications may not be allowed. This is described in detail below in the flow steps for RCA system 110.

Operational modes that may be supported include: 1) Purely convective RRT with simultaneous pre-dilution and post-dilution hemofiltration for both 24-hour CVVH and intensive 4-5 hour HVHF therapy (FIGS. 8a and 8b); 2) Purely diffusive RRT with only net ultrafiltration for both 24-hour SLED and conventional 4-5 hour IHD (FIGS. 5a and 5b); 3) Post-dilution hemofiltration (online post-HDF) for outpatient 4-5 hour therapy with high blood flows and a desire to maximize clearance and control cost (FIGS. 7a and 7b); 4) Pre-dilution hemofiltration (online pre-HDF or CVVHDF) for 24-hour CRRT with a desire to deliver both convective and diffusive clearance and minimize clotting (FIGS. 6a and 6b); 5) Optional single needle operational mode for all extended therapy (CRRT or nocturnal therapy) modalities. The greatest benefit of this mode is that it ensures that blood withdrawal from the patient is immediately halted if an access needle disconnection occurs. In contrast, when two needles are used, in the case of a venous access disconnection, there is a potential for a catastrophic bleed as the machine may keep aspirating blood through the arterial needle.

For each of these modalities with appropriate prescriptions, the plasma small solute clearance can be calculated and verified periodically with a novel online conductivity dialysance method according to the present invention. Assuming access recirculation is monitored and measured by the hematocrit sensors 150, 152, the whole blood clearance for solutes like urea can also be inferred from the data. This will provide the clinician with unprecedented flexibility and precision in the selection of the small solute hourly clearance goal as well as the degree of convective versus diffusive blood purification. Control programs deriving the prescriptions for each operational mode are developed allowing for complete automation of the prescription writing. The total therapy fluid flow will usually not exceed 250% of the total plasma flow or about 160% of the total blood flow regardless of the purification method used. Such fluid efficiency is fully comparable with what is achieved with current traditional clinical dialysis prescriptions.

Fundamentals of the RCA prescription according to the present invention are as follows. Sufficient plasma total calcium to citrate ratio must be achieved for effective anticoagulation. The total Ca (mM) to citrate (mM) ratio may range between 2 to 4 in the extracorporeal circuit. Part of the citrate may be provided as acid citrate in the anticoagulant infusion (to further enhance anti-coagulation through acidification of thrombin and other coagulation cascade proteins and increase the ultrafilterable fraction of calcium by disrupting its binding to albumin). The plasma flow may be monitored online with a hematocrit and blood flow sensor module 150, 152. This will allow the calculation of the delivered calcium load into the circuit and will define the necessary anticoagulant infusion rate. Access recirculation may also be monitored by the hematocrit sensor 150, 152.

The prescription should eliminate the possibility of citrate accumulation even in the complete absence of liver metabolism (liver failure). This may be achieved by keeping the citrate plasma dialysance above 60-80% of the plasma flow in the extracorporeal circuit and correlating it with the amount of citrate infused into a liter of circuit plasma and the citrate concentration in the therapy fluid used. The target plasma total calcium level should be defined (usually 2-2.5 mmol/L depending on the serum albumin concentration) by the operator. This will have an indirect impact on the systemic plasma ionized Ca content in steady state. The ultrafilterable and dialyzable fraction of total calcium should be selected (this will range from 0.7 to 0.95 depending of the calcium to citrate ratio, albumin level and pH in the circuit). The plasma albumin level may be further considered as it will impact the systemic ionized Ca level at the targeted total systemic plasma Ca level. The systemic citrate level will have minimal impact, even in ICU patients with liver failure, because citrate accumulation beyond 2 to 3 mM levels cannot occur when filter performance is maintained at the specified fluid flow rates. Prescriptions and therapy fluid compositions may be provided that allow exact mass balance calculations for citrate, calcium and magnesium, sodium and bicarbonate (and trace metal minerals).

In the following description, a glossary of the abbreviations used is as follows:

Csys: calculated steady state systemic plasma citrate concentration in a patient with zero citrate metabolism (liver failure; worst case scenario in RCA)

E: apparent circuit post-anticoagulant infusion arterial plasma citrate to therapy fluid citrate concentration difference reduction ratio during a single filter pass ("plasma citrate extraction ratio"); (ECit, ECa)

DCit: apparent citrate plasma dialysance (DCit* when expressed for the adjusted QBCit during calculations and DCit when expressed for the unadjusted QP)

DCond: apparent "summary conductivity solute" whole blood dialysance. This value may be predicted from filter KoACond, Qb, Qd, and Quf and/or determined by the sodium citrate bolus based measurement or by the traditional online conductivity dialysance measurement method (for high blood flow treatment sessions; this latter method is not discussed here being prior art and not applicable in SLED)

QB: the effective arterial blood water flow for the solute analyzed; QBCond is closely equal to the arterial whole blood water flow for conductivity and QBCit is closely equal to arterial blood plasma water flow for citrate. In the case of citrate, for the calculation of "E" the plasma water volume is adjusted for the free water shifts between the RBCs and the plasma space in response to the hypertonic citrate anticoagulant and DCit* is calculated with these adjustments. Once E=DCit*/QBCit (=DCit/QP) is derived, the unadjusted QP and DCit can be used to simplify the subsequent calculation of Csys.

QP: The arterial blood plasma flow without adjustment for the effects of the hypertonic anticoagulant infusion (These shifts are accounted for during the calculation of E).

Cinf: The increase in the arterial plasma citrate concentration as a result of the anticoagulant infusion, before any pre-filter replacement fluid infusion or adjustment for water shifts between blood fluid compartments. (These shifts are accounted for during the calculation of E).

Hgb: hemoglobin concentration in the arterial blood

Qpre: pre-filter replacement fluid flow rate

Qpost: post filter replacement fluid flow rate

Qd: dialysis fluid flow rate

Quf: net ultrafiltration (negative fluid balance goal plus the citrate and Ca infusion rates)

QCa/Mg: the flow rate of the calcium and magnesium infusion

Qtf: total therapy fluid flow rate (=Qd in SLED)

DCond: "conductivity solute" dialysance determined by the sodium citrate bolus based measurement DCit: the calculated citrate dialysance (DCit* when expressed for the adjusted QBCit during calculations and DCit when expressed for the unadjusted QP)

Ddiff: the calculated diffusive component of the measured total dialysance (DdiffCond, DdiffCit); in SLED the diffusive dialysance is equal to the total dialysance KoA: mass transfer area coefficient; measure of filter performance specific to solute (KoACond, KoACit)

a and S: solute diffusivity and sieving coefficients; aCond; aCit, SCond; SCit, f: correction factor to derive the dialyzable/filterable fraction of the total plasma Ca For the control program for RCA system 110, the flow steps may include:
1) Start Machine in RCA Mode
2) a) Select Treatment Type: Sustained Low-Efficiency Dialysis (SLED), Hemodiafiltration (pre-HDF or post-HDF), or Pure hemofiltration (pre-CVVH or Pre+post-CVVH).
   b) Select Treatment Duration: 10-hour or 24-hour.
   c) Select Access Connection: Regular versus Single-Needle.
3) a) Machine advises filter, tubing, anticoagulant and calcium solutions and RCA acid concentrate.
   b) Confirm all disposables are as advised by the machine
   c) Connect tubing to dialyzer.
   d) Connect infusion pumps.
   e) Prime system with priming solution.
   f) Test system integrity (current machine protocol).
4) RCA priming checks: performed with the circuit arterial and venous ends connected in recirculation mode.
   a) Confirm conductivity of therapy fluid is at target with RCA Mode specific lesser dilution of the acid concentrate.
   b) Alarm if conductivity is abnormal: inappropriate acid concentrate for RCA treatment.
   c) Confirm citrate infusion loading onto the citrate pump by turning on the citrate pump and measuring the increase in conductivity in the drain circuit of the dialyzer.
   d) Alarm: it is not the citrate infusion solution that is loaded onto the citrate pump based on effluent conductivity changes.
   e) Confirm calcium infusion loading onto the calcium pump by turning on the calcium pump and measuring the increase in conductivity in the drain circuit of the dialyzer.
   f) Alarm: it is not the calcium infusion solution that is loaded onto the $Ca^{2+}$-pump based on effluent conductivity changes.
5) Input Patient Information.
   a) Sex, height, age, weight (minimum data is weight) (if Watson volume and $V_E$ calculations are desired).
   b) Minimum data is systemic hemoglobin and albumin concentration.
6) Select SLED, HDF, or HF
For SLED:
7) Treatment information advised by software based on prior selections.
   a) Confirm: Filter type (determines expected KoACond, KoACit, SCond, SCit).
   b) Input: Maximal access blood flow rate expected (QB).
   c) Confirm: Dialysate fluid flow rate (HD and HDF 200% QB; CVVH 200% QP).
   d) Input: Total net ultrafiltration desired per treatment (during 10 or 24 hours).
   e) Confirm: Set dialysis machine alarm parameters.
   f) Confirm: Type of citrate anticoagulant solution (ICU versus OPD; likely uniform).
   g) Confirm: Type of calcium solution (ICU versus OPD, likely uniform).
   h) Confirm: Maximum citrate level in systemic blood allowed (2.0-4.0 mM).
   i) Confirm: Dialysis acid and base concentrates used.
8) Connect the patient
9) Safety checks after initial patient connection in isolated HD mode.
   a) Start treatment, confirm citrate infusing in the arterial limb by watching the effluent conductivity.
   b) Measure access recirculation with automated online hemodilution or temperature technique.
   c) Measure baseline in vivo KoACond at QB 150-300 and QD 300-600 (ml/min) in 12-hour SLED.
   d) Compare with expected value for selected specific filter; alert operator if significant difference.
   e) Calculate baseline in vivo KoACit from the above measurement
   f) Measure baseline in vivo KoACond at QB (priming solution) 75-150 and QD 150-300 (ml/min) in 24-hour SLED.
   g) Compare with expected value for selected specific filter; alert operator if significant difference.
   h) Calculate baseline in vivo KoACit from the above measurement (in the 12-hour mode both dialysate bolus based and blood bolus based DCond will be measured).
10) Display Confirmation Alarms.
   a) Alarm if more than 10-15% recirculation is detected; the treatment will still be safe, but less effective for uremic clearance.
   b) Measure Hgb concentration with the online sensor (Alarm if more than 20% different from initially provided value).
   c) Alarm if citrate not on arterial limb of circuit (confirm during bolus).
   d) Alarm if filter Dcond more than 10-20% different from expected in vivo value and possibly refuse the filter.
   e) Alarm if the expected and the detected replacement fluid conductivity values at the RCA Mode dilution of the hyponatric RCA acid concentrate do not match.
11) Analyze input data.
   a) Determine prescription and machine settings with in vivo DCond.
   b) Display machine generated QB, Cinf, Qd Quf, QCit1, QCa/Mg.
   c) Display expected DCond (ml/min)(if using weight-adjusted prescribing).
   d) Display expected maximum Csys.
   e) Display expected Ca replacement infusion dose (mmol/hour) for circuit $Ca^{2+}$ losses (prescriptions can have uniform QB and DCond versus weight adjusted).
For HDF:
7) Treatment Information advised by software based on prior selections.
   a) Input: Dialyzer type (determines expected KoACond, KoACit, SCond, SCit).
   b) Input: Maximum hemoconcentration allowed in the circuit (define in the range 50-60%).
   c) Input: Therapy fluid summary flow rate (200% of QB).
   d) Input: Total clearance goal for CRRT (DCond based Kt/V or just Kt).
   d) Input: Total net ultrafiltration desired per treatment (or over 24 hours).
   f) Input: Set dialysis machine alarm parameters.
   g) Input: Type of citrate solution (ICU versus OPD; likely uniform).
   h) Input: Type of calcium solution (ICU versus OPD, likely uniform).
   i) Input: Maximum citrate level in systemic blood allowed (2.0-4.0 mM).
   j) Input: Dialysis acid and base concentrates used.
8) Connect the patient
9) Safety checks after initial patient connection in isolated HD mode.
   a) Start treatment, confirm citrate infusing in the arterial limb by watching the effluent conductivity.
   b) Measure access recirculation with online hemodilution technique.

c) Measure baseline in vivo KoACond at QB 150-300 and QD 300-600 (ml/min) in 12-hour SLED.

d) Compare with expected value for selected specific filter; alert operator if significant difference.

e) Calculate baseline in vivo KoACit from the above measurement.

f) Measure baseline in vivo KoACond at QB (priming solution) 75-150 and QD 150-300 (ml/min) in 24-hour SLED.

g) Compare with expected value for selected specific filter; alert operator if significant difference.

h) Calculate baseline in vivo KoACit from the above measurement (in the 12-hour mode both dialysate bolus based and blood bolus based DCond will be measured).

10) Display Confirmation Alarms.

a) Alarm if more than 10-15% recirculation is detected; the treatment will still be safe, but less effective for uremic clearance.

b) Measure Hgb concentration with the online sensor (Alarm if more than 20% different from initially provided value).

c) Alarm if citrate not on arterial limb of circuit (confirm during bolus).

d) Alarm if filter Dcond more than 10-20% different from expected in vivo value (and possibly refuse the filter).

e) Alarm if the expected and the detected replacement fluid conductivity values at the RCA Mode dilution of the hyponatric RCA acid concentrate do not match.

11) Analyze input data and change to HDF operational mode.

a) Determine post-dilution possible as % of QB with set hemoconcentration limit.

b) If CRRT, always use pre-HDF, Qpre 30% of QB and the rest of the therapy fluid as QD.

c) If short therapy, use post-HDF with Qpost 20% of QB if hemoconcentration limit allows.

d) Otherwise, use pre-HDF for short therapy as well with Qpre 30% of QB.

e) Determine prescription and machine settings based on treatment goals, patient data and the blood bolus based DCond and if available the dialysate bolus based DCond values.

f) Display QB, Cinf, Qpre (pre-HDF) or Qpost (post-HDF), Quf, QCit1, QCa/Mg.

g) Display expected total DCond (ml/min)

h) Display expected maximum Csys.

i) Display expected circuit Ca loss (mmol/hour) before replacement infusion (prescriptions can have uniform QB and DCond versus weight adjusted).

For HF:

7) Treatment Information advised by software based on prior selections.

a) Input: Dialyzer type (determines expected KoACond, KoACit, SCond, SCit).

b) Input: Maximum hemoconcentration allowed in the circuit (define in the range 50-60%).

c) Input: Therapy fluid summary flow rate (150% of QB).

d) Input: Total clearance goal for CVVH (DCond based Kt/V or just Kt).

e) Input: Total net ultrafiltration desired per treatment (or over 24 hours).

f) Input: Set dialysis machine alarm parameters.

g) Input: Type of citrate solution (ICU versus OPD; likely uniform).

h) Input: Type of calcium solution (ICU versus OPD, likely uniform).

i) Input: Maximum citrate level in systemic blood allowed (2.0-3.0 mM).

j) Input: Dialysis acid and base concentrates used.

8) Connect the patient

9) Safety checks after initial patient connection in isolated HD mode.

a) Start treatment, confirm citrate infusing in the arterial limb by watching the effluent conductivity.

b) Measure access recirculation with online hemodilution technique.

c) Measure baseline in vivo KoACond at QB 150-300 and QD 300-600 (ml/min) in 12-hour SLED.

d) Compare with expected value for selected specific filter; alert operator if significant difference.

e) Calculate baseline in vivo KoACit from the above measurement.

f) Measure baseline in vivo KoACond at QB (priming solution) 75-150 and QD 150-300 (ml/min) in 24-hour SLED.

g) Compare with expected value for selected specific filter; alert operator if significant difference.

h) Calculate baseline in vivo KoACit from the above measurement (in the 12-hour mode both dialysate bolus based and blood bolus based DCond will be measured).

10) Display Confirmation Alarms.

a) Alarm if more than 10-15% recirculation is detected; the treatment will still be safe, but less effective for uremic clearance.

b) Measure Hgb concentration with the online sensor (Alarm if more than 20% different from initially provided value).

c) Alarm if citrate not on arterial limb of circuit (confirm during bolus).

d) Alarm if filter Dcond more than 10-20% different from expected in vivo value (and possibly refuse the filter).

e) Alarm if the expected and the detected replacement fluid conductivity values at the RCA Mode dilution of the hyponatric RCA acid concentrate do not match.

11) Analyze input data.

a) Determine post-dilution possible as % of QB with set hemoconcentration limit.

b) Determine prescription and machine settings based on treatment goals, patient data and the blood bolus based DCond and if available the dialysate bolus based DCond values.

c) Program Qpost for the above maximum post-filtration, minus (Qcit1+QCa/Mg+Quf) for maximum citrate clearance with a given QB and total Qtf. The Qpre is Qtf (150% of QB)−Qpost.

d) Determine prescription and machine settings.

e) Display QB, Cinf, Qpre and Qpost, Quf, Qcit1, QCa/Mg.

f) Display expected DCond (ml/min) and expected maximum Csys.

g) Display expected circuit Ca loss (mmol/hour) before replacement infusion (prescriptions can have uniform QB and DCond versus weight adjusted).

For ALL OPERATIONAL MODES:

12) Calcium Dosing.

a) DCit is essentially equal to DCa*f correction for dialyzable fraction (0.95 to 0.8 depending on albumin level and Cinf).

b) Target systemic plasma total Ca (mM) is defined: Use Csys (0.25 mM Ca/1 mM citrate), systemic albumin (0.2 mM Ca/1 g/dL) and target systemic ionized Ca (target Cai=1.00 mM when systemic citrate is assumed to be equal to Csys=3).

c) Circuit Ca loss in steady state is equal to DCa*(Target systemic total Ca−Catf), where Catf is the calcium concentration in the fresh therapy fluid (mM).

d) QCa/Mg is easily calculated from the circuit Ca loss and Ca concentration of the Ca infusion solution.

e) At start, the operator may have to give 1-4 amps of Ca-gluconate over 1-2 hours to bring the systemic ionized Ca close to 1.25-1.5.

13) Continuous safety check.

a) Citrate solution is properly on the citrate pump and arterial limb is arterial (expected constant step-up in effluent conductivity from baseline Ctf conductivity) (Alarm if citrate bag changed to calcium or saline or access connection reversed during operation based on effluent conductivity monitoring with all the above IV fluids having different conductivity).

b) Input Ctf constant in RCA Mode when proper, unique RCA acid and standard base concentrates are used (Alarm if non-RCA acid concentrate is being supplied at any time).

c) Input: Online measured total Dcond from standard operation and estimated Cp (Alarm if filter performance is declining to prompt bolus clearance interrogation and/or filter change).

d) Input: Measured access blood flow rate: current (QB) (Alarm: when QB is changed because of access issues recalculate all pump speeds and fluid flows).

e) Input: Measured hemoglobin concentration (Alarm: when changed by more than 10% alert operator to possible bleeding or over-ultrafiltration; recalculate prescription, recommend to operator CBC check, net ultrafiltration target revision).

14) Hourly safety check: input data.

a) Input: online measured total Dcond (blood bolus based and when possible dialysate bolus based methods both.

b) Input: Measured circuit blood flow rate: current (QB).

c) Input: Set therapy fluid flow rate (usually 150-200% of QB).

d) Input: Measured hemoglobin concentration.

e) Input: Set total net ultrafiltration.

15) Recalculation of the prescription.

a) Calculate: DdiffCond, KoACond, KoACit, DdiffCit, Total DCit.

b) Calculate the maximum possible citrate in systemic blood (Csys; 2.0-4.0 mM).

c) Alarm if Csys more than 3 mM and address as follows: Change filter if KoACit is >than 40-60% less than target for filter. Reduce Cinf if filter performance is within limits (or increase filter size). Re-measure clearance and recalculate Csys until calculated Csys<=4 mM.

d) Display current clearance after all changes: DCond (in ml/min)

e) Adjust QB, QD, Qcit, QCa/Mg, NetUf, and Qpre and or Qpost as applicable.

16) Other alarms.

a) Citrate bag is about to run out: (if the machine measures bag weight or knows bag volume and logs new bag setups).

b) Calcium bag is about to run out: (if the machine measures bag weight or knows bag volume and logs new bag setups).

c) RCA acid concentrate is about to run out: (if the machine measures the acid concentrate reservoir weight).

d) The treatment goal (total time or total clearance or total net UF has been reached): in 12-hour treatments.

RCA system 110 may contain an online sensor system (OSS) for measuring calcium, magnesium and citrate in the ultrafiltrate. The same flow steps detailed above apply to such a system, except that data from the OSS may be used to adjust the calcium infusion according to systemic citrate and calcium levels. As explained herein, the calcium, magnesium and citrate values measured from the ultrafiltrate by the OSS can be used to back-calculate the values in the patient's plasma. As also explained, the kinetic curve of systemic plasma citrate concentration can be used to derive the exact value of the liver clearance of citrate as well as the volume of distribution of citrate, $V_E$. Using the above parameters, systemic citrate levels can be accurately predicted at any future T time point. The calcium and citrate pump as well as the entire prescription including the therapy fluid bicarbonate concentration (when flexible) can then be completely controlled by the machine software.

Filter performance can be monitored both by conductivity as well as citrate clearance measurements. The direct citrate clearance measurements again enable complete precision in calcium and citrate dosing. Since calcium exits through the hemofilter almost entirely as Ca-citrate complex, the measured citrate dialysance will be nearly equal to the total calcium dialysance. The slightly lower Ca-dialysance will be due to the Gibbs-Donnan effect and the minimal albumin-bound Ca in the circuit (about 5-20% depending on the amount of citrate infused in the arterial limb of the circuit, the acidity of the citrate infusion and the plasma albumin level). At any point where blood bolus based conductivity dialysance is measured, blood bolus based citrate dialysance will also be measured simultaneously with the OSS when available on the machine.

Turning now to another aspect of the present invention, home nocturnal dialysis is a re-discovered, expanding method of RRT. Most experts believe that it is the best method of RRT, resulting in excellent uremic and blood pressure control, freedom from most dietary restrictions otherwise mandatory for ESRD patients on 3 times-per-week dialysis, and resulting in fewer hospitalizations, lesser use of phosphate binders and most importantly better quality of life. Nevertheless, only a minute fraction of ESRD patients are currently on nocturnal dialysis.

The most important reasons for the limited use of nocturnal dialysis include the following. Highly effective anticoagulation is mandatory during 8-12-hour treatments to prevent clotting of the extracorporeal circuit and associated alarms and sleep disruption. The only agent in common use, heparin, has significant side effects and a systemic bleeding risk that increases with higher doses. In addition, single needle operational mode is preferred to lessen the risk of major bleeding in the event of permanent access disconnection. This again requires powerful anticoagulation. Complex online dialysis fluid generation systems are expensive to deploy and maintain in the home, and online clearance measurements that could be used to monitor efficacy and compliance have not been widely adapted to slow nocturnal dialysis. Furthermore, RCA has not been developed for home treatments. Still further, biofilm formation and bacterial contamination of components of the dialysis system is a major concern, and costs must not exceed markedly the overall costs of 3 times weekly in-center dialysis.

According to the present invention, an RCA home system 210 (FIGS. 17a-17d) may be designed as an RRT device that also doubles to deliver automated RCA for home nocturnal dialysis. One purpose of the present invention is to provide a device that can deliver previously unprecedented high convective or diffusive clearances and can be operated by laypersons in home settings without the need for highly complex treatment protocols. RCA home system 210 is a modified version of the RCA system 110 that is specifically re-designed for the unique challenges of home RRT. Therefore, components of system 210 that are similar to components of system 110 are identified with like reference numerals except for the substitution of a "2" prefix.

RCA home system 210 according to the present invention may include a combination of various CRRT and dialysis machine hardware components arranged in a unique design, two special modes of operation of the device (simultaneous pre- and post-dilution hemofiltration and continuous sustained low efficiency dialysis (c-SLED)), and a software control module. System 210 may also include a sensor module 256 to measure citrate, calcium and magnesium levels online to ensure the maximum accuracy, fluid efficiency and safety of treatment prescriptions. System 210 may use a novel replacement fluid concentrate, a novel citrate anticoagulant, and a novel single premixed calcium plus magnesium infusion which were designed to fully exploit the system's capabilities. RCA home system 210 may resemble a traditional hemodialysis machine and can be constructed from hemodialysis machine components except for online citrate sensor 256 as described below. Most elements have been discussed above with reference to the RCA system 110 of the present invention.

RCA home system 210 can safely provide at least up to 12 liters per hour of convective clearance to patients without relying on the liver to metabolize citrate. The system design prevents citrate accumulation in the patient, while maintaining highly efficient anticoagulation of the extracorporeal circuit 212. A control program may be used to derive a safe treatment prescription according to treatment goals selected by the operator. An online citrate sensor 256 may be used to eliminate the risk of citrate accumulation (that may occur only with declining filter performance in SLED mode) and doubles as an online delivered clearance and liver metabolic function monitor.

System 210 according to the present invention is shown in FIGS. 17a and 17b for a machine capable of pre- and post-dilution CVVH for maximal fluid efficiency and in FIGS. 17c and 17d for an even simpler machine that performs only pre-dilution CVVH or SLED depending on the tubing connection. The common features with RCA system 110 are either not repeated or repeated only briefly herein. The most important differences and novel elements are detailed below.

RCA home system 210 may include a single, sterile bag 280 (e.g., 5 liter plastic) that may contain a novel, single component, about 30-50× electrolyte concentrate. The hemofiltration replacement fluid may be diluted from this concentrate by mixing it with ultrapure water generated by a water treatment module of the RCA online system 210. The online fluid generation follows well-established design from currently existing dialysis machines. However, instead of the traditional two bags, system 210 according to the present invention requires only one concentrate chamber or bag 280 that contains all electrolytes necessary except calcium and magnesium. This is a major departure from current fluid mixing systems. The single concentrate reduces complexity of the fluid circuit and makes the dilution procedure very precise and safe with conductivity monitoring of the ready-to-use replacement fluid as the established safety check for the degree of dilution. Since day-to-day flexibility in therapy fluid sodium and bicarbonate concentration is not needed in home nocturnal dialysis programs, this simplicity of fluid generation has no significant clinical drawbacks. Individual prescriptions can still be attained if the manufacturer provides several individual single-component concentrates with moderately variable final potassium, bicarbonate, and possibly phosphate contents. The appropriate concentrate can be selected for the patient about once monthly, similar to the selection of peritoneal dialysis fluid composition and prescription for patients on peritoneal dialysis.

RCA home system 210 may include two highly precise volumetric infusion pumps 234, 244 which may have dedicated air in line detectors and line clamps (not shown), optionally color-coded and with special tubing to deliver the citrate anticoagulant and the calcium plus magnesium infusions as described below with reference to FIGS. 9-16. Infusion lines 228, 242 may have special end connections that will only attach to the appropriate solution bags 232, 246 and at the other end will be welded to the entry points in extracorporeal circuit 212 to minimize the risk of disconnection from the circuit 212 and wrong connection of infusate bags 232, 246. Pumps 234, 244 may be designed to accept only the right type of infusate tubing and may be fully coordinated with the operation of blood pump 222 and other fluid pumps. This again prevents accidental connection of the wrong infusate in the wrong place and also ensures that citrate and calcium plus magnesium infusions are stopped when the machine blood pump 222 and/or replacement fluid pump 264 are not operating. In addition, the fluid bags 232, 246 may be manufactured to be significantly different in weight and size as well as in the color of the plastic and/or legend to further reduce the chance of accidental wrong connection.

RCA home system 210 may utilize Doppler-based fluid flow and hematocrit monitors or alternatively optical hematocrit sensors 250, 252 on the arterial and venous blood lines 214, 218 as well as possibly on the replacement fluid line 228 and effluent fluid line 224 for maximal precision in ensuring that the set blood flow rate on blood pump 222 matches the actual blood flow delivered by the action of the blood pump 222 and all other fluid flows (pre-filter fluid flow, effluent flow, venous blood flow and net ultrafiltration amount) are all the same as defined by the machine settings. All crystalloid fluid pumps may be volumetric for precise control of fluid flow rates.

An online citrate, calcium and magnesium sensor 256 may be provided in the effluent fluid line 224. This sensor array 256 allows for the derivation of the citrate, calcium and magnesium level in the patient's systemic blood. In one safe operational mode of RCA home system 210 (more than 66% citrate extraction), citrate accumulation can only occur if the filter performance declines. Laboratory testing is not available in the home setting. For maximum safety, the indirect data from the online conductivity clearance monitor may not be sufficient in the home setting. However, the online citrate and calcium sensor 256 may warn of any change in systemic citrate and calcium levels in real time and prompt the patient and or the remote monitoring personnel to review and adjust the treatment settings to ensure the safe continuation of the RRT treatment. Sensor 256 may also serve as an online clearance module, may provide information for the fine-tuning of the calcium plus magnesium dosing and monitor the metabolic function of the liver.

RCA home system 210 may include disposable, sterile fluid circuits which may include the replacement fluid and effluent fluid balancing chambers 262 of the RRT machine 260. While the ultrapure dialysate generation module is not sterile, starting with a sterile concentrate will greatly reduce the risk of bacterial contamination in the final dialysate. Water from this module and also the generated replacement fluid may pass through low flux sterilizing filters 282 with pore size small enough to prevent the passage of whole bacteria or endotoxins and pyrogens derived from bacteria. If the implementation of the disposable sterile balancing chamber 262 is too costly, the fresh online replacement fluid may be filter-sterilized after passing through the usual, non-disposable, fixed balancing chamber. The filter sterilization may be necessary to allow direct infusion of the online replacement fluid into the RRT circuit blood space. These concerns are less pronounced in the nocturnal SLED diffusive operational mode of the device, where the online fluid remains separated from the blood space by the membrane of hemofilter 216. Specially designed dialysis catheters, access needles, circuit tubing and connectors may also be utilized as described elsewhere herein. Single needle operational mode is as previously discussed for RCA system 110.

The elements of the CRRT machine 260 include, but are not limited to, hemofilter 216, usual fluid and blood circuit tubes, conductivity monitors, fluid heating element, blood leak detector, and air detectors as used on conventional RRT machines RCA home system 210 according to the present invention further includes an operational mode of pre- and post-dilution CVVH, marked isolated pre-dilution CVVH or SLED with a single, online generated calcium and magnesium free fluid to maximize single pass citrate (and coincident calcium) extraction on the filter 216. Initially, the RCA online system-controlled concentrated citrate infusion may reduce ionized calcium in the systemic blood entering the arterial limb 214 of the extracorporeal circuit 212. This blood may then be diluted with the essentially calcium-free pre-filter fluid. The original hematocrit, blood volume and electrolyte composition may then be restored by ultrafiltration on the hemofilter 216 except that the blood leaving the filter 216 will have a 50-75% reduced total calcium and magnesium as well as uremic solute content (the actual reduction is precisely determined by the treatment settings) and a low ionized calcium level preventing blood clotting. Finally, before the blood is returned to the patient, the RCA online system-controlled calcium plus magnesium infusion restores normal total calcium and magnesium levels. This procedure will usually be performed with blood flows in the range of 150-300 ml/minute during 8-12-hour nocturnal CVVH or SLED.

As described above, RCA home system 210 may utilize an essentially calcium and magnesium free pre-filter online-generated replacement fluid. The online fluid generation is simpler and safer since all the remaining electrolytes including phosphate and bicarbonate can now be combined into a single concentrate bag 280 making the fluid generation system safer and simpler. An integrated IV pump 244 may be provided to administer a premixed calcium plus magnesium containing infusion. System 210 may control this pump 244 to deliver the supplemental calcium and magnesium in a fixed ratio in coordination with the RRT prescription and monthly patient chemistry values. A novel dosing program may be used to drive the pump 244. The online calcium and citrate sensor 256 may alarm if a machine failure or calcium plus magnesium line disconnection was to cause hypocalcemia (or hypercalcemia if too much infusion is given).

In accordance with the present invention, a combination of tri-sodium citrate and acid citrate in the pre-dilution fluid may be implemented with the fluid conductivity further manipulated by the addition of sodium chloride for safety monitoring purposes. The present invention further contemplates a mandatory addition of phosphate to the pre-filter replacement fluid (or dialysis fluid) concentrates. This eliminates the need for monitoring serum phosphate levels and for separate intravenous phosphate administration. Phosphate losses can be very large and can quickly lead to severe hypophosphatemia with high daily (nocturnal) clearance goals unless the phosphate is provided in the replacement fluid. Since calcium and magnesium are essentially not present in the RRT fluid concentrate, phosphate can be added commercially, preserving physiologic phosphate levels in the therapy fluid and consequently in the patient. Finally, phosphate is also a calcium chelator and may result in a further minor reduction in the ionized calcium level in the circuit. If stored in a single compartment with bicarbonate, phosphate may be provided in a pH-adjusted buffered form to avoid the possibility of $CO_2$ gas or carbonate generation by reacting with bicarbonate.

Integrated online hematocrit sensors 250, 252 may be provided straddling the pre-dilution fluid connection 230 on the arterial limb 214 of the blood circuit 212. The online hematocrit sensors 250, 252 allow minute-to-minute calculation of the plasma volume in the blood flowing into the circuit 212. This ensures the most accurate and possibly continuously adjusted dosing of citrate to achieve the target citrate to plasma calcium ratio. Another benefit of the hematocrit sensor 250, 252 is that it can be utilized for periodic automated monitoring for catheter recirculation using an induced hemodilution-based technique. This allows the correction of measured clearances for access recirculation when this phenomenon is present. Detecting recirculation in the access early is important to ensure full exposure of the circuit to uremic blood from the patient and in correctly performing clearance calculations using the OSS. Further, in a method according to the present invention, the described online hematocrit sensor pair 250, 252 can also be used to derive the delivered blood flow in the arterial limb 214 of the circuit 212 by analyzing the hemodilution induced by the infusion of a known amount of pre-filter replacement fluid. The pre-filter fluid may be delivered by existing highly accurate volumetric pumping technology. The observed hemodilution in response to a known amount of pre-filter fluid infusion will allow the precise back calculation of the delivered blood flow that was diluted in this fashion. Finally, the hematocrit sensor 250, 252 as a blood volume monitor may detect blood volume contraction in the patient due to excessive ultrafiltration and may alert the patient and stop the net fluid removal before resultant hemodynamic compromise could develop.

RCA home system 210 may further include integrated Doppler sensors to monitor fluid flow rates in the arterial blood line 214, venous blood line 218, pre-filter fluid line 228, and effluent fluid line 224. These fluid flows are predetermined by the settings of the machine With modern machine technology using precise volumetric pumps on the crystalloid fluid lines (but using a non-occlusive roller pump as usual on the blood line to avoid hemolysis) and the generally lower flow rates utilized during CRRT, clinically significant, more than 10% deviations from the preset flow rates are unlikely. The machine 260 has multiple safeguards against deviations from the prescribed fluid flow rates. These include the balancing chamber 262 for correlating the effluent and the replacement fluid flows, the duplicate hematocrit sensors 250, 252 to monitor delivered blood flow as well as the ratio of delivered blood flow to pre-filter fluid flow, and finally the Doppler sensor system. The simultaneous use of all of these measures ensure the safe operation of RCA home system 210 according to the present invention that utilizes a strict coordination of the flow rates of the various fluids it utilizes. Finally, continuous, precise monitoring of the patient's systemic citrate and calcium levels through the composition of the effluent fluid will provide yet another, ultimate level of safety for the procedure.

Effluent line 224 of RCA home system 210 may contain an OSS that can indirectly monitor the systemic concentration of citrate, calcium and magnesium. This module can analyze the ultrafiltrate and derive the patient's plasma citrate and total calcium and magnesium level continuously with mathematical precision and display it in real time. The OSS may alarm when dangerously rising citrate levels or abnormal (low or high) total calcium levels are detected. Measuring citrate may also serve as a basis for a novel online clearance module, filter patency monitor and liver function monitor. The concepts used to implement the citrate sensor 256 are also applicable to other ultrafilterable solutes. Monitoring of sodium, glucose, pH, bicarbonate and $CO_2$ as well as any ultrafilterable small solute level is also possible.

The design, fluids, and control program of the RCA home system 210 eliminate all of the risks of RCA as described below. RCA home system 210 may include all of the safety features of RCA System 110 as discussed herein. The modifications of home system 210, most notably the single-chamber concentrate 280 and the OSS will address additional risks unique to the home treatment environment as follows:

1) Metabolic alkalosis: The baseline acid-base chemistry is expected to be normal in stable home patients. The therapy fluid bicarbonate of 25-40 may be selected about once monthly and will depend on the weekly equivalent clearance delivered, baseline liver function and endogenous acid generation rate (protein nutrition). The single chamber concentrate 280 will reduce complexity and will prevent erroneous bicarbonate or sodium settings by the operator as these will be largely fixed with a single concentrate.

2) Metabolic acidosis: see above for metabolic alkalosis.

3) Hypocalcemia 1 (due to net calcium loss from the patient): The ultrafiltrate total calcium and magnesium losses are precisely calculable in the RCA home system 210. The online total calcium sensor module 256 may be necessary for catastrophic system failures (for example, disconnection or leakage of the calcium plus magnesium replacement infusion) in the home. This sensor module will remove all concerns related to calcium, magnesium and citrate levels in the patient's plasma. This module will eliminate the need for laboratory monitoring of the patient's systemic total and ionized calcium and magnesium levels during RCA. The fundamental principle of the sensor 256 is simultaneous determination of free ionized calcium, free ionized magnesium and free ionized citrate levels in the effluent fluid of the circuit. This allows for the mathematical derivation of the total calcium content of the effluent fluid with clinically sufficient accuracy.

4) Hypocalcemia 2 (due to citrate accumulation): Safe prescriptions prevent citrate accumulation even in the absence of liver metabolism by providing for a 66-75% citrate extraction on the hemofilter in a single pass. The OSS will derive the systemic citrate level in real time and will detect a rise in citrate levels accurately before the systemic ionized calcium level could drop by more than 0.25 mmol/L. A kinetic program may analyze the RRT prescription (fluid compositions and flow rates as well as blood flow rate). It also may utilize anthropometric data to predict the citrate volume of distribution in the patient. Data from the OCM allows filter clearance calculations. Finally, an estimate of the patient's citrate clearance in L/minute may also be derived from the measured systemic citrate curve. This will allow the prediction of the citrate curve after a prescription change.

5) Rebound hypercalcemia (due to release of calcium from citrate after CVVH is stopped): The RCA home system 210 may not allow home treatment prescriptions to continue without modification if the patient's detected systemic citrate level exceeds 3.0 mmol/L. This will ensure that systemic citrate levels stay <=3.0 mM corresponding to about maximum 0.75 mM chelated calcium that could be released after RCA is stopped in all patients who can metabolize citrate. (Most patients will have 1 mM plasma citrate and about 0.25 mM Ca chelated by citrate in the steady state). The RCA protocol may be designed to keep systemic ionized Ca levels around 1-1.25 and therefore the highest calcium level after RCA is stopped will be <=1.75 mM and most patients will rebound to 1.25-1.5 mM Ca levels after treatment. Utilizing the OSS, the system 210 can also provide a lower citrate and or calcium infusion rate in the last few hours of the treatment to lower the total systemic citrate and calcium levels prior to stopping the RRT.

6) Hypophosphatemia: Depending on the achieved equivalent weekly clearance and dietary habits, the single bag concentrate 280 may have varying amount of phosphate, to suit the individual patient.

7) Nursing errors: The RCA home system 210 may be designed to be fully automated and provide home nocturnal RRT with citrate anticoagulation without any intervention from nurses or other health care personnel.

8) Rare: Ionized hypomagnesemia: Magnesium dosing may be fully coordinated with calcium. The only variable, the molar ratio of calcium to magnesium may be fine tuned in the range of 2:1 to 2:0.5 with more clinical experience in the future. Similar to the current clinical practice of having several acid concentrates with different calcium to magnesium molar ratios, it is likely that the calcium and magnesium infusion according to the present invention will have to be formulated as two or three distinct varieties with slightly different Ca:Mg molar ratios in the above range to accommodate the individual patient.

9) Declining filter performance: The conductivity-based OCM as well as the OSS monitoring the citrate bolus-based online clearance can detect this complication and alert the operator that the filter needs to be replaced.

10) Trace metal depletion: Cationic trace metal supplementation may be provided with the calcium infusion to restore precise mass balance for these trace solutes. Any trace metal incompatible with the calcium infusion can be provided in the citrate anticoagulant infusion in an adjusted concentration.

11) Access disconnection: Needle disconnection can be safely detected if a single needle operational mode is used in combination with a novel circuit tubing connector to access a permanent access for daily nocturnal dialysis.

12) Wrong connection of citrate, calcium or acid concentrate or blood circuit to patient: These errors may be prevented by the hardware design of the system 210 as well as through conductivity monitoring-based safety checks.

13) Disconnection of the calcium and or citrate infusion: This can be completely prevented by appropriate circuit tubing design (non-disconnectable, physically continuous infusion to blood line connection). The disconnection of the citrate infusion can also be detected by monitoring the circuit effluent conductivity and or citrate concentration. As a major improvement, disconnection of the calcium infusion can now be detected with the OSS through detecting decreasing systemic calcium levels despite normal functioning of the rest of the RCA home system 210. The optical hematocrit sensors 250, 252 can detect access recirculation and can enable the correction of blood bolus-based clearance measurements as well as the correction of derived systemic citrate and calcium levels for this phenomenon.

The novel therapy fluid used by the RCA home system 210 is described below. All concentrations and dilutions including, but not limited to, 1×, 5× 10×, and 50× formulations are fully contemplated in accordance with the present invention.

Novel Single Pre- and Post-Filter Replacement Fluid (or Dialysate in Nocturnal-Sled Mode):

| Pre-filter fluid (with 37X dilution used) | 1X fluid mmol/L | 1X fluid mEq/L |
|---|---|---|
| Sodium | 138 | 138 |
| Potassium | 4 | 4 |
| HCO3— | *27 | 27 |
| Chloride | 112.3 | 112.3 |
| Calcium | 0 | 0 |
| Magnesium | 0 | 0 |
| Phosphate (HPO4—: H2PO4— = 20:1) | *1.35 | *2.7 |
| Dextrose | 5.5 | 5.5 |

The most likely concentrate composition is provided above, wherein values denoted with an * may be slightly modified based on clinical experience. The manufacturer may modestly vary the potassium, sodium and bicarbonate content of the concentrate to best suit the individual patient. This will result in a range of combinations of the electrolytes in the final ready to use online generated fluid similar to several compositions of peritoneal dialysis bags being available to patients on peritoneal dialysis.

The ranges of possibilities in the 1× therapy fluid composition are provided below:

| | Therapy fluid 1X (mmol/L) |
|---|---|
| Sodium | 130-150 |
| Potassium | 2-4 |
| HCO3— | 20-40 |
| Chloride | 90-135 |
| Calcium | 0-0 |
| Magnesium | 0-0 |
| Phosphate (HPO4—: H2PO4— = 20:1) | 0-1.5 |
| Dextrose | 5.5-11 |

The provided concentrate is an important component of RCA home system 210 of the present invention. The lower potassium and higher bicarbonate concentrates are proposed for the few patients who want only every other day nocturnal therapy. The phosphate may be provided as a tri-basic and di-basic salt, pH-adjusted to be compatible with bicarbonate and to avoid $CO_2$ gas generation by virtue of being in the same concentrate container. (The zero range for phosphate may only be needed when 3× weekly brief 3-6 hours outpatient treatments are done with the RCA home system 210 and fluids).

A novel control program that monitors all sensor data and ensures a safe prescription based on treatment goals, mode of operation (pre- and post-dilution CVVH versus c-SLED as selected by the operator), and possibly patient variables input from the sensor devices (OSS) may be utilized according to the present invention. The control module has the capability to completely automate the safe functioning of the RCA home system 210 but is proposed in the default operational mode primarily as a safety and alarm tool with no authority to automatically change treatment settings (other than stop the machine if needed during an alarm).

The control program that may be used by the RCA home system 210 may be essentially identical to the control program of RCA system 110, wherein data from the OSS may be used to adjust the calcium infusion according to systemic citrate and calcium levels. When the RCA home system 210 is implemented as shown in FIGS. 17a-17b, the operational modes of pre- and post-dilution CVVH and SLED can be used as discussed for system 110. For the implementations in FIGS. 17c-17d, the SLED mode is unchanged; however, CVVH may only be performed in isolated marked (66%) pre-dilution mode. Modified calculations from the pre- and post-ultrafiltration mode as discussed for RCA system 110 with post-infusion being zero can still be used. The program simplifies the use of the device and allows for exact and automated calculation of the prescribed treatment variables including blood flow, citrate anticoagulant infusion rate, pre filter fluid flow, and degree of dilution of the pre-filter fluid during online generation as well as the rate of the calcium plus magnesium supplemental infusion. Once or a few times monthly, the physician may program the treatment modality, the duration and the frequency of the treatments and the hourly clearance goals and can provide data on measured hemoglobin and albumin levels as well as the patient's liver function (usual liver clearance) as determined from prior treatments.

In the default mode, the program will generate a prescription based on a markedly high pre-dilution (with or without post-dilution depending on the system design) with a pre-filter fluid flow to plasma flow ratio of 2:1 that will not allow dangerous citrate accumulation in the systemic plasma of the patient even in the absence of liver metabolism. All patients can safely reach up to 100-200 ml/kg/hr treatment goals with such a prescription. The clearance goal is expressed corrected for the degree of pre-dilution. More fluid efficient prescriptions that utilize lesser amounts of pre-dilution of the patient's blood in the arterial limb 214 of the circuit 212 would rely on the liver to clear some of the systemic citrate. If such prescriptions are allowed, should a sudden and unexpected reduction in liver function occur, the provided citrate and calcium sensor 256 may detect citrate accumulation and the resulting danger of ionized hypocalcemia before this complication could develop to a clinically significant degree. The generated alarm may contact the remote monitoring center to warn about the liver function and will trigger the machine to default to safe treatment parameters.

The dextrose content and pH of various fluids used by the systems and methods described herein is now addressed. The dextrose concentration and pH has an important influence on the formation of glucose degradation products (GDPs) during heat sterilization. The presence of GDPs may have an adverse impact on the biocompatibility of the fluids used by the systems according to the present invention, and therefore the fluid designs may be modified as described below to eliminate this potential problem. Prior art systems for RCA do not utilize dextrose in a way that minimizes GDP formation during heat sterilization of the CRRT fluids as in the present invention for RCA.

Multiple pre-mixed sterile solutions have been described herein to be infused either as pre-dilution or post-dilution replacement fluids or to be used as dialysis fluid during CRRT. The dextrose content of these fluids has been specified to be in the range of about 5.5 to 11 mM and the pH in the range of about 5-9 depending on the specific fluid. However, during heat sterilization, GDPs may form and reduce the biocompatibility and general clinical suitability of these fluid formulations. GDP generation during heat sterilization may be minimized when the dextrose concentration is high and the pH is in the 2-2.5 range. GDP formation in the pre-dilution and post-dilution replacement fluids or fresh dialysate can be eliminated by omitting the dextrose from all of these fluid bags and instead adding it to the single calcium and magnesium infusion which may be pH-adjusted to a value around 2-2.5. In an alternative or simultaneous implementation, dextrose can be also added to the concentrated citrate anticoagulant infusion. The citrate bag may then be manufactured as a two-compartment bag, with the dextrose highly concentrated in the smaller compartment and pH-adjusted to a value around 2-2.5, possibly with hydrochloric acid. Since only 1-2 bags of concentrated citrate will typically be used per 24 hours (or per treatment in general), this does not represent a significant increase in manufacturing costs or clinical burden of use compared to the other fluid designs and use protocols described herein.

The compositions and concentration ranges contemplated according to the present invention are provided below. The fluids are explained first in general and then grouped and shown in detail for a specific CRRT device hardware implementation. While specific compositions are provided, the exact concentrations are meant to be illustrative and not limiting. In general, a range of at least +/−25% variation may be possible in all electrolyte concentrations provided and is fully contemplated in accordance with the present invention. It is understood that the fluids may be provided in a 1×, 5×, 10×, 50×, or any other concentrated or diluted ratio of the fluid components described herein. Again, for any description of solutions and fluids herein, except where expressly indicated, all numerical quantities in this description indicating amounts of material or conditions of reaction and/or use are understood as modified by the word "about" in describing the broadest scope of the present invention. Furthermore, the phrase "essentially free" is understood to mean that only trace amounts of a material, compound, or constituent may be present.

Fluid Composition of the Concentrated Citrate Anticoagulant
General Composition:

| Concentrated Citrate Anticoagulant: about 4% w/v total citrate; optionally a mixture of basic and acid citrate | mmol/L | mEq/L |
|---|---|---|
| Sodium Chloride | 0-2000 | 0-2000 |
| Total Citrate | 20-1000 | 60-3000 |
| Trisodium (Basic) Citrate | 20-1000 | 60-3000 |
| Citric Acid | 0-333 | 0-1000 |
| Sodium Bicarbonate | 0-1000 | 0-1000 |
| Phosphate (usually $H_2PO_4^-$; $HPO_4^{2-}$ when bicarbonate is present) | 0-50 | 0-50 (mmol) |
| Hydrochloric acid (to adjust the pH if needed) | 0-10 | 0-10 |
| Dextrose (D-glucose) (pH-adjusted to 2-2.5) | 0-2000 | NA |
| Optional trace elements, iron, other nutrients | As needed | NA |
| Optional solutes for online dialysance measurements | As needed | NA |
| Optional solutes for body metabolism and/or elimination kinetic studies | As needed | NA |

The fluid labeling nomenclature is: Citrate(B/A)Na(X)Bic(X)D(X)P(X)
where,
B=Basic citrate content (mmol/liter)
A=Acid citrate content (mmol/liter)
Na=Sodium content (mmol/L)
Bic=Bicarbonate content (mmol/liter)
D=Dextrose content (mmol/liter)
P=Phosphate content (mmol/liter)

In one implementation, bicarbonate may be present next to basic citrate. This fluid may be used for patients with severe pre-existing metabolic acidosis and or severely compromised citrate metabolism to maintain bicarbonate delivery by the circuit even when using a standard 20-24 mmol/L bicarbonate replacement fluid. Also fully contemplated is the addition of any metabolizable carbohydrate monomer or polymer molecule (one implementation being dextrose), such as to the citrate anticoagulant used pre-filter (or to any of the other fluid used in the RCA systems according to the present invention), to specifically modulate and inhibit protein aggregation, protein limiting membrane formation, and filter membrane protein fouling in the hemofilter during RRT including dialysis, hemo-diafiltration and pure hemofiltration. When dextrose is used, the fluid chamber containing this compound may have a small volume (about 10% of the total bag volume) and the dextrose chamber pH may be adjusted to about 2-2.5, according to one aspect of the invention by adding hydrochloric acid (HCl) as appropriate (about <=4 mmol/l concentration or <=2 mmol total/500 ml smaller dextrose chamber in a 5 liter dual-chamber bag). The phosphoric acid or citric acid may or may not be provided in the dextrose chamber (as applicable and safe) for reducing the pH.

Phosphate may be provided in this fluid, for instance when the dialysate or replacement fluids as well as the calcium infusions are phosphate-free. In another implementation (particularly when the citrate anticoagulant is phosphate-free), iron supplements can be provided here in any water soluble, non-toxic form (e.g., $Fe^{2+}$-$citrate^{3-}$) that is safe for direct infusion into blood and is compatible with all other solutes present in the specific citrate infusion formulation. The approximate amount of iron may be 0-10,000 (μg/L), wherein according to one, non-limiting aspect of the present invention, a preferred amount may be about 12.5 or 25 μg/L Fe/every 1 mmol/L citrate, or about 1750 or 3500 μg/L anticoagulant when the citrate concentration is 140 mmol/L for daily versus every other day treatment, respectively. The supplementation of the citrate-containing fluids with iron is fully contemplated in accordance with the present invention.

The concentrated citrate anticoagulant solutions may be provided, for example, in a 5-liter volume bag and may also have a different overall volume and weight than the concentrated calcium infusions to lessen the risk of accidental mix-up. The weight of the concentrated citrate solution bag may be detected by the RCA systems according to the present invention.

Fluid Composition of the Pre-Filter CitrateEasy Solutions

In anticipation of possible online generation of replacement fluids, it is understood that the fluids may be provided in a 1×, 5×, 10×, 50×, or any other concentrated to diluted ratio of the fluid components described herein. Citrate could be replaced by isocitrate or another non-toxic, metabolizable calcium chelator. Any such variations of the following fluids are also contemplated herein.

| | mmol/L | mEq/L |
|---|---|---|
| Sodium ($Na^+$) | 135-150 | 135-150 |
| Potassium ($K^+$) | 0-4 | 0-4 |
| Citrate ($Cit^{3-}$) | 4-16.67 | 12-50 |
| Bicarbonate | 0-35 | 0-35 |
| Acid citrate ($CitH_3$) | 0-10 | 0-30 |
| Chloride ($Cl^-$) | 85-130 | 85-130 |
| Calcium ($Ca^{2+}$) | 0-4.0 | 0-8.0 |
| Magnesium ($Mg^{2+}$) | 0-2.0 | 0-4.0 |
| Dextrose | 0-100.0 | 0-100.0 |
| Phosphate | 0.0-6.0 | 0.0-18.0 |
| Inulin (optional) | 0-few Mm | 0-few mM |
| PAH (optional) | 0-few mM | 0-few mM |
| Trace metals | e.g., if the trace metal is incompatible with the Ca infusion | |
| Iron (e.g., $Fe^{2+}$-$citrate^{3-}$) | 0-1000 (μg/L); about 12.5 μg/L Fe/every 1 mmol/L citrate for daily treatment | |

Iron may be introduced here, for example as a $Fe^{2+}$-$citrate^{3-}$ complex to provide at least a neural and possibly even a positive iron balance in the extracorporeal circuit as a form of iron supplementation. Iron supplemented citrate anticoagulants may be particularly useful in the outpatient setting, during chronic intermittent hemodialysis with RCA, and iron supplementation of the citrate anticoagulant infusion with any non-toxic formulation of iron suitable for direct infusion into the blood line is fully contemplated herein.

Any suitable molecule or ion safe for direct infusion into human blood can be introduced in its usual or fluoroprobe- or affinity-tag-labeled form here to allow online monitoring of filter dialysance for the specific solute as described above. All such methods are again contemplated, with dextrose being the target solute used in one specific implementation.

Fluid Labeling Nomenclature:
CitrateEasy(B/A)Na(X)L(X)BIC(X)Ca(X)K(X)P(X)D(X)
where,
B=Basic citrate content (mmol/liter)
A=Acid citrate content (mmol/liter)
L=Basic lactate content (mmol/liter)
BIC=Bicarbonate content (mmol/liter)
Na=Sodium content (mmol/liter)
Ca=Calcium content (mmol/liter)
K=Potassium content (mmol/liter)
P=Phosphate content (mmol/liter)
D=Dextrose content (mmol/liter)

Accordingly, the present invention contemplates isotonic, citrate-based pre-dilution fluids with anticoagulant activity. The total acid content may be variable to accommodate different patient chemistries. The fluids may be essentially calcium- and magnesium-free for the greatest clinical anticoagulant effect (where applicable). Calcium and magnesium may be added with careful formulations for systems lacking a Ca pump. Variability in citrate dosing may be achieved while keeping the pre-dilution the same by connecting two citrate bags which may be of the same geometrical design and total fluid volume, for instance vertically hanging from the same height attached to a single fluid scale simultaneously, such as with a large-bore, "Y" connector, to the pre-dilution fluid line. If the bags have different total citrate content, the average pre-dilution fluid citrate content will change depending on the ratio of the high-versus low-citrate bags (2:0, 1:1 and 0:2 bag ratio options). Variability in citrate dosing may also be achieved by varying the plasma flow to pre-dilution fluid flow ratio and this method is also contemplated during the use of these fluids according to the present invention.

Phosphate may be added with careful formulation to avoid crystal precipitation with Ca or Mg (where applicable). Dextrose may be added for various purposes. When dextrose is added, it may be provided in a concentrated form and pH-adjusted to 2-2.5, such as to prevent GDP formation during heat sterilization. Double chamber bags may be used to supply dextrose when needed. The pre-dilution fluids may be supplemented with other solutes (trace minerals, water-soluble, non-plasma-protein-bound renal function markers and, in general, any solute amenable for online filter dialysance measurements) as described herein and all such modifications are fully contemplated. When Raman spectroscopy is used to detect a concentration of a specific marker solute in the blood at any arbitrary point in the blood circuit (instead of monitoring the filter effluent where these solutes may not be present), partially or completely protein bound markers for kinetic elimination studies may also be provided with any of the pre-filter or post-filter fluid infusions and the use of Raman detection of such solutes is fully contemplated.

Fluid Composition of the BicarbEasy Solutions:

In anticipation of possible online generation of replacement fluids, it is understood that the fluids may be provided in a 1×, 5×, 10×, 50×, or any other concentrated to diluted ratio of the fluid components described herein.

|  | mmol/L | mEq/L |
|---|---|---|
| Sodium (Na$^+$) | 120-150 | 120-150 |
| Potassium (K$^+$) | 0-4 | 0-4 |
| Bicarbonate | 20-60 | 20-60 |
| Chloride (Cl$^-$) | 85-120 | 85-120 |
| Calcium (Ca$^{2+}$) | 0-4 | 0-8 |
| Magnesium (Mg$^{2+}$) | 0-2.0 | 0-4.0 |
| Phosphate (HPO$_4^{2-}$) | 0-3 | 0-6 |
| Dextrose | 0-50.0 | 0-50.0 |

Fluid labeling nomenclature: BicarbEasy(X)Na(X)Ca(X)K(X)P(X)L(X)D(X)
where,
X=Bicarbonate content (mmol/liter)
Na=Sodium content (mmol/liter)
Ca=Calcium content (mmol/liter)
K=Potassium content (mmol/liter)
P=Phosphate content (mmol/liter)
L=Lactic acid content (mmol/liter)
D=Dextrose content (mmol/liter)

Accordingly, the present invention contemplates isotonic or near-isotonic bicarbonate-based post-dilution fluids. The fluids may be essentially calcium- and magnesium-free for greatest clinical anticoagulant effect (where applicable). In one implementation, the essentially dextrose-, calcium- and magnesium-free fluids can be manufactured in a single compartment sterile bag without the risk of Ca-carbonate and Mg-carbonate precipitation and/or GDP formation during heat sterilization. For systems lacking a concentrated Ca pump, calcium and magnesium may be added with careful formulations, the use of an acid (where applicable), and a dual-chamber bag design. Variability in bicarbonate dosing may be achieved by connecting 2 bicarbonate bags which may be of the same geometrical design and total fluid volume, for example vertically hanging from the same height on a single fluid scale simultaneously, by a large-bore, "Y" connector to the post-dilution fluid line. If the bags have different total bicarbonate content, the average post-dilution fluid bicarbonate content will change depending on the ratio of the high-versus low-bicarbonate bags (e.g., 2:0, 1:1 and 0:2 bag ratio options). The same principle may be applied when the machine has a concentrated citrate pump and both the pre-dilution and post-dilution pumps supply bicarbonate-based fluids.

Phosphate may be added with careful formulation to avoid crystal precipitation with Ca or Mg (where applicable). Dextrose may be added for various purposes. When dextrose is added, it may be provided in a concentrated form and pH-adjusted to 2-2.5, such as to prevent GDP formation during heat sterilization. Double chamber bags, and possibly hydrochloric acid in clinically negligible amounts, may be used to supply dextrose at low pH when needed. The post-dilution fluids may be supplemented with other solutes (trace minerals, plasma-protein-bound or non-plasma-protein bound renal function markers and, in general, any solute amenable for online filter dialysance and/or body solute kinetics measurements), and all such modifications are contemplated herein.

Fluid Composition of the Electrolyte Concentrates Used for Online Generation of Replacement Fluid or Fresh Dialysis Fluid:

Reference is made to the special compositions of acid and base concentrates and dry powder electrolyte or other solute formulations described herein. Since all components in the final 1× dialysis fluids discussed below are chemically compatible with careful adjustment of the pH of any molecules capable of forming a buffer system, any separation of the listed components of the final 1× dialysis fluid into concentrates and or dry powder formulations suitable for any online dialysate generating system are contemplated herein.

In some formulations, the removal of dextrose affords easier dextrose dialysance calculations and allows heat sterilization of the acid concentrates without concerns about GDP formation. The provision of the dextrose (when present) in a high concentration, such as 150-200 mM dextrose (before dilution) in a 35× acid concentrate with pH adjusted to 2-2.5, such as by hydrochloric acid, may allow heat sterilization with minimal GDP formation. The acid concentrates may also be provided in dual-chamber bags with dextrose separate from any solutes that cannot be heat sterilized with it in a single chamber safely. The present invention also contemplates the provision of dextrose (when used) in a separate chamber with the pH adjusted in the range of about 2-2.5 with a clinically negligible amount of hydrochloric acid (which chamber may or may not also contain the phosphoric acid and any of the other pH-compatible electrolytes) with bicarbonate in another chamber in the single concentrate formulation aimed for simple home dialysate generation as described herein, with a dual-chamber bag design to lessen the risk of GDP production during heat sterilization.

The Ranges for the Individual Components are Provided Below:

| Replacement or dialysis fluid acid concentrate with phosphate components after mixing with the base concentrate and water to 1X | 1X final fluid composition; mmol/L | 1X fluid component from the acid concentrate; mEq/L |
| --- | --- | --- |
| Sodium | 120-150 | 80-120 |
| Potassium | 2-4.0 | 2-4.0 |
| Chloride | 80-130 | 80-130 |
| Bicarbonate | 20-40 | 0 |
| Calcium | 0-3 | 0-6 |
| Magnesium | 0-1.5 | 0-3 |
| Phosphate, $HPO_4^{2-}$ (Phosphoric acid or $NaH_2PO_4$ pH adjusted to <5 in acid concentrate) | 0-1.5 | 0-4.5 (0-1.5 mM) |
| Acetate or lactate may be used when phosphate is essentially zero (Acetic or lactic acid in acid concentrate) | 0-4 | 0-4 |
| Dextrose | 0-11 | 0-11 (mmol) |

Fluid labeling nomenclature: RCA Acid Concentrate Na(X)K(X)P(X)D(X)
where,
Na=Sodium content (mmol/liter)
K=Potassium content (mmol/liter)
P=Phosphate content (mmol/liter)
D=Dextrose content (mmol/liter)

All content is expressed in mmol/liter concentration after dilution with water and mixing with the corresponding base concentrate according to the standard proportioning ratios of the specific dialysis machine. For example, on the SLED-capable Fresenius 2008, 35× acid concentrate with final bicarbonate set for 23 and sodium set for 140, the acid concentrate may be prepared so that, with the above mixing, the resulting final 1× replacement fluid Na is 128 and final bicarbonate is about 24, appropriate for online pre- and post-dilution CVVH with high dose citrate when the combined pre- and post-dilution replacement therapy flow is prescribed equal to 100% of the total blood flow. Conversely, setting the final sodium to 144 and bicarbonate to 25 will then result in a final sodium concentration of about 132.4 mmol/l and bicarbonate of about 26 mmol/l, appropriate for online, automated pre- and post-dilution CVVH with high dose citrate when the combined pre- and post-dilution replacement therapy flow is prescribed equal to 150% of the total blood flow. For SLED operation, setting the final sodium to 152 and bicarbonate to 25 will then result in a final sodium concentration of about 139.6 mmol/l and bicarbonate of about 26 mmol/l, suitable for automated SLED with citrate. Small amounts of citrate, calcium and magnesium may also be added as described previously herein.

Finally, with the use of the classic two (acid and base) concentrate proportioning system, it is possible to provide magnesium in the acid concentrate to result in a final RCA 1× dialysis or replacement fluid magnesium concentration of about 1 mM (range of about 0-1.5 mM). This allows the use of magnesium-free calcium infusion with calcium dosing independent of magnesium dosing. Phosphate supplements in this system can still be provided in the acid concentrate (for example, as phosphoric acid) or, when the acid concentrate is phosphate-free, with the citrate anticoagulant, with the bicarbonate concentrate, or in the calcium infusion, all discussed herein. When phosphate is provided in a fluid containing calcium and/or magnesium, the fluid pH may be adjusted to pH 4 or less to avoid crystal precipitation. The above variations in the delivery of magnesium by the RCA systems according to the present invention are fully contemplated herein.

Fluid Composition of the Concentrated Calcium Infusion

This is a concentrated calcium and magnesium chloride infusion (with, for example, 0.5× diluted and 2×, 4× up to 20× concentrated formulations) with a, for example, 2.5:1 (range 1:1 to 4:1) molar ratio of calcium and magnesium.

General Composition:

| | mmol/L | mEq/L |
| --- | --- | --- |
| Calcium: | 10-1000 | 20-2000 |
| Magnesium: | 0-500 | 0-1000 |
| Sodium | 0-2000 | 0-2000 |
| Chloride | 28-5000 | 28-5000 |
| Hydrochloric acid (in the dextrose chamber) | 0-10 | 0-10 |
| Phosphate ($H_3PO_4$:$H_2PO_4^-$ in a 1:1 molar ratio) | 0-50 | 0-50 (mmol) |
| Dextrose | 0-1000 | 0-1000 (mmol) |
| Trace elements | as needed | NA |
| Biologically important solutes | as needed | NA |

Trace elements and any other biologically important solute may be added in a molar ratio to calcium that may be the same as in the ultrafiltrate during CVVH with RCA at a time point when the systemic blood plasma has normal trace element, biologically important solute and total calcium content as adjusted for the albumin and 0.5-2 mM citrate level. When phosphate is provided here, the fluid may be formulated with the pH adjusted to be <=3 to avoid crystal precipitation and, according to one aspect of the invention, the calcium may not exceed 100 mM and the magnesium may not exceed 50 mM concentration. Furthermore, when the dialysis acid concentrates contain magnesium, all concentrated calcium infusions as discussed herein may be formulated without magnesium, with or without the addition of phosphate, and with or without the necessary adjustments to the sodium chloride content to maintain the overall conductivity similar to the calcium infusion fluids with magnesium and all such adjustments are contemplated.

Iron supplements with water soluble, non-toxic formulations of iron that are suitable for direct infusion into the blood may be provided here (particularly when phosphate is absent and as long as the formulation does not release any toxic free iron in the presence of excess calcium and magnesium and an acid pH) in the range of 0-6000 μg/L, providing about 100 μg/L Fe for every 1 mmol/L calcium with, according to one non-limiting aspect of the present invention, a preferred concentration of 5000 μg/L Fe when the Ca concentration is 50 mmol/L, and all such modifications are also contemplated herein.

The concentrated calcium solutions may be provided, for example, in a 3-liter volume bag and specifically with a different overall volume and weight than the concentrated citrate infusions to lessen the risk of accidental mix-up. The weight of the concentrated calcium solution bag may be detected by the RCA systems according to the present invention.

Fluid labeling nomenclature: Calcium(X)Mg(X)Na(X)D(X)P(X)
where,
X=Calcium content (mmol/liter)
Mg=Magnesium content (mmol/liter)
Na=Sodium content (mmol/liter)
D=Dextrose content (mmol/liter)
P=Phosphate content (mmol/liter)

Figure 35:
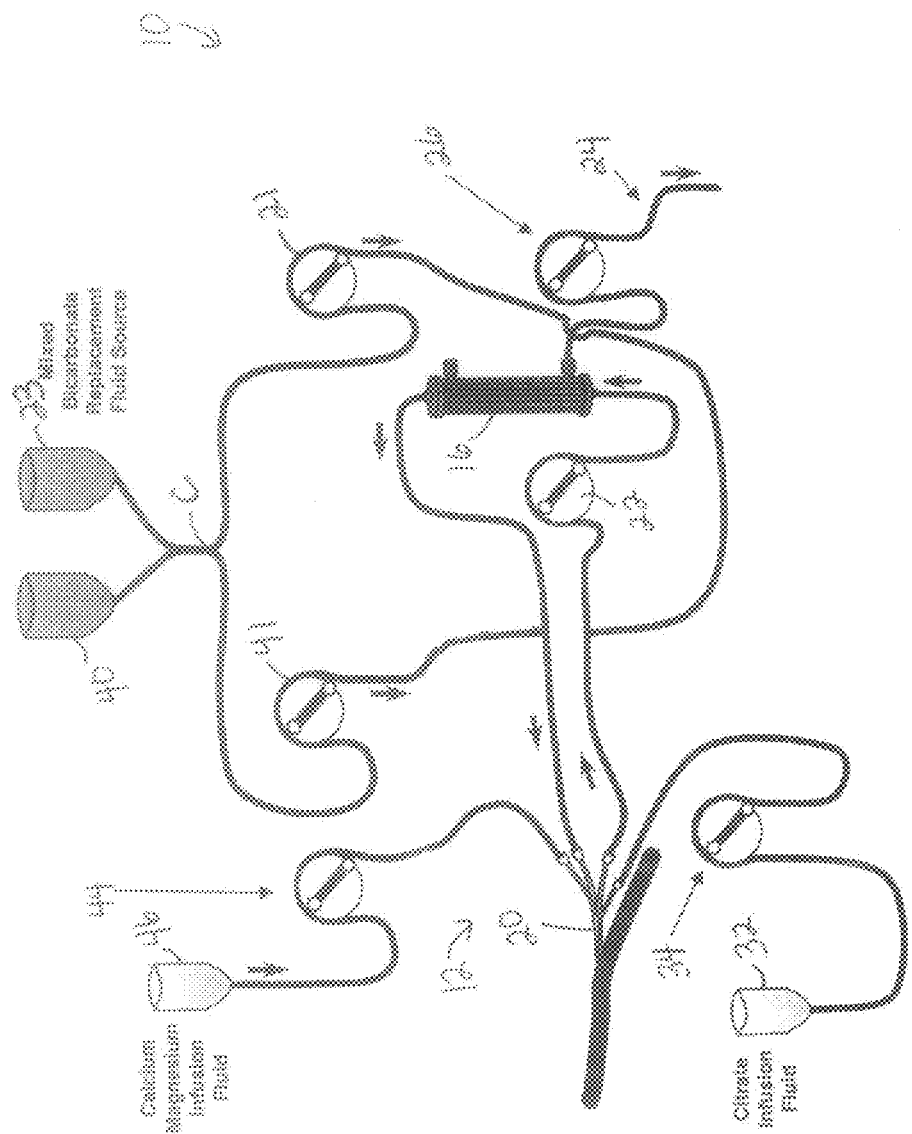
FIG. 35 depicts a system for pre- and post-veno-venous hemofiltration (CVVH) with regional citrate anticoagulation (RCA) for a machine with six fluid pumps including concentrated citrate and calcium pumps and a single source for bicarbonate pre- and post-dilution replacement fluid infusions according to the present invention.

Implementations for specific RRT devices will now be described. With reference to FIG. 35, a system 10 for CRRT with pre-packaged fluids is depicted with simultaneous pre- and post-veno-venous hemofiltration (CVVH) with RCA for a machine with six fluid pumps, including a concentrated citrate pump 34 and a calcium pump 44. Similar to the system described above with reference to FIGS. 3-4, pump 34 (which may include an air detector) may pump a concentrated citrate anticoagulant 32, pump 21 may pump a bicarbonate-based pre-dilution fluid mixed from bags 23 and 40, pump 22 is the blood pump, pump 26 is the total ultrafiltrate pump, pump 41 may pump a bicarbonate-based post-dilution fluid mixed from bags 23 and 40, and pump 44 (which may include an air detector) may pump a concentrated calcium and magnesium infusion that may optionally contain dextrose. The replacement fluid may be mixed from bags 23 and 40, which may be connected by a large bore, "Y"-shaped mixing connector C having at least two connections to bags 23 and 40, and one single mixed fluid outflow tract that later again bifurcates to become the pre-dilution and post-dilution replacement lines, as shown in FIG. 35. Further, bags 23 and 40 may be positioned and drained in a single outflow tract so that the rate of fluid flow from each bag is predictably about equal (for instance, when all bags 23 and 40 are of the same bag design and dimensions with equal total fluid volume and are hanging by gravity from the same fixed height point). The replacement fluids in bags 23 and 40 may or may not have the same sodium and bicarbonate content and other composition. Other components of system 10 have been described previously herein.

Citrate120/20Na560D210:

This fluid may be used when there is no severe preexisting metabolic acidosis. It may be manufactured as a two-compartment bag 32. The dextrose may be in a separate, smaller chamber to ensure a higher concentration, with the pH adjusted to about 2-2.5, possibly with a clinically negligible amount of hydrochloric acid, to minimize the production of GDPs during heat sterilization. The citric acid may or may not be in the same compartment with the dextrose. The high sodium and dextrose content may be optimized for online conductivity and dextrose dialysance measurements. During pre- and post-dilution hemofiltration, this fluid can be used with essentially dextrose-free replacement fluids and an essentially dextrose-free concentrated calcium infusion. When the citrate fractional extraction is above 0.80 (e.g., during sustained low efficiency dialysis (SLED)), it should be used with either dextrose-containing replacement fluids and/or a dextrose-containing concentrated calcium infusion.

| Concentrated Acid Citrate Anticoagulant: about 4% w/v total citrate; a mixture of basic and acid citrate in a 6:1 molar ratio | mmol/L | mEq/L |
| --- | --- | --- |
| Sodium Chloride | 200 | 200 |
| Total Citrate | 140 | 420 |
| Trisodium (Basic) Citrate | 120 | 360 |
| Citric Acid | 20 | 60 |
| Dextrose (D-glucose) (pH-adjusted to 2-2.5) | 210 | 210 (mmol) |

Citrate120/20Na560D0:

This is a single chamber, essentially dextrose-free variation of the above fluid. It should be used with either dextrose-containing replacement fluids and/or a dextrose-containing concentrated calcium infusion.

| Concentrated Acid Citrate Anticoagulant: about 4% w/v total citrate; a mixture of basic and acid citrate in a 6:1 molar ratio | mmol/L | mEq/L |
| --- | --- | --- |
| Sodium Chloride | 200 | 200 |
| Total Citrate | 140 | 420 |
| Trisodium (Basic) Citrate | 120 | 360 |
| Citric Acid | 20 | 60 |
| Dextrose (D-glucose) | 0 | 0 (mmol) |

Citrate140/0Na560Bic140D210:

This fluid may be used when there is severe preexisting metabolic acidosis. It may be manufactured as a two-compartment bag 32. The dextrose may be in a separate, smaller (about 10% of the total volume) chamber to ensure a higher concentration, with the pH adjusted to about 2-2.5 by hydrochloric acid to minimize the production of GDPs during heat sterilization. The high sodium and dextrose content may be optimized for online conductivity and dextrose dialysance measurements. During pre- and post-dilution hemofiltration, this fluid can be used with essentially dextrose-free replacement fluids and an essentially dextrose-free concentrated calcium infusion. When the citrate fractional extraction is above 0.75 (e.g. during SLED), it should be used with either dextrose-containing replacement fluids and/or a dextrose-containing concentrated calcium infusion.

| Concentrated Basic Citrate Anticoagulant: about 4% w/v basic citrate with bicarbonate | mmol/L | mEq/L |
| --- | --- | --- |
| Sodium bicarbonate | 140 | 140 |
| Total Citrate | 140 | 420 |
| Trisodium (Basic) Citrate | 140 | 420 |
| Citric Acid | 0 | 0 |
| Hydrochloric acid (HCl; in the small dextrose chamber to adjust pH to 2-2.5) | 0.4 | 0.4 |
| Dextrose (D-glucose) | 210 | NA |

Citrate140/0Na560Bic140D0:

This is a single chamber, essentially dextrose-free variation of the above fluid. It should be used with either dextrose-containing replacement fluids and/or a dextrose-containing concentrated calcium infusion.

| Concentrated Basic Citrate Anticoagulant: about 4% w/v basic citrate only | mmol/L | mEq/L |
|---|---|---|
| Sodium Bicarbonate | 140 | 140 |
| Total Citrate | 140 | 420 |
| Trisodium (Basic) Citrate | 140 | 420 |
| Citric Acid | 0 | 0 |
| Dextrose (D-glucose) | 0 | NA |

In one implementation, all of the above citrate anticoagulant solutions may be provided with phosphate at a concentration of about 35 mmol/L. In the acid citrate formulations, it may be provided as NaH2PO4 salt, whereas in the basic citrate formulations it may be provided as Na2HPO4 salt during the manufacturing process. The final sodium concentration would be the same, 560 mM with adjustments made to the NaCl content as needed. The low pH of the separate dextrose compartment (where applicable) may be maintained in the phosphate-containing formulations as well, such as with the use of hydrochloric acid.

BicarbEasy24Na128Ca0K2/4P0.75D0:

This fluid may be preferred for patients with no evidence of severe pre-existing metabolic acidosis. This fluid can also be used for patients with essentially zero citrate metabolism, as long as the bicarbonate-supplemented citrate anticoagulant is used with it (Citrate140/0Na560Bic140D0 or Citrate140/0Na560Bic140D210).

|  | mmol/L | mEq/L |
|---|---|---|
| Sodium (Na$^+$) | 128 | 128 |
| Potassium (K$^+$) | 2 or 4 | 2 or 4 |
| Bicarbonate | 24 | 24 |
| Chloride (Cl$^-$) | 104.5 or 106.5 | 104.5 or 106.5 |
| Calcium (Ca$^{2+}$) | 0 | 0 |
| Magnesium (Mg$^{2+}$) | 0 | 0 |
| Phosphate (HPO$_4^{2-}$) | 0.75 | 1.5 |
| Dextrose | 0 | 0 |

Dextrose is essentially absent in keeping with the assumed use of a standard dextrose-supplemented concentrated citrate and/or calcium infusion. The phosphate may be pH-adjusted to about 8.4 between the di-basic and mono-basic salt form to be compatible with the bicarbonate in the fluid without $CO_2$ generation, or may be simply added as $Na_2HPO_4$ for easier manufacturing with a negligible amount of $Na_2CO_3$ formed upon mixing with bicarbonate. The sodium may be low to compensate for the use of the hypertonic citrate solution. This fluid assumes that about 7-8 mmol of citrate is added to each liter of plasma in the arterial limb of the extracorporeal circuit. The bicarbonate is 24 since higher daily clearance goals in general require the use of lower bicarbonate concentrations in the post-filter fluid (as long as citrate metabolism is not impaired) to avoid metabolic alkalosis. When citrate metabolism is impaired, extra bicarbonate may be provided by the basic citrate anticoagulant with bicarbonate. Essentially, all clinical scenarios can be covered by the acid and basic citrate anticoagulants and the use of the BicarbEasy24Na128Ca0K2/4P0.75D0 fluid.

BicarbEasy32Na128Ca0K2/4P0.75D0:

Rather than using a bicarbonate-supplemented citrate anticoagulant, an alternate approach may be to use a replacement fluid with higher bicarbonate content. This fluid may be preferred for patients with evidence of shock liver and/or severe preexisting metabolic acidosis.

|  | mmol/L | mEq/L |
|---|---|---|
| Sodium (Na$^+$) | 128 | 128 |
| Potassium (K$^+$) | 2 or 4 | 2 or 4 |
| Bicarbonate | 32 | 32 |
| Chloride (Cl$^-$) | 96.5 or 98.5 | 96.5 or 98.5 |
| Calcium (Ca$^{2+}$) | 0 | 0 |
| Magnesium (Mg$^{2+}$) | 0 | 0 |
| Phosphate (HPO$_4^{2-}$) | 0.75 | 1.5 |
| Dextrose | 0 | 0 |

All of the considerations discussed for BicarbEasy24Na128Ca0K2/4P0.75D0 apply except that the bicarbonate concentration may be higher to correct any pre-existing severe metabolic acidosis faster and/or to compensate for the lack of systemic bicarbonate generation from citrate when citrate metabolism is impaired. Initially, while the systemic bicarbonate is less than 24, this fluid may be used together with the basic citrate anticoagulant (Citrate140/0Na560Bic140D0 or Citrate140/0Na560Bic140D210). When the metabolic acidosis has resolved, this fluid can be used with the acid citrate anticoagulant Citrate120/20Na560D210 or Citrate120/20Na560D0 even in the absence of citrate metabolism.

Any of the above two replacement fluids may be used alone or together with the other fluid with a different bicarbonate content (FIG. 35, bags 23 and 40). In addition, when the two fluids are used simultaneously, the ratio of the different bags may be 1:1, and further ratio variations may be possible if more than two fluid bags can be connected simultaneously. These variations, when applied properly as guided by the control program according to the present invention, allow the flexible adjustment of the overall bicarbonate delivery according to the individual needs of the specific patient.

Calcium50Mg20Na140D0:

| CaCl2 and MgCl2 infusion in venous limb near catheter | mmol/L | mEq/L |
|---|---|---|
| Calcium | 50 | 100 |
| Magnesium | 20 | 40 |
| Sodium | 140 | 140 |
| Chloride | 280 | 280 |
| Dextrose | 0 | 0 (mmol/L) |

This fluid assumes the use of either a dextrose-enriched citrate anticoagulant with a citrate extraction ratio at or below 0.75, or the use of dextrose-containing replacement or dialysis fluids. The different total conductivity and absent dextrose may help the machine detect when the calcium infusion is incorrectly connected pre-filter by resulting in a lower filter effluent 24 conductivity and dextrose content. These methods are specifically contemplated herein.

Calcium50Mg20Na140D125:

| CaCl2 and MgCl2 infusion in venous limb near catheter | mmol/L | mEq/L |
|---|---|---|
| Calcium | 50 | 100 |
| Magnesium | 20 | 40 |
| Sodium | 140 | 140 |
| Chloride | 280 + 4 | 280 + 4 |
| Hydrochloric acid (HCl; to adjust pH to 2.4) | 4 | 4 |
| Dextrose | 125 | NA |

This fluid assumes the use of either an essentially dextrose-free citrate anticoagulant or a citrate extraction ratio above 0.75, in both cases without the use of dextrose-containing replacement or dialysis fluids. The different total conductivity and the different dextrose content (from both the essentially dextrose-free and dextrose supplemented citrate anticoagulant) may help the machine detect when the calcium infusion is incorrectly connected pre-filter by resulting in a different (lower) conductivity and different dextrose content change of the filter effluent fluid 24 during bolus operation of the citrate pump. The fluid designs with these methods are specifically contemplated herein.

Figure 36:
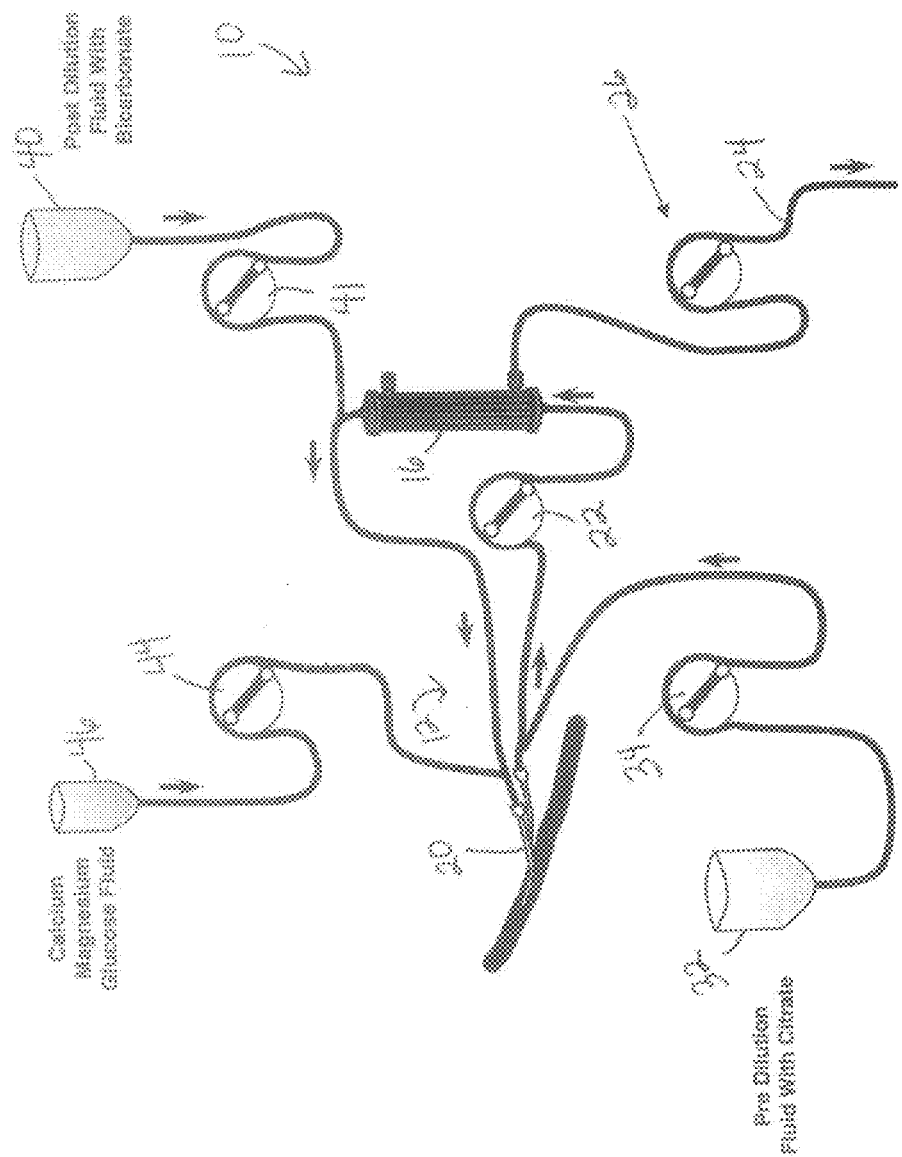
FIG. 36 depicts a system for pre- and post-veno-venous hemofiltration (CVVH) with RCA for a machine with five fluid pumps including a concentrated calcium infusion pump according to the present invention.

Referring now to FIG. 36, a system 10 is depicted for a CRRT circuit based on simultaneous pre- and post-venovenous hemofiltration (CVVH) with RCA for a machine with five fluid pumps including a concentrated calcium infusion pump 44. Similar again to FIGS. 3-4 above, pump 34 may pump an isotonic citrate-based pre-dilution solution 32, pump 22 is the blood pump, pump 26 is the total ultrafiltrate pump, pump 41 may pump a bicarbonate-based post-dilution fluid 40, and pump 44 may pump a concentrated calcium and magnesium infusion that may optionally contain dextrose. Other components of system 10 have been described above.
CitrateEasy14/2Ca0K2/4P0.75D0:

This is an acidic, high citrate fluid with phosphorus added, wherein a mode of operation may be simultaneous pre- and post dilution CVVH. This fluid may not be for patients with shock liver and an inability to attain >=66% citrate extraction and/or preexisting severe metabolic acidosis.

|  | mmol/L | mEq/L |
|---|---|---|
| Sodium ($Na^+$) | 140 | 140 |
| Potassium ($K^+$) | 2 or 4 | 2 or 4 |
| Citrate ($Cit^{3-}$) | 14 | 42 |
| Acid citrate | 2 | 6 |
| Chloride ($Cl^-$) | 100.25 or 102.25 | 100.25 or 102.25 |
| Calcium ($Ca^{2+}$) | 0 | 0 |
| Magnesium ($Mg^{2+}$) | 0 | 0 |
| Phosphate ($H_2PO_4^-$) | 0.75 | 0.75 (mmol/L) |
| Dextrose | 0 | 0 |

In this fluid, dextrose may be removed to allow heat sterilization in a single chamber bag 32 without the production of GDPs. The removal of both calcium and magnesium is important to the maximal anticoagulant effect and for the safe addition of phosphate to the fluids at the point of manufacture. Finally, the sodium may be 140 for greater acceptance by clinicians. This value may be increased to 145 if clinical results (mild hyponatremia) mandate. This fluid assumes the use of a dextrose supplemented Ca-infusion.
CitrateEasy14/2Ca0K2/4P0.75D22:

One variation of the above fluid may be manufactured as a two-compartment bag 32 with a smaller compartment containing dextrose pH adjusted to 2-2.5, possibly with hydrochloric acid (either citric acid or phosphoric acid, both, or neither may also be in this compartment). In general, in all CitrateEasyD22 fluids, the phosphate may or may not be supplied with the dextrose in a small (about 10% of final bag volume) compartment as phosphoric acid. When the seal is broken, the final composition may be:

|  | mmol/L | mEq/L |
|---|---|---|
| Sodium ($Na^+$) | 140 | 140 |
| Potassium ($K^+$) | 2 or 4 | 2 or 4 |
| Citrate ($Cit^{3-}$) | 14 | 42 |
| Acid citrate | 2 | 6 |
| Chloride ($Cl^-$) | 100 or 102 | 100 or 102 |
| Calcium ($Ca^{2+}$) | 0 | 0 |
| Magnesium ($Mg^{2+}$) | 0 | 0 |
| Phosphoric acid ($H_3PO_4$) | 0.75 | 0.75 (mmol/L) |
| Dextrose | 22 | 22 (mmol/L) |

This fluid may have several benefits. Proper loading of the pre-dilution pump 34 with citrate-containing fluid (and the proper mixing of the two chambers of that fluid) may be confirmed by monitoring the dextrose level of the filter effluent 24 in response to a small pre-dilution fluid bolus (different effluent effect from the essentially dextrose-free bicarbonate containing fluids can be detected regardless of the patient's plasma dextrose level; usually there will be an increase in effluent dextrose levels, unless the patient is grossly hyperglycemic, >22 mM). The present invention also provides the ability to use blood bolus-based dextrose dialysance measurements for filter performance monitoring (important when a diffusive element of clearance is present in the CRRT prescription, e.g. continuous veno-venous hemodiafiltration).
CitrateEasy16/0Ca0K2/4P0.75D0:

This is an alkaline, high citrate fluid with phosphate added, which may be for patients with pre-existing severe metabolic acidosis who can attain >=66% citrate extraction. One mode of operation may be simultaneous pre- and post dilution CVVH. For patients with pre-existing severe metabolic acidosis who can attain >=66% citrate extraction. This fluid works with BicarbEasy25/50Ca0/K2/4P1G0.

|  | mmol/L | mEq/L |
|---|---|---|
| Sodium ($Na^+$) | 140 | 140 |
| Potassium ($K^+$) | 2 or 4 | 2 or 4 |
| Citrate ($Cit^{3-}$) | 16.0 | 48 |
| Acid citrate | 0 | 0 |
| Chloride ($Cl^-$) | 93.25 or 95.25 | 93.25 or 95.25 |
| Calcium ($Ca^{2+}$) | 0 | 0 |
| Magnesium ($Mg^{2+}$) | 0 | 0 |
| Phosphate ($H_2PO_4^-$) | 0.75 | 0.75 (mmol/L) |
| Dextrose | 0 | 0 |

Dextrose may be removed to allow heat sterilization in a single chamber bag 32 without the production of GDPs. The acid citrate may be eliminated so as not to worsen any pre-existing acidosis. This fluid assumes the use of a dextrose-supplemented Ca-infusion and the presence of marked acidemia in the systemic blood.
CitrateEasy16/0Ca0K2/4P0.75D22:

In one variation, the above fluid may be manufactured as a two-compartment bag 32 with a smaller compartment containing dextrose (and optionally any of the other solutes that allow the pH to be adjusted and could be supplied there safely) at a pH of about 2-2.5, possibly adjusted by hydrochloric acid. After breaking the seal, the final dextrose concentration would be about 22 mM as explained for CitrateEasy14/2Ca0K2/4P0.75D22 above.
CitrateEasy7/1Ca0K2/4P0.75D0:

This is the pre-dilution fluid with less citrate added, and can be used for patients with shock liver and an inability to attain >66% citrate extraction (indefinite use). This fluid works with BicarbEasy25/50Ca0K2/4P0.75D0.

|  | mmol/L | mEq/L |
| --- | --- | --- |
| Sodium (Na$^+$) | 140 | 140 |
| Potassium (K$^+$) | 2 or 4 | 2 or 4 |
| Citrate (Cit$^{3-}$) | 7 | 21 |
| Acid citrate | 1 | 3 |
| Chloride (Cl$^-$) | 120.25 or 122.25 | 120.25 or 122.25 |
| Calcium (Ca$^{2+}$) | 0 | 0 |
| Magnesium (Mg$^{2+}$) | 0 | 0 |
| Phosphate (H$_2$PO$_4^-$) | 0.75 | 0.75 |
| Dextrose | 0 | 0 |

CitrateEasy7/1Ca0K2/4P0.75D22:

In one variation, the above fluid may be manufactured as a two-compartment bag 32 with a smaller compartment containing dextrose (and optionally any of the other solutes that allow the pH to be adjusted and could be supplied there safely) at a pH of 2-2.5, possibly adjusted by hydrochloric acid. After breaking the seal, the final dextrose concentration may be 22 mM as explained for CitrateEasy14/2Ca0K2/4P0.75D22 above.

BicarbEasy25Ca0K2/4P0.75D0:

This fluid may be used in combination with CitrateEasy14/2Ca0K2/4P1 for patients with no evidence of shock liver or severe preexisting metabolic acidosis.

|  | mmol/L | mEq/L |
| --- | --- | --- |
| Sodium (Na$^+$) | 140 | 140 |
| Potassium (K$^+$) | 2 or 4 | 2 or 4 |
| Bicarbonate | 25 | 25 |
| Chloride (Cl$^-$) | 115.5 or 117.5 | 115.5 or 117.5 |
| Calcium (Ca$^{2+}$) | 0 | 0 |
| Magnesium (Mg$^{2+}$) | 0 | 0 |
| Phosphate (HPO$_4^{2-}$) | 0.75 | 1.5 |
| Dextrose | 0 | 0 |

Dextrose may be absent to allow the use of a standard dextrose-supplemented Ca infusion. The phosphate may be pH-adjusted to about 8.4 between the di-basic and mono-basic salt form to be compatible with the bicarbonate in the fluid without CO$_2$ or Na$_2$CO$_3$ generation. If pure Na$_2$HPO$_4$ is used to provide phosphate when preparing the solution, a clinically negligible amount of Na$_2$CO$_3$ (about 0.05 mmol/L) will be generated upon mixing with the bicarbonate buffered solution. Finally, higher treatment goals in general require the use of lower bicarbonate concentrations in the post-filter fluid (as long as citrate metabolism is not impaired) to avoid metabolic alkalosis.

BicarbEasy50Ca0K2/4P0.75D0:

This fluid may be used for patients with shock liver and/or until severe metabolic acidosis is corrected.

|  | mmol/L | mEq/L |
| --- | --- | --- |
| Sodium (Na$^+$) | 140 | 140 |
| Potassium (K$^+$) | 2 or 4 | 2 or 4 |
| Bicarbonate | 50 | 50 |
| Chloride (Cl$^-$) | 90.5 or 92.5 | 90.5 or 92.5 |
| Calcium (Ca$^{2+}$) | 0 | 0 |
| Magnesium (Mg$^{2+}$) | 0 | 0 |
| Phosphate (HPO$_4^{2-}$) | 0.75 | 1.5 |
| Dextrose | 0 | 0 |

All considerations apply as for BicarbEasy25Ca0K2/4P0.75D0. The bicarbonate may be very high to compensate for the bicarbonate lost in the ultrafiltrate through the circuit and for the lack of liver conversion of citrate into bicarbonate in a shock liver patient.

Figure 37:
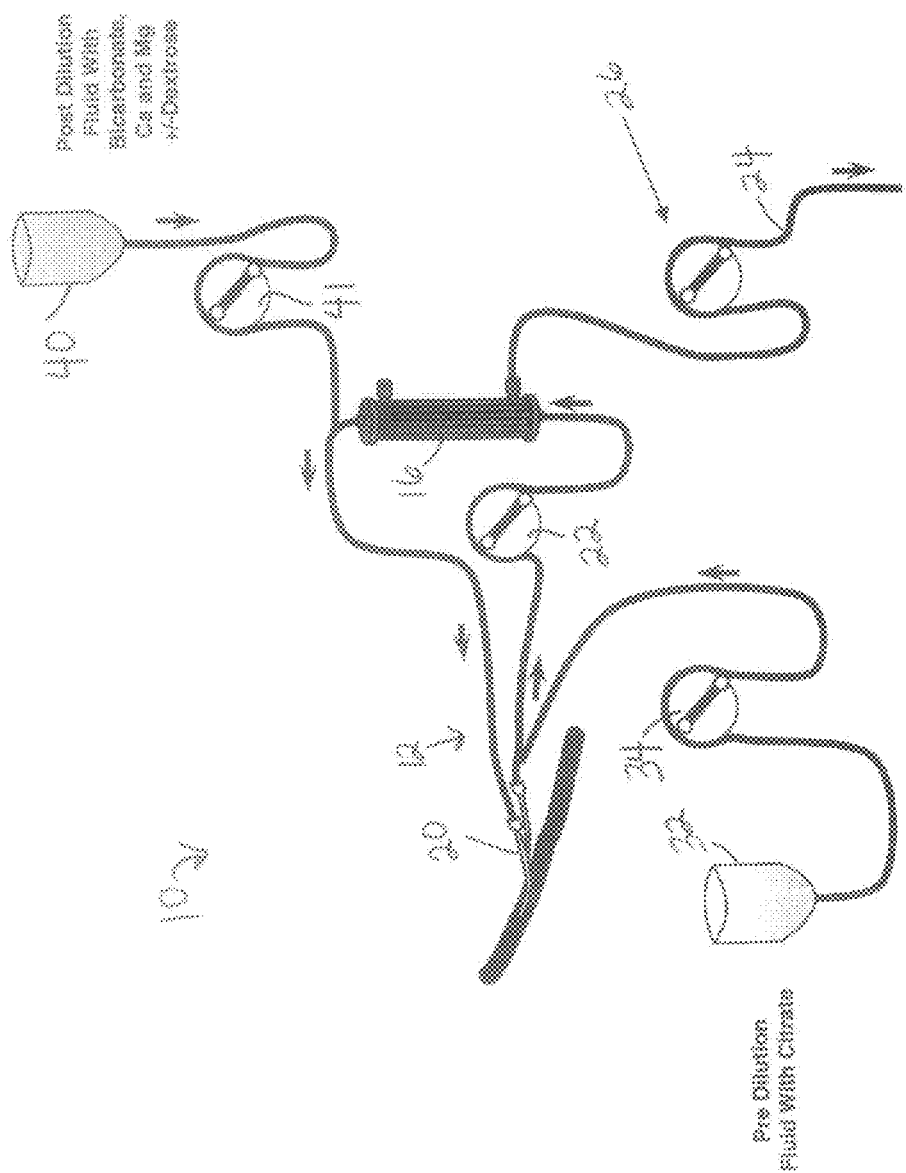
FIG. 37 depicts a system for pre- and post-veno-venous hemofiltration (CVVH) with RCA for a machine with four fluid pumps according to the present invention.

Turning now to FIG. 37, a system 10 is depicted using a CRRT circuit for simultaneous pre- and post-veno-venous hemofiltration (CVVH) with RCA for a machine with four fluid pumps without a concentrated calcium or citrate infusion pump. With reference to FIG. 2 above, pump 34 may pump an isotonic citrate-based pre-dilution solution 32, pump 22 is the blood pump, pump 26 is the total ultrafiltrate pump, and pump 41 may pump a bicarbonate-based, post-dilution fluid 40 that includes calcium, magnesium and optionally dextrose. Other components of system 10 have been described above.

CitrateEasy14/2Ca2K2/4P3D0:

This fluid is a variation for a pre- and post-dilution system without a fifth (calcium) pump. The high citrate fluid has more phosphorus added, with one mode of operation being simultaneous pre- and post-dilution CVVH. This fluid may not be for patients with shock liver and an inability to attain >=66% citrate extraction and/or preexisting severe metabolic acidosis. This fluid works with BicarbEasy25/50Ca2.25/K2/4P0D11.

|  | mmol/L | mEq/L |
| --- | --- | --- |
| Sodium (Na$^+$) | 140 | 140 |
| Potassium (K$^+$) | 2 or 4 | 2 or 4 |
| Citrate (Cit$^{3-}$) | 14.0 | 42 |
| Acid citrate | 2 | 6 |
| Chloride (Cl$^-$) | 102.5 or 104.5 | 102.5 or 104.5 |
| Calcium (Ca$^{2+}$) | 2 | 4 |
| Magnesium (Mg$^{2+}$) | 0.75 | 1.5 |
| Phosphate (H$_2$PO$_4^-$) | 3 | 3 |
| Dextrose | 0 | 0 |

Dextrose was removed to allow heat sterilization in a single chamber bag 32 without the production of GDPs. More phosphate was added as the post-filter fluid 40 will have calcium and bicarbonate and therefore may not have phosphate at the point of manufacturing. This fluid assumes the use of a dextrose-containing post-dilution replacement fluid 40. Calcium and phosphate are stable in the same bag 32 as the pH is around 6.6 and calcium is chelated by citrate.

CitrateEasy 14/2Ca2K2/4P3D22:

In one variation, the above fluid may be manufactured as a two-compartment bag 32 with a smaller compartment containing dextrose pH adjusted to about 2-2.5, possibly with hydrochloric acid (the citric acid or the phosphoric acid, both, or neither may also be in this compartment). After breaking the seal, the final dextrose concentration may be 22 mM as explained for CitrateEasy14/2Ca0K2/4P0.75D22 above.

CitrateEasy16/0Ca2K2/4P3D0:

This is an alkaline high citrate fluid with more phosphorus added, wherein one mode of operation is simultaneous pre- and post dilution CVVH with pre-existing severe metabolic acidosis. This fluid may not be for patients with shock liver and an inability to attain >=66% citrate extraction. This fluid works with BicarbEasy25/50Ca2.25/K2/4P0D11.

|  | mmol/L | mEq/L |
| --- | --- | --- |
| Sodium (Na$^+$) | 140 | 140 |
| Potassium (K$^+$) | 2 or 4 | 2 or 4 |
| Citrate (Cit$^{3-}$) | 15.5 | 46.5 |
| Acid citrate | 0.5 | 1.5 |
| Chloride (Cl$^-$) | 98 or 100 | 98 or 100 |
| Calcium (Ca$^{2+}$) | 2 | 4 |
| Magnesium (Mg$^{2+}$) | 0.75 | 1.5 |
| Phosphate (H$_2$PO$_4^-$) | 3 | 3 |
| Dextrose | 0 | 0 |

Dextrose was removed to allow heat sterilization in a single chamber bag 32 without the production of GDPs. More phosphate is added as the post-filter fluid 40 will have calcium with bicarbonate without citrate, and therefore cannot have phosphate. The acid content is reduced. This fluid assumes the use of a dextrose-containing post-dilution replacement fluid 40. Calcium and phosphate are stable in the same bag 32 as the pH is around 6.8-7.0 after all buffer systems equilibrate and calcium is chelated by citrate.

CitrateEasy16/0Ca2K2/4P3D22:

In one variation, the above fluid may be manufactured as a two-compartment bag 32 with a smaller compartment containing dextrose pH-adjusted to about 2-2.5, possibly with hydrochloric acid. After breaking the seal, the final dextrose concentration may be 22 mM as explained for CitrateEasy14/2Ca0K2/4P0.75D22 above.

CitrateEasy7/1Ca2K2/4P3:

This is a low citrate fluid with more phosphate added, and can be used for patients with shock liver and an inability to attain >66% citrate extraction (indefinite use) and/or preexisting severe metabolic acidosis (initial use). This fluid works with BicarbEasy25/50Ca2.5K2/4P0.

|  | mmol/L | mEq/L |
| --- | --- | --- |
| Sodium (Na$^+$) | 140 | 140 |
| Potassium (K$^+$) | 2 or 4 | 2 or 4 |
| Citrate (Cit$^{3-}$) | 7 | 21 |
| Acid citrate | 1 | 3 |
| Chloride (Cl$^-$) | 124.5 or 126.5 | 124.5 or 126.5 |
| Calcium (Ca$^{2+}$) | 2 | 4 |
| Magnesium (Mg$^{2+}$) | 0.75 | 1.5 |
| Phosphate (H$_2$PO$_4^-$) | 3 | 3 |
| Dextrose | 0 | 0 |

The safety of the phosphate-containing CVVH fluid is predicted based on inorganic fluid chemistry principles, namely that calcium and magnesium do not precipitate with phosphate in the presence of excess citrate and a mildly acidic pH. The addition of more phosphate will eliminate hypophosphatemia, even with a calcium-containing and therefore essentially phosphate-free post-filter bicarbonate fluid 40.

CitrateEasy7/1Ca2K2/4P3D22:

In one variation, the above fluid may be manufactured as a two-compartment bag 32 with a smaller compartment containing dextrose, pH-adjusted to about 2-2.5, possibly with hydrochloric acid (the citric acid may or may not also be in this compartment). After breaking the seal, the final dextrose concentration may be 22 mM, as explained for CitrateEasy16Ca0K2/4P0.75D22 above.

BicarbEasy25Ca2.5K2/4P0D0:

This fluid may be utilized in combination with CitrateEasy14/2Ca2K2/4P3G22 for patients with no evidence of shock liver or severe pre-existing metabolic acidosis.

|  | mmol/L | mEq/L |
| --- | --- | --- |
| Sodium (Na$^+$) | 140 | 140 |
| Potassium (K$^+$) | 2 or 4 | 2 or 4 |
| Bicarbonate | 27 | 27 |
| Chloride (Cl$^-$) | 122 or 124 | 122 or 124 |
| Calcium (Ca$^{2+}$) | 2.5 | 5 |
| Magnesium (Mg$^{2+}$) | 1 | 2 |
| Phosphate (H$_2$PO$_4^-$) | 0 | 0 |
| Hydrochloric acid | 2 | 2 (mmol/L) |
| Dextrose | 0 | 0 |

The dextrose may be removed when a high dextrose pre-filter fluid 32 is used. This allows the confirmation of the proper pre-filter and post-filter fluid connections through the monitoring of the dextrose level of the filter effluent 24 with the pre-filter fluid bolus technique. The high calcium and magnesium ensures mass balance of these ions in the circuit in the absence of a concentrated calcium pump. The phosphate is removed. The bicarbonate should be separated from the calcium, magnesium and hydrochloric acid in a traditional two-chamber bag 40. Higher treatment goals allow (and require) the use of lower bicarbonate concentrations in the post-filter fluid 40 as long as citrate metabolism is not impaired, to avoid metabolic alkalosis. The hydrochloric acid may be added to ensure a pH around 7-7.4 after mixing of the two chamber contents at the point of use, to lessen the risk of carbonate precipitation. The bicarbonate content is before mixing with the hydrochloric acid; after mixing it will be 25.

BicarbEasy25Ca2.5K2/4P0D11:

This fluid may be used when the pre-filter fluid 32 is essentially dextrose-free and in the absence of a concentrated calcium (and dextrose) pump. Correct loading of the pre-filter 34 and post-filter fluid pumps 41 may again be confirmed by the differential effects of these fluids on the filter effluent 24. The smaller compartment containing dextrose, calcium and magnesium with hydrochloric acid may have a pH of about 1.5-2.

BicarbEasy50Ca2.5K2/4P0D0:

This fluid may be used for patients with evidence of shock liver or severe preexisting metabolic acidosis.

|  | mmol/L | mEq/L |
| --- | --- | --- |
| Sodium (Na$^+$) | 140 | 140 |
| Potassium (K$^+$) | 2 or 4 | 2 or 4 |
| Bicarbonate | 53 | 53 |
| Chloride (Cl$^-$) | 96 or 98 | 96 or 98 |
| Calcium (Ca$^{2+}$) | 2.5 | 5 |
| Magnesium (Mg$^{2+}$) | 1 | 2 |
| Phosphate (H$_2$PO$_4^-$) | 0 | 0 |
| Hydrochloric acid | 3 | 3 (mmol/L) |
| Dextrose | 0 | 0 |

All considerations explained for BicarbEasy25Ca2.5K2/4P0D0 apply. The high bicarbonate concentration may be needed in the absence of citrate metabolism. The hydrochloric acid may be added to ensure a pH around 7-7.4 after mixing of the contents at the point of use, to lessen the risk of carbonate precipitation. The bicarbonate content is before mixing with the hydrochloric acid; after mixing it will be 50. The dextrose content is essentially zero when the pre-filter fluid dextrose is 22 mM.

BicarbEasy50Ca2.5K2/4P0D11:

This fluid may be used when the pre-filter fluid 32 is essentially dextrose-free and in the absence of a concentrated calcium (and dextrose) pump. Correct loading of the pre-filter 34 and post-filter fluid pumps 41 may again be confirmed by the differential effects of these fluids on the filter effluent 24. The smaller compartment containing dextrose, calcium and magnesium with hydrochloric acid may have a pH of about 1.5-2.

Figure 38:
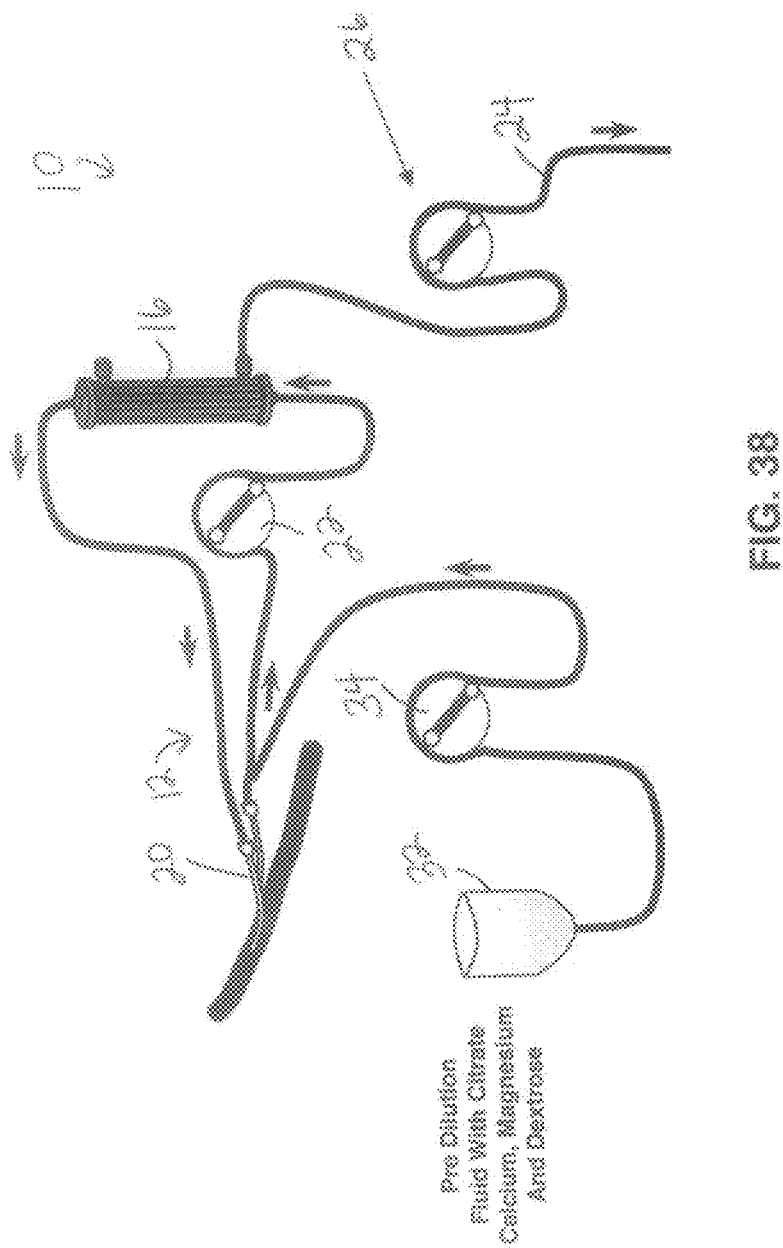
FIG. 38 depicts a system for isolated pre-dilution veno-venous hemofiltration (CVVH) with RCA for a machine with three fluid pumps according to the present invention.

FIG. 38 illustrates a system 10 using a CRRT circuit for isolated pre-dilution veno-venous hemofiltration (CVVH) with RCA for a machine with three fluid pumps. With reference to FIG. 2 described previously herein, pump 34 may pump an isotonic citrate-based pre-dilution solution 32 which also may have calcium, magnesium and dextrose added, pump 22 is the blood pump, and pump 26 is the total ultrafiltrate pump. Other components of system 10 have been described above.

CitrateEasy14/2Ca2.25K2/4P0.75D0:

This fluid has calcium and magnesium added, wherein one mode of operation is isolated pre-dilution CVVH with a 2-liter arterial circuit limb plasma flow to 1-liter pre-dilution fluid flow ratio. This fluid may not be for patients with impaired liver function. The low 33% citrate extraction due to the absence of post-filtration may argue for the use of the online citrate sensor 56 for safe treatments.

|  | mmol/L | mEq/L |
| --- | --- | --- |
| Sodium ($Na^+$) | 140 | 140 |
| Potassium ($K^+$) | 2 or 4 | 2 or 4 |
| Citrate ($Cit^{3-}$) | 14 | 42 |
| Acid citrate | 2 | 6 |
| Chloride ($Cl^-$) | 105.75 or 107.75 | 105.75 or 107.75 |
| Calcium ($Ca^{2+}$) | 2.25 | 4.5 |
| Magnesium ($Mg^{2+}$) | 1 | 2 |
| Phosphate ($H_2PO_4^-$) | 0.75 | 0.75 |
| Dextrose | 0 | 0 |

The addition of both calcium and magnesium ensures mass balance for these ions. The anticoagulant effect is reduced but still good due to the excess amount of citrate. Similarly, the very low ionized calcium levels and acidic pH in the fluid bags 32 allow the safe addition of phosphate by the manufacturer as well. Separate dextrose and bicarbonate administration by the health care team to the patient may or may not be needed.

CitrateEasy9/1L15Ca2.25K2/4P0.75D0:

This fluid has calcium and magnesium added, wherein one mode of operation is isolated pre-dilution CVVH with 1-liter arterial circuit limb plasma flow to 1-liter pre-dilution fluid flow ratio. This fluid may not be for patients with impaired liver function. The fairly low 50% citrate extraction due to the absence of post-filtration may argue for the use of the online citrate sensor 56 for safe treatments.

|  | mmol/L | mEq/L |
| --- | --- | --- |
| Sodium ($Na^+$) | 140 | 140 |
| Potassium ($K^+$) | 2 or 4 | 2 or 4 |
| Citrate ($Cit^{3-}$) | 9 | 27 |
| Acid citrate | 1 | 3 |
| Lactate | 15 | 15 |
| Chloride ($Cl^-$) | 106.75 or 108.75 | 106.75 or 108.75 |
| Calcium ($Ca^{2+}$) | 2.25 | 4.5 |
| Magnesium ($Mg^{2+}$) | 1 | 2 |
| Phosphate ($H_2PO_4^-$) | 0.75 | 0.75 |
| Dextrose | 0 | 0 |

The addition of both calcium and magnesium ensures mass balance for these ions. The anticoagulant effect is reduced but still good due to the excess amount of citrate. Similarly, the very low ionized calcium levels and acidic pH in the fluid bags 32 allow the safe addition of phosphate by the manufacturer as well. Separate dextrose and bicarbonate administration by the health care team to the patient may or may not be needed. The total metabolizable alkali content (citrate plus lactate) is about 42 mEq/L.

CitrateEasy14/2Ca2.25K2/4P1D5.5; CitrateEasy9/1L16Ca2.25K2/4P1D5.5:

The above fluids may be provided with 5.5 mM (final concentration) dextrose. The dextrose may be provided in a separate, smaller fluid chamber, pH-adjusted possibly by hydrochloric acid (dual chamber bag 32 design) to minimize GDP production during heat sterilization by increasing the dextrose concentration and keeping the pH in the 2-2.5 range in the smaller fluid chamber. The dextrose may or may not be provided together with phosphoric and/or citric acid where pH-compatible and safe.

CitrateEasy10/0BIC10Ca2.25K2/4P0.75D0; CitrateEasy10/0BIC10Ca2.25K2/4P0.75D5.5:

The above fluids may be provided with all basic citrate and 10 mmol/L bicarbonate instead of lactate. The pH of the fluid in the bicarbonate-containing chamber may be adjusted to around 8.4. Ca and Mg phosphate precipitation may be prevented by chelation of the Ca and Mg by the excess citrate. In one variation, the fluid may be supplemented by 5.5 mmol/L (final concentration) dextrose. The dextrose may be provided in a separate, smaller fluid chamber (dual chamber bag 32 design) to minimize GDP production during heat sterilization by increasing the dextrose concentration (by reducing the chamber size) and keeping the pH in the 2-2.5 range in the smaller fluid chamber, possibly by the addition of hydrochloric acid. The phosphate (phosphoric acid form) may or may not be in the glucose chamber as well.

In one implementation, the system shown in FIG. 38 can be used in isolated pre-dilution mode with a separate calcium infusion pump connected to the venous limb of the circuit and operated by the health care team. The fluid CitrateEasy4/0BIC24Ca0K2/4P0.75D0 may be utilized for the system and clinical use:

|  | mmol/L | mEq/L |
| --- | --- | --- |
| Sodium ($Na^+$) | 140 | 140 |
| Potassium ($K^+$) | 2 or 4 | 2 or 4 |
| Citrate ($Cit^{3-}$) | 4 | 12 |
| Acid citrate | 0 | 0 |
| Bicarbonate | 24 | 24 |
| Chloride ($Cl^-$) | 104.5 or 106.5 | 104.5 or 106.5 |
| Calcium ($Ca^+$) | 0 | 0 |
| Magnesium ($Mg^+$) | 0 | 0 |
| Phosphate ($HPO_4^-$) | 0.75 | 1.5 |
| Dextrose | 0 | 0 |

This single chamber fluid may work with a nurse-controlled, separate Calcium50Mg20Na140D125 infusion to restore the calcium, magnesium, and dextrose lost during CVVH. Isolated pre-dilution ultrafiltration may be utilized as the operational mode, wherein the fluid flow rate may always be equal to the blood flow rate for the simplest clinical protocol. The calcium infusion rate can be easily determined from a table based on blood flow, hemoglobin value, net ultrafiltration, and desired total systemic calcium. At a QB of 75 ml/min, the fluid flow would be 4.5 L/hour, resulting in about 100 liters of fluid used daily and about 50 liters of pre-dilution adjusted urea clearance in 24 hours. While this may be a relatively fluid inefficient clinical protocol, the operational simplicity and the availability of a commercial device that could easily run such treatments may compensate for this, and this fluid and method are fully contemplated according to the present invention.

FIG. 39 illustrates a system 110 for pre- and post-venovenous hemofiltration (CVVH) with RCA and online sterile replacement fluid generation in a modification of a commercial HD machine 1n general, the same concentrated citrate and calcium infusion fluids may be used here as described for the CRRT hardware platform described above with reference to FIG. 35. The main difference is that a single, online generated replacement fluid may be used by this system 110 for simultaneous pre- and post-replacement fluid infusion. When the replacement fluid is generated from separate bicarbonate and acid concentrates, the final sodium and bicarbonate concentrations can be adjusted flexibly as described above. Components of system 110 have been described previously herein with reference to FIG. 8a.

This system 110 may target a citrate extraction ratio of >=0.75. Therefore, an essentially dextrose-free replacement fluid and a dextrose-containing calcium infusion 146 may be used when the citrate anticoagulant 132 contains dextrose as proposed in one implementation. The fluids used may include Citrate120/20Na560D210 (likely two-chamber bag 132 for dextrose sterilization) and Citrate140/0Na560Bic140D210 (likely two-chamber bag 132 for dextrose sterilization) as explained above with reference to FIG. 35. Calcium50Mg20Na140D0 and Calcium50Mg20Na140D125 may also be provided as explained above with reference to FIG. 35. Additional fluids are described below.

RCA-CVVH Acid Concentrate Na(128)K(2-4)P(0.75)D(0):

This is an acid concentrate with phosphate dedicated to simultaneous pre- and post-dilution CVVH with daily therapy and high clearance goals. The generated online fluid sodium is 128 (when the machine is set for 140 sodium and the bicarbonate is about 24 when it is set for 23; the exact composition of the acid concentrate is then easily calculated from knowing the specifics of the proportioning system and usual concentrates used by the specific dialysis machine modified for RCA). This acid concentrate differs from the non-RCA standard acid concentrates in that the sodium content is about 10% lower so that the 1× online replacement fluid sodium is about 8% lower than the nominal setting on the machine. The potassium (and phosphate) concentrations are also reduced to result in 2 or 4 K and 0.75 mM phosphate at the lower bicarbonate settings used. The actual final replacement fluid sodium may be varied online based on the sodium dialysance achieved as well as the degree of pre-filter hypernatremia induced by the anticoagulant citrate infusion. For example, with online CVVH, the concentrate may provide a final replacement fluid composition including about 132 mmol/L sodium, about 107.5-111 mmol/L chloride, and about 25 mmol/L bicarbonate.

| Replacement fluid acid concentrate with phosphate components after mixing with the base concentrate and water to 1× | 1× final fluid composition; mmol/L | 1× acid fluid component; mEq/L |
|---|---|---|
| Sodium | 128 | 102 |
| Potassium | 2-4.0 | 2-4.0 |
| Chloride | 104.25-106.25 | 104.25-106.25 |
| Bicarbonate | 24 | 0 |
| Calcium | 0 | 0 |
| Magnesium | 0 | 0 |
| Phosphate, $HPO_4^{2-}$ (Phosphoric acid or $NaH_2PO_4$ pH-adjusted to <5 in acid concentrate) | 0.75 | 0.75 mM |
| Dextrose | 0 | 0 (mmol) |

To generate this 1× composition, the machine may be set for a target Na about 140 and target bicarbonate 22 with the above concentrate composition. This 1× replacement fluid assumes the use of the high sodium anticoagulant citrate infusions to achieve sodium mass balance in the circuit.

RCA-CVVH Acid ConcentrateNa(128)K(2-4)P(0)D(0):

The essentially phosphate-free version of the above acid concentrate can be utilized when higher phosphate removal is desired and hypophosphatemia is not a concern. This concentrate is suitable for intermittent treatment, a few hours long, with high-volume CVVH. If phosphoric acid is not used, acetic acid, lactic acid, or hydrochloric acid may be used in the acid concentrate instead to yield about 2 mM concentration in the final 1× fluid (for acetate or lactate after mixing with bicarbonate) or about 0.1 mM concentration in the final 1× fluid (for hydrochloric acid, neutralized by bicarbonate to sodium chloride 0.1 mM).

RCA-CVVH Acid Concentrate Na(128)K(2-4)P(0.75)D(5.5/11);

RCA-CVVH Acid Concentrate Na(128)K(2-4)P(0)D(5.5/11):

The above acid concentrates can also be provided supplemented with dextrose (according to the fixed concentrate proportioning ratios of the specific dialysis machine with the final 1× fluid sodium is set to the nominal 140 value and the bicarbonate is set to the nominal 23 value to result in a 128 Na and 24 HCO3) to yield 5.5 mM or 11 mM final dialysis fluid dextrose content. These sterile acid concentrates may be manufactured in a single chamber bag with the pH adjusted to about 2-2.5, such as to minimize GDP formation. In the case of the phosphoric acid-containing concentrate (pH around 2), pH adjustment may not be needed as long as heat sterilization of dextrose with phosphoric acid is acceptable in a single chamber. The essentially phosphoric acid-free acid concentrate may contain acetic acid, lactic acid, or hydrochloric acid instead as explained for RCA-CVVH Acid Concentrate Na(128)K(2-4)P(0)D(0).

With reference to FIG. 40, a modification of a currently available dialysis machine is depicted with pumps and fluid connections shown for 24-hour sustained low efficiency dialysis (SLED) or 4-5 hour intermittent hemodialysis (IHD) with RCA and online dialysis fluid generation. Components of system 110 have been described above with reference to FIG. 5a. It is understood that the fluids described herein may also be used during any form of hemodiafiltration. Calcium50Mg20Na140D0 and Calcium50Mg20Na140D125 are as described above with reference to FIG. 35. Other fluids are described below.

Citrate120/20Na560D210 (likely two-chamber bag for dextrose sterilization):

As explained above with reference to FIG. 35, when the dextrose fractional extraction is above 0.75 (e.g. during sustained low efficiency dialysis (SLED)), it should be used with either dextrose-containing replacement fluids and/or a dextrose-containing concentrated calcium infusion.

Citrate120/20Na560D0:

As explained above with reference to FIG. 35, this fluid is the single chamber, essentially dextrose-free variation of the above fluid. It should be used with either dextrose-containing replacement fluids and/or a dextrose-containing concentrated calcium infusion.

Citrate140/0Na560Bic140D210 (likely two-chamber bag for dextrose sterilization):

As explained above with reference to FIG. 35, when the dextrose fractional extraction is above 0.75 (e.g. during SLED), it should be used with either dextrose-containing replacement fluids and/or a dextrose-containing concentrated calcium infusion.

Citrate140/0Na560Bic140D0:

As explained above with reference to FIG. 35, this fluid is the single chamber, essentially dextrose-free variation of the above fluid. It should be used with either dextrose-containing replacement fluids and/or a dextrose-containing concentrated calcium infusion.

RCA-SLED Acid Concentrate Na(128)K(2-4)P(0.75)D(0):

This is an acid concentrate with optional phosphate dedicated to SLED or intermittent hemodialysis. The fluid sodium content is identical to the RCA-CVVH Acid Concentrate Na(128)K(2-4)P(0.75)D(0). The generated online fluid sodium is 140 (when the machine sodium is set for 153, and the bicarbonate is about 26 when it is set for 24; the exact composition of the acid concentrate is then easily calculated from knowing the specifics of the proportioning system and usual concentrates used by the specific dialysis machine modified for RCA). This acid concentrate differs from the RCA-CVVH concentrates in that the potassium, phosphate, and optional dextrose concentrations were further reduced about 10% to result in 2 or 4 K and 0.75 mM phosphate at the higher nominal total sodium settings and low bicarbonate settings used during SLED. The actual final dialysis fluid sodium may be varied online based on the sodium dialysance achieved as well as the degree of pre-filter hypernatremia induced by the anticoagulant citrate infusion. Such variations in the final 1× fluid sodium are most likely to be needed during high-per-minute clearance, intermittent HD when lower fractional sodium dialysance (DNa/QB) and lower citrate extraction ratio is achieved and will be selected by the prescription writing program.

| Dialysis fluid acid concentrate with phosphate components after mixing with the base concentrate and water to 1× | 1× final fluid composition; mmol/L | 1× acid flui component; mEq/L |
|---|---|---|
| Sodium | 140 | 112 |
| Potassium | 2-4.0 | 2-4.0 |
| Chloride | 114.25-116.25 | 114.25-116.2 |
| Bicarbonate | 26.25 | 0 |
| Calcium | 0 | 0 |
| Magnesium | 0 | 0 |
| Phosphate, $HPO_4^{2-}$ (Phosphoric acid or $NaH_2PO_4$ pH-adjusted to <5 in acid concentrate) | 0.75 | 0.75 mM |
| Dextrose | 0 | 0 (mmol) |

RCA-SLED Acid Concentrate Na(128)K(2-4)P(0)D(0):

The essentially phosphate-free version of the above acid concentrate can be utilized when higher phosphate removal is desired and hypophosphatemia is not a concern. This concentrate is suitable for intermittent, few-hour-long, high-clearance HD. The essentially phosphoric acid-free acid concentrate may contain acetic acid, lactic acid, or hydrochloric acid instead as explained for RCA-CVVH Acid Concentrate Na(128)K(2-4)P(0)D(0).

RCA-SLED Acid Concentrate Na(128)K(2-4)P(1)D(5.5/11);

RCA-SLED Acid Concentrate Na(128)K(2-4)P(0)D(5.5/11):

The RCA-SLED acid concentrates can be also provided supplemented with dextrose (according to the fixed concentrate proportioning ratios of the specific dialysis machine, when the final 1× fluid sodium is set to the nominal 153 value and the bicarbonate is set to the nominal 25 value to result in a 140 Na and 26 HCO3) to yield 5.5 mM or 11 mM final dialysis fluid dextrose content. The essentially phosphoric acid-free acid concentrate may contain acetic acid, lactic acid, or hydrochloric acid instead as explained for RCA-CVVH Acid Concentrate Na(128)K(2-4)P(0)D(0). These acid concentrates may be manufactured in a single or dual chamber bag with the pH adjusted, such as by hydrochloric acid as needed to about 2-2.5 to minimize GDP formation in the dextrose-containing chamber during heat sterilization. In the case of the phosphoric acid containing concentrate (pH around 2), pH adjustment may not be needed as long as heat sterilization of phosphoric acid and dextrose together is found to be safe.

Referring now to FIG. 41, the systems of FIGS. 39-40 can also be implemented with a single concentrate-based online 1× replacement and or dialysis fluid generation module as described above with reference to FIGS. 17a-17d. The following concentrates can be used with this system:

RCA-CVVH Single Concentrate Na(128)BIC(24)K(2-4)P(0.75)D(0):

| Replacement fluid single concentrate with phosphate components after mixing the two chambers of the concentrate and adding water to 1× | Acid chamber contribution to 1× final fluid composition; mmol/L | Base chamber contribution to 1× final fluid composition; mmol/L | Mixed chamber contribution to 1× final fluid composition; mmol/L |
|---|---|---|---|
| Sodium | 0 | 128 | 128 |
| Potassium | 0 | 2-4 | 2-4 |
| Chloride | 0 | 104-106 | 104-106 |
| Bicarbonate | 0 | 24 | 24 |
| Calcium | 0 | 0 | 0 |
| Magnesium | 0 | 0 | 0 |
| Phosphate ($HPO_4^{2-}$) | 0 | 0-1 ($HPO_4^{2-}$) | 0-1 ($HPO_4^{2-}$) |
| Hydrochloric acid (if needed for pH 2-2.5 in the acid chamber) | 0-0.012 | 0 | 0-0.012 |
| Dextrose | 0-11 | 0 | 0-11 |

The separation of the solutes in a two-chamber bag as above may be needed if heat sterilization is performed with a dextrose-containing concentrate. The dextrose compartment may contain about 10% of the final concentrate volume and may be pH-adjusted to 2-2.5 with hydrochloric acid alone. Phosphate (when used) may then be provided as 100% $Na_2HPO_4$ in the bicarbonate-containing chamber. Alternatively, when phosphate is used, about 5-10% of the total amount may be provided as phosphoric acid in the acid, dextrose-containing chamber, 80-90% as $Na_2HPO_4$ in the basic chamber, and 5-10% as $Na_3PO_4$ (equal to the molar amount of phosphoric acid) in the basic chamber. Upon mixing the chambers, the concentrate pH will be in the 8.2-8.4 range without excessive CO2 gas formation. Hydrochloric acid may not be needed to lower the pH in the dextrose compartment when phosphoric acid is used (if it is found to be safe to heat sterilize phosphoric acid and dextrose together). When the dextrose content is essentially zero, all solutes can be mixed in a single bag chamber. Acetic acid, lactic acid, or hydrochloric acid may not be needed when a single chamber, dextrose-free bag is used. However, heat sterilization of such single bags may be desirable to prevent bacterial growth, as the concentrate pH will be around 8.4. When a single chamber concentrate is used, the phosphate (when used) is provided as an approximately 20:1 molar mixture of $Na_2HPO_4$ and $NaH_2PO_4$ salts pH-adjusted to about 8.4 to avoid CO2 gas generation in the concentrated bicarbonate solution. For ease of manufacturing, 100% $Na_2HPO_4$ may be used to provide phosphate when preparing the concentrate. In this scenario, a clinically negligible amount of $Na_2CO_3$ (about 1.75 mmol/L at 35× and 0.05 mmol/L at a final 1× dilution) will be generated after mixing the phosphate in the bicarbonate buffered concentrate.

The exact concentrate composition is defined by the above target 1× concentrations and the proportioning ratio of the single-concentrate online fluid generation system. In one implementation, dextrose is essentially absent. Essentially dextrose-free fluids assume the use of either a dextrose-supplemented citrate anticoagulant and/or a dextrose-supplemented calcium infusion. The concentrate may be provided in a dual-chamber bag, separating bicarbonate from phosphoric acid or acetic or lactic acid. When dextrose is present, it may be provided in a smaller chamber in the dual-chamber concentrate bag, separate from the bicarbonate and other electrolytes except possibly the phosphoric or acetic or lactic acid. This allows a high dextrose concentration and pH-adjusted to around 2-2.5, such as with hydrochloric acid, for heat sterilization to minimize GDP production during the process.

RCA-SLED Single Concentrate Na(128)BIC26K(2-4)P (0.75)D(0-11):

| Dialysis fluid single concentrate with phosphate components after mixing the two chambers of the concentrate and adding water to 1× | Acid chamber contribution to 1× final fluid composition; mmol/L | Base chamber contribution to 1× final fluid composition; mmol/L | Mixed chamber contribution to 1× final fluid composition; mmol/L |
|---|---|---|---|
| Sodium | 0 | 140 | 140 |
| Potassium | 0 | 2-4 | 2-4 |
| Chloride | 0 | 114-116 | 114-116 |
| Bicarbonate | 0 | 26 | 26 |
| Calcium | 0 | 0 | 0 |
| Magnesium | 0 | 0 | 0 |
| Phosphoric acid | 0-0.1 ($H_3PO_4$) | 0-1 ($HPO_4^{2-}$) | 0-1 ($HPO_4^{2-}$) |
| Acetic acid, lactic acid, or hydrochloric acid (may be used when dextrose is present and phosphoric acid is essentially absent) | 0-0.02 (HCl) (0.05 acetic or lactic acid) | 0 | 0-0.02 (HCl) 0-0.05 (acetate or lactate) |
| Dextrose | 0-11 | 0 | 0-11 |

This fluid has the same concentrate sodium content as the RCA-CVVH Single Concentrate Na(128)BIC(24)K(2-4)P (0.75)D(0). However, with about 10% lesser dilution during the online generation of the 1× dialysis fluid, the final 1× sodium will be about 140 mmol/L. The concentrate phosphoric acid (or acetic acid, lactic acid, or hydrochloric acid), potassium, and dextrose (when applicable) content would also have to be adjusted to achieve the target 1× concentrations as required by the dialysis machine specific concentrate dilution ratio.

Finally, a circuit priming solution is also proposed for calibration of the Online Sensor System 256:

|  | mmol/L | mEq/L |
|---|---|---|
| Sodium ($Na^+$) | 130-150 | 130-150 |
| Citrate ($Cit^{3-}$) | 1-20 | 3-60 |
| Chloride ($Cl^-$) | 100-140 | 100-140 |
| Calcium ($Ca^{2+}$) | 0.5-10 | 1-20 |
| Magnesium ($Mg^{2+}$) | 0.25-5 | 0.5-10 |
| Dextrose | 0-50 | 0-50 |

According to one non-limiting aspect of the present invention, a preferred composition may be:

|  | mmol/L | mEq/L |
|---|---|---|
| Sodium ($Na^+$) | 140 | 140 |
| Citrate ($Cit^{3-}$) | 6 | 18 |
| Chloride ($Cl^-$) | 127 | 127 |
| Calcium ($Ca^{2+}$) | 1.8 | 3.6 |
| Magnesium ($Mg^{2+}$) | 0.7 | 1.4 |
| Dextrose | 11 | 11 (mmol) |

This solution will prime the circuit at the start of the procedure and will allow the filter effluent sensor array 256 to test the accurate functioning of the safety sensors for dextrose, citrate, calcium and magnesium.

The modification of the dextrose content allows large-scale, commercial production of the fluids according to the present invention, without concerns about the generation of GDPs during heat sterilization. The addition of online dextrose dialysance based filter performance monitoring may allow complete automation of citrate anticoagulation sooner, even before the ultimate safety element, the online citrate sensor, is commercially available.

During the operation of RCA systems 10, 110, 210 according to the present invention, the arterial and venous blood flow, as well as the citrate and calcium infusions are precisely controlled by the system without any intervention from the health care personnel. This design affords the safe use of special catheter or circuit tubing connector designs as shown in FIGS. 9-16. These accessories may replace or connect to standard blood circuit tubing in current clinical use. The special blood circuits, access catheters or circuit tubing connectors may introduce the citrate anticoagulant as early as possible into the arterial blood pathway and reverse the anticoagulant effect by the calcium infusion into the venous blood pathway as late as possible. These designs are possible as the blood flow as well as the citrate and calcium infusion flows are now precisely controlled and monitored by the dialysis machine instead of the human operator. The new blood circuits can come with special end connectors or can be completely integrated with the citrate and calcium delivery systems.

FIGS. 9a and 9b illustrate a triple lumen access catheter 300 having a first lumen 302 representing an arterial blood withdrawal path, a second lumen 304 representing a venous blood return path, and a third lumen 306 representing an arterial infusion path. Third lumen 306 may be in fluid communication with first lumen 302 via an opening 308 in the lumen wall that allows for injection of an infusion solution. According to one aspect of the present invention, opening 308 may be provided near the entrance 310 of first lumen 302 used to withdraw blood from the patient, wherein third lumen 306 may have a cap 312 or other closure at that end. The infusion solution may contain the citrate (or other) anticoagulant, and the infusion solution line (not shown) may have an air detector. Catheter 300 allows the introduction of citrate anticoagulant into the arterial blood as early as possible.

FIGS. 10a and 10b illustrate a quadruple lumen catheter 314 having a first lumen 316 representing an arterial blood withdrawal path, a second lumen 318 representing a venous blood return path, and a third lumen 320 representing an arterial infusion path, and a fourth lumen 322 representing a venous infusion path. Third lumen 320 may be in fluid communication with first lumen 302 via an opening 324 in the lumen wall that allows for injection of an infusion solution, such as citrate anticoagulant. Fourth lumen 322 may be in fluid communication with second lumen 318 via an opening 326 in the lumen wall that allows for injection of an infusion solution, such a calcium solution. According to one aspect of the present invention, opening 324 may be provided near the entrance 328 of first lumen 316 used to withdraw blood from the patient, wherein third lumen 320 may have a cap 330 or other closure at that end. Likewise, opening 326 may be provided near the exit 332 of second lumen 318 used to return blood to the patient, wherein fourth lumen 322 may have a cap 334 or other closure at that end. Therefore, using catheter 314 citrate may be infused into the arterial line to immediately provide anticoagulation of the blood entering the extracorporeal circuit. In order to provide anticoagulation throughout the entire circuit, calcium which reverses citrate anticoagulation, may be infused in the venous return line at the last possible location before blood is returned to the patient. The infusion solution lines (not shown) may have air detectors.

FIG. 10c illustrates a quadruple lumen vascular access catheter 314 according to another aspect of the present invention which connect to arterial blood line 14, 114, venous blood line 18, 118, citrate infusion line 28, 128 and calcium infusion line 42, 142 which may have different lengths and/or colors and which may be fused at a fixed point so that the circuit 12, 112 may only be connected together in the correct position. This arrangement ensures that the anticoagulant is always infused into the arterial line 14, 114 and the venous infusion solution is always delivered into the venous blood returned to the patient. The infusion solution lines 28, 128, 42, 142 may have air detectors (not shown).

As illustrated in FIG. 10d, quadruple lumen vascular access catheter 314 may include connectors 340 of different configurations, such as with the male and female line connectors reversed and of different colors. The catheter connection ends correspond to connection ends of the complementary type for the dialysis arterial and venous blood tubing 14, 114, 18, 118 as well as the anticoagulant and calcium infusion lines 28, 128, 42, 142. Therefore, the arterial and venous blood ports as well as the medication infusion ports may all be color-coded and mutually incompatible to prevent errors stemming from line reversal or other misconnection. This ensures that the circuit 12, 112 can only be connected with the catheter 314 in the correct configuration and that the anticoagulant is always infused into the arterial line and the venous infusion solution is always delivered into the venous blood returned to the patient. The infusion solution lines may have air detectors. The citrate and calcium ports on catheters 300 and 314 may have safety valve mechanisms to prevent air aspiration if one or both of the infusion lines disconnect, and the blood pump continues to run. Catheter 314 may be designed for short (3-5 hours long) IHD sessions with RCA where achieving high blood flows and hourly clearance goals is necessary.

A triple lumen catheter 350 with a single blood path (FIGS. 14a-14d) may be used for clinical applications where a high blood flow is not mandatory and a smaller diameter catheter (possibly even in a peripheral vein) may be acceptable. In this catheter 350, blood flow direction is alternating in a single lumen. A central lumen 352 may be used to withdraw blood from the patient during a first, arterial pump cycle, then on the next, venous pump cycle infuse blood back into the patient. A second lumen 354 representing an arterial cycle infusion pathway in communication with central lumen 352 may be used to infuse citrate anticoagulant or another solution into the incoming blood during the arterial pump cycle. During the venous cycle, a third lumen 356 representing a venous cycle infusion pathway in communication with central lumen 352 may be used to infuse calcium or another infusion into the blood before reentry into the circulation. The calcium infusion line may be clamped during the arterial pump cycle, and the anticoagulant infusion line may be clamped during the venous pump cycle.

As with catheters 300 and 314, the anticoagulant may be introduced into central lumen 352 via an opening 358 in the lumen wall at the tip of the catheter 350, such that the blood receives anticoagulant at the exact point where it enters the extracorporeal circuit. In order to provide anticoagulation throughout the entire circuit, calcium which reverses citrate anticoagulation, may be introduced into central lumen 352 via an opening 360 in the lumen wall at the tip of the catheter 350. Also as above, second lumen 354 and third lumen 356 may be provided with a cap 362 or 364, respectively, or other closure. As shown in FIGS. 14b and 14d, catheter 350 according to the present invention may accommodate blood tubing and infusion lines with different arterial and venous connectors.

This smaller catheter 350 may be particularly suited for heart failure patients who could benefit from 12-24-hour ultrafiltration with RCA using a peripheral vein access, and in whom placement of a large dialysis catheter for conventional access is difficult to justify because of the associated risk of complications. Catheter 350 requires a dialysis machine that is capable of the single needle dialysis operational mode (this is an optional module on modern dialysis machines). An additional benefit of this symmetrical design is that mixed up connection of the arterial and venous blood lines and/or the citrate and calcium infusion lines cannot result in any clinical complication as long as the temporal coordination between the blood pumping cycles and the citrate and calcium pumping cycles is preserved. The asymmetrical connector designs of FIG. 14d may only be needed if a dedicated RCA blood circuit tubing is used with asymmetrical blood and infusion line end designs.

Permanent accesses (arterio-venous fistulas and grafts) are very rarely utilized for CRRT because of fears of unnoticed venous access needle disconnection and subsequent catastrophic blood loss in the ICU. Similar concerns surround the use of permanent accesses in home nocturnal dialysis programs. In a two-needle dialysis session, when the venous needle disconnects (slips out of the access), the machine may not alarm and can cause massive blood loss with continued arterial pumping. As a solution, the catheter described above (FIGS. 14a-14d) can also be implemented as a circuit tubing connector that attaches to a single needle that is inserted into a permanent vascular access (single needle dialysis operational mode is required), which may be embodied as a quintuple lumen circuit connector 366 with a single blood path (FIGS. 15a-15d).

FIGS. 15a-15d illustrate a connector 366 (e.g., plastic) according to the present invention for circuit priming and to attach to a single vascular access needle from a standard dialysis blood line set and standard medication infusion lines for use with single needle dialysis operational mode. The central lumen 368 may be used to withdraw blood from the patient during an arterial pump cycle, then on the next, venous pump cycle infuse blood back into the patient. A needle connection 370 may be disposed on one end of central lumen 368. Connector 366 includes an arterial blood port 372 in fluid communication with central lumen 368 and arranged to be connected to an arterial blood line, a venous blood port 374 in fluid communication with central lumen 368 and arranged to be connected to a venous blood line, an arterial cycle infusion port 376 in fluid communication with central lumen 368 and arranged to be connected to an arterial infusion line for injection an infusion (e.g., citrate anticoagulant) during the arterial pump cycle, and a venous cycle infusion port 378 in fluid communication with central lumen 368 and arranged to be connected to a venous infusion line for injection of an infusion (e.g., calcium) during the venous pump cycle. Arterial and venous blood ports 372, 374 and arterial and venous infusion ports 376, 378 may branch outwardly from central lumen 368 as shown. In addition, needle connection 370 may be capped for circuit priming.

According to one aspect of the present invention, arterial and venous infusion ports 376, 378 may be closer to needle connection 370 than are arterial and venous blood ports 372, 374. With this configuration, the blood may receive anticoagulant as it enters the extracorporeal circuit, and may receive calcium as it leaves the circuit to be returned to the patient. As above, the venous infusion pump may be turned off during the arterial pump cycle, and the citrate infusion pump may be turned off during the venous pump cycle.

The design of connector 366 has the same benefits as far as mixed up connection of blood and/or medication lines are concerned as single lumen catheter 350 described above. The most important added benefit is that the connector 366 allows single needle dialysis to be performed on a permanent access. This operational mode is particularly suited for extended therapy sessions (e.g., nocturnal dialysis and CRRT) where a high blood flow is not needed, but the risk of a catastrophic bleed from access needle disconnection is greater. In the single needle mode, if the needle disconnects, the system may sense air in the arterial limb of the circuit with the next arterial (or intake) cycle and may alarm immediately, essentially eliminating the risk of a major unnoticed bleeding in the event of needle disconnection.

Figure 15A:
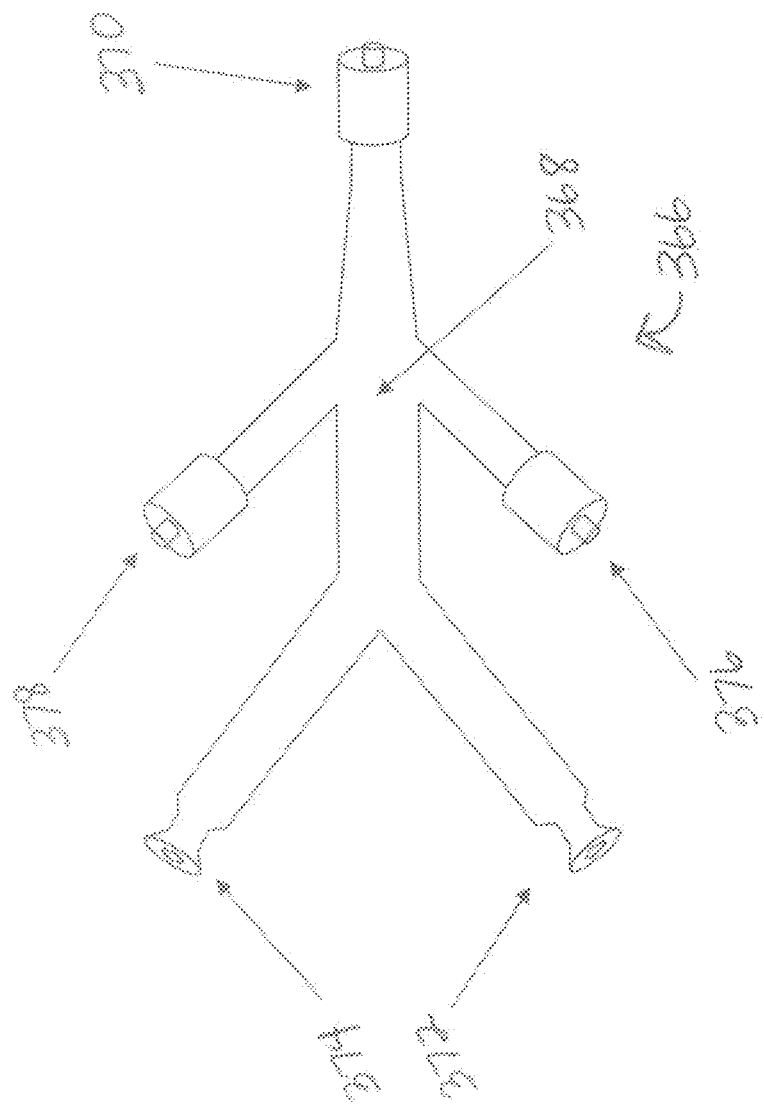
FIG. 15a illustrates a connector according to the present invention for circuit priming and for attachment to a single vascular access needle from a dialysis blood line set and medication infusion lines for use with single needle dialysis operational mode.
Figure 15B:
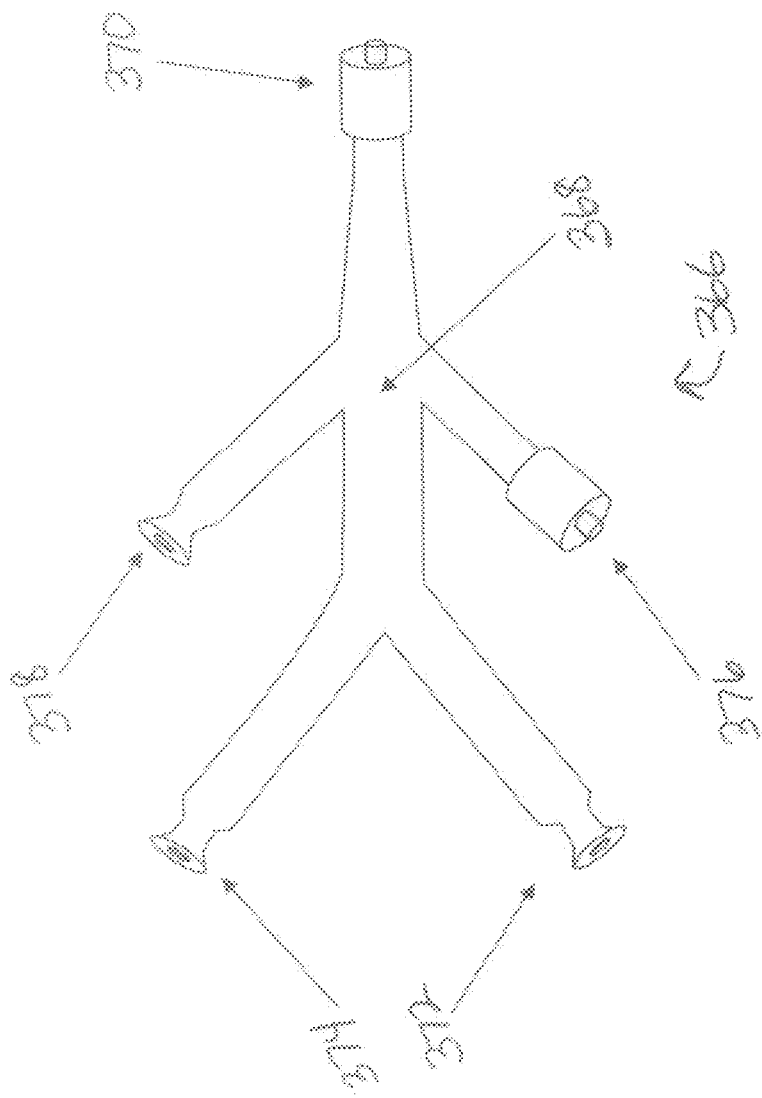
FIG. 15b illustrates a connector according to the present invention for circuit priming and for attachment to a single vascular access needle from a dialysis blood line set for use with single needle dialysis operational mode.
Figure 15C:
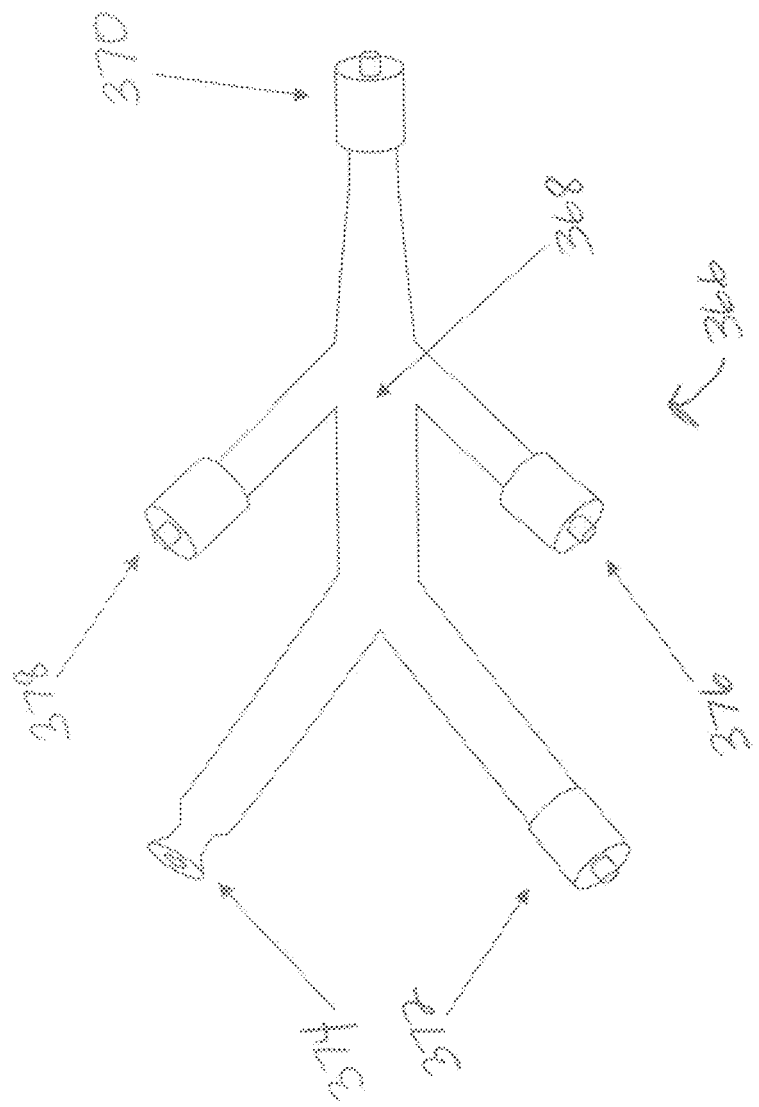
FIGS. 15c and 15d illustrate a connector according to the present invention for circuit priming and for attachment to a single vascular access needle from a citrate-dedicated dialysis blood line for use with single needle dialysis operational mode.
Figure 15D:
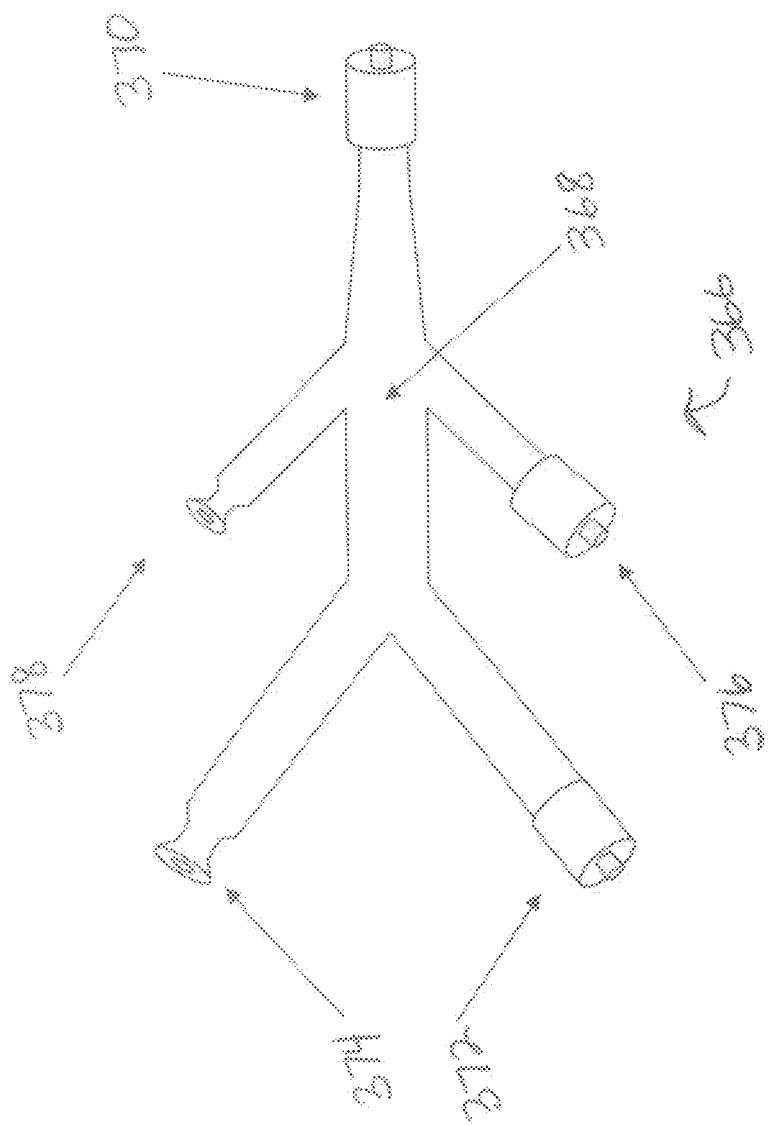

The connectors depicted in FIGS. 15a-15b connect to blood lines with symmetrical ends with the connector of FIG. 15a accommodating infusion lines with identical ends and the connector of FIG. 15b accommodating infusion lines with asymmetrical ends. The connectors depicted in FIGS. 15c-15d accommodate a citrate-dedicated blood circuit and connect to blood lines with asymmetrical ends, with the connector of FIG. 15c accommodating infusion lines with identical ends and the connector of FIG. 15d accommodating infusion lines with asymmetrical ends. Finally, these devices may be very useful during the initial circuit priming and safety check step. All lines can be connected, and the needle connection can be attached to a priming solution line to prime and test the system. After testing is complete, the priming line may be removed and the needle connected.

Special blood circuits, blood circuit connectors, and medication infusion lines designed for two-needle or conventional double lumen dialysis catheter access treatments with RCA according to the present invention are shown in FIGS. 11a-11b, 12a-12b, 13, and 16a-16b.

FIG. 11a illustrates connectors 380, 382 (e.g., plastic) according to the present invention which may be used as a kit to attach standard dialysis blood lines (independent arterial and venous blood circuit ends) for dialysis using separate arterial and venous needles. Connector 380 may be an arterial connector which includes a central lumen 384, a needle connection 386, and an arterial infusion port 388 for the infusion of citrate or other anticoagulant at the point where blood enters the extracorporeal circuit. A similar connector 382, with the male and female connectors reversed, may be a venous connector which includes a central lumen 390, a needle connection 392, and a venous infusion port 394 for the infusion of calcium at the point where blood is returned to the patient. The orientation of the male and female connectors may be maintained from the beginning to the end of each infusion line. As above, the location of the arterial and venous infusion ports 388, 394 provides anticoagulation throughout the entire circuit. FIG. 11a depicts a configuration where the blood ports 396, 398 are the same but the infusion ports 388, 394 are different. FIG. 11b depicts both the blood ports 396, 398 and infusion ports 388, 394 having different configurations, which may be used to attach a citrate-dedicated dialysis blood tubing (different arterial and venous blood circuit ends).

FIG. 12a illustrates an arterial infusion line connector 500 according to an aspect of the present invention which may be used to attach a citrate-dedicated dialysis arterial blood line using separate arterial and venous needles. Connector 500 includes a central lumen 502, a needle connection 504, an arterial blood port 506, and an arterial infusion port 508. As shown, arterial infusion port 508 and citrate infusion line 28, 128, 228 may be integrated into one unit, preventing accidental anticoagulant infusion disconnection. Citrate infusion line 28, 128, 228 may have a specific key segment 510 configured to be received by citrate pump 34, 134, 234 (and not calcium pump), as well as a specific bag connector 512 configured to be received by the citrate bag (and not calcium bag). This arrangement provides anticoagulation throughout the entire circuit and ensures that the citrate can only be infused into the arterial limb of the blood circuit.

Figure 12B:
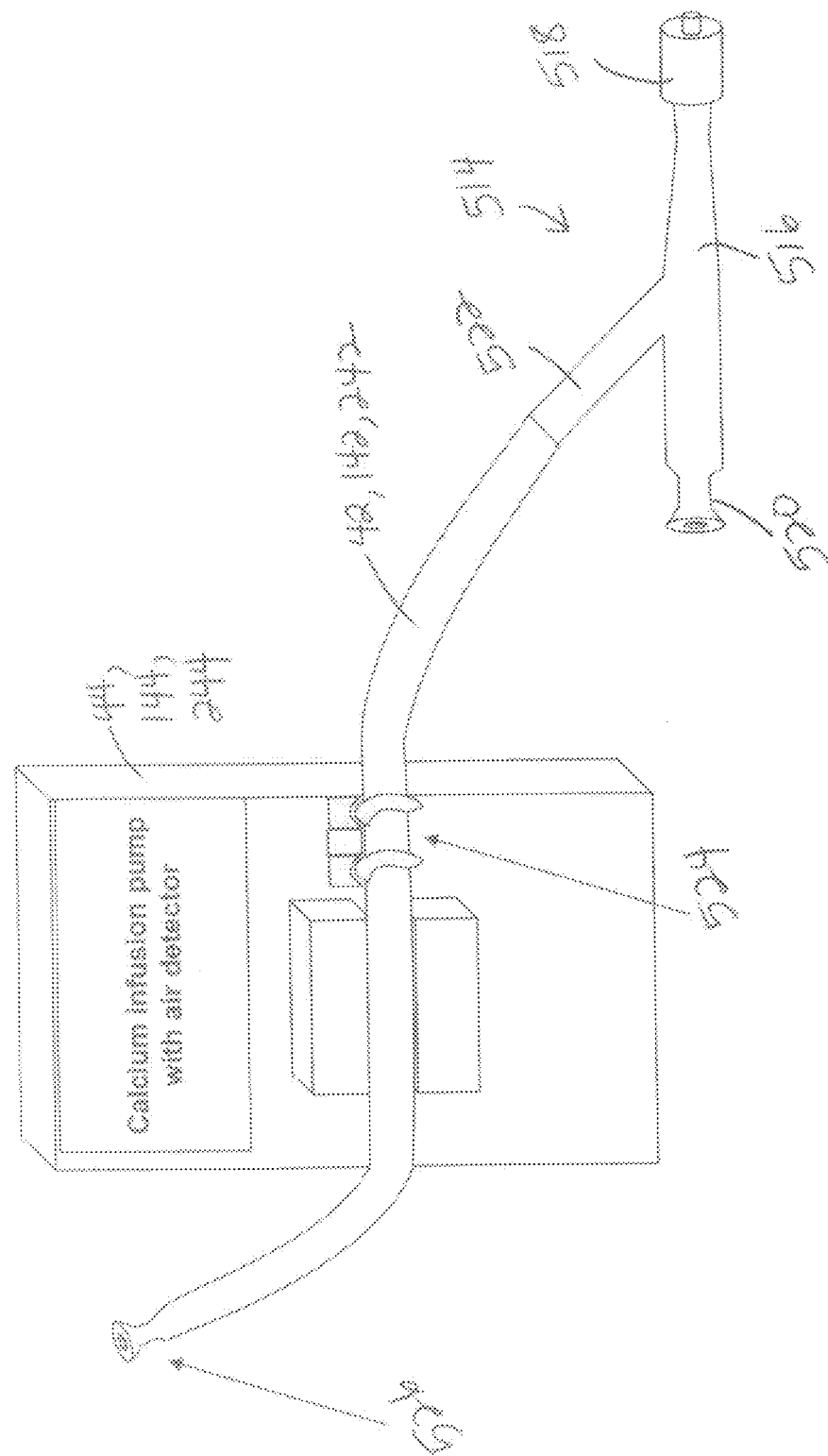
FIG. 12b illustrates a venous infusion line connector according to the present invention which may be used to attach a standard or citrate-dedicated dialysis venous blood line using separate arterial and venous needles.

FIG. 12b illustrates a venous infusion line connector 514 according to an aspect of the present invention which may be used to attach a standard or citrate-dedicated dialysis venous blood line using separate arterial and venous needles. Connector 514 includes a central lumen 516, a needle connection 518, a venous blood port 520, and a venous infusion port 522. As shown, venous infusion port 522 and calcium infusion line 42, 142, 242 may be integrated into one unit, preventing accidental calcium infusion disconnection. Calcium infusion line 42, 142, 242 may have a specific key segment 524 configured to be received by calcium pump 44, 144, 244 (and not citrate pump), as well as a specific bag connector 526 configured to be received by the calcium bag (and not citrate bag). If a citrate dedicated blood tubing is used, the calcium can only be infused into the venous limb of the blood circuit.

Figure 13:
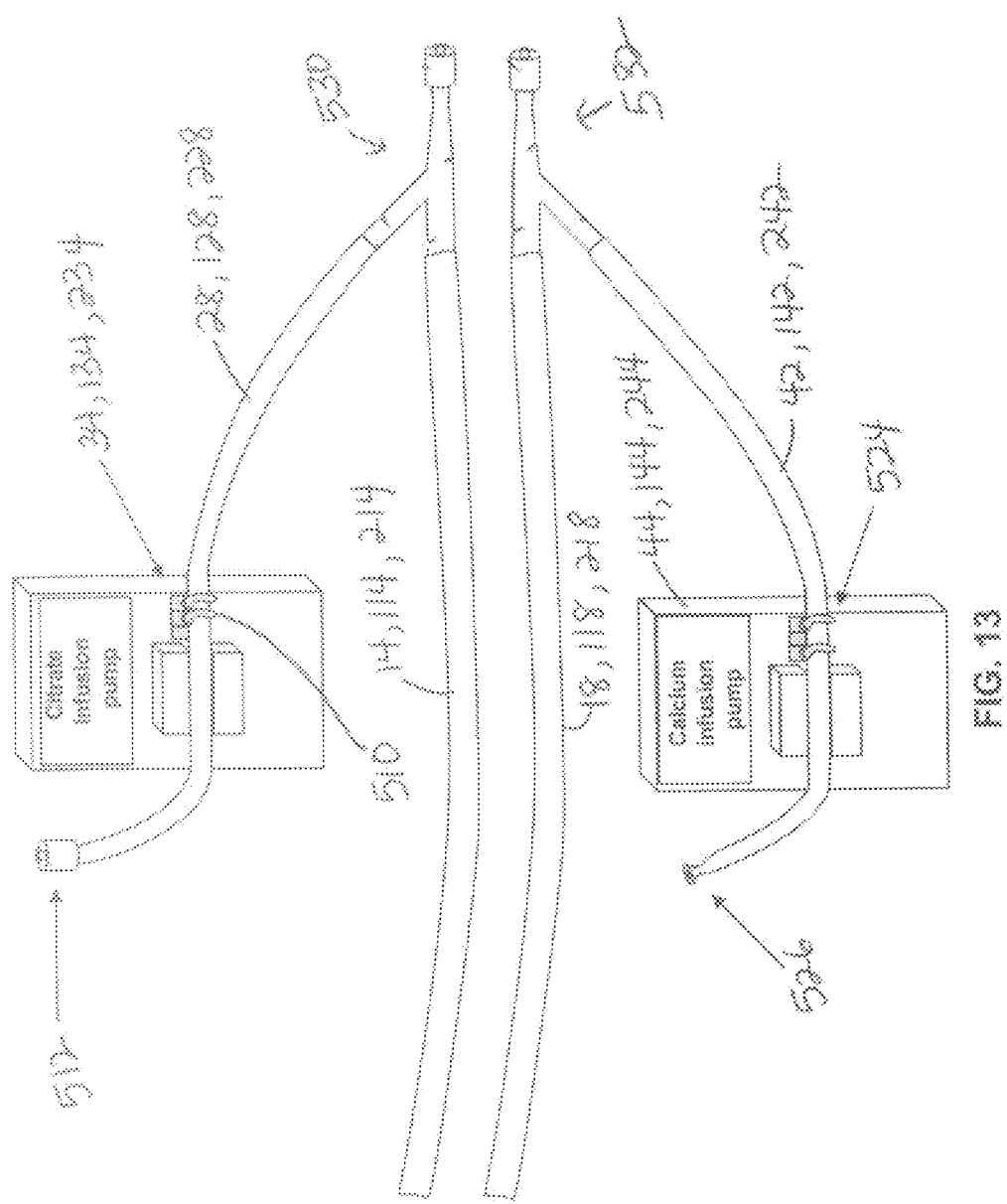
FIG. 13 illustrates citrate-dedicated blood circuit tubing with integrated arterial and venous medication infusion line connectors according to the present invention which may be used to connect the extracorporeal circuit to the patient using separate arterial and venous access needles or a double lumen hemodialysis catheter.

FIG. 13 illustrates citrate-dedicated blood circuit tubing with integrated arterial and venous medication infusion line connectors 530, 532 according to the present invention which is used to connect the extracorporeal circuit to the patient using separate arterial and venous access needles or a traditional double lumen hemodialysis catheter. The advantages to this configuration are that the connectors 530, 532, blood lines 14, 114, 214 and 18, 118, 218, and infusion lines 28, 128, 228 and 42, 142, 242 are integrated into one unit, preventing accidental citrate or calcium infusion disconnection. Integration of the citrate infusion line 28, 128, 228 with the arterial connector 530 and the calcium infusion line 42, 142, 242 with the venous connector 532 ensures that anticoagulant only enters the blood circuit in the arterial limb and calcium only enters the venous limb.

Figure 16A:
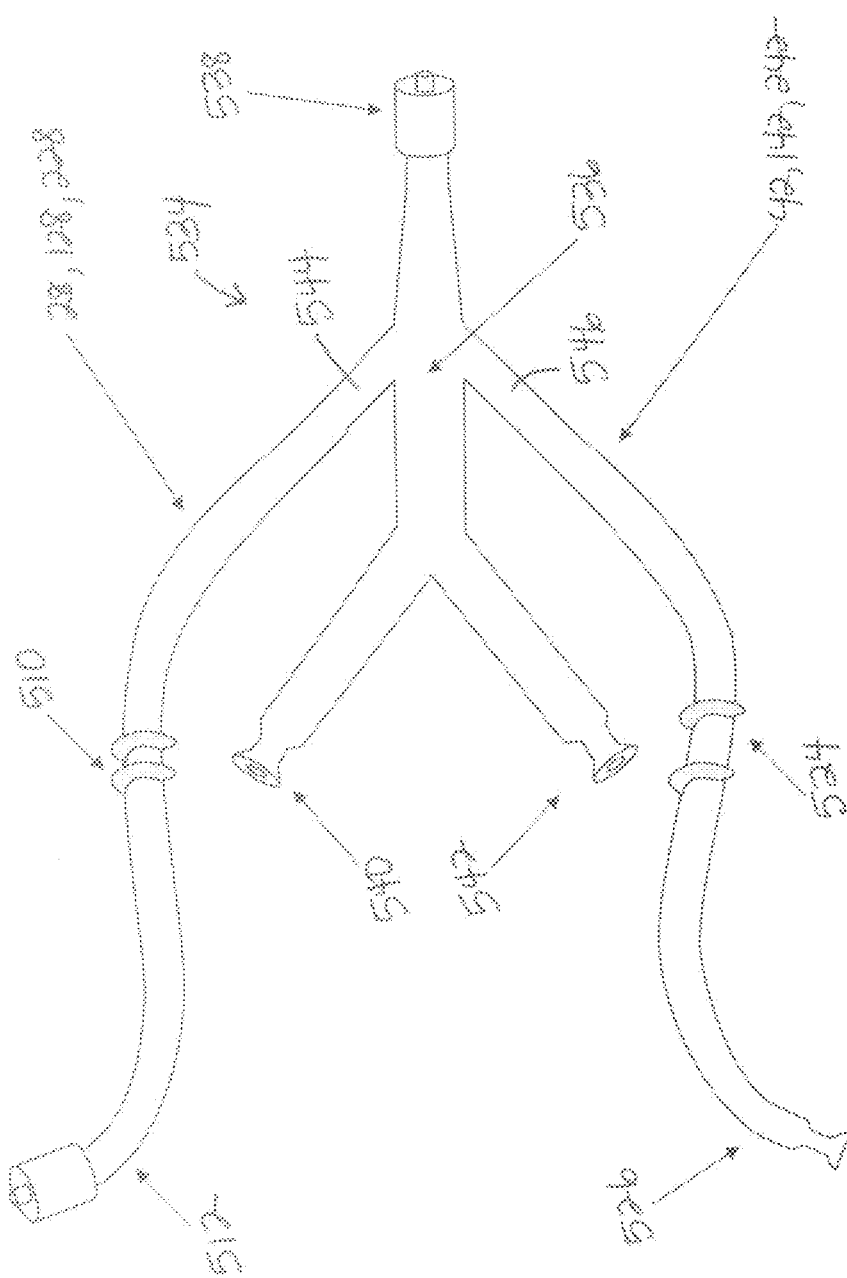
FIG. 16a illustrates a connector according to the present invention for attachment to a single vascular access needle or to a single lumen catheter from a dialysis blood line for use with single needle dialysis operational mode.
Figure 16B:
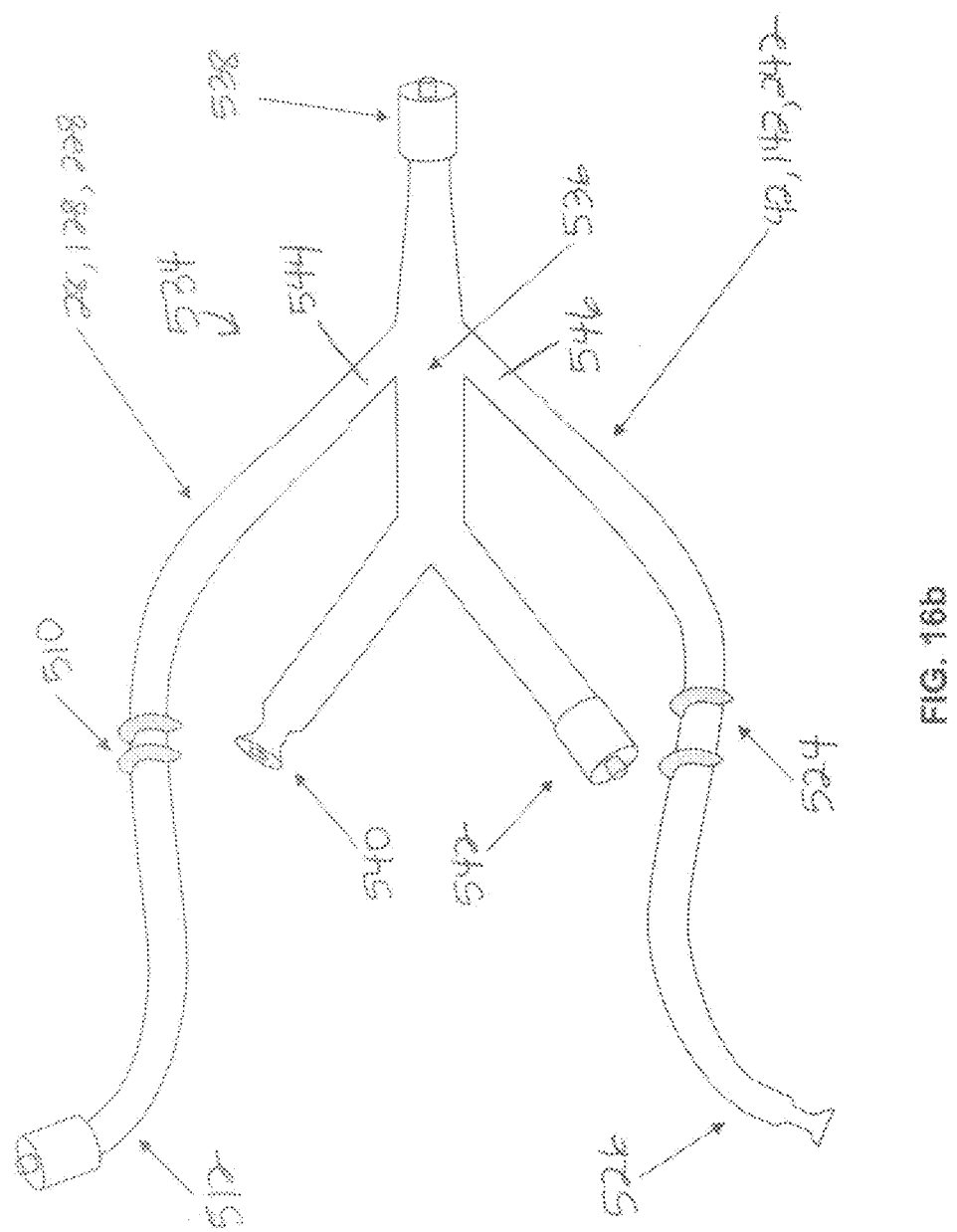
FIG. 16b illustrates a connector according to the present invention for attachment to a single vascular access needle or to a single lumen catheter from a citrate-dedicated dialysis blood line for use with single needle dialysis operational mode.

FIGS. 16a-16b illustrate a connector 534 (e.g., plastic) according to the present invention to attach to a single vascular access needle or to a single lumen catheter from a standard dialysis blood line for use with single needle dialysis operational mode. Connector 534 includes a central lumen 536, needle connection 538, arterial blood port 540, venous blood port 542, arterial infusion port 544, and venous infusion port 546. Arterial infusion port 544 may be integrated with arterial infusion line 28, 128, 228, and venous infusion port 546 may be integrated with venous infusion line 42, 142, 242, eliminating the chance of infusion line disconnection. FIG. 16a depicts arterial and venous blood ports 540, 542 having the same configuration, and FIG. 16b depicts arterial and venous blood ports 540, 542 having different configurations, such as for accommodating citrate-dedicated blood circuit ends.

In the above embodiments, the medication infusion lines may be made of rigid plastic material that minimizes changes in the filling volume of the lines with the pumping cycles to guarantee the greatest accuracy of infusate delivery. The connection to the citrate or calcium infusion solution bag should be above the pumping segment and air detector portions of the IV infusion pumps, so that accidental disconnection from or emptying of the bag would be detected immediately by detecting air in the line.

The catheters and connectors according to the present invention which may be used for RCA may maximize anticoagulation efficiency and (in the case of the single needle tubing connector) will allow safe use of permanent vascular accesses for 12 to 24 hour CRRT or home nocturnal hemodialysis. The single lumen catheter for RCA may allow the more common use of a peripheral vein for isolated UF with RCA for example for volume overloaded heart failure patients in whom placement of a traditional access catheter may be deemed too aggressive. When high blood flows and hourly clearances are not needed but accidental venous access disconnection could be fatal as in CRRT and nocturnal dialysis, a triple lumen RCA catheter or a single needle plastic adapter, each with a single blood pathway and symmetrical or asymmetrical (to accommodate asymmetrical infusion line ends) citrate- and calcium infusion connections may be used. Proper coordination of the arterial (aspiration) blood pump cycle with activation of the citrate infusion pump and the venous (re-infusion) blood pump cycle with the activation of the calcium infusion pump ensures proper circuit anticoagulation as well as the reversal of the anticoagulation just when the processed blood is returned into the patient. In the event of access disconnection, the machine alarms when a pressure change is detected and/or air is aspirated into the blood line in the arterial (aspiration) cycles following the disconnection, preventing clinically significant blood loss.

The citrate and the calcium bags may have different and mutually incompatible connection locking mechanisms to completely prevent inadvertent wrong connection of the bags. In addition, the total conductivity of the citrate and calcium infusions will be substantially different. This will help detect wrong connection of the bags through the online clearance-monitoring tool or by direct conductivity measurements of the infusates themselves. Conductivity monitoring of the anticoagulant infusion line and the calcium plus magnesium infusion line by any method to detect the presence of inappropriate fluid conductivity and hence inappropriate fluid flowing in these tubing segments is fully contemplated according to the present invention.

The conductivity-based online clearance monitor according to the present invention is now discussed in further detail.

Traditional safety monitoring with laboratory measurements of total and ionized calcium and Lytes 7 with anion gap every 6 hours (as in the current clinical protocols in use) is not sufficient for treatments with high hourly clearance goals. While traditional laboratory monitoring is insufficient to ensure the safety of RCA with high hourly clearance goals, such goals are becoming the standard of care and are easily achieved with online fluid generation at a reasonable cost. However, if the prescription is carefully written and the various fluid flows and compositions are defined appropriately, RCA with high clearance goals will keep all major electrolyte values in the normal range. The only variable in the system 10, 110, 210 that could often be a cause of complications is the possibly declining filter performance, for example with progressive protein fouling of the membrane and/or clotting of the fiber bundle. Therefore, in the absence of a commercially available online citrate and/or ionized calcium sensor, online filter clearance (performance) monitoring in conjunction with safe prescriptions may be utilized for patient safety in the implementation of online safety monitoring for the RCA system 10, 110, 210 according to the present invention.

In order to write a safe prescription that prevents systemic citrate accumulation even in shock-liver (anhepatic) patients, the present invention includes a calculation method whereby the maximal systemic citrate concentration that can develop in the absence of citrate metabolism is calculated for any RRT prescription. The principles of writing a safe prescription are explained below. In essence, the maximum possible systemic citrate level during RCA with a given prescription needs to be calculated. The abbreviations used are as follows:

$C_{Cit}$: the concentration of citrate in the anticoagulant fluid
$Q_{Cit}$: the flow rate of the anticoagulant fluid
$C_{sys}$: steady state systemic plasma citrate concentration in a patient with zero citrate metabolism
$C_{ven}$: the plasma citrate concentration in the blood circuit venous limb before the blood is returned to the patient
E: apparent circuit post-anticoagulant infusion arterial plasma citrate to therapy fluid citrate concentration difference reduction ratio during a single filter pass ("plasma citrate extraction ratio")
$D_{Cit}$: apparent citrate plasma dialysance ($D_{Cit}^*$ when expressed for the adjusted $Q_{BCit}$ during calculations and $D_{Cit}$ when expressed for the unadjusted $Q_P$)
$D_{Cond}$: apparent "summary conductivity solute" whole blood dialysance (this value may be predicted from filter $KoA_{Cond}$, Qb, Qd, $Q_{pre}$, $Q_{post}$ and $Q_{uf}$ and/or determined by the sodium citrate bolus based measurement or by the traditional online conductivity dialysance measurement method (for high blood flow treatment sessions))
$Q_B$: the effective blood flow for the solute analyzed; $Q_{BCond}$ is closely equal to the arterial whole blood water flow for conductivity and $Q_{BCit}$ is closely equal to arterial blood plasma water flow for citrate. In the case of citrate, for the calculation of "E" the plasma water volume is adjusted for the free water shifts between the RBCs and the plasma space in response to the hypertonic citrate anticoagulant and the mildly hypotonic pre-filter online therapy fluid infusion (when applicable) and $D_{Cit}^*$ is also calculated with these adjustments. Once $E=D_{Cit}^*/Q_{BCit}$ ($=D_{Cit}/Q_P$) is derived, the unadjusted $Q_p$ and $D_{Cit}$ can be used to simplify the subsequent calculation of $C_{Sys}$.
$Q_P$: The arterial blood plasma flow without adjustment for the effects of the hypertonic anticoagulant infusion (These shifts are accounted for during the calculation of E).

$C_{tf}$: Citrate concentration in the therapy fluid $C_{inf}$: The increase in the arterial plasma citrate concentration as a result of the anticoagulant infusion, before any pre-filter replacement fluid infusion or adjustment for water shifts between blood fluid compartments. (These shifts are accounted for during the calculation of E). $C_{inf}=C_{Cit}/(Q_{BCit}/Q_{Cit})$.

Figure 18:
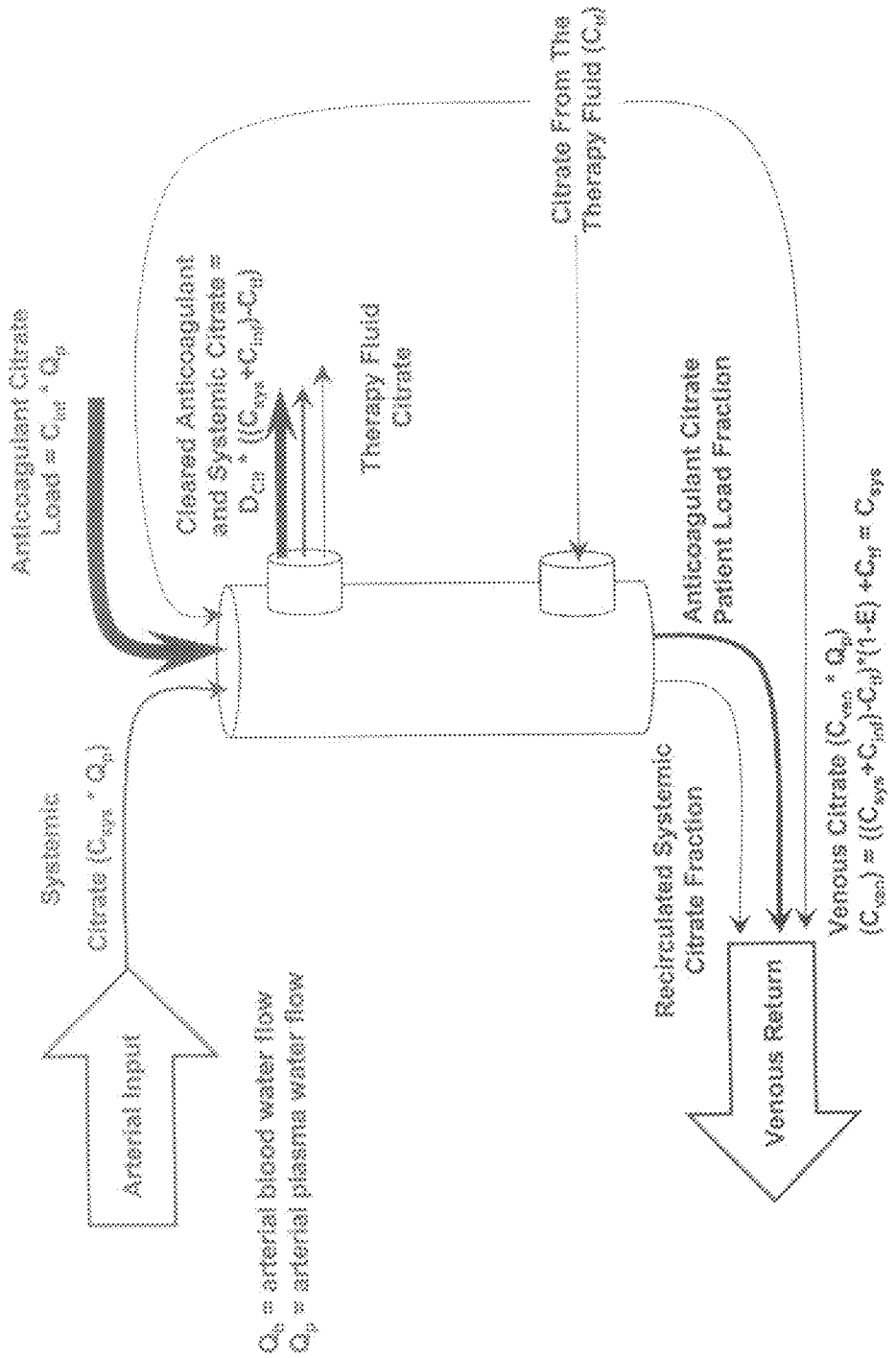
FIG. 18 depicts a calculation according to the present invention of the maximum possible systemic citrate level during RCA.

In the anhepatic patient, there is no systemic citrate metabolism and citrate clearance is solely through the extracorporeal circuit, where FIG. 18 illustrates an explanation of the calculation of the maximum possible systemic citrate level during RCA. In the anhepatic patient, the steady state is reached when $C_{sys}=C_{ven}$. If the variable E is defined as: $E=C_{inf}/(((C_{sys}+C_{inf})-C_{tf})$ then $((C_{sys}+C_{inf})-C_{tf})^*(1-E)+C_{tf}=C_{sys}$ will be true. Rearrangement yields $C_{sys}=C_{inf}^*(1-E)/E+C_{tf}$. In the steady state, the anticoagulant load $Q_p^*C_{inf}=D_{Cit}^*((C_{sys}+C_{inf})-C_{tf})$, the plasma water citrate dialysance multiplied by the citrate concentration gradient between the anticoagulated arterial plasma and the therapy fluid. Rearrangement yields $D_{Cit}/Q_P=(C_{inf}/(C_{sys}+C_{inf}-C_{tf}))=E$. $D_{Cit}$ can be calculated from $D_{Cond}$; the $D_{CondB}$ (whole blood conductivity dialysance) is measured by the online clearance module. The flows $Q_B$ and $Q_P$ are known. Finally, $C_{sys}$ is calculated from E, $C_{tf}$ and $C_{inf}$.

Therefore, the steady state is reached when the new citrate loaded into the combined patient and CRRT circuit space is equal to the net citrate removed from the patient and CRRT circuit combined in the circuit effluent as shown in Equation 1:

$$\text{Citrate load}=Q_P^*C_{inf}=D_{Cit}^*((C_{sys}+C_{inf})-C_{tf})=\text{Citrate removal} \qquad 1:$$

The citrate removal is by definition the apparent plasma citrate dialysance multiplied by the citrate concentration gradient. For simplicity, after calculating E we use $Q_P$ and the apparent plasma $D_{Cit}$ (instead of QBCit and DCit*) without adjustment for water shifts between blood fluid compartments as these adjustments were made during the calculation of E.

Rearrangement yields Equation 1*:

$$(C_{inf}/((C_{sys}+C_{inf})-C_{tf}))=D_{Cit}/Q_P=E \qquad 1^*:$$

$D_{Cit}/Q_P=D_{Cit}^*/Q_{BCit}$ can be calculated from the measured total $D_{Cond}$ (see below); the $D_{Cond}$ (apparent whole blood conductivity dialysance) is measured by the online dialysance module and $Q_{BCond}$ and $Q_{BCit}$ are known. When calculating $D_{Cit}^*$ from $D_{Cond}$, the differences in the summary sieving and diffusivity coefficients for the negatively charged citrate and citrate-Ca or citrate-Mg complexes (probably slightly above 1) as compared to the summary sieving and diffusivity coefficients for conductivity (equal to 1) are considered. In general, a low estimate for E can usually be calculated online if the online conductivity dialysance can be measured during RRT with RCA with clinically acceptable accuracy (method described below).

Using the definition of E as: $E=(C_{inf}/((C_{sys}+C_{inf})-C_{tf}))$ and some rearrangement, Equation 2 will then be true:

$$((C_{sys}+C_{inf})-C_{tf})^*(1-E)+C_{tf}=C_{sys} \qquad 2:$$

Alternatively, in the anhepatic patient, the steady state also means that $C_{sys}=C_{ven}$, in other words the venous blood plasma citrate concentration returning to the patient will be equal to the arterial (systemic) plasma citrate concentration before the infusion of the fresh anticoagulant (we ignore the effects of the minimal net ultrafiltration). Therefore, Equation 2 again follows with a different logic using the initial definition of E:

$$C_{ven}=C_{sys}=((C_{sys}+C_{inf})-C_{tf})^*(1-E)+C_{tf} \qquad 2:$$

Finally, solving Equation 2 for $C_{sys}$ yields Equation 3:

$$C_{sys}=C_{inf}^*(1-E)/E+C_{tf} \qquad 3:$$

A few examples for calculating $C_{sys}$ with Equation 3 are given below. During pre-post-dilution CVVH for CRRT, the maximal practical E will be about 0.75. If the therapy fluid has no citrate in it, ($C_a=0$), then even with very strong anticoagulation with $C_{inf}=7.5$ mM the $C_{sys}$ will be 2.5 mM or less (less if there is liver metabolism of citrate). If the therapy fluid has citrate with $C_{tf}=1.2$, then with lesser, but still strong, anticoagulation with $C_{inf}=6$ the $C_{sys}$ will be 3.2 mM or less (less if there is liver metabolism of citrate). When using the RCA system 10, 110, 210 according to the present invention, the maximal practical E may be about 0.66. The $C_{inf}$ can be calculated according to its definition and will be 8 mM with the CitrateEasy16 fluid and a 2 liter plasma to 1 liter CitrateEasy16 fluid flow ratio. Both the pre-dilution fluid and the post-dilution fluid then can be thought of as replacement fluids with $C_{tf}=0$. The maximum $C_{sys}$ will be 4 mM or less (if there is liver metabolism).

During pre-dilution CVVHDF or pure SLED for CRRT, the maximal practical E will be about 0.85. Even if the therapy fluid has citrate in it, ($C_{tf}=1.2$) and even with very strong anticoagulation with $C_{inf}=7.5$ the $C_{sys}$ will be 2.7 mM or less (less if there is liver metabolism of citrate). If the therapy fluid has no citrate with $C_{tf}=0$ and even with very strong anticoagulation with $C_{inf}=7.5$ the $C_{sys}$ will be 1.5 mM or less (less if there is liver metabolism of citrate).

During high volume pre-post hemofiltration (HVHF), intermittent hemodialysis (IHD) or postHDF with high blood and therapy fluid flow rates, the maximal attainable E can be as low as 0.6-0.7. Under these circumstances, the anticoagulation intensity, $C_{inf}$ must be reduced to about 4-5 mM and $C_{tf}$ should be preferably zero or maximum 0.8 mM. Also, a filter with the highest surface area, flux and resultant citrateKoA may be utilized. All of these alterations ensure that $C_{sys}$ remains in the 2-3 range even in the absence of liver function (not mentioning the fact that it is unlikely that a patient with no liver metabolism of citrate would be encountered in the outpatient setting).

In summary, in Equation 3 control over all the variables is possible. By selecting the appropriate citrate pump speed for a given arterial blood plasma flow, $C_{inf}$ may be defined. By carefully designing the therapy fluid concentrate, $C_{tf}$ may be selected. By using an appropriate filter and blood flow and therapy fluid flow rates and a database of $D_{Cond}$ and $D_{Cit}$ values predicted from these variables, E can be programmed to the target 0.6-0.9 range, as long as the filter performance remains unchanged from baseline. This last prerequisite is important to the continued safety of the RCA after the start of the procedure. Finally, a low estimate for E can be monitored online by monitoring $D_{Cond}$ online and calculating E. The need for online filter performance monitoring may require that the RCA system 10, 110, 210 according to the present invention have an online clearance module that works at all blood and therapy fluid flows, including the low flows typically used for CRRT. The only possible exception may be in the operational mode of pre- and post-dilution hemofiltration as here the all-convective citrate clearance is highly reliable and is easily calculated.

The present invention provides a novel online conductivity dialysance monitor (OCM) for RRT with RCA. A commercially available module essentially determines conductivity dialysance by altering the conductivity of the fresh dialysis fluid and measuring the subsequent conductivity change of the spent dialysate (see U.S. Pat. Nos. 6,702,774 and 6,939, 471). Common to all previous implementations is the concept of varying the sodium concentration (and conductivity) of the fresh dialysate by about 10% and measuring the reflection of these programmed variations in the conductivity of the spent dialysate. This approach is not feasible with the low therapy fluid flow rates of CRRT.

Using the currently available methods, changing the composition of the fresh dialysate takes a very long time at the low dialysate flow rates typically used for CRRT. The rate of change is related to the ratio of the dialysate flow rate ($Q_d$) and the volume of the concentrate mixing chamber and dialysate tubing $V_m$, ratio=$Q_d/V_m$. At the low dialysate flow rates used in CRRT, the pumping of the dialysate also becomes intermittent, causing further difficulties in the measurement. Finally the effects of access-, cardiopulmonary- and systemic recirculation may all become more pronounced. At the very high fractional plasma clearance rate (K) needed for the safe removal of citrate (K>=80% of blood circuit plasma flow ($Q_p$)), even large changes in the fresh dialysate conductivity will cause only modest (<=30% of the change in the fresh fluid), and therefore difficult to precisely measure changes in the effluent fluid conductivity. Finally, theoretically the KoA (mass transfer area coefficient; a standardized measure of membrane performance) of the membrane could be determined at a conveniently higher $Q_d$, using techniques of the current art. However, this KoA would not be the same as the KoA present at the low $Q_d$ values of CRRT because of fluid layering and channeling effects that develop at those low flow rates.

The current art does not utilize the possibility of introducing a bolus of concentrated sodium citrate or other conductive solution into the arterial limb 14, 114, 214 of the blood circuit 12, 112, 212. Hemodialysis machines in current clinical use do not have integrated sodium pumps on the blood circuit. However, the citrate pump 34, 134, 234 necessary for anticoagulant administration in the RCA system 10, 110, 210 according to the present invention may in essence be a concentrated sodium solution pump and is eminently suited for the purpose of online conductivity dialysance monitoring. Therefore, in a fundamental departure from the practiced art, the present invention includes a novel modification of conductivity-based hemofilter clearance monitoring in which the conductivity dialysance may be determined by using the concentrated sodium citrate pump 34, 134, 234 to modulate the incoming blood sodium citrate content (and thereby conductivity) by means of a small bolus of trisodium citrate infusion (as opposed to modulating the fresh therapy fluid sodium concentration, which will be kept constant). The effects of such modulation are a precise and immediate change in the arterial blood plasma sodium citrate concentration and conductivity, as shown in FIG. 19 for the calculation of the effect of the sodium citrate bolus, and an almost immediate change in the filter effluent fluid sodium content and conductivity, as shown in FIGS. 20a-20b.

Figure 19:
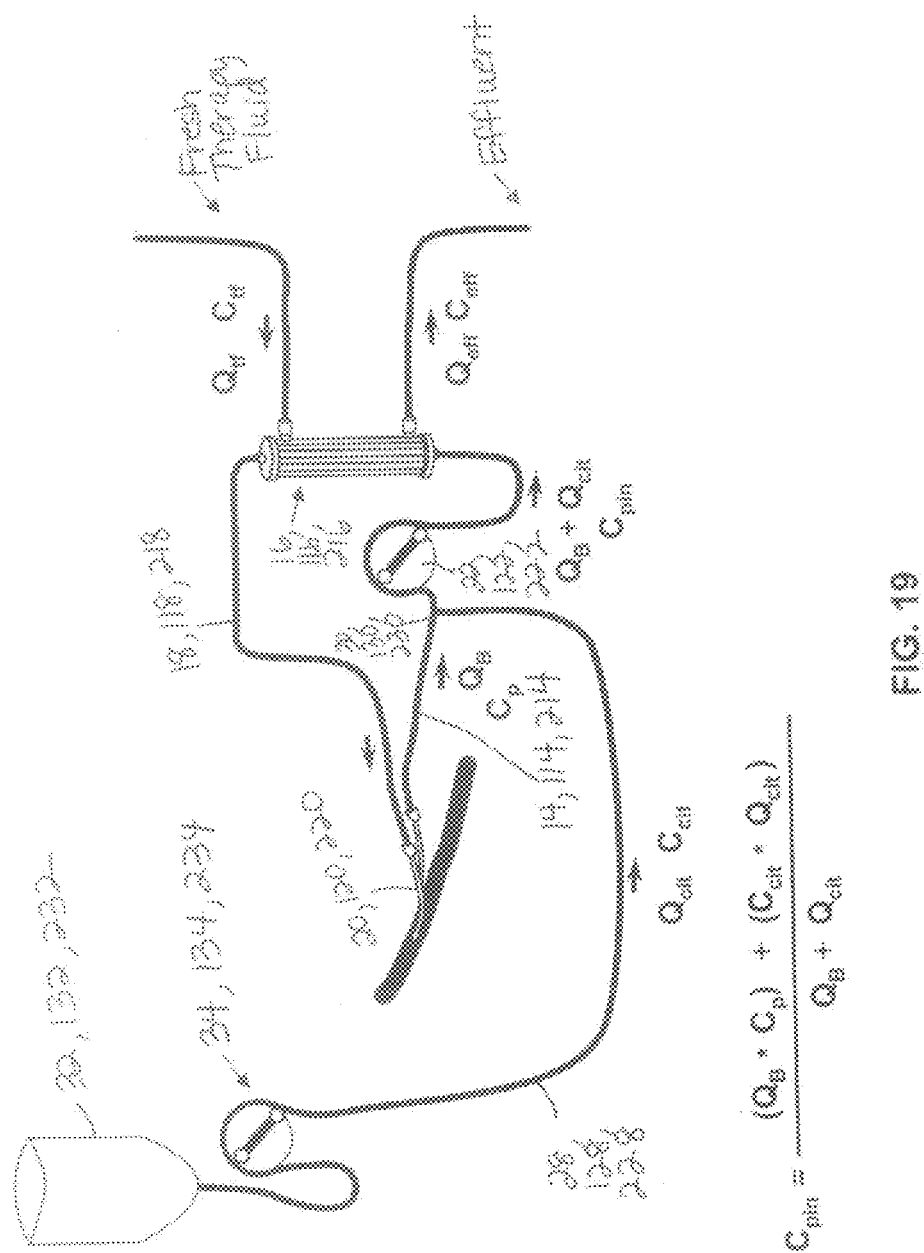
FIG. 19 depicts a calculation according to the present invention of the conductivity of plasma ($C_{pin}$) in the arterial limb of the extracorporeal circuit entering the hemodialyzer.
Figure 20A:
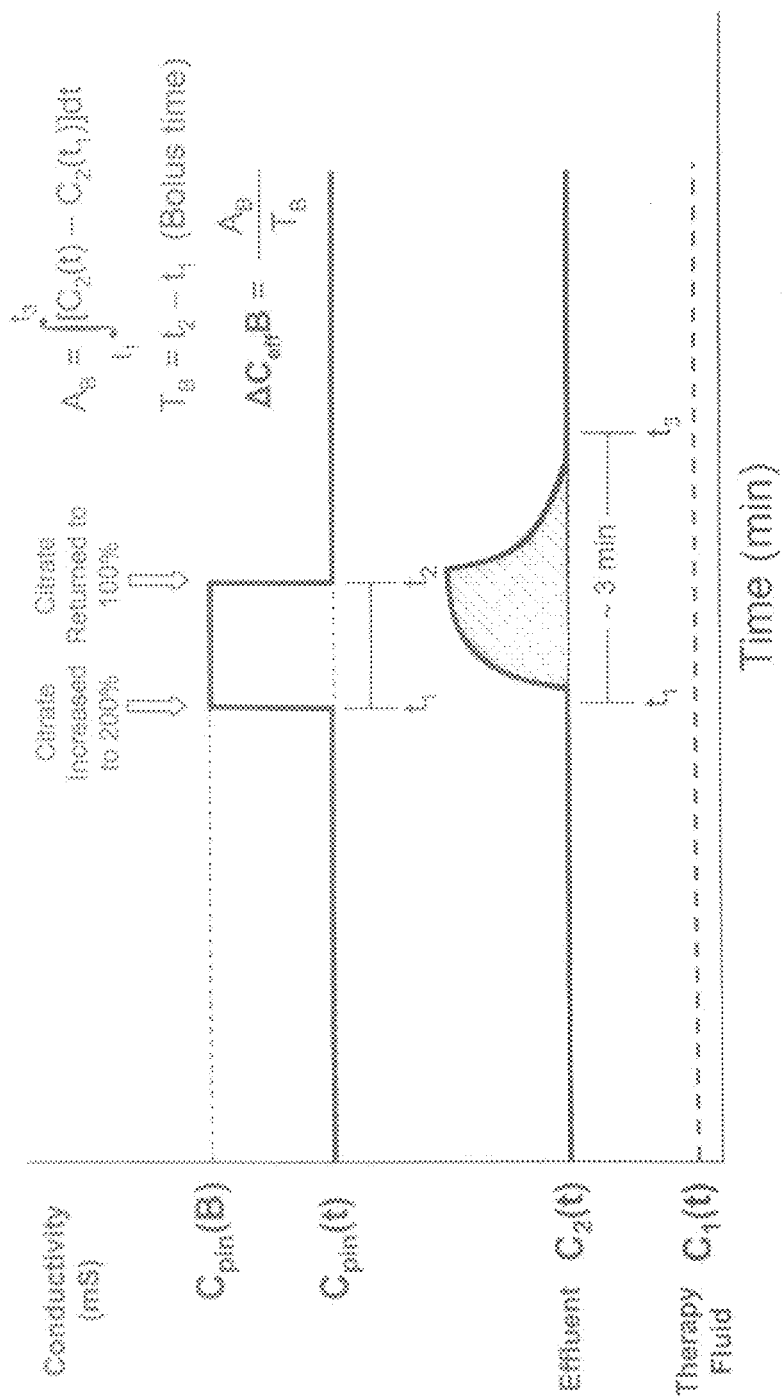
FIG. 20a illustrates an OCM in accordance with the present invention.

In particular, FIG. 19 illustrates a calculation of the conductivity of plasma ($C_{pin}$) in the arterial limb of the extracorporeal circuit entering the hemodialyzer. All parameters are known or measured values except $C_p$ and hence $C_{pin}$. FIG. 20a illustrates an online clearance monitor in accordance with the present invention. A conductivity sensor C1 can be placed in the therapy fluid line before the fluid is infused into the filter (into the dialysate and/or the blood compartment). A second conductivity sensor C2 can be placed in the effluent line of the dialysis machine. Increasing the concentration of sodium citrate (and possibly sodium chloride or sodium bicarbonate) and hence the conductivity of the blood plasma ($C_{pin}$) entering the dialyzer for a short period of time ($T_B=t_2-t_1$; bolus method) produces a corresponding response in the sodium concentration and hence the conductivity measured in the effluent, $C_2(t)$. Data from the transient increase in effluent conductivity can be used to determine the dialyzer conductivity dialysance online. The $C_2(t)-C_1(t)$ (inter-bolus) persistent difference can also be used for less accurate but truly continuous monitoring of conductivity dialysance and hence filter performance in between boluses. (Differences in $C_1(t)$, $C_2(t)$ and $C_{pin}(t)$ are not to scale). During the positive bolus method, QB may be reduced to keep (QB+Qcit) unchanged.

Figure 20B:
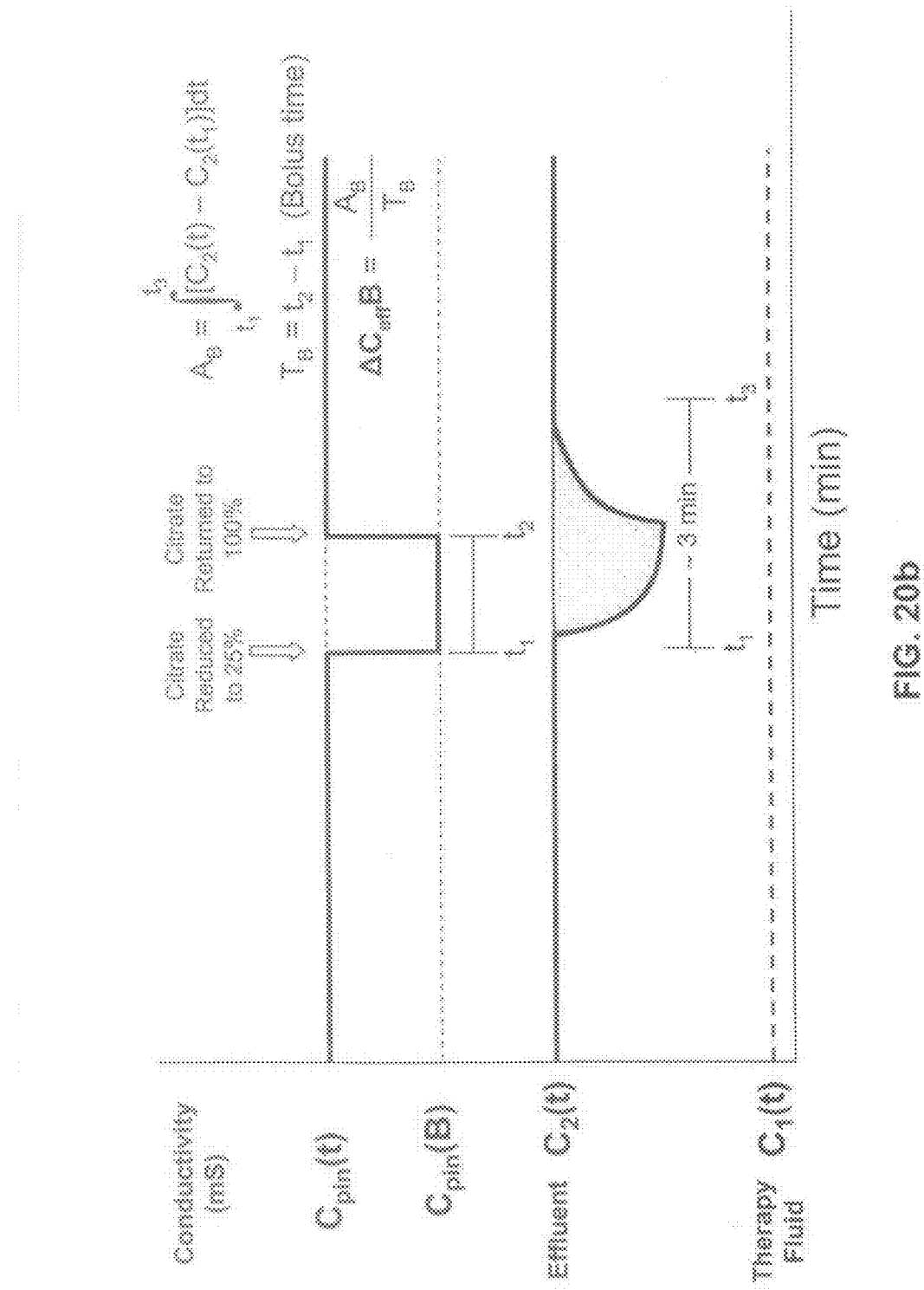
FIG. 20b illustrates an OCM in accordance with another aspect of the present invention.

FIG. 20b also illustrates an online clearance monitor in accordance with the present invention. Decreasing the concentration of the anticoagulant sodium citrate (and sodium chloride or sodium bicarbonate possibly with it) and hence the conductivity of the blood plasma ($C_{pin}$) entering the dialyzer for a short period of time ($T_B=t_2-t_1$; "negative bolus" method) produces a corresponding response in the sodium concentration and hence the conductivity measured in the effluent, $C_2(t)$. Data from the transient decrease in effluent conductivity can be used to determine the dialyzer conductivity dialysance online. The $C_2(t)-C_1(t)$ difference can also be used for less accurate but truly continuous monitoring of filter performance in between boluses. (Differences in $C_1(t)$, $C_2(t)$ and $C_{pin}(t)$ are not to scale). Also, both $A_B$ and $\Delta C_{eff}B$ are negative values as expected for the negative bolus method. During the negative bolus method, QB may be increased to keep (QB+Qcit) unchanged.

The rate of change of the effluent conductivity will be related to the ratio $Q_b/V_f$, where $Q_b$ is the arterial blood flow rate and $V_f$ is the blood filling volume of the filter. This ratio is much larger than the $Q_d/V_m$ mentioned earlier in the description of prior art, and ensures that the method will be practical for the low fluid flow rates prevalent in CRRT prescriptions. The magnitude of the change will be related to the ratio of $Q_b/Q_d$ and usually will be about 50-80% of the change in the plasma conductivity, allowing precise measurements. Due to the 90-100% fractional extraction of the conductivity bolus in the CRRT operational mode, cardiopulmonary and systemic recirculation is predicted to have an insignificant effect on the measurement, particularly if a high-low bolus technique is used. Access recirculation may have a more marked effect; however, this can be corrected for by measuring the degree of recirculation with the hematocrit sensor. Overall, the apparent conductivity dialysance measured by the blood side bolus and dialysate side sensor method will give a comparably accurate indirect tool to monitor conductivity (and indirectly citrate and urea) dialysance as the prior art. This method, however, will work at very low QB values and will not result in salt loading of the patient, both improvements over prior art.

The following equations show the calculation of the apparent conductivity dialysance for all treatment modalities as measured from effluent conductivity changes and the calculation of the target safety variable true filter $D_{Cit}$ from the true filter $D_{Cond}$ which, in turn, can be calculated from the measured $D_{Cond}$. These calculations are performed assuming no access, cardiopulmonary or systemic recirculation during the novel conductivity dialysance measurement procedure.

These conductivity dialysance calculations may be expressed for total blood water flow, since following the infusion of hypertonic citrate into the plasma space, water and urea will quickly cross red blood cell (RBC) membranes to continuously equilibrate tonicity, osmolality and conductivity between the plasma and RBC space in the extracorporeal circuit. The dialysance calculations for citrate should be expressed with plasma water flow and plasma water dialysance, also accounting for the temporary water shifts between the RBC space and the plasma space in response to the hypertonic citrate infusion and the hypotonic pre-filter replacement fluid infusion when used. $Q_B$ in this regard is always the effective blood water flow for the specific solute being investigated. Such prerequisites are apparent to those skilled in the art and such modified calculations, while not shown for all possible variations, are also fully contemplated according to the present invention.

In the first step, the total true filter $D_{Cond}$ is obtained. (The effect of access- and cardiopulmonary recirculation on the measurement of conductivity dialysance and the calculation of the true filter $D_{Cond}$ is discussed later.) Next, the diffusive dialysance component of the total apparent dialysance is calculated (where applicable). Once the diffusive dialysance is known, the $KoA_{Cond}$ of the filter can be calculated. The $KoA_{Cond}$ is converted to $KoA_{Cit}$ based on the known constant diffusivity constants for conductivity and citrate. Using the $KoA_{Cit}$, $Q_{BCit}$ (as adjusted for water shifts between the fluid spaces of whole blood and the pre-filter replacement fluid flow) and $Q_D$, the diffusive component of the total apparent $D_{Cit}^*$ is calculated. Finally, the total $D_{Cit}^*$ is derived by adding the convective dialysance component (when applicable) to the diffusive component calculated earlier. Once $D_{Cit}^*$ is known, $E_{Cit}$ and maximum $C_{sys}$ can be determined as shown herein regarding writing a safe prescription for RCA. The terms used in the equations are defined below:

$Q_B$: effective arterial blood water flow ($Q_{BCond}$, $Q_{Bcit}$, adjusted arterial blood plasma water flow for citrate)
Hgb: hemoglobin concentration in the arterial blood
$Q_P$: arterial plasma flow
$C_p$: "conductivity solute" concentration in the plasma water entering the filter without citrate infusion
$C_{pin}(1)$: "conductivity solute" concentration in the plasma entering the filter with normal citrate infusion rate
$C_{pin}(t)$: "conductivity solute" concentration in the plasma entering the filter during the citrate bolus at "t" time point
$C_{pin}(B)$: "conductivity solute" concentration in the plasma entering the filter during the citrate bolus
$C_{Cit}$: "conductivity solute" concentration in the citrate anticoagulant
$Q_{Cit}(1)$: flow rate of the citrate anticoagulant during normal conditions
$Q_{Cit}(B)$: flow rate of the citrate anticoagulant during the temporary sodium citrate bolus
$Q_{pre}$: pre-filter substitution fluid flow rate
$Q_{post}$: post-filter substitution fluid flow rate
$Q_d$: dialysis fluid flow rate
$Q_s$: total substitution fluid flow rate
$Q_{uf}$: net ultrafiltration (negative fluid balance goal plus the citrate and Ca infusion rates)
$Q_{tf}$: total therapy fluid flow rate ($=Q_d+Q_s$)
$C_{ef}(1)$: "conductivity solute" concentration of the effluent fluid during baseline citrate anticoagulation conditions
$C_{ef}(t)$: "conductivity solute" concentration of the effluent fluid during the temporary sodium citrate bolus at "t" time point
$A_B$: the total amount of increased "conductivity or solute" appearing in the effluent in response to the sodium citrate bolus delivered by the anticoagulant pump
$T_B$: the exact duration of the citrate pump running faster to deliver the citrate bolus
$DC_{ef}(B)$: the time averaged effluent "conductivity solute" concentration increase during the citrate bolus
$C_{ef}(B)$: the time averaged effluent "conductivity solute" concentration during the citrate bolus
$C_{tf}$: "conductivity solute" concentration of the fresh therapy fluid $D_{Cond}$: "conductivity solute" dialysance determined by the sodium citrate bolus based measurement
$D_{Cit}$: the calculated citrate dialysance ($D_{Cit}^*$ when expressed for the adjusted $Q_{BCit}$ during calculations and $D_{Cit}$ when expressed for the unadjusted $Q_P$)
$D_{diff}$: the calculated diffusive component of the measured total dialysance ($D_{diffCond}$, $D_{diffCit}$)
KoA: mass transfer area coefficient; measure of filter performance specific to solute ($KoA_{Cond}$, $KoA_{Cit}$)
S: summary solute sieving coefficient $S_{Cond}$, $S_{Cit}$
a: summary solute diffusivity coefficient (Gibbs-Donnan factor; $a_{Cond}$, $a_{Cit}$)

The summary conductivity of the blood and the fresh and spent therapy fluids is essentially provided by sodium ions with their accompanying small solute (chloride, bicarbonate, phosphate and citrate) anions. Equation (1) defines the apparent conductivity dialysance under baseline operating conditions (modified from published art):

$$D_{cond} = (QD + Qs + Quf)\frac{(Ceffl - Ctf)}{a_{cond}(Cpin1 - Ctf)} \quad (1)$$

To largely reduce the effect of the unknown Cp (affecting Cpin1) in the calculation, the bolus method may be used. For greatest accuracy (as allowed by the precision of the blood pump), during the citrate bolus the total filter blood water flow, $Q_b+Q_{Cit(B)}$ is kept constant by temporarily decreasing the $Q_B$ by the bolus to baseline anticoagulant infusion rate difference (QcitB−Qcit1) (about 1-5% decrease over the baseline $Q_B$ depending on how concentrated the anticoagulant solution is) and the $Q_{tf}$ is kept unchanged. Under such conditions, the $D_{Cond}$ will remain practically constant during the bolus.

When the citrate bolus is given, the effluent conductivity as a function of time, $C_{ef}(t)$ will first rise and then fall as shown in FIG. 20a. (A negative bolus method implemented by reducing the citrate infusion as shown in FIG. 20b is also possible). Integrating the change in conductivity from baseline ($C_{ef}(t)-C_{ef}(1)$) by dt from the time point, $t_1$ at the start of the bolus to the time point, $t_3$ after the bolus when the effluent conductivity returns to baseline, and then dividing it by the duration of the citrate bolus infusion, $T_B$ yields the time averaged increase of effluent conductivity over baseline corresponding to the bolus, $DC_{ef}B$. Adding this value to $C_{ef(1)}$ yields the time averaged effluent conductivity during the citrate bolus, $C_{ef(B)}$.

By defining $C_{ef(B)}$ in this manner, Equation (2) is true after all data is collected from the bolus:

$$D_{cond} = (Qd + Qs + Quf)\frac{(CeffB - Ctf)}{a_{cond}(CpinB - Cpin1)} \quad (2)$$

It is known that $a_{Cond}$ is equal to 1 when the "hypothetical summary solute" conductivity is being studied. Equations (1) and (2) can be rearranged and combined to eliminate $C_{tf}$; the result is Equation (3):

$$D_{cond} = (Qd + Qs + Quf)\frac{(CeffB - Ceff1)}{a_{cond}(CpinB - Cpin1)} \quad (3)$$

In Equation (3), all variables are either set on the machine ($Q_d$, $Q_s$ and $Q_{uf}$) or are measured and calculated ($C_{ef}B$, $C_{ef}1$).

The denominator ($C_{pin}B - C_{pin}1$) can be calculated (ignoring the temporary and fully reversing osmotic water shifts between the red blood cell volume and the plasma volume of the blood in response to the hypertonic sodium citrate anticoagulant infusion and subsequent hypotonic therapy fluid exposure) as follows from Equations (4), (5) and (6) (see FIGS. 19, 20a, and 20b):

$$Cpin1 = \frac{(Qb \cdot Cp) + (Qcit1 \cdot Ccit)}{(Qb + Qcit1)} \quad (4)$$

Similarly, Equation (5) when lowering QB during the bolus as discussed above:

$$CpinB = \frac{(Qb - QCitB + Qcit1) \cdot Cp) + (QcitB \cdot Ccit)}{(Qb + Qcit1)} \quad (5)$$

Using Equations (4) and (5) to express ($C_{pin}B - C_{pin}1$), after rearrangement yields Equation (6):

$$(CpinB - Cpin1) = \frac{(QcitB - Qcit1)(Ccit - Cp)}{(Qb + Qcit1)} \quad (6)$$

In Equation (6), all variables are known except $C_p$. However, since the electrolyte composition and therefore the conductivity of the human plasma is strictly regulated, in one approach $C_p$ is assumed approximately equal to 14 mS+−1.5 mS. The relative error range this assumption introduces into the calculation will depend on the value of $C_{cit}$. If the $C_{Cit}$ value is very large (highly concentrated citrate solution with additional sodium chloride or sodium bicarbonate (550 mM or higher sodium content), the error introduced by the estimated Cp will be ±1-3% at most. Such errors will be further reduced as the treatment returns the patient's plasma electrolyte composition towards normal in a few hours and $C_p$ approximates the normal 14 mS. In a second solution to the problem of $C_p$ being unknown, $D_{Cond}$ is first calculated using the assumed value of $C_p$ as described above in Equation (6) and then (3). The calculated $D_{Cond}$ is then inserted into Equation (1) and Equation (1) is solved for $C_{pin}1$. Subsequently, $C_{pin}1$ is inserted into Equation (4) and Equation (4) is solved for $C_p$. The so derived $C_p$ is then re-inserted into Equation (6) and Equation (6) is re-solved for ($C_{pin}B - C_{pin}1$). This value is then re-inserted into Equation (3) to recalculate the $D_{Cond}$. These steps may be performed recursively by a computing module until the individual final values for $D_{Cond}$ and $C_p$ are approximated within 0.1%. Finally, a third variation of the technique is contemplated, during which conductivity is also measured on the arterial and venous blood lines without direct physical contact with the blood or compromising sterility. This allows for maximal precision of the clearance measurements, but requires some novel detection elements.

Using the value obtained from Equation (6) it is now possible to solve Equation (3) and derive the value of $D_{Cond}$. The $D_{Cond}$ value obtained for conductivity dialysance can be converted into blood clearance values for urea and other small solutes, taking into account how the Gibbs-Donnan effect may influence the movement of negative versus positive ions as compared to the neutral, non-ionic solute urea or the summary charge neutral "hypothetical summary conductivity solute". Once the apparent or total, $D_{Cond}$ conductivity dialysance is known, it is possible to calculate the diffusive dialysance, $D_{diffCond}$ component as described in prior art and published in the literature (however, the effect of any access recirculation if present must be removed first, as discussed below).

For any solute during intermittent hemodialysis with some net ultrafiltration ($Q_{uf}$) and during post-dilution hemodiafiltration with $Q_{post}$ post replacement fluid rate and $Q_{uf}$ net ultrafiltration, $D_{diff}$ is derived by using Equation (7) (where we assume QB is the effective blood water flow for the specific solute and the solute specific sieving coefficient, S is used):

$$D_{diff}(postHDF) = (Qb)\frac{D_{Total} - S(Qpost + Quf)}{Qb - S(Qpost + Quf)} \quad (7)$$

For any solute during pre-dilution hemofiltration with $Q_{pre}$ replacement fluid rate and $Q_{uf}$ net ultrafiltration, $D_{diff}$ is derived by using Equation (8) (where we again assume QB is the effective blood water flow for the specific solute corrected for the effects of water shifts between the RBC and plasma space and the infusion of the pre-filter replacement fluid and we use the solute specific sieving coefficient, S:

$$D_{diff}preHDF = (Qb + Qpre)\frac{\left(\frac{(Qb + Qpre)}{Qb}D_{Total} - S(Qpre + Quf)\right)}{(Qb + Qpre - S(Qpre + Quf))} \quad (8)$$

Equation (8) can be deduced from Equation (7) if one considers pre-dilution hemofiltration to be a special case of simple dialysis with net ultrafiltration where the new $Q_b^*$ is equal to $Q_b + Q_{pre}$, the pre-dilution corrected $D_{Total}^*$ is equal to $D_{Total} \cdot ((Q_b + Q_{pre})/Q_b)$ and net ultrafiltration becomes $Q_{pre} + Q_{uf}$. In the special case of simultaneous pre- and post-dilution hemofiltration, when $Q_d = 0$ and the solute sieving coefficient is S, Equation (3) still applies:

$$D_{Total} = (Q_{pre} + Q_{post} + Q_{uf}) \cdot ((C_{eff}B - C_{eff}1)/(S \cdot (C_{pin}B - C_{pin}1)))$$

Since this operational mode involves no dialysis, $D_{diff}$ is zero and is not calculated, and $D_{Total}$ can also be expressed as:

$$D_{Total} = S \cdot (Q_{pre} + Q_{post} + Q_{uf}) \cdot (Q_b/(Q_b + Q_{pre}))$$

From this:

$$D_{TotalCit} = D_{TotalCond} \cdot (S_{Cit}/S_{Cond}) \cdot (Q_P/Q_B) \cdot ((Q_B + Q_{Pre})/(Q_P + Q_{Pre}))$$

From these equations, it is apparent that a decline of the small solute apparent dialysance is unlikely in pure convective renal replacement therapy as long as the target total ultrafiltration of $Q_{pre} + Q_{post} + Q_{uf}$ is achieved, unless S changes markedly, which is not probable due to the highly predictable nature of small solute movement with purely convective blood purification. Dialysance for individual solutes is calculated by knowing their S sieving coefficients and the total ultrafiltration rate. (The apparent S value may change modestly for electrically charged solutes depending on the ratio of the pre-dilution ($Q_{pre}$) and post-dilution ($Q_{post}$) replacement fluid flow rates and this may have to be considered in the electrolyte mass balance calculations when selecting the therapy fluid composition for various ratios of $Q_{pre}$ and $Q_{post}$ fluid flows.)

Once the $D_{diffCond}$ has been determined from the total $D_{Cond}$ measured at a given (effective) $Q_b$ and $Q_d$, the KoACond of the filter membrane can be calculated as published in the literature, (see Equations (9.1) and (9.2)) and can be compared to the expected value provided by the filter manufacturer and/or established in vivo by local user experience.

In pure dialysis and post-dilution HDF, Equation (9.1):

$$KoACond = \left(\frac{Qb \cdot Qd}{(Qb - Qd)}\right) \cdot \ln\left(\frac{Qd(Qb - Ddiff)}{(Qb)(Qd - Ddiff)}\right) \quad (9.1)$$

In pre-dilution HDF, Equation (9.2):

$$KoACond = \left(\frac{QbQpre)Qd}{(Qb + Qpre - Qd)}\right) \cdot \ln\left(\frac{Qd(Qb + Qpre - Ddiff)}{(Qb + Qpre)(Qd - Ddiff)}\right) \quad (9.2)$$

The KoACond changes measured as a function of time while keeping the therapy parameters unchanged for any given filter will allow the detection of declining filter performance and impending clotting. The KoACond is converted to KoACit as shown in Equation (9.3):

$$KoACit = \frac{KoACond \cdot a_{Cit}}{a_{Cond}} \quad (9.3)$$

Knowing the KoACit allows the calculation of the DdiffCit from the effective $Q_{BCit}$ for citrate and the Qpre and Qd fluid flow rates prescribed, as shown in Equations (10.1) and (10.2). In pure dialysis and post dilution HDF, Equation (10.1) is used where QB now denotes $Q_{BCit}$ and KoA denotes KoACit:

$$D_{diff}Cit = QBCit \frac{e^{KoA \frac{(Qd-Qb)}{(Qd \cdot Qb)}} - 1}{e^{KoA \frac{(Qd-Qb)}{Qd \cdot Qb}} - \frac{Qb}{Qd}} \quad (10.1)$$

In pre-dilution HDF, Equation (10.2) is used where QB now denotes $Q_{BCit}$ and KoA denotes KoACit:

$$D_{diff}Cit = (Qb + Qpre) \frac{e^{KoA \frac{Qd-(Qb+Qpre)}{Qd \cdot (Qb+Qpre)}} - 1}{e^{KoA \frac{Qd-(Qb+Qpre)}{Qd \cdot (Qb+Qpre)}} - \frac{(Qb+Qpre)}{Qd}} \quad (10.2)$$

Finally, the obtained $D_{diff}Cit$ can be inserted into Equation (7) or (8) with the $Q_{pre}$ or $Q_{post}$ and $Q_{uf}$ values as appropriate, and the equations can be solved to derive the total $D_{Cit}^*$. Here the S sieving coefficient will now be specific for citrate, $S_{Cit}$. The obtained total $D_{Cit}^*$ is used to derive $E=D_{Cit}^*/QB_{Cit}$. The obtained E allows the calculation of the safety parameter, Csys as described herein regarding safe prescriptions for RCA.

In summary, in the novel arterial circuit limb blood-bolus method according to the present invention, conductivity dialysance may be measured by inducing a precise, calculated change in the input plasma conductivity entering the hemofilter and measuring the response in the filter effluent fluid. Conductivity dialysance may then be converted into citrate dialysance as shown in the above equations. The feasibility of such conversion depends on the in vivo ratio of the diffusivity coefficients for conductivity and citrate. This ratio is estimated to be about 3, and in the range of 2 to 4. The citrate dialysance, in turn, defines the maximum possible systemic citrate level with a given treatment prescription, which is the safety parameter that is desired to be maintained and monitored. In a variation of the technique, in the event that it is not desirable to increase the input solute concentration, conductivity dialysance can be measured by introducing a calculated decrease in the input solute concentration and measuring the change in conductivity of the filter effluent fluid. All of the equations remain unchanged because both ($C_{eff}B - C_{eff}1$) and ($C_{pin}B - C_{pin}1$) in Equation (3) will be negative when the input concentration is decreased (and QB is appropriately increased) (FIG. 20b).

Any method that induces a known change to the dialyzer input blood composition, which results in a measurable change in the composition of the effluent fluid of the hemofilter can be used to measure the dialysance of the hemofilter and then calculate citrate dialysance and is fully contemplated in accordance with the present invention. The present invention also contemplates methods that induce a change in the input blood composition and measure the effects on the filter output blood composition.

The effect of access recirculation on the online conductivity dialysance may also be measured by the method according to the present invention. Below, the differential impact of access recirculation on the online conductivity dialysance based filter clearance measurements is reviewed when performed with the traditional, fresh dialysis fluid conductivity bolus method versus the circuit arterial limb blood-bolus method of the present invention (see FIG. 21). The following will be presumed:

1) The dialysis fluid bolus method, when possible to execute with the high/low step functions as described in Kidney International, Vol. 66, Supplement 89 (2004), pp. S3-S24, will be considered equivalent to the effective dialysance of the circuit that includes the effects of the possibly present access as well as cardiopulmonary recirculation ($D_{eff2}$) and systemic conductivity recirculation will be assumed negligible.

2) The access recirculation will be measured with a hematocrit sensor (hemodilution) or thermal sensor (thermodilution) based method prior to any online clearance measurement.

3) When venous catheter access is used, only access recirculation may be present ($D_{eff1}$). Both methods will allow the calculation of the true filter dialysance, $D_{Filter}$ before it is altered by any recirculation.

4) When a permanent access is used, at least with circuit blood flows up to 300 ml/min, our blood bolus based method will measure $D_{Bolus}$. Assuming that significant systemic and cardiopulmonary recirculation is not present with our method (this is reasonable with single pass conductivity extraction >=80% with $Q_B$<=300 ml/min) and measuring access recirculation will allow the derivation of the true filter dialysance, $D_{eff}$ as well as the effective dialysance altered by access recirculation only, $D_{eff1}$. This is the data needed for citrate kinetics calculations.

5) In a permanent access, the dialysate bolus method will measure $D_{eff2}$. Even if the access recirculation R and the permanent access blood flow $Q_{AC}$ is measured (for instance with the use of the reverse blood line connector device and the hemodilution or thermodilution technique) in the absence of the cardiac output CO, $D_{Filter}$ cannot be calculated.

Figure 21:
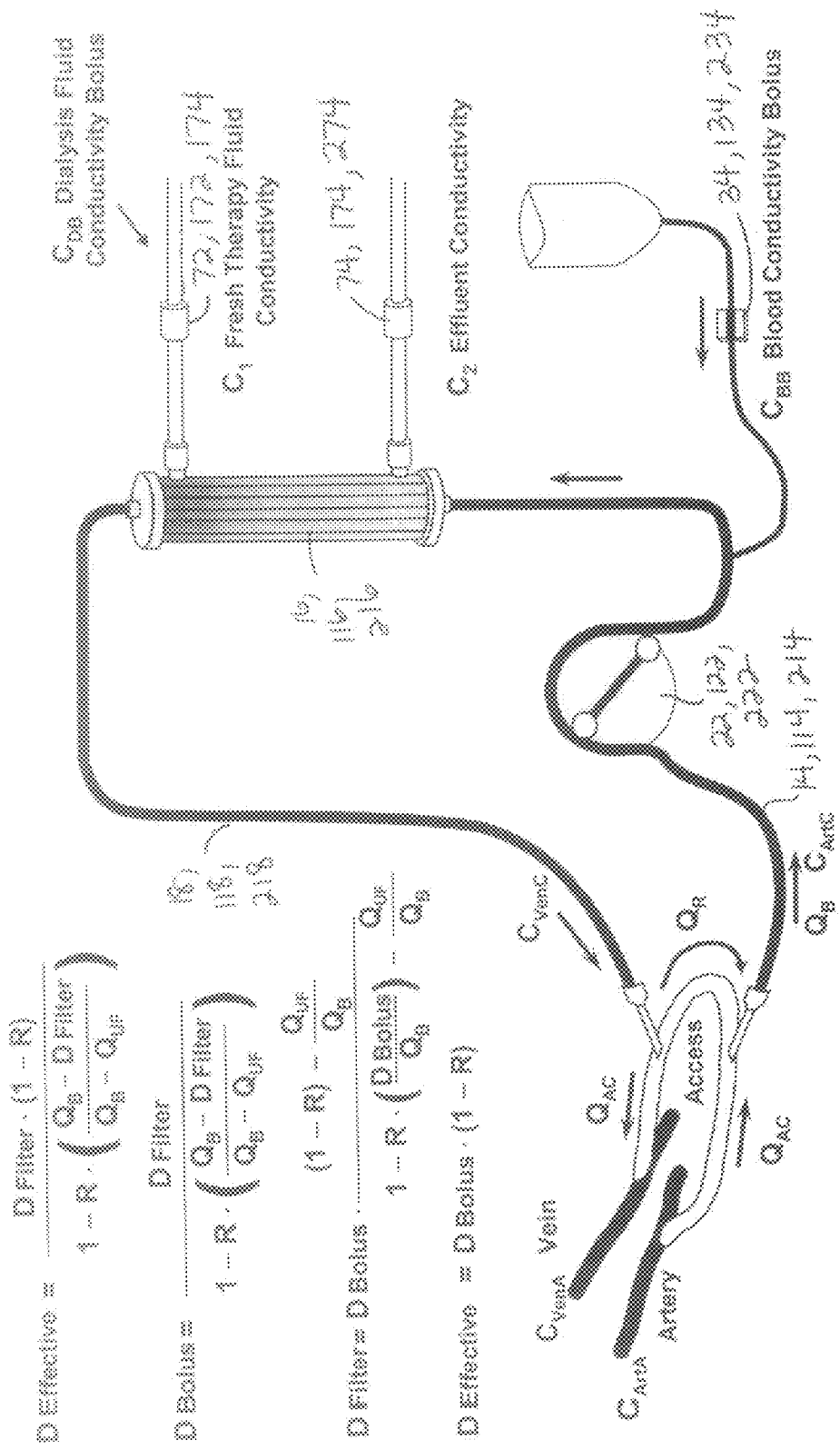
FIG. 21 depicts a comparison according to the present invention of the effects of permanent access recirculation on the fresh dialysis fluid conductivity bolus-based online dialysance measurement ($D_{effective}$) versus the circuit arterial limb blood conductivity bolus-based online dialysance measurement ($D_{Bolus}$)

The terms used in the equations are defined below, wherein the calculations are depicted in FIG. 21:

$Q_B$: effective circuit arterial whole blood water flow for conductivity ($Q_{BCond}$), adjusted arterial blood plasma water flow for citrate, ($Q_{Bcit}$)

$Q_{AC}$: effective access whole blood water flow for conductivity ($Q_{ACCond}$), adjusted arterial blood plasma water flow for citrate, ($Q_{ACcit}$)

$C_{AC}$: "conductivity solute" concentration in the plasma water in the access $C_{ArtR}$: "conductivity solute" concentration in the plasma water entering the filter (pre-dilution removed), as modified by recirculation $C_{ArtRS}$: "conductivity solute" concentration from the access arterial blood in the plasma water entering the filter (pre-dilution removed), as modified by recirculation $C_{ArtRB}$: "conductivity solute" concentration from the arterial limb bolus infusion in the plasma water entering the filter (pre-dilution removed), as modified by recirculation $C_{Ven}$: "conductivity solute" concentration in the plasma water exiting the filter $C_B$: "conductivity solute" concentration step-up in the plasma entering the filter over plasma entering the arterial limb of the blood circuit during the citrate bolus $C_{Cit}$: "conductivity solute" concentration in the citrate anticoagulant $Q_{Cit(B)}$: flow rate of the citrate anticoagulant during the temporary sodium citrate bolus $Q_{pre}$: pre-filter substitution fluid flow rate $Q_{uf}$: net ultrafiltration $Q_R$: the recirculating circuit venous limb blood R: the recirculation ratio defined as $R=Q_R/Q_B$ $D_{Filter}$: true filter "conductivity solute" dialysance $D_{Eff2}$: effective "conductivity solute" dialysance affected by access and cardiopulmonary recirculation and determined by the dialysate bolus based measurement $D_{Bolus}$: measured "conductivity" dialysance affected by access but not cardiopulmonary recirculation and determined by the blood bolus based measurement $D_{Eff1}$: effective "conductivity" dialysance determined from $D_{Bolus}$ by correcting for access recirculation only FIG. 21 is a comparison of the effects of permanent access (depicted; however, the calculations are also fully applicable to catheter access) recirculation on the fresh dialysis fluid conductivity bolus based online dialysance measurement ($D_{effective}$) versus the circuit arterial limb blood conductivity bolus based online dialysance measurement ($D_{Bolus}$). $D_{Filter}$ is the intrinsic filter dialysance with the effects or access recirculation removed. Cardiopulmonary and systemic recirculation is ignored. R is equal to $Q_R/Q_B$ and can be measured online by hemodilution or thermodilution methods.

$$DEffective = \frac{DFilter \cdot (1-R)}{1 - R \cdot \left(\frac{Q_B - DFilter}{Q_B - Q_{UF}}\right)} \quad \text{Equation 1}$$

This describes the relationship between Deff1 and Dfilter with R access recirculation. Deff1 is measured by the dialysis fluid bolus method if the cardiopulmonary recirculation is negligible or absent as is the case with venous catheter access. It was derived as follows:

Deffective*CAc=CArtRS*Dfilter (1.1)

Cven=CArtRS*(Qb−Dfilter)/(QB−QUF) (1.2)

CArtRS=R*Cven+(1−R)*CAc (1.3)

CArtRS=CAc*(1−R)/(1−R((Qb−Dfilter)/(QB−QUF)) (1.4)

$$DBolus = \frac{DFilter}{1 - R \cdot \left(\frac{Q_B - DFilter}{Q_B - Q_{UF}}\right)} \quad \text{Equation 2}$$

This describes the relationship between Dbolus and Dfilter with R access recirculation. Dbolus is measured by the circuit arterial limb bolus method if the cardiopulmonary recirculation is negligible or absent as is the case with venous catheter access and in general with this method when the QB is <=300 and QD is 150-200% of QB with a large surface area, high flux filter. R is measured online with the hemodilution or thermodilution technique. This Equation 2 is novel according to the present invention and is derived as follows:

Dbolus*CB=CArtRB*Dfilter (2.1)

Cven=CArt*(Qb−Dfilter)/(QB−QUF) (2.2)

CArtRB=R*Cven+(1−R)*CAc+CB (2.3)

CAc=0 (reasonable when single pass bolus extraction is >=80% or if we examine the recirculation effects on the bolus in isolation) (2.4)

CArtRB=CB/(1−R((Qb−Dfilter)/(QB−QUF)) (2.5)

Combining Equations 2.1 and 2.5 and rearranging yields Equation 2.

$$Dfilter = Dbolus \cdot \frac{(1-R) - \frac{Q_{UF}}{Q_B}}{1 - R \cdot \left(\frac{Dbolus}{Q_B}\right) - \frac{Q_{UF}}{Q_B}} \quad \text{Equation 3}$$

This equation is derived from Equation 2 by simple rearrangement and solution for Dfilter. The Dfilter conductivity dialysance can be separated into diffusive and convective component, the diffusive component converted into citrate diffusive dialysance and finally summary citrate dialysance calculated as described earlier. Subsequently, Dbolus citrate and Deff1 citrate can be calculated using effective QB as plasma water flow for citrate.

Deffective=Dbolus·(1−R) Equation 4

This equation follows from Equations 1 and 2. As discussed above, Dbolus is measured by the novel blood bolus method according to the present invention. Deffective ($D_{eff1}$) can then be calculated using the measured R value. If a venous catheter access is used, Deff1 will be equal to the effective urea clearance. $D_{eff1}$ must be converted into $D_{eff2}$, the effective urea clearance including a correction for cardiac output when a permanent (arterial) access is used:

$D_{eff2}=(1/(1+D_{eff1}/(CO-Q_{AC})))*D_{eff1}$ Equation 5

As mentioned, in a permanent access, the dialysate bolus method will measure $D_{eff2}$. The blood bolus method according to the present invention will measure $D_{Bolus}$ and will allow the calculation of $D_{eff1}$ if the access recirculation R is measured. Finally, if the permanent access blood flow $Q_{AC}$ is measured (for instance with the use of the reverse blood line connector device and the hemodilution or thermodilution technique), Equation 5 allows the calculation of the cardiac output CO with some simple rearrangements.

$CO=((D_{eff1}*D_{eff2})/(D_{eff1}-D_{eff2}))+Q_{AC}$ Equation 6

The method according to the present invention may allow the measurement of the cardiac output with clinically useful accuracy. The present invention contemplates use of this method with a dialysis machine with the appropriate sensor equipment, access connection reversal device and the cannulation of a permanent access to measure the cardiac output of a patient during treatment.

The online sensor system (OSS) according to the present invention will now be further described.

In recent years there has been expansive growth in the field of sensor technology. There are a multitude of new sensors that measure various substances including glucose, electrolytes, and macromolecules. Most of these sensors can be produced to scale to work with very small fluid samples. The greatest hurdle for these sensors in transitioning to human clinical use is the safety and regulatory concerns any device that comes into direct contact with human blood or tissue fluids must alleviate. The present invention provides an online sensor system (OSS) which is designed to overcome this problem as a sampling device that generates plasma ultrafiltrate for analysis by downstream sensor arrays, thereby allowing the indirect measurement of any filterable substance in the blood circulation.

Figure 22:
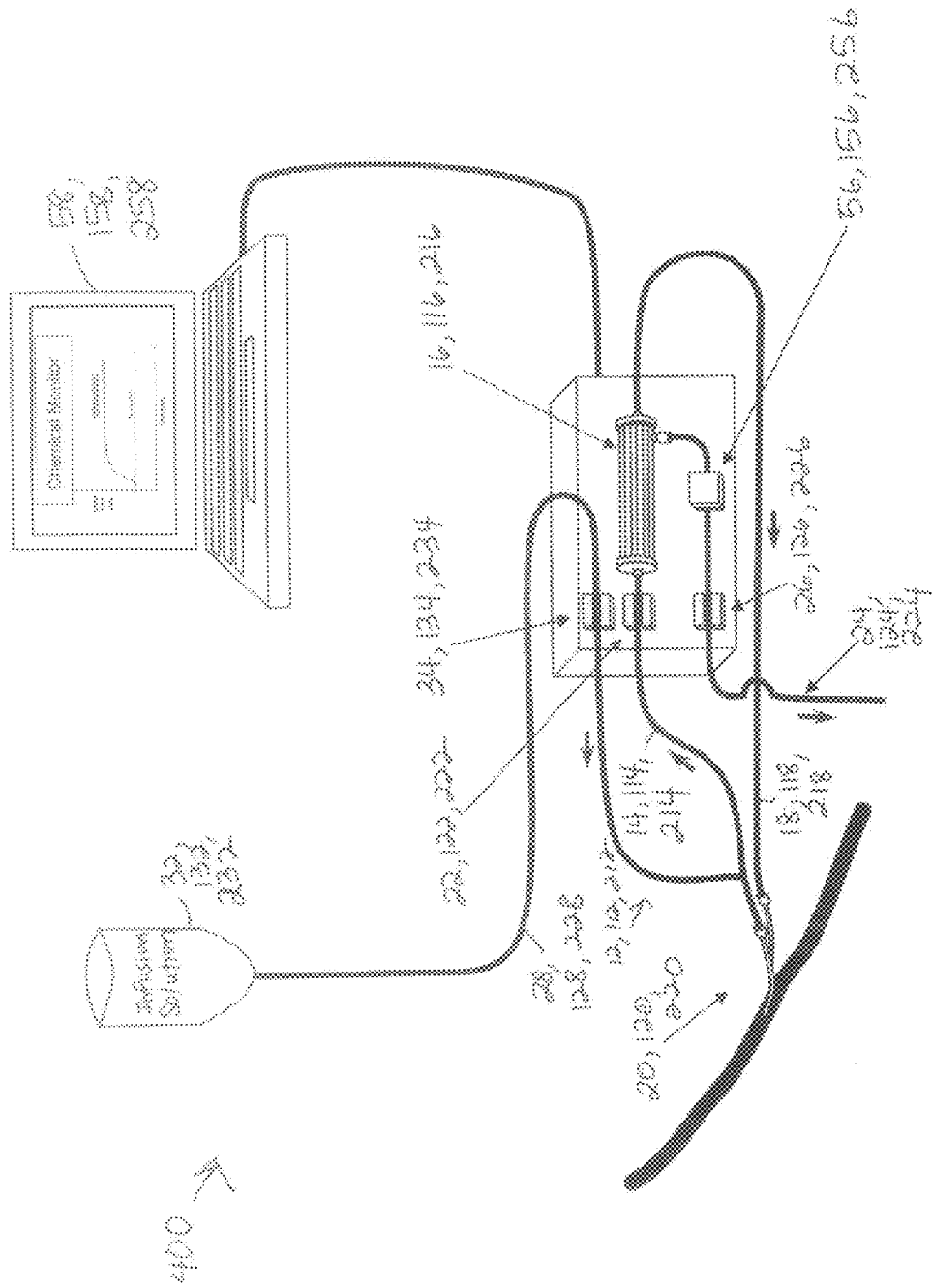
FIG. 22 illustrates a basic hemofiltration circuit according to the present invention which may be used to extract a small amount of ultrafiltrate for chemical analysis.

The sensors placed into the OSS do not come in direct contact with human blood; instead they analyze a fluid sample obtained by ultrafiltration of circulating blood. An illustration of a basic hemofiltration circuit for OSS 400 which may be used to extract a small amount of ultrafiltrate for chemical analysis is shown in FIG. 22. Blood is drawn into the circuit from the patient's access catheter 20, 120, 200 by the blood pump 22, 122, 222. An infusion pump 34, 134, 234 may add a small amount of infusion solution (e.g., anticoagulant) to the blood to prevent the circuit from clotting, wherein the blood then passes through the hemofilter 16, 116, 216 and returns to the patient. A small amount of fluid, ultrafiltrate, may be extracted from the blood passing through the hemofilter 16, 116, 216 by the ultrafiltration pump 26, 126, 226. Hemofilter 16, 116, 216 may be a miniature hemofilter or a simple two compartment hemofilter. The chemical composition of the ultrafiltrate can then be analyzed for a single analyte or multiple different analytes using a sensor array 56, 156, 256. The concentration of the analyte in the blood can then be determined since the dilution of the blood is known (this will be usually less then 10%) and the sieving of the solute through the hemofilter 16, 116, 216 is known. The OSS 400 can be implemented with any existing device that extracts ultrafiltrate from body fluids. Specific application of a CRRT circuit as an OSS to measure patient plasma levels of citrate, calcium, magnesium, glucose, inulin and para-aminohippuric acid (PAH) is provided according to the present invention. For patients not receiving CRRT, a small (e.g., 2×3 inch-size) OSS system is described herein that can be attached to a peripheral intravenous catheter and can store sufficient anticoagulant and ultrafiltrate to provide 1-2 ml of ultrafiltrate hourly during a 24-hour period of intermittent, hourly operation. Such sample size is more than adequate for the novel sensor technologies.

One advantage of OSS 400 according to the present invention is that it is very safe because the ultrafiltrate is discarded after the measurements and therefore possible contaminants or allergens in the sensor array 56, 156, 256 part of the circuit cannot come into contact with the patient. Devices for detecting an analyte in blood have been developed, however those devices bring the sensors into direct contact with blood in vivo by coupling the device with a venous flow device, such as an extracorporeal membrane oxygenator or hemodialysis machine. A sensor in contact with human blood will require sterilization and adherence to safety procedures to minimize risks to patients. Contact with human blood will result in biofouling of the sensor, which will possibly reduce sensor performance. Coatings added to sensor surfaces to limit degradation and improve performance have the added risk of possible adverse patient reactions. It will be mandatory for blood contact sensors to go through FDA testing to ensure that they do not cause anaphylaxis in patients. Since the OSS 400 according to the present invention uses an ultrafiltrate of the blood, large molecules such as proteins remain in the blood and are not available to foul sensor surfaces and thereby reduce performance. The OSS 400 eliminates the need for anaphylaxis testing because once the ultrafiltrate passes the sensor 56, 156, 256 it may be completely discarded. The use of OSS 400 can markedly accelerate the time from development of a specific sensor to transitioning to human clinical use either in the testing and development phase or for routine patient care.

OSS 400 according to the present invention may have different implementations. In one embodiment, the OSS 400 may be provided as a compact device (e.g., 2×3 inch-size) for ease of use and immediate applicability for hospitalized patients (and possibly even for outpatients for 24-48 hours; as a "chemical Holter monitor"). This form of the OSS 400 only requires a small peripheral IV for access to the patient's venous blood and is designed to serve as a safe plasma-sampling device. In another embodiment, the OSS 400 may be provided as a full size CRRT machine OSS. The effluent fluid line 24, 124, 224 in such a circuit may be used to provide samples for the sensor array 56, 156, 256 of the OSS 400. Importantly, in this implementation, more complex assessment of the patient's condition beyond simple plasma concentration measurements is possible, including measuring renal and liver clearances of various substances and thereby monitoring renal and liver function online, in real time.

The implementation of the OSS 400 as a small ultrafiltration circuit attached to a peripheral (venous) IV line may be used for patients not receiving CRRT therapy. This embodiment of the OSS 400 includes a small hemofiltration device that may extract only a few milliliters of ultrafiltrate per hour from a miniature extracorporeal circuit. A basic hemofiltration circuit which may be used to extract a small amount of ultrafiltrate for chemical analysis is shown in FIG. 22. Catheter 20, 120, 220 may comprise a small, double lumen intravenous catheter which may be placed in a suitable vein. Blood may be removed from the patient using the arterial pump 22, 122, 222 at a few milliliters per minute. At the same time, the infusion pump 34, 134, 234 may add anticoagulation solution to the blood at an appropriate rate to prevent clotting. Anticoagulated blood from the arterial limb 14, 114, 214 of the circuit may be pumped through a miniature hemofilter 16, 116, 216 and ultrafiltrate may be extracted from the blood by the ultrafiltration pump 26, 126, 226. Sensors 56, 156, 256 in the ultrafiltration circuit may analyze the ultrafiltrate for the selected analytes.

Figure 23:
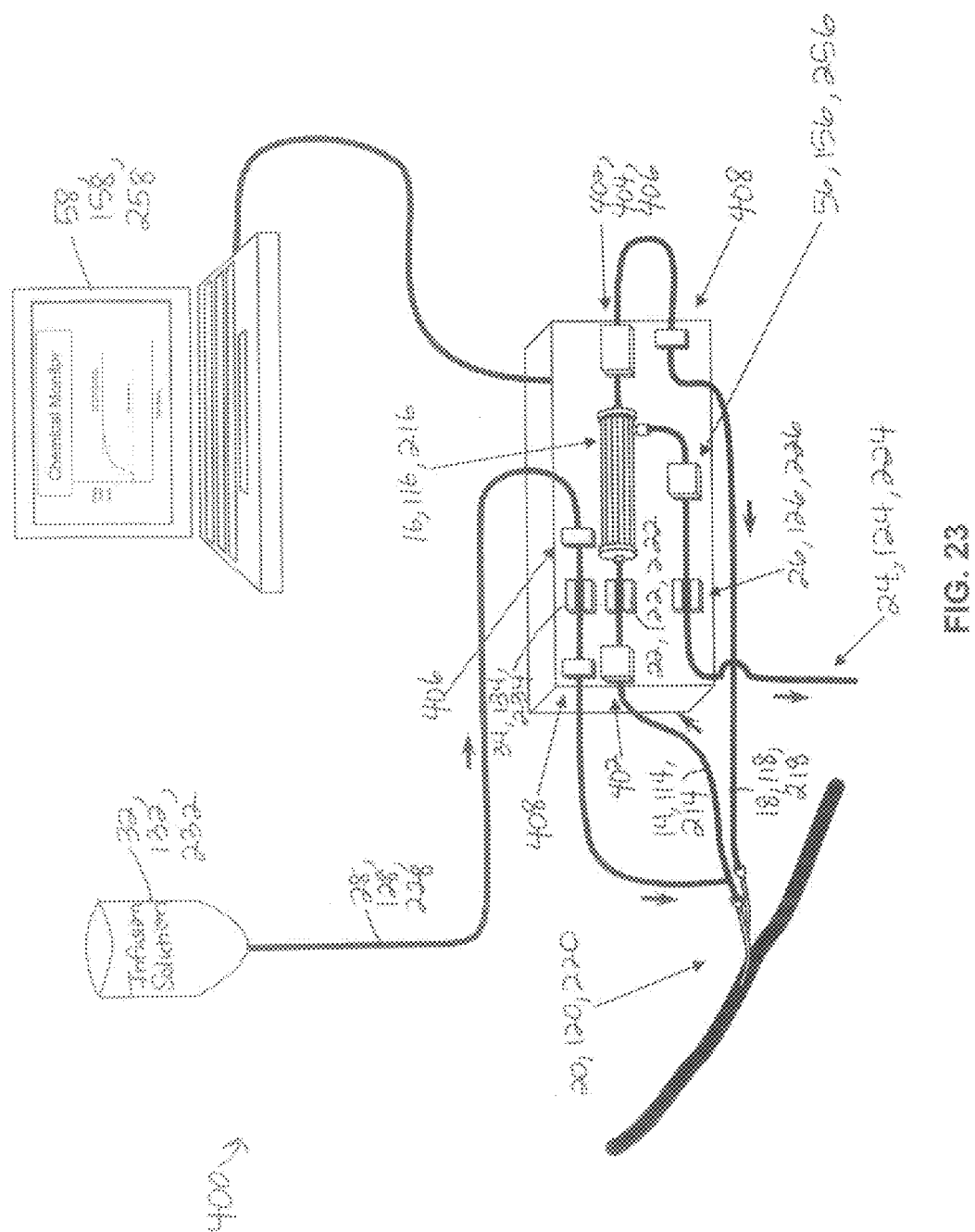
FIG. 23 illustrates a complete hemofiltration circuit according to the present invention which may be used to extract a small amount of ultrafiltrate for chemical analysis.
Figure 24:
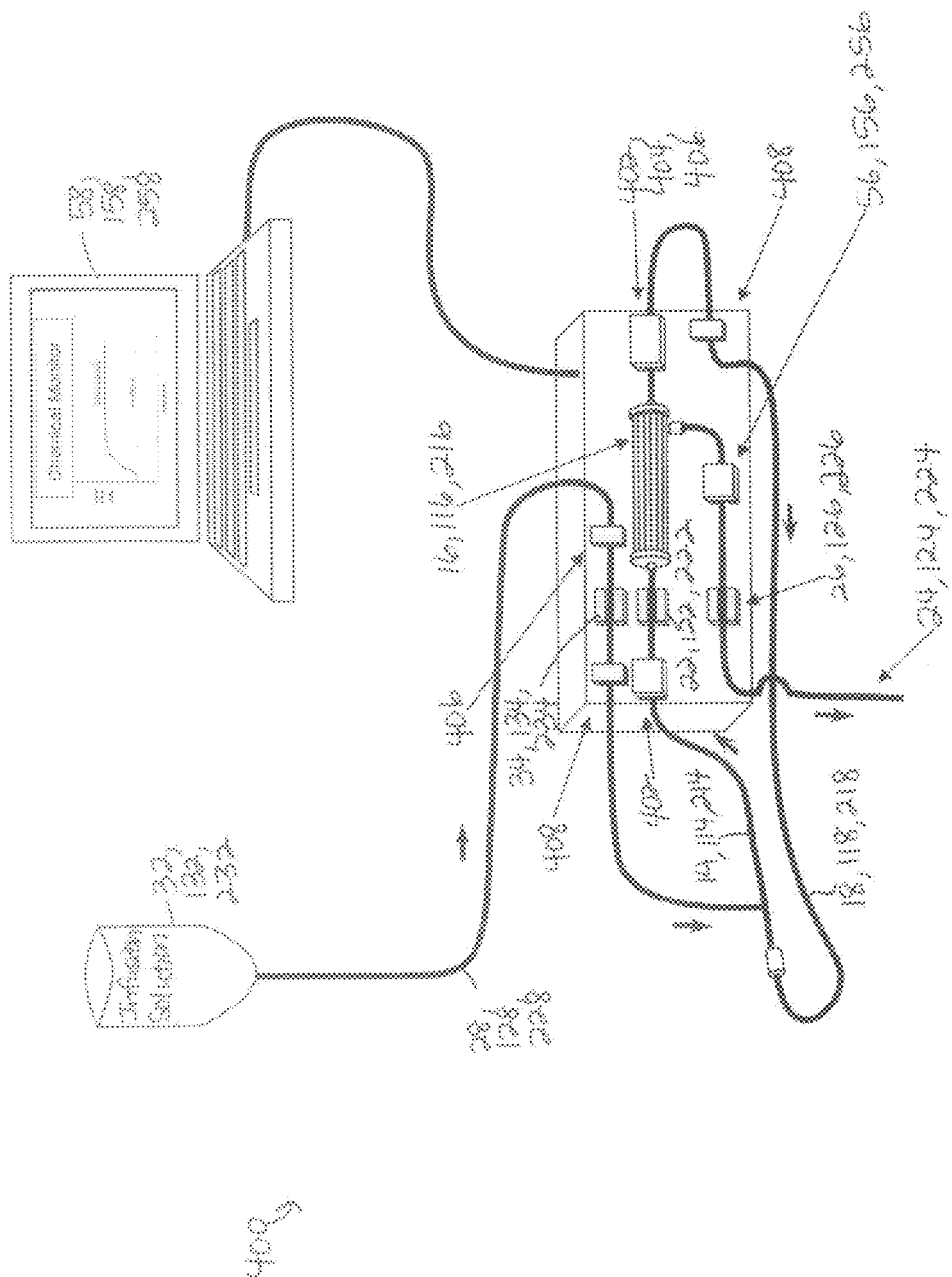
FIG. 24 illustrates a hemofiltration circuit according to the present invention which may be used for priming and initial testing of pumps and pressure transducers.

FIG. 23 shows a more complete hemofiltration circuit according to the present invention which may be used to extract a small amount of ultrafiltrate for chemical analysis. Arterial and venous pressure sensors 402, air-in-fluid detectors 404, a blood in circuit detector 406 and line clamps 408 may be added to provide patient safety. FIG. 24 shows a hemofiltration circuit which may be used for priming and initial pressure testing of pumps and pressure transducers. All three pumps may have very precise flow rates which allows for accurate calculation of blood analyte concentrations.

The OSS 400 according to the present invention can operate is a continuous mode or in an intermittent mode in which samples are collected at pre-selected intervals. In intermittent mode, the entire circuit can be refilled with the anticoagulant solution. If the infusion pump 34, 134, 234 is run at a slightly higher rate than the arterial pump 22, 122, 222, the entire extracorporeal circuit 12, 112, 212 will be filled with anticoagulation solution. Running the infusion pump 34, 134, 234 for a short period of time after the blood pump 22, 122, 222 is stopped and the blood line is clamped will direct fluid into the access catheter, filling it with anticoagulation solution. Only a minuscule volume of infusion fluid is needed for anticoagulation of the circuit, which avoids the risk of infusing an excess amount of anticoagulant into the patient. When acid citrate anticoagulant is used, the approximately 5.4 pH of the anticoagulant-filled circuit will also prevent bacterial growth in the event of a contamination.

Figure 25:
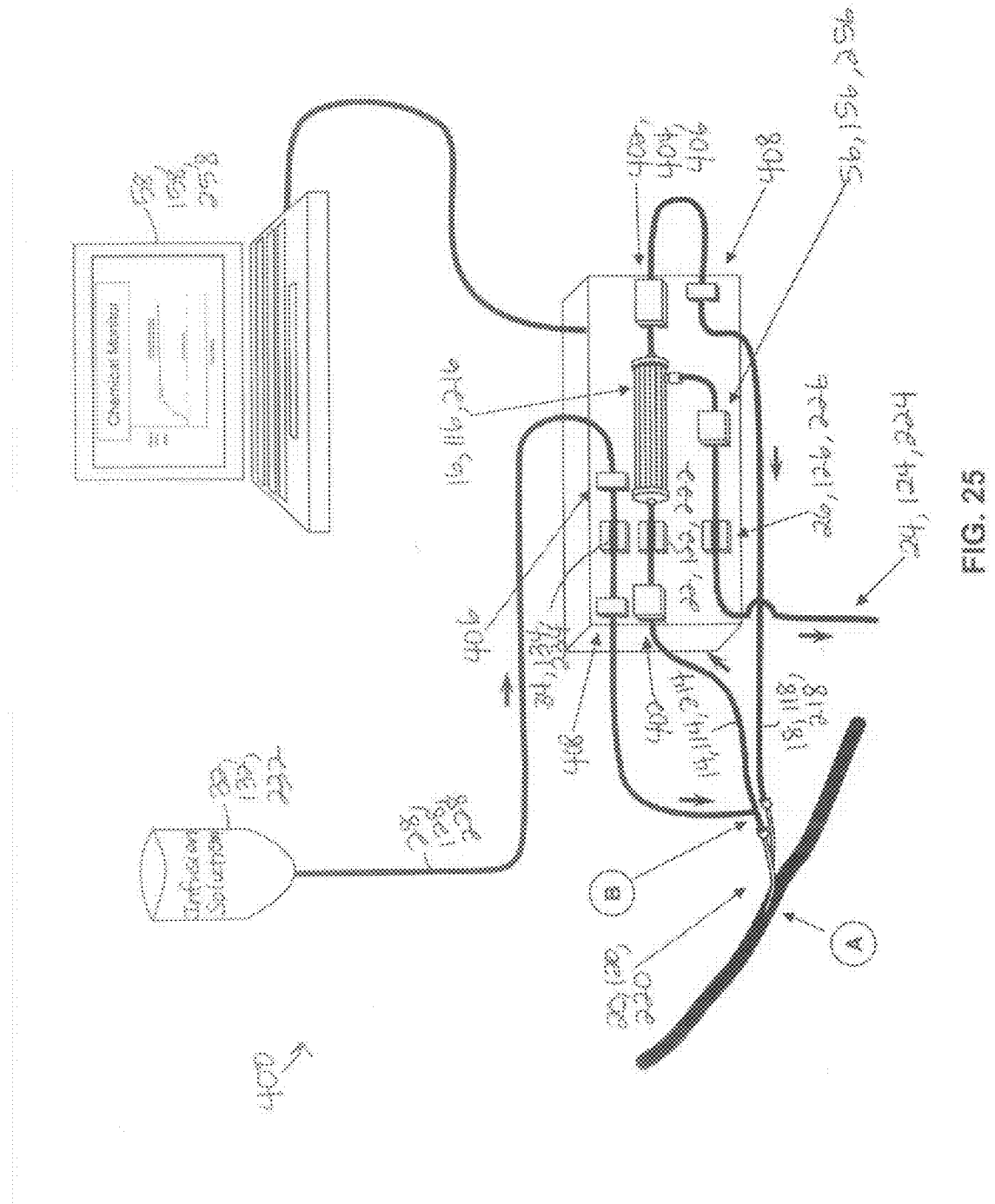
FIG. 25 illustrates a complete hemofiltration circuit according to the present invention which may used to extract a small amount of ultrafiltrate for chemical analysis.

During continuous operation, the section of the circuit between point A and point B in FIG. 25 is not exposed to the infusion solution containing an anticoagulant. To address this situation, a triple lumen venous catheter with an infusion port at the tip of the withdrawal lumen may be utilized, such as catheter 300 depicted in FIG. 9). This triple lumen catheter 300 allows an anticoagulant solution to be infused through a hole in the lumen wall directly into the entrance of the arterial blood withdrawal path. Since the venous return path contains anticoagulant, the entire triple lumen catheter 300 is continuously exposed to anticoagulant. FIG. 26 shows triple lumen catheter 300 in the OSS hemofiltration circuit according to the present invention.

For a case where a sensor requires complete isolation of the ultrafiltrate because the testing procedure requires reagents that are very hazardous to the patient, one of the backflow prevention devices 410, 412, 414 in FIG. 27 can be used such that the ultrafiltrate extracted from the blood the fluid can be isolated from the patient circuit. In one implementation (FIG. 27a), an air gap device 410 may be used where the input fluid enters a chamber 416 from the top and falls through an air space. If for any reason the sensor system 56, 156, 256 causes a backflow to occur, the ultrafiltrate will flow harmlessly out of an opening 418 to the air. This solution may be applicable when the OSS 400 is used in a fixed orientation to gravity, for instance as part of a large CRRT circuit. For the compact size OSS which may be attached to the patient's body and not have a fixed orientation to gravity, one of the two valve-system-based backflow prevention devices can be used (FIGS. 27b-27c). In FIG. 27b, a device 412 including a series of two or more one way valves 420 can be used, such that if the first valve fails, the second valve must also fail before backflow can occur.

Figure 28B:
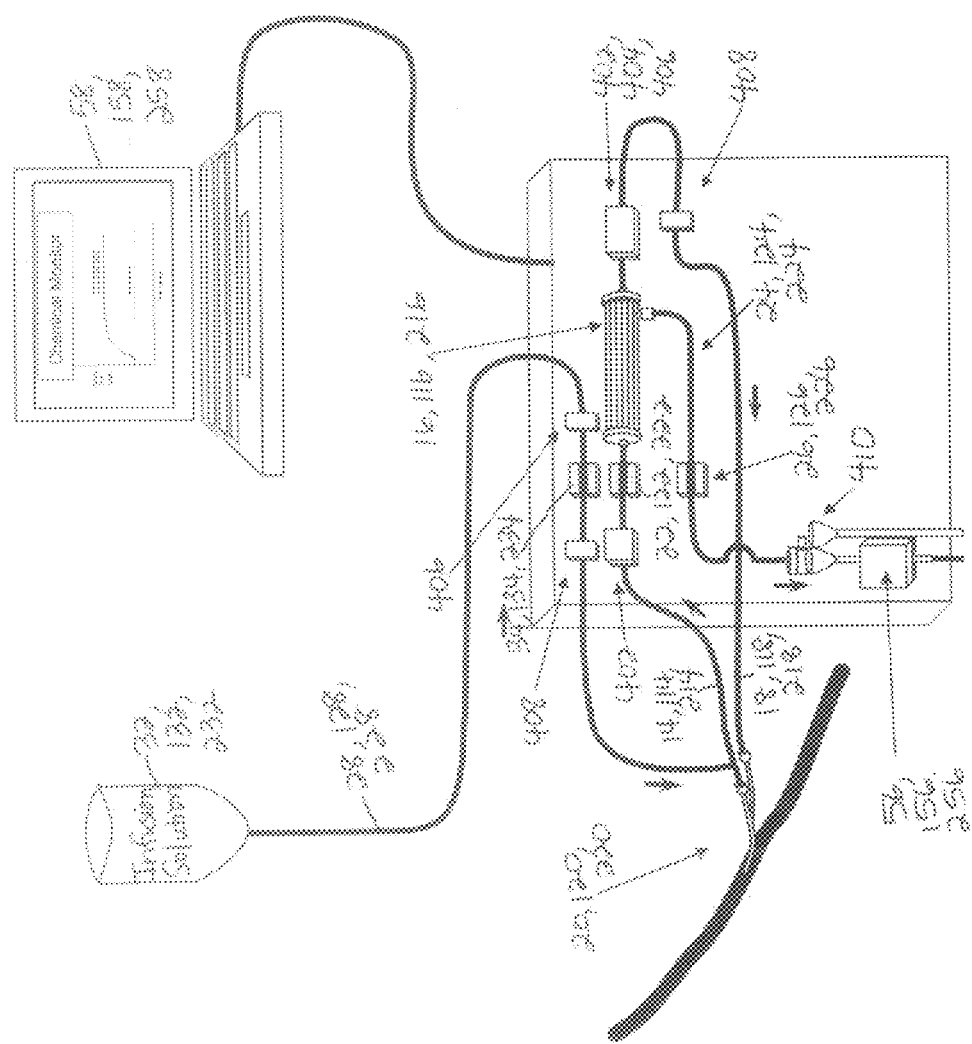
FIG. 28b illustrates a hemofiltration circuit according to the present invention showing a possible location for an air gap backflow prevention device.

In FIG. 27c, a reduced pressure zone device 414 is illustrated, wherein the input pressure must exceed a set pressure P to open valve 422, and fluid in a reduced pressure zone 424 is approximately P−0.19P because a pressure of P−0.2P is required to open valve 426. Any initial backflow is stopped by valve 426. If valve 426 fails, backflow is prevented by valve 422 and any increase in pressure above P−0.15P opens valve 428 and the backflow is diverted out of the device 414. The use of one of these devices 410, 412, 414 ensures that if for any reason the OSS 400 causes a backflow to occur, the ultrafiltrate will flow harmlessly out through the backflow opening where it is collected and sent to the drain. FIGS. 28a and 28b show possible locations for backflow prevention devices 414 and 410, respectively.

The compact size OSS 400 according to the present invention may be easily connected to a peripheral vein of the patient and can be transported with the patient if needed. It is very safe to use because sensors 56, 156, 256 do not come in direct contact with human blood and after analyte measurements are made the ultrafiltrate is sent to the drain. The data obtained may be stored for later retrieval and or may be transmitted by a wireless connection.

The OSS 400 according to the present invention may also be implemented as part of an extracorporeal blood circuit 12, 112, 212 used to provide CRRT in the ICU. The OSS 400 can be implemented with any existing device that extracts an ultrafiltrate from body fluids. Specific application of a CRRT circuit as an OSS to measure patient plasma levels of glucose, citrate, calcium, magnesium, inulin and para-aminohippuric acid (PAH) is described herein. Importantly, when the OSS 400 is implemented as part of a CRRT circuit, truly online, continuous measurement of the plasma concentration of any filterable solute for which a specific sensor is available becomes possible. Thus, kinetic analysis of the solute concentration curve as a function of time becomes clinically feasible without the need for onerous frequent blood sampling. The kinetic data provides a wealth of new information, ensures monitoring of the liver metabolic function, and may possibly allow measuring the glomerular filtration rate and renal plasma flow in real time. Such methods are not currently available and are needed clinically.

Figure 29A:
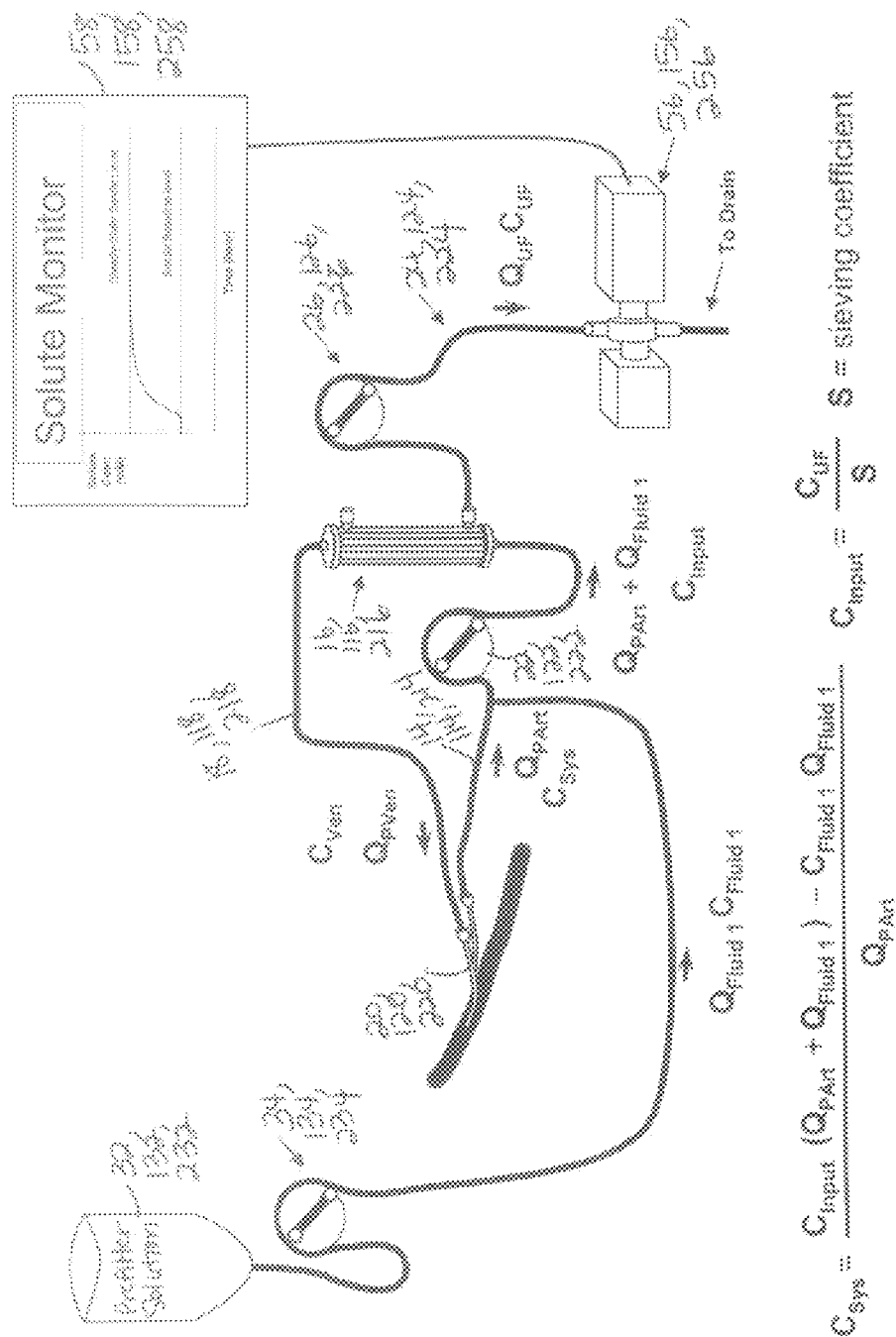
FIG. 29a depicts a configuration according to the present invention for deriving the patient systemic solute level ($C_{Sys}$) by measuring the ultrafiltrate solute concentration $C_{UF}$ and dividing by the hemofilter sieving coefficient S for the specific solute.
Figure 29B:
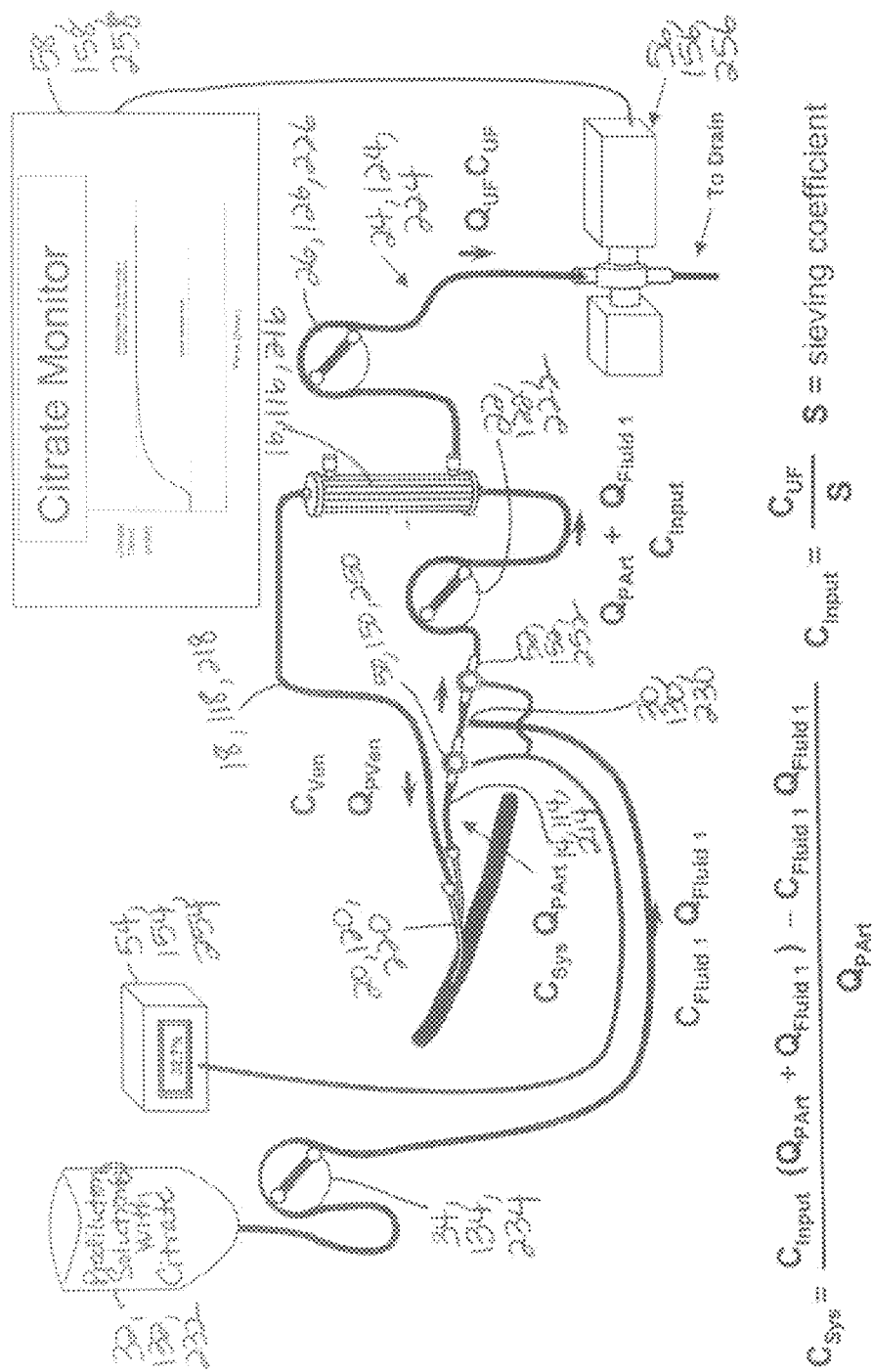
FIG. 29b depicts a configuration according to the present invention for deriving the patient systemic citrate level $C_{Sys}$ by measuring the ultrafiltrate citrate concentration $C_{UF}$.
Figure 20C:
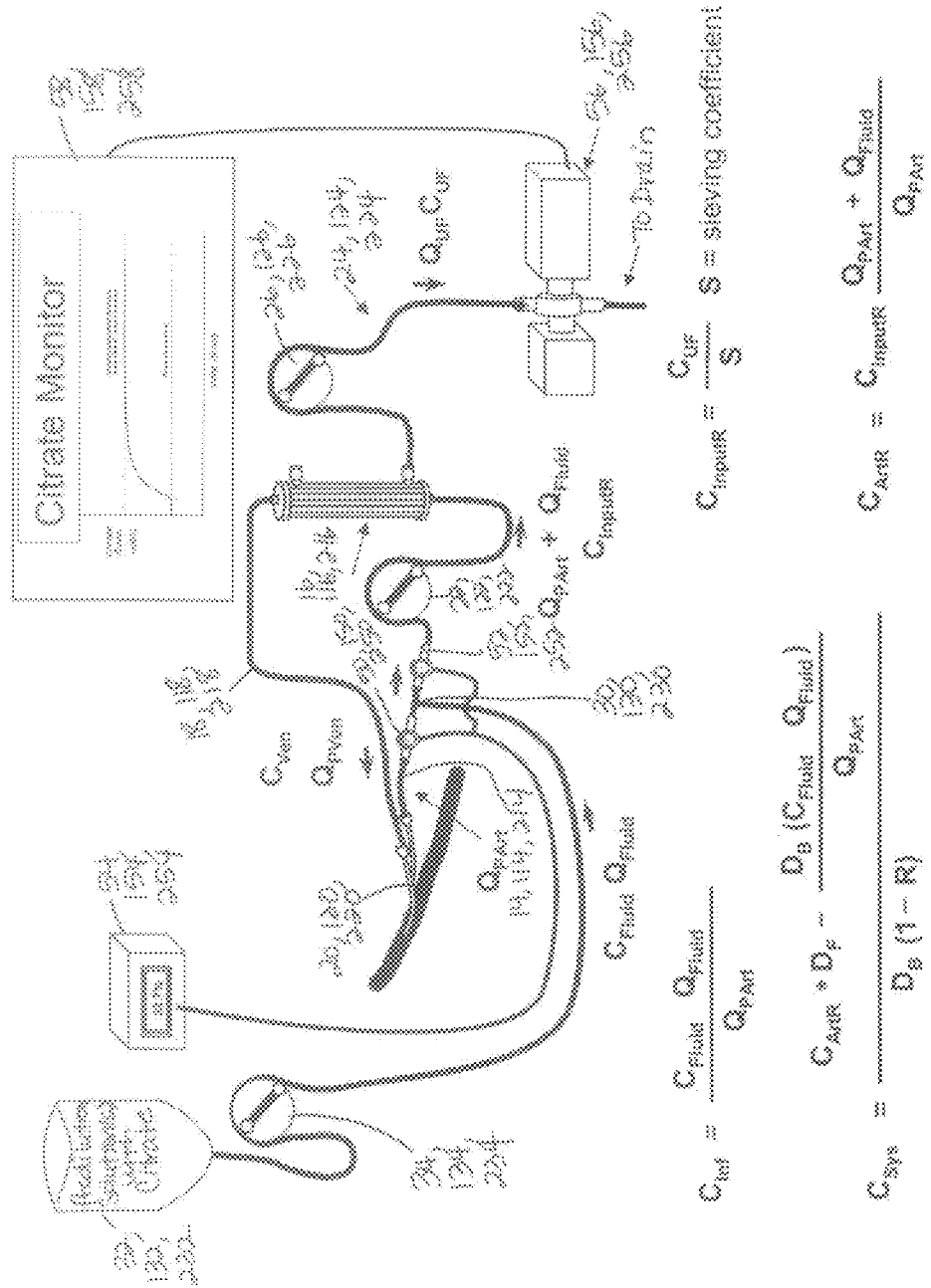

This implementation of the OSS 400 according to the present invention in an RRT circuit is clinically immediately available, by minor modification of existing RRT devices and by placing the sensor array 56, 156, 256 into the effluent line of an RRT device. The OSS 400 may be best implemented integrated into the RCA systems according to the present invention and described herein which were either designed solely or have the option to deliver purely convection-based, high dose RRT with fully effective RCA. FIGS. 29a-29c show the OSS 400 integrated into the RCA system according to the present invention running in either isolated pre-dilution or simultaneous pre- and post-dilution hemofiltration mode (only the pre-dilution flow relevant to the OSS application is shown). The sensor 56, 156, 256 is placed into the effluent fluid line carrying ultrafiltrate (and or dialysate) away from the hemofilter.

In particular, FIG. 29a illustrates a configuration for deriving the patient systemic solute level ($C_{sys}$) by measuring the ultrafiltrate solute concentration $C_{UF}$ and dividing by the hemofilter sieving coefficient S for the specific solute. All other parameters are known values and the $C_{sys}$ is calculated according to the formulas shown. Access recirculation is not present. FIG. 29b illustrates a configuration for deriving the patient's systemic citrate level $C_{Sys}$ by measuring the ultrafiltrate citrate concentration $C_{UF}$. $C_{Sys}$ can be calculated knowing the arterial plasma flow $Q_{PArt}$ rate, citrate infusion flow $Q_{Fluid1}$ rate, citrate concentration of the infusion solution $C_{Fluid1}$ and the filter sieving coefficient for citrate S. The hematocrit sensors 50, 150, 250 and 52, 152, 252 allow the calculation of the plasma citrate concentration by contributing to the measurement of the delivered arterial plasma flow and by measuring access recirculation (assumed not present here). FIG. 29c Illustrates a configuration for deriving the patient's systemic citrate level $C_{Sys}$ by measuring the ultrafiltrate citrate concentration $C_{UF}$ when the increase in citrate concentration from the anticoagulant infusion in the arterial limb plasma with the pre-dilution effect removed is $C_{Inf}$, access recirculation is R=$Q_{PR}/Q_P$ and filter citrate dialysance with recirculation effects removed is $D_F$, plasma citrate bolus dialysance with recirculation is $D_B$ and filter systemic citrate effective clearance with recirculation is $D_E$ where $D_E = D_B * (1-R)$. All variables are known or can be measured and or calculated as shown before. The calculations can be applied for any solute for which the above parameters are known, measured and or calculated.

The effluent fluid contains a wealth of information on the patient's plasma solute composition, but in current clinical practice it is discarded without any further analysis. This fluid is a clear crystalloid with a small amount of albumin, small peptides, and cytokines also present. The transparency and minimal viscosity of the effluent fluid provide for an ideal environment for an optical- and/or chemical sensor array. The OSS 400 according to the present invention may operate in a manner such that solute concentrations are converted to light (optical) signals by solute-specific, possibly disposable, chemical-optical transducer systems (chips or optrodes) that are exposed to the effluent flow, such as in a possibly disposable, light transparent flow-through chamber. Readout of the optical signals may be done through the light-transparent wall of the chamber or through the optical filament part of the optrode by a fixed, excitation light generating (if needed) and optical signal capturing and analyzing module. Multiple light wavelengths may be used simultaneously for both excitation and readout on an unlimited number of sufficiently small emitting, capturing and analyzing modules.

In a modification of this method, Raman scatter spectroscopy may be used on the effluent line and the specific solutes may be identified by their unique Raman spectra. Quantification may be possible by measuring the signal intensity of specific spectral peaks. The advantage of this method is that solute specific chemical-optical probes are not needed as specificity is provided by the unique Raman spectra of the target solute. Citrate will be in a large molar excess compared to most other molecules in the effluent and it may be possible to quantitate it with Raman scatter spectroscopy, possibly even differentiating free citrate, Ca-citrate and Mg-citrate. The present invention contemplates the use of Raman scatter spectroscopy to monitor systemic solute levels through monitoring the RRT circuit effluent fluid, with the specific example of measuring all species of citrate in the effluent.

Finally, the fluid here is waste fluid and will not be exposed to the patient's blood again, eliminating any chance of any elements of the sensor getting into direct or indirect contact with the patient. This is completely ascertained when a backflow prevention safety device 410, 412, 414 (as shown in FIG. 27) is added before the effluent is exposed to the sensors 56, 156, 256. Finally, the effluent tubing 24, 124, 224 can easily be modified to allow the connection of the OSS 400 in this segment of the CRRT circuit.

The calculation of systemic solute levels from solute levels measured in the ultrafiltrate including corrections for the effects of access recirculation when present is described below. Once real-time measurement of a solute is provided in the effluent, a special software calculator may be used to determine the contribution of solute entering the extracorporeal circuit from the systemic circulation of the patient (the systemic plasma solute level) and the contribution of solute freshly infused into the CRRT circuit pre-filter (if the solute is contained in the pre-filter infusion(s), as may be the case for glucose, citrate, inulin and PAH). This calculation requires that the extracorporeal circuit plasma flow to summary pre-filter fluid infusion ratio remain constant for the time of the calculation and is very reliable when only convective clearance is used, as in the RCA systems according to the present invention.

In the RCA system, plasma flow may be monitored in real time by the online hematocrit sensors and possibly by a Doppler-based system as well as shown in FIGS. 29a-29b. The pre-filter fluid infusion rate is also known in real-time, as the pre-filter fluid pump 34, 134, 234 of the machine delivers it and it also may be monitored by the function of the Doppler and hematocrit sensors 50, 150, 250 and 52, 152, 252. Therefore, the contribution of solute freshly infused into the circuit blood plasma can be calculated in real time. The calculation also relies on the sieving coefficient of the solute being known. Such information has been published for glucose and citrate in the literature and can easily be measured for most small solutes including inulin and PAH. The sieving characteristics of a given solute on the specific filter used are not likely to change as long as effective anticoagulation is used, and can also be monitored by the OCM for conductivity or citrate. Thus, in the RCA system, under steady operational parameters, the solute concentration measured by the OSS in the ultrafiltrate can be immediately used to provide the solute level present in the patient's systemic blood. The exact calculations for any filterable solute are shown in FIG. 29a and for the specific example of citrate in FIG. 29b. The calculations can be provided for CVVHD, CVVHDF and c-SLED as well, as long as measurements are done for the given filter type at fixed dialysate, ultrafiltrate and blood flow and pre-filter fluid infusion rates assuming that the solute transfer properties of such RRT circuits are defined and monitored by a precise online clearance monitor. However, purely convective clearance may be preferred in this method for greater reliability of solute transport.

The OSS 400 can be integrated with the RRT device to send an alarm to the operator when a critical (high or low) threshold of systemic plasma solute concentration is breached and possibly to automatically adjust treatment settings to correct the solute level abnormality. A clinical assessment of the patient with full laboratory parameters may also follow. Finally, falsely abnormal solute levels in the blood entering the extracorporeal circuit due to recirculation at the catheter tip can be detected by the recirculation detection feature of the online hematocrit sensors 50, 150, 250 and 52, 152, 252 which may be integrated into the RCA system, and corrections in the calculations are possible, eliminating false solute level alarms with or without an intervention on the recirculating access as indicated (FIG. 29c and as explained below).

The terms used in the equations are defined below, and the physical layout of the OSS 400 with the key calculations is shown in FIGS. 29a-29b and for recirculation in FIG. 29c:

$Q_{AC}$: effective access blood water flow specific for the solute measured $Q_B$: effective circuit arterial blood water flow specific for the solute measured; arterial blood plasma water flow for citrate, ($Q_{PArt}$)

$C_{Sys}$ (same as $C_{AC}$): solute concentration in the effective blood water in the arterial limb of the access $C_{ArtR}$: solute concentration in the plasma water entering the filter (pre-dilution removed), as modified by recirculation $C_{ArtRSys}$: solute concentration portion from the access arterial blood in the plasma water entering the filter (pre-dilution removed), as modified by recirculation $C_{ArtRInf}$: solute concentration portion from the arterial limb solute (citrate) infusion in the plasma water entering the filter (pre-dilution removed), as modified by recirculation $C_{InputR}$: The solute concentration in the plasma water entering the filter; this is $C_{ArtR}$ adjusted for pre-dilution $C_{UF}$: The solute concentration in the ultrafiltrate exiting the filter $C_{Inf}$: solute concentration step-up in the effective blood water of the blood entering the filter over the blood entering the arterial limb of the blood circuit during citrate infusion, with pre-dilution removed $C_{Fluid}$: summary solute concentration in the pre-filter fluids $Q_{Fluid}$: summary flow rate of the pre-filter fluids $Q_R$: the recirculating circuit venous limb blood effective water flow (solute specific)

R: the recirculation ratio defined as $R=Q_R/Q_B$; (measured by hemodilution or thermodilution)

$D_{Filter}$: true filter solute dialysance (calculated)

$D_{Bolus}$: measured solute dialysance affected by access but not cardiopulmonary recirculation and determined by the blood bolus based measurement for conductivity (OCM) or citrate (citrate sensor)

$D_{Eff1}$: effective solute dialysance determined from $D_{Bolus}$ by correcting for access recirculation only S: summary solute sieving coefficient ($S_{Cond}$, $S_{Cit}$, $S_{Solute}$)

These Calculations Assume:

1) All the equations presented and or used in the section on access recirculation effects on conductivity dialysance based online clearance measurements are referenced here as needed 2) Access recirculation, R, is measured online.

3) While the general term D, (dialysance) is used, all clearance is convective for greater predictability of small to medium size solute movement. However, this method limitation is not mandatory.

4) $D_{Bolus}*$ is measured for conductivity and or citrate and $D_{Filter}*$ is calculated.

5) $D_{Filter}*/Q_B >= 0.8$ and $Q_B$ is $<=300$ ml/min so that cardiopulmonary and systemic recirculation can be neglected.

6) The sieving coefficient is known for both the solute used to measure $D_{Bolus}*$ as well as the solute for which the systemic concentration needs to be determined.

7) $D_{Filter}*$ is converted to $D_{Filter}$ using the sieving coefficient of the "solute" used for measuring $D_{Bolus}*$ and the sieving coefficient of the target solute to be measured as well as knowing the effective blood water flows for both solutes. (These calculations are discussed with reference to the OCM where in a specific example $D_{Conductivity}$ is converted into $D_{Citrate}$).

8) The target solute $D_{Filter}$ and R is used to calculate the target solute $D_{Bolus}$ and $D_{effective1}$.

Specific equations used in the calculations are as follows:

$$C_{InputR} = \frac{C_{UF}}{S} \quad S = \text{sieving coefficient} \quad \text{Equation 1}$$

The $C_{UF}$ is measured by the OSS and S is known for the target solute.

$$C_{ArtR} = C_{InputR} \frac{Q_{PArt} + Q_{Fluid1}}{Q_{PArt}} \quad \text{Equation 2}$$

$C_{ArtR}$ is derived by adjusting $C_{InputR}$ for the effects of the pre-dilution with $Q_{Fluid}$.

$$C_{Inf} = \frac{C_{Fluid}Q_{Fluid}}{Q_{PArt}} \quad \text{Equation 3 (by definition)}$$

The recirculating solute fluxes originating from the systemic circulation ($C_{Sys}$) and from the blood bolus infusion can be conceptually separated (if the post-dilution fluid and or the dialysis fluid target solute concentration is zero as it is for citrate, calcium and magnesium) and Equation 4 follows by definition:

$$D_{Bolus}*C_{Inf}+D_{eff1}*C_{Sys}=C_{ArtRSys}*D_{filter}+C_{ArtRInf}*D_{filter}=C_{ArtR}*D_{Filter}$$

In Equation 4, $C_{ArtR}$ is derived from measuring $C_{UF}$, and $D_{Bolus}$, $D_{eff1}$, $D_{filter}$ is either directly measured or calculated.

Using $D_{eff1}=D_{Bolus}*(1-R)$ and solving Equation 4 for $C_{Sys}$ (equivalent to $C_{AC}$ or "arterial" access solute concentration) yields $$C_{Sys} = \frac{C_{ArtR}*D_F - \frac{D_B(C_{Fluid}Q_{Fluid})}{Q_{PArt}}}{D_B(1-R)} \quad \text{Equation 5}$$

In one implementation, the physical design of the access device used for the OSS 400 and the low $Q_B/Q_{AC}$ ratio is expected to eliminate access recirculation. However, the above novel calculations are provided when the OSS 400 is implemented as part of a (convective) RRT circuit where recirculation, although rare, may occur and its elimination may not be clinically immediately possible. Specific examples for the clinical use of OSS 400 integrated into a CRRT circuit for the simple measurement of systemic blood glucose and citrate levels are provided below.

For systemic blood glucose monitoring, patients with ARF in the ICU often have diabetes and/or various degrees of liver dysfunction. In such patients, tight glycemic protocols for blood sugar control are often difficult to administer safely and can have a high rate of hypoglycemic complications. Since these patients will often have baseline mental status changes as well and may be sedated and their liver's ability to respond to hypoglycemia may be compromised, a real risk of catastrophic hypoglycemic events is apparent. Frequent blood sugar monitoring by standard clinical methods is costly, labor intensive and may be inconvenient to the patient. Reliable glucose sensors have been developed by several companies in the quest for creating the "artificial endocrine pancreas" and are currently in preclinical or clinical trials. They all have to satisfy FDA safety regulations delineated for devices that come into direct contact with human blood or body fluids inside the body. However, such safety concerns would not apply if the sensors were deployed in the OSS allowing immediate human clinical trials of the clinical feasibility and value. These sensors could be immediately placed in the effluent line of a CRRT circuit.

For systemic blood citrate (and calcium) level monitoring, RCA during the delivery of CRRT (and possibly home nocturnal dialysis in the future) is emerging in the literature as the anticoagulation method of choice. In all applications of RCA in any form of RRT, there is a significant amount of citrate infused into the extracorporeal circuit. A portion of the citrate infused into the circuit ultimately enters the patient and is converted into bicarbonate by the metabolic action of the liver. When the liver function is markedly compromised, citrate is not converted, with consequent systemic citrate accumulation and hypocalcemia, hypomagnesemia and metabolic acidosis. In-coordinate prescriptions can also lead to net calcium gain or loss in the circuit, leading to further complications. In current clinical practice, laboratory values including Lytes 7 and total and ionized calcium are measured every 6 hours to detect a lack of citrate metabolism and abnormalities of calcium homeostasis. This increases the cost of RCA and does not provide complete safety as citrate accumulation can occur in 1-2 hours with sudden, marked changes in liver function with the current RRT prescriptions targeting higher treatment goals and fluid flows than in the past. Laboratory monitoring is obviously not an option in the home setting.

The online citrate, calcium and magnesium sensor according to the present invention may detect systemic citrate, calcium and magnesium level changes in real time before clinically significant derangements could occur, completely eliminating concerns about these solutes. This is likely to increase physician use of RCA in RRT in the ICU and may allow deployment of RCA in the home setting with the RCA home system described herein. The online citrate, calcium and magnesium sensor can easily provide online clearance measurements. Finally, the dosing of the replacement calcium plus magnesium infusion in RCA for CVVH is in part determined by the systemic citrate level, and the online citrate sensor can provide this information continuously.

The online citrate sensor is an implementation of the OSS with a specific optical citrate sensor that is placed into the CRRT circuit effluent fluid line carrying ultrafiltrate and or dialysate away from the hemofilter (FIG. 29b). Citrate present in the ultrafiltrate and/or dialysate fluid will be in the 0 to 15 mM range under normal operating conditions. In one example, the citrate sensor may utilize luminescence from a complex of citrate with a europium-based ligand (e.g., Chemical Communications 2005, pages 3141-3143: Parker et al, "A pH-insensitive, ratiometric chemosensor for citrate using europium luminescence"). This sensor technology is based on allowing citrate to reversibly associate with a europium ion-based complex. During spectrophotometry, the citrate-europium complex is exposed to an excitation light source and luminescence is measured at different wavelengths. The citrate concentration in the sample is determined by ratiometric analysis, calculating the ratio of the luminescence intensities at the different wavelengths. This citrate sensor technology has no interference from phosphates, lactate or bicarbonate, has a response time in the millisecond range and is not affected by pH changes in the range of 4.8-8.0. In accordance with the present invention, the abundant, clear crystalloid CRRT effluent fluid is eminently suitable for spectrophotometry analysis online. As the detection relies on luminescence changes with europium and citrate association and dissociation, there is no consumption of reagents (if the europium ligand is immobilized in the flow-through detection chamber) or fading as with electrode or enzyme based methods of citrate detection published by others in the past. The published optical system was fine-tuned to the 0-3 mM citrate concentration; however this may be adjustable by changing the amount and chemical design of the europium complex used.

Figure 30A:
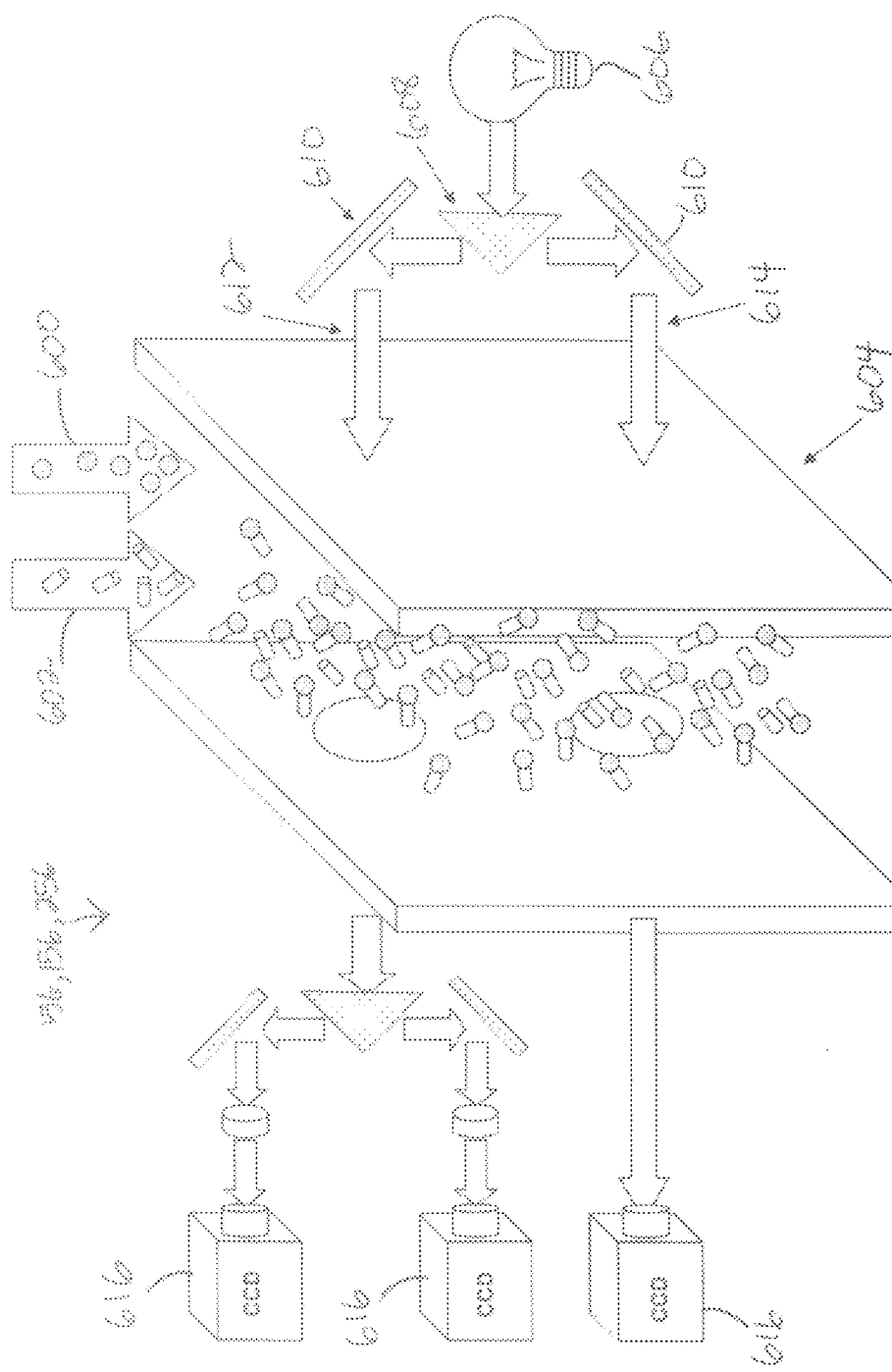
FIG. 30a is a schematic illustration of a citrate, calcium and magnesium sensor according to the present invention for use in a continuously flowing fluid circuit.
Figure 30B:
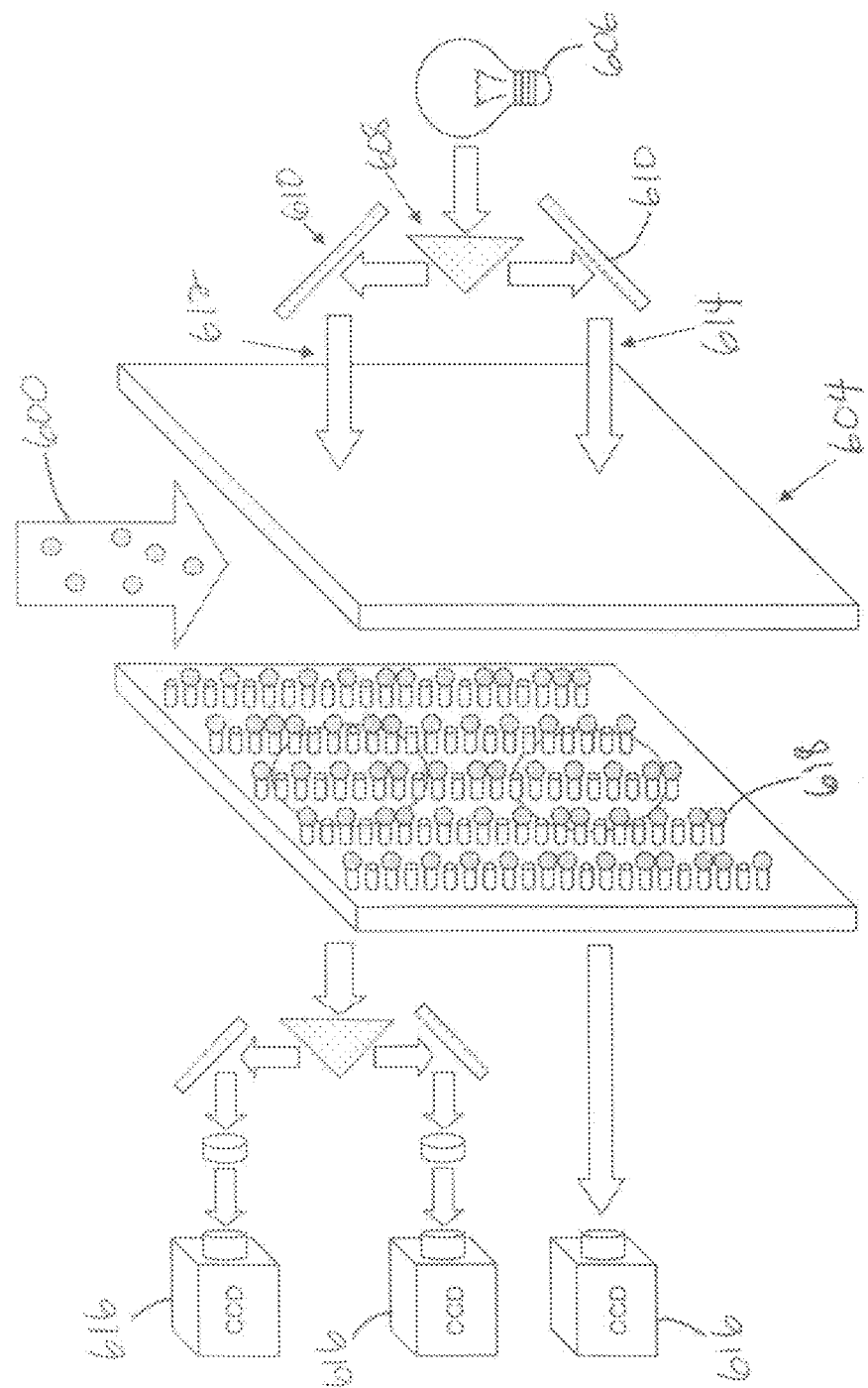
FIG. 30b is a schematic illustration of a citrate sensor according to the present invention for use in a continuously flowing fluid circuit.

In accordance with the present invention, the sensor 56, 156, 256 may be created by either diverting a small amount of the CRRT effluent 600 (<1 ml/minute to conserve reagents) for mixing with the europium-ligand containing detection reagent 602 in a flow-through light transparent chamber 604 (FIG. 30a) or by covalently immobilizing the detector europium complex onto the wall of a flow-through light transparent chamber 604 in the fluid pathway of the entire effluent (FIG. 30b). FIG. 30a illustrates a citrate, calcium and magnesium sensor 56, 156, 256 according to the present invention for use in a continuously flowing fluid circuit. The system mixes the opto-chemical probes 602 and the drain fluid 600 containing citrate, calcium and magnesium before making optical measurements. A light source 606, prism 608, and mirrors 610 create a measurement optical path 612 and a control optical path 614. Probe binding results in changes in light absorption and or emission at specific wavelengths, where changes in light intensity may detected by optical detectors 616 (e.g., charge coupled devices) and converted into electronic signals. The total citrate, calcium and magnesium concentrations may be determined by a processing unit using calculations based on the obtained data. FIG. 30b illustrates a citrate, calcium and magnesium sensor 56, 156, 256 for use in a continuously flowing fluid circuit which utilizes chemical probes 618 immobilized, such as in a hydrophilic polymer film that coats surfaces, in a light transparent cuvette 604. The probes 618 bind citrate, calcium and magnesium which freely diffuse between the drain fluid 600 and the cuvette 604, where probe binding results in changes in light intensity that may be used to determine the total citrate, calcium and magnesium concentrations as above.

Due to the tight coordination of the europium ion into the complex covalent bond chemical structure of the ligand (akin to the coordination of the iron (Fe) ion in the heme group), a sensor 56, 156, 256 based on the europium ligand-coated chamber 604 should be very stable for days of continuous operation. The flow through chamber 604 may be locked into a spectrophotometer module on the machine that provides excitation light 606 (e.g., at 384 nm wavelength) and luminescence detection 616 (e.g., at 579 nm and 616 nm wavelengths). For patient safety and increased accuracy, two citrate sensors may be used. Sensor values may be compared and, if they deviate by a predefined value, the system will signal an alarm to prompt corrective measures. One light transparent chamber 604 with two optical paths 612, 614 could be used for the system as shown (FIGS. 30a and 30b).

There are multiple other chemical-optical sensing technologies which may also be used for citrate (see, for example, Anslyn et al, Tetrahedron, Volume 59, Number 50, 8 Dec. 2003, pp. 10089-10092(4)) and may form the basis of the optical-chemical transducer part of the online citrate sensor according to the present invention. However, it is understood that the application of simultaneous monitoring of citrate, calcium and possibly magnesium levels in effluent fluids of extracorporeal blood treatment devices is fully contemplated according to the present invention, regardless of the specific sensing technology used. One physical implementation includes a combination of possibly disposable, optical-chemical transducers and possibly fixed, non-disposable optical excitation, readout and analysis modules, wherein the latter may be separated from the effluent fluid by a light-transparent, sterile/fluid barrier (flow through chamber). Once real-time measurement of citrate, calcium and magnesium is provided in the effluent, a software module may determine the systemic citrate concentration based on the methodology described herein for any filterable solute in general. Specific use of the data obtained are described below.

For detection of systemic citrate accumulation due to lack of liver metabolism, the machine can send an alarm to the operator when a critical threshold of systemic plasma citrate concentration is exceeded. A clinical assessment of the patient and the CRRT treatment with full laboratory parameters can then follow with appropriate changes to the care of the patient. Increasing citrate levels in the blood entering the extracorporeal circuit due to recirculation at the catheter tip can be detected by the recirculation detection feature of the online hematocrit sensor which may be integrated into the RCA system of the present invention, thereby eliminating false citrate alarms and allowing for exchange of the dysfunctional access catheter in a timely manner.

The online citrate sensor may be used to guide the calcium plus magnesium infusion dosing. During the operation of the RCA system according to the present invention (and in other CRRT systems with RCA), the ultrafiltrate calcium content and magnesium concentration is equal to the total patient systemic plasma calcium or magnesium concentration adjusted for the degree of pre-dilution with the calcium and magnesium free pre-filter fluid, respectively. The high clearance goals achieved with the RCA System ensure that only chloride, albumin, lactate, bicarbonate and citrate can persist as anions in high concentrations in the patient's plasma. Other anions including phosphate will be quickly reduced to physiologic levels by the effects of the CVVH procedure, and systemic pH will also approximate the normal 7.4. The anion beta-hydroxybutirate can be eliminated by administering glucose and insulin if needed. Under these conditions, the patient's systemic total and ionized calcium and magnesium levels can be programmed as long as the only clinically significant variable, the current systemic plasma citrate level is known, which may be provided by the online citrate and calcium sensor according to the present invention. (Lactate, the other patient-specific clinically-variable anion does not seem to affect ionized Ca levels sufficiently to be of clinical concern). Since the systemic blood citrate level is derived by the online citrate sensor and the plasma albumin concentration of the patient is known from laboratory studies (and is unlikely to fluctuate quickly), a desirable total systemic plasma calcium and magnesium concentration can be targeted (a constant fraction of which, in turn, will appear in the ultrafiltrate as net loss from the patient) to keep the ionized calcium (and magnesium) in the physiologic range. Using this programming of calcium and magnesium replacement, all patients may be at target ionized calcium values with much lesser need for frequent monitoring of their laboratory parameters. It is also of importance that the sieving coefficient of calcium and magnesium in the RCA system may be near 1.0 (different from 0.6 in regular CVVH without citrate) due to the unique RCA fluid design of the present invention and the fact that only convective clearance may be used.

Next, an online filter clearance (performance) and patency monitor is described. Accuracy of the online citrate and calcium sensor according to the present invention can be easily tested by deploying the sensor in duplicate and by varying the circuit plasma flow to citrate anticoagulant infusion ratio by changing the blood flow rate and pre-filter fluid flow rate ratio (citrate blood bolus based method). This will result in an immediate and predictable change in the ultrafiltrate citrate level. The changes measured by the sensor can be compared with the predicted changes to monitor filter patency and sensor accuracy. Ideally, the sensor is checked initially at the time of the priming of the circuit with a modified saline solution that contains Ca, Mg and citrate at the start of the CRRT procedure. Subsequent measurements should match the initial filter and sensor performance. Once the citrate clearance is known (particularly in a purely convection based RRT treatment as delivered with the RCA systems), the clearance of any solute with a known sieving coefficient on the specific type of hemofilter used can be easily calculated. This will be of great value to pharmacists with the increasingly widespread use of high clearance targets in RRT protocols and concomitant very effective removal of various medications. The signal to baseline ratio of the citrate based online clearance monitor can be as high as 1:1 (by doubling the citrate infusion rate temporarily), possibly ensuring more accurate measurements than existing technology can provide (depending on the resolving ability of the citrate and calcium sensors as well). The current gold standard online clearance method relies on varying the sodium concentration of the dialysate and detecting the changes by monitoring the conductivity of the circuit effluent. The data obtained mainly reflects the movement of the small solute sodium and may be of lesser value when the clearance of middle to large size molecules is investigated. In contrast, when OSS technology of the present invention for high molecular weight inulin is used (see below), the filter online clearance of middle and large molecular weight solutes can also be monitored, which cannot be accomplished by other devices currently in clinical use. Monitoring such clearance may become important in the future to follow the efficacy of the removal of cytokines and antibiotics through the filter with high volume CVVH.

Finally, it should be noted that in the event of a citrate sensor malfunction, the RCA system according to the present invention will still continue to operate and provide RCA for RRT in a safe default mode relying on their safe prescription algorithms and OCM modules for the monitoring of filter performance and hence, indirectly, citrate clearance.

The clinical use of the OSS according to the present invention integrated into a CRRT circuit to obtain systemic solute concentration kinetic curves as a function of time to calculate and monitor liver metabolic function, glomerular filtration rate and renal plasma flow with specific examples for citrate, inulin and PAH monitoring is now described. Despite significant advances in ICU therapy, the mortality of acute renal failure (ARF) requiring renal replacement therapy has remained essentially unchanged in the past decades at very high levels, particularly when ARF is caused by acute tubular necrosis (ATN) in the setting of the systemic inflammatory syndrome (SIRS) with or without multi-organ dysfunction syndrome (MODS). Emerging data suggests that the very early (within 0-24 hours of the start of the acute kidney injury (AKI), initiation of high dose convective CRRT may have a favorable impact on patient survival and recovery of renal function. It is expected that in the future, high dose CVVH will be started earlier for a broader group of patients as long as difficulties of the procedure are overcome (as described with reference to the RCA system according to the present invention).

However, the new treatment approach will create new clinical dilemmas as well. Many patients will be non-oliguric, and with the high clearance goals, traditional markers of renal function including blood urea nitrogen (BUN) and creatinine will be in the normal or near normal range. Furthermore, the levels of these solutes are also influenced by a multitude of factors other then renal function including, but not limited to, the amount of muscle mass and muscle breakdown for creatinine, and tissue catabolism, the use of corticosteroids, and the presence or absence of gastrointestinal bleeding for BUN. Precise information on renal function will be indispensable for proper medication and CRRT dosing and to know when renal recovery has occurred to the degree that the CRRT could be stopped. As a result, the development of new, clinically feasible methods to assess glomerular filtration rate and renal function will be necessary.

Similarly, currently there is no reliable, inexpensive clinical method to follow liver parenchymal function in critically ill patients. Laboratory tools in current use provide only indirect assessment and may take 12-24 hours to reflect marked changes in liver function. The only alternate to routine chemistry testing, the ICG-Pulsion technology and device, is fairly costly, does not provide continuous data, and has failed to gain wide-spread use to date. More accurate and real-time assessment of liver function is needed for the safety of RCA that usually depends on primarily the liver to clear the bulk of the citrate entering the patient's body. Timely information on the metabolic function of the liver would also be helpful in the management of acutely ill liver failure patients being evaluated for liver transplantation and in the post-liver transplantation period.

The present invention provides a method of kinetic analysis of systemic concentration curves obtained by the OSS as a function of time for various solutes that can be used to determine liver metabolic function, glomerular filtration rate, and renal tubular secretory function in real time, online. The description below reviews the theoretical principle of solute kinetic modeling as relevant to the clinical tool according to the present invention, utilizing the specific example of citrate. The use of two additional specific substances are then briefly reviewed that could be of immediate interest in clinical practice.

An explanation of the theoretical principle of single pool kinetic modeling of solute (e.g. citrate) loading into the apparent solute volume of distribution of the patient treated with CRRT and clearance of the solute (e.g. citrate) from the patient by the CRRT circuit and body clearance mechanisms (metabolism and/or elimination by the liver and/or kidneys) is described below. While citrate is used in this example, the equations are applicable to any water-soluble substance.

Figure 31:
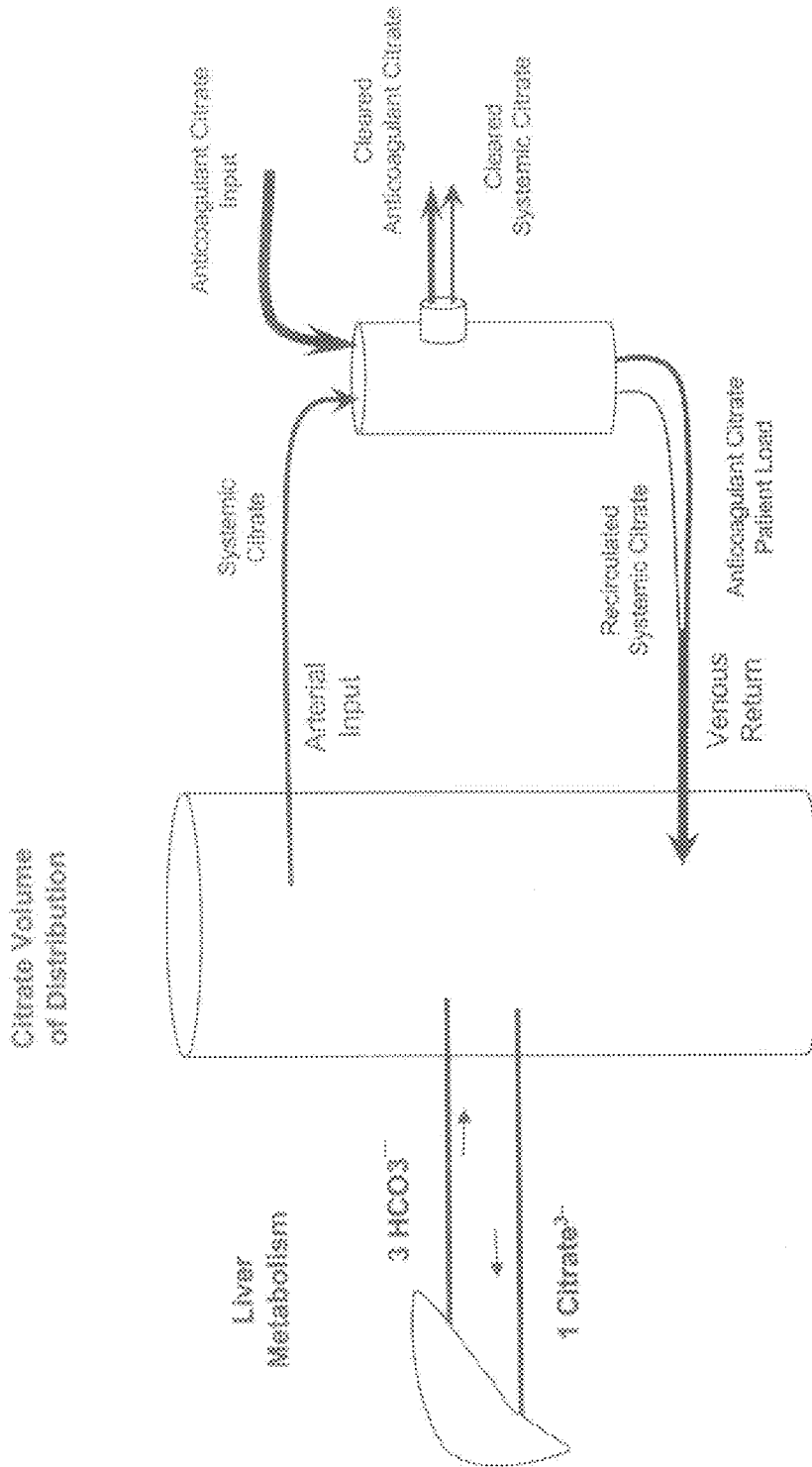
FIG. 31 is a schematic illustration of systemic citrate kinetics during citrate anticoagulation including citrate generation, citrate body clearance and citrate filter clearance in accordance with the present invention.
Figure 32:
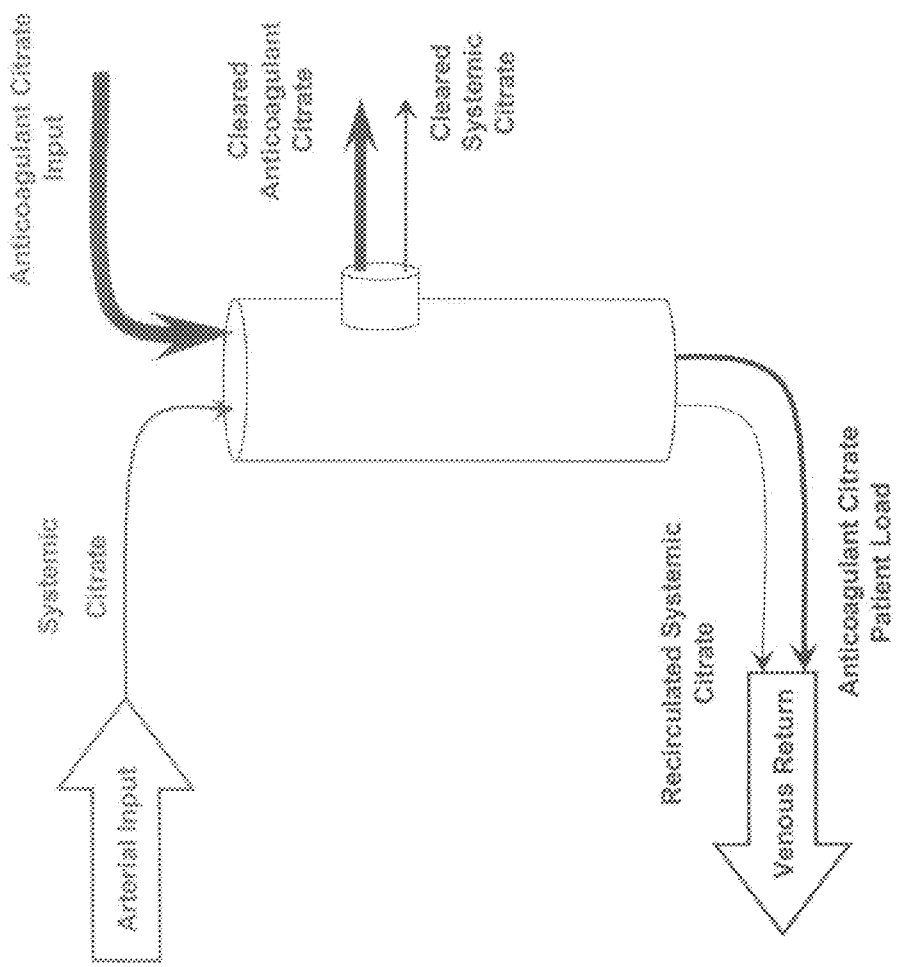
FIG. 32 is a schematic illustration of solute fluxes in the extracorporeal circuit during CRRT according to the present invention using citrate as a small solute example.

Citrate loading (generation) into the patient in CRRT occurs through the infusion of new anticoagulant into the circuit. The systemic citrate kinetics during citrate anticoagulation are shown including citrate generation, citrate body clearance and citrate filter clearance, including the citrate mass balance fluxes in the patient and the extracorporeal circuit, are shown in FIG. 31. These concepts can be generalized to any solute that enters the body and/or is produced in the body at a steady rate and is cleared from the body through a concentration dependent mechanism by metabolism and/or elimination by filtration and/or secretion by the liver, kidney and/or the CRRT circuit as applicable. FIG. 32 is an explanation of solute fluxes in the extracorporeal circuit during CRRT using citrate as a small solute example, wherein the citrate load in the circuit is the fraction of the newly infused anticoagulant that is not cleared on the filter in a single pass (further correction is needed when access recirculation is present). When the blood flow, anticoagulant flow, net ultrafiltration amount, and replacement fluid flows as well as the filter performance are constant, this amount is also constant. Citrate removal from the patient is the summary of the citrate cleared from the systemic blood of the patient on the hemofilter and the citrate cleared by the patient's body, predominantly by metabolism in the liver. These mass fluxes of citrate can be described by equations as shown below. The definitions of the parameters used in the calculations are as follows:

$C_{(t)}$ (mmol/L): the patient's systemic plasma citrate concentration at "t" time point after CVVH started $C_{(0)}$ (mmol/L): the plasma citrate concentration at the start of CRRT with RCA, defined as zero $C_{(steady)}$ (mmol/L): the plasma citrate concentration when the steady state is reached $T_{(90\%)}$ (minutes): the time it takes to build up the plasma citrate level to 90% of the steady state value $V_{(d)}$ (L): the patient's volume of citrate distribution (predicted to be equal to the extracellular fluid volume)

G (mmol/min): the net citrate load into the patient from the pre-filter fluid after passing through the filter K (L/min): the total clearance of citrate from the patient's body that is the summary of:

$K_{(b)}$ (L/min): the body clearance or metabolism of citrate (the equivalent of $K_r$ in the urea equation)

$K_{(f)}$ (L/min): filter clearance of systemic citrate

B (L/min): the net change in V per minute (net ultrafiltration rate)

$Q_B$: effective circuit arterial blood water flow specific for the solute measured; arterial blood plasma water flow for citrate, ($Q_{PArt}$)

$C_{Inf}$: citrate concentration step-up in the effective blood water entering the filter during baseline anticoagulation over the effective blood water citrate concentration entering the arterial limb of the blood circuit with pre-dilution removed $C_{Bolus}$: citrate concentration step-up in the effective blood water entering the filter during the citrate bolus over the effective blood water citrate concentration entering the filter with baseline anticoagulation, with pre-dilution removed $Q_R$: the recirculating circuit venous limb blood effective water flow (solute specific)

R: the recirculation ratio defined as $R=Q_R/Q_B$; (measured by hemodilution or thermodilution)

$D_{Bolus}$: measured solute dialysance affected by access but not cardiopulmonary recirculation and determined by the blood bolus based measurement for conductivity (OCM) or citrate (citrate sensor)

$D_{Eff1}$: effective solute dialysance determined from $D_{Bolus}$ by correcting for access recirculation only R is measured as discussed previously herein. Using the citrate, calcium and magnesium sensor features of the OSS according to the present invention as well as the novel citrate blood bolus-based online clearance method described herein for conductivity and fully applicable for citrate (after making the adjustments for the effective QB being QP for citrate), citrate DBolus is measured and Deffective1 is calculated. The following will be true:

1·G=Cinf*(QBCit−DBolus)

2·K(f)=Deffective1=DBolus*(1−R)

The change in the systemic concentration of citrate as a function of time will be determined by the difference in the positive citrate flux into the patient (G) that is constant and the negative citrate removal flux (filter and body clearance multiplied by the systemic citrate concentration), which negative flux is variable and is determined by the changing systemic citrate level. The mathematical formula is shown in equation 1.

$$d(CV)/dt = G-(K_{(b)}+K_{(f)})*C \text{ (single pool, variable volume citrate equation)} \quad 1)$$

This equation will be clearly familiar to nephrologists. This is, in fact, the well-known formula for the single pool kinetic modeling of urea removal during hemodialysis. The following differences should be noted:

a. G is body generation of urea whereas it is a steady patient load of citrate here b. Urea distributes in total body water whereas citrate distributes only in the extracellular volume (ECV)

c. Urea clearance is defined as whole blood volume per minute and citrate as plasma volume per minute (following from their respective volumes of distribution)

d. The relative importance of G and $K_{(b)}$ is much greater for citrate during RCA for RRT than for urea during traditional hemodialysis However, none of these differences will affect the applicability of the equation or its solution. Single pool modeling can be reliably used as the rate of solute transfer per hour is fairly low in CRRT and the citrate volume of distribution is the ECV with rapid equilibration from the intravascular space (intracellular levels are kept low mandatorily by metabolism to prevent interference with intracellular calcium signaling and probably by the lack of high capacity transmembrane carriers in most tissues except the liver and to a lesser degree skeletal muscle.) The mathematical solution developed for urea single pool kinetic modeling will therefore be applicable to predicting systemic citrate levels at any time point of the RCA for CVVH treatment. The solution of Equation 1 yields Equation 2:

$$C=C_{(0)}((V-B*t)/V)\exp(((K_{(b)}+K_{(f)}+B)/B)+(G/(K_{(b)}+K_{(f)}+B)))*(1-((V-B*t)/V)\exp((K_{(b)}+K_{(f)}+B)/B) \quad 2)$$

Fortuitously, the net ultrafiltration per hour (B) in CRRT is relatively negligible when compared to the ECV of the patient and the equation can be simplified by eliminating B while preserving clinically adequate accuracy to give the solution for a single pool, fixed volume citrate kinetic model (Equation 3):

$$C = C_{(0)} e\text{-}\exp((K_{(b)}+K_{(f)})*t/V) + (G/(K_{(b)}+K_{(f)}))* (1-e\text{-}\exp((K_{(b)}+K_{(f)})*t/V)) \quad 3)$$

FIG. 33 illustrates plasma citrate concentration in the patient during RCA. The systemic plasma citrate concentration kinetic curve predicted by Equation 3 can be obtained by the OSS of the present invention when implemented as a citrate sensor in the effluent line of a CRRT circuit. In the clinical setting, all variables that determine the shape of the kinetic curve of the individual patient can be exactly defined by the treatment operational mode and the CRRT fluid composition(s) as well as circuit blood and CRRT fluid flow rates and/or measured by the online blood bolus dialysance method described herein. The parameters are constant ($C_{(0)}$, $K_{(f)}$ and G) or near constant ($V_{(d)}$) at fixed circuit plasma and CRRT fluid flow rates. The $V_{(d)}$ can be estimated fairly accurately from anthropometric data. Therefore, for a given patient, the $K_b$ value can be mathematically derived from the systemic citrate concentration curve imaged by the online citrate sensor according to the present invention. Any subsequent change in the $K_{(b)}$ will result in predictable changes in the systemic plasma citrate concentration and will be detected in real time by monitoring this variable, $C_{(t)}$, by the OSS. Clinically important predictions of Equation 3 are as described below.

In steady state when the systemic citrate concentration is constant, the citrate load is equal to citrate removal, Equation 4:

$$G = C_{(steady)} * (K_{(b)}+K_{(f)}) \quad 4)$$

It follows that $C_{(steady)}$ is defined only by the CRRT treatment settings defining G and $K_{(f)}$ and the patient's citrate metabolism $K_{(b)}$ and is not influenced by the citrate volume of distribution, Equation 5:

$$C_{(steady)} = G/((K_{(b)}+K_{(f)})) \quad 5)$$

It is then shown that if a CRRT prescription is provided that achieves more than 70% single pass clearance of the anticoagulant citrate infusion on the filter, proportionally keeping G low and $K_{(f)}$ high, the $C_{(steady)}$ cannot exceed 2 mmol/L even if $K_{(b)}$ is zero (consistent with no metabolism of citrate by the patient's liver), regardless of the magnitude of prescribed clearance goals (if $C_{Inf}$ is around 5-6 mM). Such a prescription is important to the safety of RCA in RRT when the liver function is either unknown or is known to be severely compromised. Such prescriptions in current clinical practice are limited to the mainly diffusive treatments of CVVHDF with high dialysate flow rates and c-SLED. Safe prescriptions based on purely convective clearance accomplishing high treatment goals are provided for the first time by the dosing programs of the RCA system and method according to the present invention.

When a CRRT prescription is used that allows for dangerous citrate accumulation if the patient's liver is not metabolizing citrate (such prescriptions are more fluid and cost efficient and could be used for about 90% of patients who do not have liver failure), it is important to know clinically how long an individual patient needs to be monitored closely after the initiation of RCA for CRRT to reliably determine whether he or she can metabolize the infused citrate, particularly if the online citrate sensor of the present invention is not used. Assuming the systemic citrate concentration at the start of the RCA, $C_{(0)}$ is zero, the time to reach 90% of the predicted $C_{(steady)}$ based on the assumed liver function, $T_{(90\%)}$ can be calculated, as in Equation 6:

$$T_{(90\%)} = (V_{(d)} * \ln(10))/(K_{(b)}+K_{(f)}) \quad 6)$$

This equation shows that a patient with liver failure with $K_{(b)}$ zero, large ECV ($V_{(d)}$) and a CRRT prescription with a low clearance goal (and resultant low G and $K_{(f)}$) may take up to 5-10 hours to reach toxic citrate levels, but nevertheless will reach these levels eventually. Monitoring should cover this period and adequacy of liver metabolism should not be concluded based on relatively low citrate levels in the first few hours of treatment. Using these concepts, all patients with insufficient liver function at start can be correctly identified in the first few hours of RCA with CRRT, particularly when the OSS is used to monitor citrate levels and $K_{(b)}$ in real time.

Figure 34A:
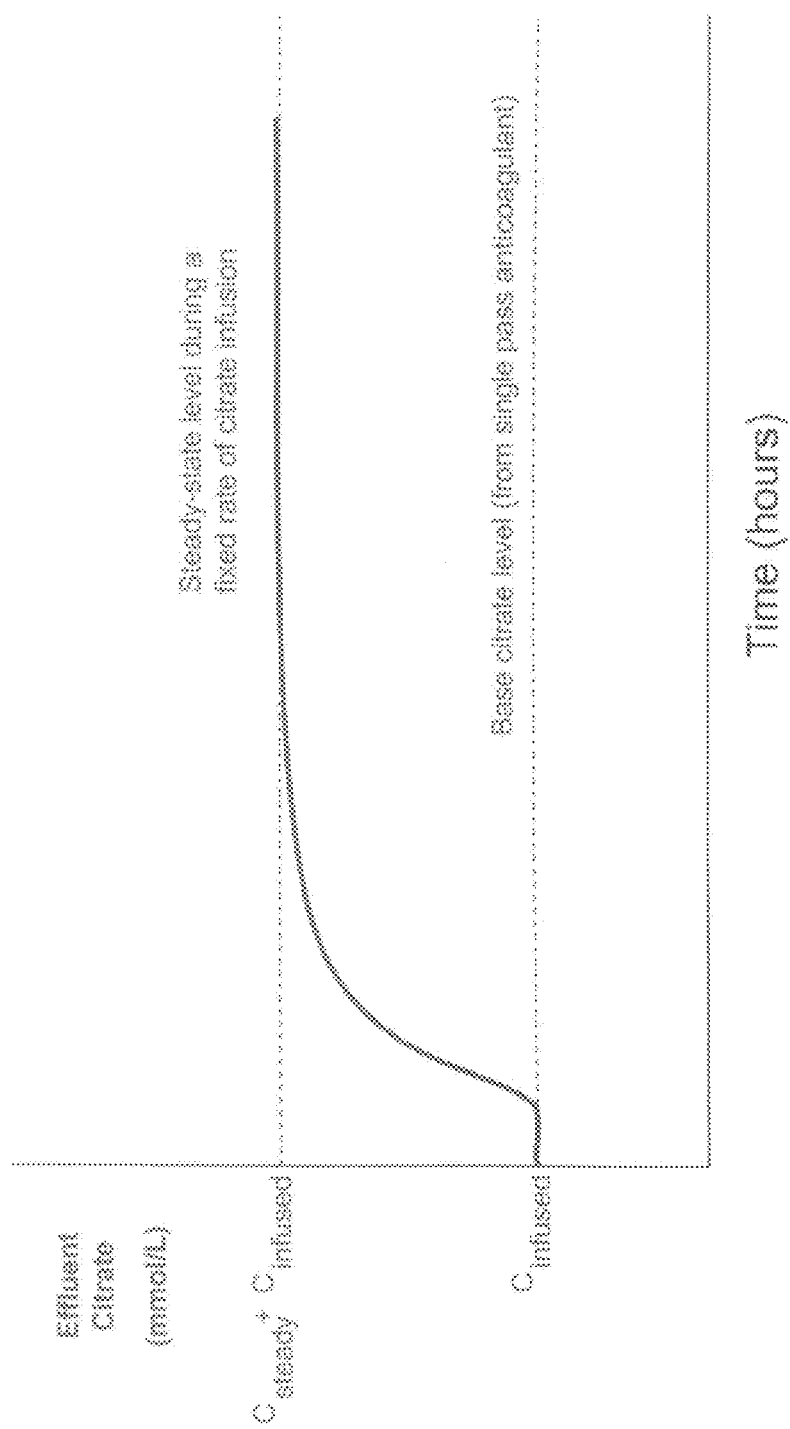
FIG. 34a is a graph depicting citrate concentration measured by a citrate sensor in the drain circuit of a renal replacement therapy machine utilizing RCA with fixed CRRT prescription settings according to the present invention that result in the development of a citrate steady state determined by the CRRT settings and the patient's citrate metabolism.

An example of imaged systemic citrate plasma concentration curves as a function of time are provided in FIG. 34a (normal operation of CRRT with RCA). FIG. 34a illustrates citrate concentration measured by a citrate sensor in the drain circuit of an RRT machine utilizing RCA with fixed CRRT prescription settings that result in the development of a citrate steady state determined by the CRRT settings and the patient's citrate metabolism. FIG. 34b illustrates citrate concentration measured by a citrate sensor in the drain circuit of a dialysis machine utilizing RCA. When the patient experiences hepatic failure and no longer metabolizes citrate, the steady state is disrupted and the plasma and ultrafiltrate citrate concentration will increase until another markedly higher steady-state citrate level is reached. The magnitude of change in the citrate level will depend on the CRRT settings. In FIG. 34b, when after a period of normal operation of RCA with CRRT the liver function of the patient changes (deteriorates) suddenly (for instance, a previously stable patient tolerating RCA for CRRT well may develop liver failure after a cardiac arrest and resuscitation and subsequent citrate accumulation in as little as one to two hours if the RCA for CRRT is continued). Such a complication would not be detected in time with only routine every-six-hour monitoring of total and ionized calcium levels, as is the current clinical practice. This is where the unique value of the online citrate sensor according to the present invention as a safety device may be fully realized and demonstrated.

Finally, knowing the value of $K_{(b)}$ in real time has other benefits as well. For example, it also means that citrate conversion into bicarbonate in the patient's body can be calculated exactly, allowing accurate determinations of bicarbonate mass balance during RCA for CRRT (the greatest precision is provided by the RCA system where all solute movement is convection based and all fluid flows are provided flexibly, but in tight coordination and are continuously monitored by the hematocrit and Doppler sensors and the volumetric pumps of the system). This allows for exact calculation of net bicarbonate gained or lost through the RCA for CRRT procedure with its implications for the patient's acid-base balance.

The use of the OSS according to the present invention to monitor liver function through citrate levels, glomerular filtration rate through inulin levels and renal tubular secretory function through PAH levels is now described. For all of these applications, the present invention provides a method of keeping the single pass filter extraction of the measured solute below 50% to increase the sensitivity of the method.

For monitoring liver metabolic function with the OSS, the OSS will obtain a kinetic curve of systemic plasma citrate levels as described above and once a steady state is reached, will continuously display the $C_{(steady)}$ value of systemic citrate. As shown in Equation 5:

$$C_{(steady)} = G/(K_{(b)} + K_{(f)}) \qquad 5)$$

$K_{(b)}$ is the liver clearance of citrate and has been measured to be between 0.2-0.5 L/min in ICU patients. The value of $K_{(f)}$ will be 0.03-0.07 L/min with CRRT clearance goals in the range of 20-35 ml/kg/hour as current clinical practice. Since $K_{(b)}$ is almost 10-fold greater than $K_{(f)}$, even small percent changes in $K_{(b)}$ will be sensitively reflected in the $C_{(steady)}$ value if the single pass citrate extraction on the filter is 50% or less. This makes the systemic steady state citrate level an excellent marker of liver perfusion and metabolic function. Sudden decreases in liver function will be reflected in the imaged systemic citrate level almost immediately (FIG. 34b), alerting the health care team to this complication hours before derangements of blood clotting (INR) or alterations in other liver function tests could be expected. The only currently available, distantly similar clinical method to image the liver metabolic function, the ICG-Pulsion device is based on a bolus IV injection and subsequent selective liver clearance of a fluorescent label conjugated ICG molecule with the transcutaneous imaging of the washout of the fluorescent label from the patient's circulation. This application is costly, it has caused adverse reactions, and it does not provide continuous 24-hour monitoring and so far has failed to gain a wide user base.

Monitoring renal function with the OSS with inulin and para-amino-hippuric acid (PAH) can also be accomplished according to the present invention. Traditionally, inulin has been the "gold standard solute" used to monitor glomerular filtration rate in human renal research protocols. Inulin is an inert polysaccharide of varying molecular size that is non-toxic, not metabolized by the human body and is eliminated solely by glomerular filtration without any tubular secretion or reabsorption. According to the present invention, inulin may be introduced into the CRRT circuit (and the patient) with the anticoagulant infusion pre-filter and the exact same kinetic modeling used as provided for citrate to describe its accumulation and elimination; therefore according to Equation 5:

$$C_{(steady)} = G/(K_{(b)} + K_{(f)}) \qquad 5)$$

The order of magnitude of the targeted $C_{(steady)}$ value will be defined by the sensitivity of the inulin sensor in the effluent line of the CRRT circuit and can be achieved by carefully correlating the concentration of inulin in the anticoagulant infusion with the infusion rate. If a simple, sensitive inulin sensor is not available, inulin can also be provided conjugated with a non-toxic fluorescent or another chemical label for convenient optical detection. One difficulty may be that the $K_{(b)}$ value of interest for inulin (the glomerular filtration rate of the patient in acute renal failure on CRRT) will fall in the range of 0.000 to 0.050 L/min. Obviously, most patients' GFR will be close to zero initially with the values increasing when recovery of renal function is occurring. At the same time, the $K_{(f)}$ will be around 0.03-0.07 L/min with CRRT clearance goals in the range of 20-35 ml/kg/hour as mentioned above. Since the monitored parameter $K_{(b)}$ is smaller than $K_{(f)}$ (a fixed value with a fixed CRRT prescription), the $C_{(steady)}$ inulin will be a less sensitive marker of GFR and recovery of renal function than citrate levels are of liver function. One way to improve the sensitivity of the method is by using inulin enriched in larger inulin polymers (up to molecular weight of 10-60 kiloDaltons) that may have a significant sieving phenomenon on the hemofilter but not in the glomerulus, and correspondingly may have a markedly reduced $K_{(f)}$ when compared to standard inulin with mostly smaller polysaccharide oligomers. As an added benefit, the detection of large molecular weight inulin can be used as an online clearance-monitoring tool for middle and large molecular weight solutes (for instance to predict the continued effectiveness of convective cytokine removal in sepsis). Such monitoring technology does not exist in current clinical practice.

While these maneuvers to improve the sensitivity of the inulin-based method to monitor the recovery of renal function may work, the simultaneous use of para-amino-hippuric acid (PAH) or another, water soluble and ultrafilterable, non-toxic small solute undergoing extensive tubular secretion in the kidney, may be recommended to increase the sensitivity of monitoring renal function on CRRT. PAH may be introduced into the CRRT circuit and the patient with the anticoagulant infusion following the same principles as for citrate and inulin. Equation 5 is again used to describe the relationship of the systemic steady state PAH concentration with renal PAH clearance:

$$C_{(steady)} = G/(K_{(b)} + K_{(f)}) \qquad 5)$$

PAH is a small organic acid solute that is non-toxic, cleared exclusively by the kidneys and has been extensively used in renal research protocols. Its $K_{(f)}$ will be around 0.03-0.07 L/min with CRRT clearance goals in the range of 20-35 ml/kg/hour, similar to citrate. However, PAH is cleared by the kidneys by both glomerular filtration and by a very active tubular secretory mechanism as well. As a result, PAH clearance under normal conditions is equal to the renal plasma flow and can be up to 0.6 L/minute, about 10-fold higher then $K_{(f)}$. Initially, when the patient has ARF with or without oligo-anuria and is started on CRRT, the PAH clearance may be zero. However, very significant increases can be expected with incremental recovery of kidney function and tubular secretory function. Therefore, online monitoring of the PAH $C_{(steady)}$ level may prove a sensitive and specific method for the early detection of ongoing recovery of renal (tubular) function. Similar to inulin, the order of magnitude of the targeted $C_{(steady)}$ value will be defined by the sensitivity of the PAH sensor in the effluent line of the CRRT circuit and can be achieved by carefully correlating the concentration of PAH in the anticoagulant infusion with the infusion rate. Also similarly, if a simple, sensitive PAH sensor is not available, PAH can also be provided conjugated with a non-toxic fluorescent or other chemical label (with an emission wavelength different from the fluorescent inulin label's, if the two labeled compounds are to be used simultaneously) for convenient optical detection.

The OSS according to the present invention may also be implemented as a comprehensive safety module to provide online, truly continuous display of the systemic plasma total calcium, magnesium and citrate levels during any implementation of extracorporeal blood purification using regional citrate anticoagulation. Several RRT systems have been described herein that can provide RRT with RCA safely. In these systems, appropriately designed fluid compositions and carefully programmed fluid flows ensure a predictable and neutral calcium and magnesium mass balance, and in default operational modes preclude the development of citrate accumulation even if the patient has liver failure. However, more replacement fluid efficient (and thereby more economic) prescriptions can be used for about 90% of patients who can metabolize citrate. The clinical problem is that patients can deteriorate and stop metabolizing citrate at any time during their treatment course. Online citrate level monitoring is therefore necessary with such prescriptions and can be implemented as described herein. Stable filter performance is important to the safety of diffusion based RRT with RCA prescriptions. The OCM according to the present invention may be used; however, it provides only indirect information on citrate clearance that may not suffice for the higher safety prerequisites of home RCA protocols. Finally, calcium and magnesium levels are maintained through the maintenance of mass balance in the RRT circuit. However, even with the best design, a catastrophic system failure may occur, one example being the puncture of the calcium plus magnesium replacement infusion line with subsequent failure to infuse these ions into the patient as needed. When high blood flows are utilized, such a system failure could lead to life threatening hypocalcemia within 10-20 minutes. Routine laboratory monitoring every 6 hours as done in current clinical practice will not be able to detect such a problem in a timely manner Therefore, real time (online) monitoring of calcium and magnesium levels in the systemic plasma of the patient is needed.

The present invention provides a novel, mathematically exacting, continuous monitoring method to address the above problem. The method utilizes the knowledge that the composition of the patient's systemic plasma can be back-calculated from the composition of the ultrafiltrate, knowing exactly what composition fluids and in what amounts were infused into the systemic blood in the arterial limb of the circuit before ultrafiltration and the sieving of individual solutes on the filter. This data is readily available in a given treatment. These calculations have been described previously herein, including corrections for access recirculation, when present. The method also utilizes the simultaneous measurement of ionized citrate and ionized calcium and/or ionized magnesium and/or any of their complexes with citrate. The final method and detections used may differ slightly from what is described herein based on future clinical experience, but the method according to the present invention includes the simultaneous measurement of the relevant interacting cations and anions. The method also utilizes the application of chemical and mathematical principles governing the interactions of these ions in the ultrafiltrate (these interactions have been elucidated in detail in the literature) with the specific purpose to derive the total calcium and total citrate levels in the ultrafiltrate in real time for safety monitoring of the RCA for CRRT procedure without any need to interrupt or modify the citrate anticoagulation.

The back-calculation of plasma concentration from ultrafiltrate concentration may be accomplished in CVVH and the calculations used are displayed in FIGS. 29a-29c for a solute that distributes only into the plasma volume and not into the red blood cells. Calcium and citrate both distribute in this way. The calculations can also be performed when diffusion-based clearance is used (dialysis) or when a mixture of dialysis and convection is used (hemodiafiltration), and are not discussed here as they are known to those skilled in the art using the general concept of dialysance. The use of the online clearance function of the citrate sensor according to the present invention will verify through the measured $D_{Bolus}$ (and by using the separately measured R) the accuracy of predictions of solute movement on the filter based on theoretical calculations under these more complex circumstances.

Ionized calcium in the ultrafiltrate can be measured with a calcium selective electrode. Such electrodes are in routine clinical use today and could be easily adapted to be inserted into the CRRT circuit effluent line. Unfortunately, these electrodes can be fairly error prone, require regular calibration and testing for accuracy and, with prolonged use, the electrode solutions will get depleted requiring maintenance or replacement of the electrode. While a calcium electrode may be used, the present invention also contemplates the use of no-maintenance, possibly disposable optical calcium sensors (optrodes or chemical-optical chips) for the calcium sensor. Such optrodes have been described in the literature and have many advantages over traditional calcium electrodes. Magnesium movement in the CRRT circuit parallels calcium movement. Magnesium replacement is also completely coordinated with calcium by virtue of being in the same replacement infusion solution. Therefore, only one of the two ions needs to be monitored during CRRT as there is not even any theoretical possibility of only one ion level becoming abnormal separate from the other as a consequence of the RRT procedure (it could, however, occur as a consequence of rare clinical situations and stemming from derangements in the patient's physiology). Nevertheless, if clinically desirable, duplicate monitoring could be done with a magnesium selective electrode or preferably with a magnesium selective optrode or chemical-optical chip.

One problem inherent to the measurement of calcium or magnesium by any method online (electrode or optrode or other) is that these methods detect the ionized $Ca^{2+}$ or $Mg^{2+}$ species. Unfortunately, in the citrate-rich CRRT effluent, 80-90% of calcium is bound by citrate and is not available for measurement as the ionized form. To circumvent this, periodic cessation of citrate infusion into the circuit could be considered but is not especially feasible as it involves the risk of clotting. It would also have to be done every 5-10 minutes at the highest blood flows targeted by the RCA system. The neutralization of the chelating effect of citrate by either eliminating it on an anion exchange resin or by acidifying the effluent to about pH 2 are both cumbersome and predictably prone to errors. Fortuitously, the detailed understanding of the chemical interactions of various ions in the ultrafiltrate affords a convenient and precise solution to this problem without the above undesirable maneuvers.

The solution requires the additional measurement of the free, 3-valent negatively charged citrate anion in the ultrafiltrate. This may be accomplished most conveniently by the method discussed earlier herein regarding the citrate sensor (see Parker et al. above). In that publication, the effect of competing divalent metal ions on citrate binding to the detecting complex were not investigated, but it is highly likely that the europium-ligand complex will only bind the free, trivalent negative citrate anion with high affinity and therefore will be eminently suitable for its selective detection in the CRRT effluent. In addition, the present invention also envisions the possible use of other citrate detection methods. The most promising alternative may be the method described by Anslyn et al. to detect calcium and citrate simultaneously and or building citrate optrodes where the citrate anion is bound by a specific receptor protein or antibody that was engineered to act as a molecular switch to transmit a fluoroprobe generated optical signal upon binding with citrate. The receptor peptide may have to be modified with molecular mutagenesis to optimize its specificity for the target trivalent citrate anion and increase pH independence of the binding in the range 6.5-7.5. Such molecular engineering is certainly feasible with currently available biotechnology. In general, all possible technologies that could be adapted for simple and inexpensive measurement of citrate in the effluent are fully contemplated for use with the method according to the present invention. It may also be possible to engineer receptor peptides that selectively bind the Mg-citrate and or Ca-citrate complex enabling their independent measurement. Finally, one or more different citrate sensors could be deployed simultaneously.

The CRRT effluent fluid contains a multitude of positively and negatively charged anions, many of which will interact and form complexes with each other. For the purpose of safety monitoring of the RCA for CRRT procedure, the quantitatively most important positive ions are sodium, calcium and magnesium and the quantitatively most important anions are chloride, bicarbonate, citrate, phosphate and lactate. The chemical principles governing the interactions of these anions in human plasma and ultrafiltrate were described in a series of classic physiological experiments (see Walser, J. Phys. Chem. 1961, 65, 159; Walser, Journal of Cellular & Comparative Physiology. 55:245-50, 1960 June; Walser, J Clin Invest. 1961 April; 40(4): 723-730). The scientists used ultrafiltration of plasma as a research tool; extracorporeal blood purification for renal replacement therapy was in its infancy at the time. The implications of the published science for RCA seem to have not been recognized to date. Following from the published work, the measurement of total calcium in the ultrafiltrate is accomplished as follows in Equation 7:

$$K_{CaCit-} = ((Ca^{2+})_{free} * (Cit^{3-})_{free}) / (CaCit^-) \qquad 7)$$

Where:
$K_{CaCit-}$=the dissociation constant of the ionic calcium-citrate complex (constant);
$(Ca^{2+})_{free}$=the free ionized calcium concentration (measured by the calcium sensor)
$(Cit^{3-})_{free}$=the free ionized trivalent citrate concentration (measured by the citrate sensor)
$(CaCit^-)$=the calcium-citrate ionic complex with a single negative charge The dissociation constant has a fixed value at a given temperature and ionic strength of the solution. Since the human plasma has a very narrow range of acceptable (compatible with life) ion concentrations for all major ionic species and since the pre-filter fluids also have a near physiological composition (except for the presence of citrate), the ionic strength of the CRRT effluent can be considered constant and eliminated as a variable. Also, the warming of the replacement fluid ensures that the temperature of the ultrafiltrate is kept constant near 37 C. Therefore, the $K_{CaCit-}$ dissociation constant will be a fixed value under the operating conditions of CRRT. This allows us to rearrange Equation 7 to express the amount of calcium complexed with citrate in Equation 7*:

$$(CaCit^-) = ((Ca^{2+})_{free} * (Cit^{3-})_{free}) / K_{CaCit-} \qquad 7*)$$

It is of note that all variables on the right side above are measured or constant, therefore $(CaCit^-)$ can be expressed continuously in real time. The effluent Ca also exists in complex with phosphate, lactate and bicarbonate. Complex formation with chloride does not occur. However, complex formation with phosphate will be minimized by keeping the effluent pH around 6.6-7.0 (by using acid citrate anticoagulant) at which pH most phosphate will be in the $H_2PO_4^-$ form that does not bind calcium in a significant manner. The amount of calcium bound to bicarbonate and lactate is minimal and constant, and at worst can be accounted for by a constant correction factor in the equation (designated $F_{Ca}$). Finally, the impact of high clearance CRRT will serve to normalize and standardize bicarbonate, phosphate and all other organic anion and possibly even lactate concentrations in the plasma and ultrafiltrate after a few hours of operation. Therefore, the target variable, the total calcium concentration in the effluent can be expressed as follows in Equation 8:

$$(Ca)_{total} = (Ca^{2+})_{free} + (CaCit^-) + F_{Ca} \qquad 8)$$

This can be rearranged using Equation 7* to yield Equation 8*:

$$(Ca)_{total} = (Ca^{2+})_{free} * (1 + ((Cit^{3-})_{free} / K_{CaCit-})) + F_{Ca} \qquad 8*)$$

(The $F_{Ca}$ is a minor constant factor to account for calcium bound to other anions (bicarbonate, lactate, phosphate, others) that is included for sake of completeness but is likely to be clinically not relevant.)

Similar determinations can be done for magnesium that behaves similarly to calcium except that it may bind with citrate with about 2.5 times as high affinity as shown in Equation 9:

$$(Mg)_{total} = (Mg^{2+})_{free} * (1 + ((Cit^{3-})_{free} / K_{MgCit-})) + F_{Mg} \qquad 9)$$

The variables denote the same as for calcium except that magnesium is used as the metal ion.

The $K_{CaCit-}$ and $K_{MgCit-}$ dissociation constants were previously determined at a sodium concentration of 140 mmol/L and at 25 Celsius temperature (see Am J Kidney Dis. 2005 March; 45(3):557-64; Curr Opin Nephrol Hypertens. 1999 November; 8(6):701-7). Minor adjustments will be needed as the effluent temperature will be around 37 C in clinical practice. This depends on the heat loss from the effluent fluid before contacting the sensor. A heater element on the effluent fluid line may be deployed to ensure standard measurement conditions.

Finally, with the total effluent calcium and/or magnesium concentration determined with clinically satisfactory accuracy, the back-calculation to the systemic plasma value can be performed immediately as described in FIGS. 29a-29c and as will be apparent to those skilled in the art. (If both calcium and magnesium sensing is performed, the measurements can be further checked for accuracy as follows: After several hours of CRRT, the ratio of the determined total calcium and total magnesium concentrations in the ultrafiltrate must be equal to the ratio of calcium and magnesium in the replacement fluid based on the concept of steady state and neutral mass balance, unless a significant pathophysiologic process results in the release or sequestration of calcium in the patient's body disproportionate to magnesium movement.)

As far as the measurement of total citrate in the CRRT effluent is considered, similar principles can be used to derive this value. For the complete and detailed explanation of the calculations, see Walser et al as described above. The equation for citrate is as follows in Equation 10:

$$(Cit)_{total} = (Cit^{3-})_{free} * (1 + ((Na^+)_{free} / K_{NaCit-}) + ((Ca^{2+})_{free} / K_{CaCit-}) + ((Mg^{2+})_{free} / K_{MgCit-})) \qquad 10)$$

Where the variables are:
$(Cit)_{total}$ is the total citrate concentration of the effluent;
$(Cit^{3-})_{free}$=the free ionized trivalent citrate concentration (measured by the citrate sensor);
$(Na^+)_{free}$=the free ionized sodium concentration of the effluent (after a few hours of operation of the CRRT procedure this will be normalized to a constant at 140 mmol/L and can also be derived if necessary by measuring the conductivity of the effluent with clinically sufficient accuracy);
$K_{NaCit2-}$=the dissociation constant of the ionic sodium-citrate complex (constant);
$K_{CaCit-}$=the dissociation constant of the ionic calcium-citrate complex (constant);
$K_{MgCit-}$=the dissociation constant of the ionic magnesium-citrate complex (constant);

In the clinical setting, the contribution of sodium will be constant and will likely not need to be measured, just expressed with a constant correction factor (may be denoted as an optional $F_{Cit}$). The most scientifically accurate determination of the total citrate level in the effluent requires the simultaneous measurement of the free ionized calcium, free ionized magnesium and the free trivalent ionized citrate. However, as discussed previously herein, the movement of magnesium is completely coordinated with calcium in the CRRT circuit according to the present invention. Therefore, as long as the magnesium supplement is exclusively provided as a combined, fixed ratio infusion with calcium, the contribution of magnesium bound citrate can be derived from measuring the calcium only, assuming that the ratio of total effluent calcium to total effluent magnesium will be equal to the ratio of calcium to magnesium in the combined replacement infusion. This is explained below.

Equation 11 (valid under steady state and without gross perturbations of body calcium or magnesium balance):

$$(Ca)_{total}/(Mg)_{total} = R_{Ca/Mg} \quad (11)$$

By rearranging the above, we get Equation 11*:

$$(Mg)_{total} = (Ca)_{total}/R_{Ca/Mg} \quad (11^*)$$

Where the new variable is:
$R_{Ca/Mg}$=the fixed molar ratio of calcium and magnesium in the replacement fluid (around 2-2.5; the exact value will be chosen after extensive clinical testing)

$$(Ca)_{total} = (Ca^{2+})_{free} *(1+((Cit^{3-})_{free}/K_{CaCit-})) + F_{ca} \quad (8^*)$$

$$(Mg)_{total} = (Mg^{2+})_{free} *(1+((Cit^{3-})_{free}/K_{MgCit-})) + F_{Mg} \quad (9)$$

Therefore, the solution in Equation 12 yields:

$$(Mg^{2+})_{free} = ((((Ca^{2+})_{free}*(1+((Cit^{3-})_{free}/K_{CaCit-})) + F_{Ca})/R_{Ca/Mg}) - F_{Mg})/(1+((Cit^{3-})_{free}/K_{MgCit-}))$$

The so derived $(Mg^{2+})_{free}$ than can be inserted into Equation 10 (in lieu of a measured value) to determine the total citrate concentration. An alternative is the measurement of free ionized magnesium and the derivation of calcium along the same principles, as in Equation 13:

$$(Ca^{2+})_{free} = ((((Mg^{2+})_{free}*(1+((Cit^{3-})_{free}/K_{MgCit-})) + F_{Mg})/R_{Mg/Ca}) - F_{Ca})/(1+((Cit^{3-})_{free}/K_{CaCit-})) \quad (13)$$

Where $R_{Mg/Ca}$=the fixed molar ratio of magnesium and calcium in the replacement fluid and naturally:

$$R_{Ca/Mg} = 1/R_{Mg/Ca} \quad (14)$$

However, since in rare clinical conditions, for example in hypercalcemia of malignancy or hungry bone syndrome, the mass balance of calcium and magnesium can become dissociated inside the patient's body, and also because of the vital importance of systemic ionized calcium, ionized calcium monitoring may be always performed with or without ionized magnesium monitoring).

In Equations 12 and 13, the principle was used that when two variables out of the three variables of interest (ionized Ca2+, ionized Mg2+ and ionized trivalent Cit3−) are measured, the third one can be calculated using the added information from equation 11. Using this principle, the free trivalent citrate can also be calculated, when the ionized Ca and ionized Mg is measured as long as Equation 11 applies as true (this will be the case in most clinical situations). The solution of Equations 11, 8* and 9 for the free trivalent citrate concentration yields Equation 15:

$$(Cit^{3-})_{free} = ((R_{Ca/Mg}*(Mg^{2+})_{free} + F_{Mg})) - ((Ca^{2+})_{free} + F_{Ca}))/((((Ca^{2+})_{free}*K_{MgCit-}) - (R_{Ca/Mg}*(Mg^{2+})_{free}*K_{CaCit-}))/(K_{CaCit-}*K_{MgCit-})) \quad (15)$$

Equation 15 can be used when a specific citrate sensor is not yet clinically available and as long as accurate $(Ca^{2+})_{free}$ and $(Mg^{2+})_{free}$ measurements are available with ion specific electrodes. Equation 15 further assumes that Equation 11 is true. This will be the case when there is no pathophysiologic process present in the patient's body that would result in the body absorption or release of calcium or magnesium in a ratio different from the ratio of these ions in the calcium plus magnesium replacement infusion fluid. As long as the systemic plasma ionized calcium is maintained around the physiologic 1.25 mmol/L, this will be true for the large majority of patients.

Overall, as stated earlier, the simultaneous measurement of the free ionized calcium, free ionized magnesium and the free trivalent ionized citrate may provide the best method of monitoring. However, Equation 15 can be used with commercially available calcium and magnesium electrodes and is a better solution to the problem of citrate monitoring than anything existing in current practice until an ionized citrate sensor becomes commercially available. The method according to the present invention includes the application of Equations 12, 13 and 15 or variations of these equations based on the same principles to continuously compare and verify the data provided by the proposed three different sensors. As long all of the sensors perform precisely, the measured values of $(Ca^{2+})_{free}$, $(Mg^{2+})_{free}$ and $(Cit^{3-})_{free}$ should fulfill the above equations.

Finally, with the total effluent citrate concentration determined with clinically satisfactory accuracy, the back-calculation to the systemic plasma value can be performed immediately as described in FIGS. 29a-29c and as is apparent to those skilled in the art.

The above calculations are obviously not meant to be performed by the clinician at the bedside. However, when the OSS according to the present invention delivers the above measured values in real time, a small computer integrated into the OSS can easily be programmed to process the data as above and display the effluent values in real time. The calculation of the systemic plasma values then requires the OSS to have information about the treatment settings (fluid flows and composition). This data can be provided by integrating the OSS into the CRRT device or could be entered manually (as these variables typically do not need frequent changes during the RCA for CRRT procedure) if the OSS is implemented as a stand-alone citrate and calcium sensing safety device.

The OSS according to the present invention may improve the safety of RCA for RRT as follows. The generalized concept of the OSS is outlined for the safe monitoring of any water soluble, filterable substance in the effluent line of the OSS circuit that is either normally present in the body or is introduced by IV infusion through the fluid infusion pathway of the CRRT circuit or by other means. One immediately feasible specific example is the online monitoring of tight glycemic protocols. The OSS as a citrate sensor may be designed as a safety monitor for real-time, online detection of citrate accumulation in the patient who is receiving RCA during the delivery of CRRT whether in the form of continuous veno-venous hemofiltration (CVVH), continuous veno-venous hemodialysis (CVVHD) or continuous veno-venous hemodiafiltration (CVVHDF). The sensor eliminates the need for frequent laboratory testing to detect this complication and is equally adaptable to intermittent hemodialysis (IHD) and continuous sustained low efficiency dialysis (c-SLED) performed with RCA as well.

Figure 34C:
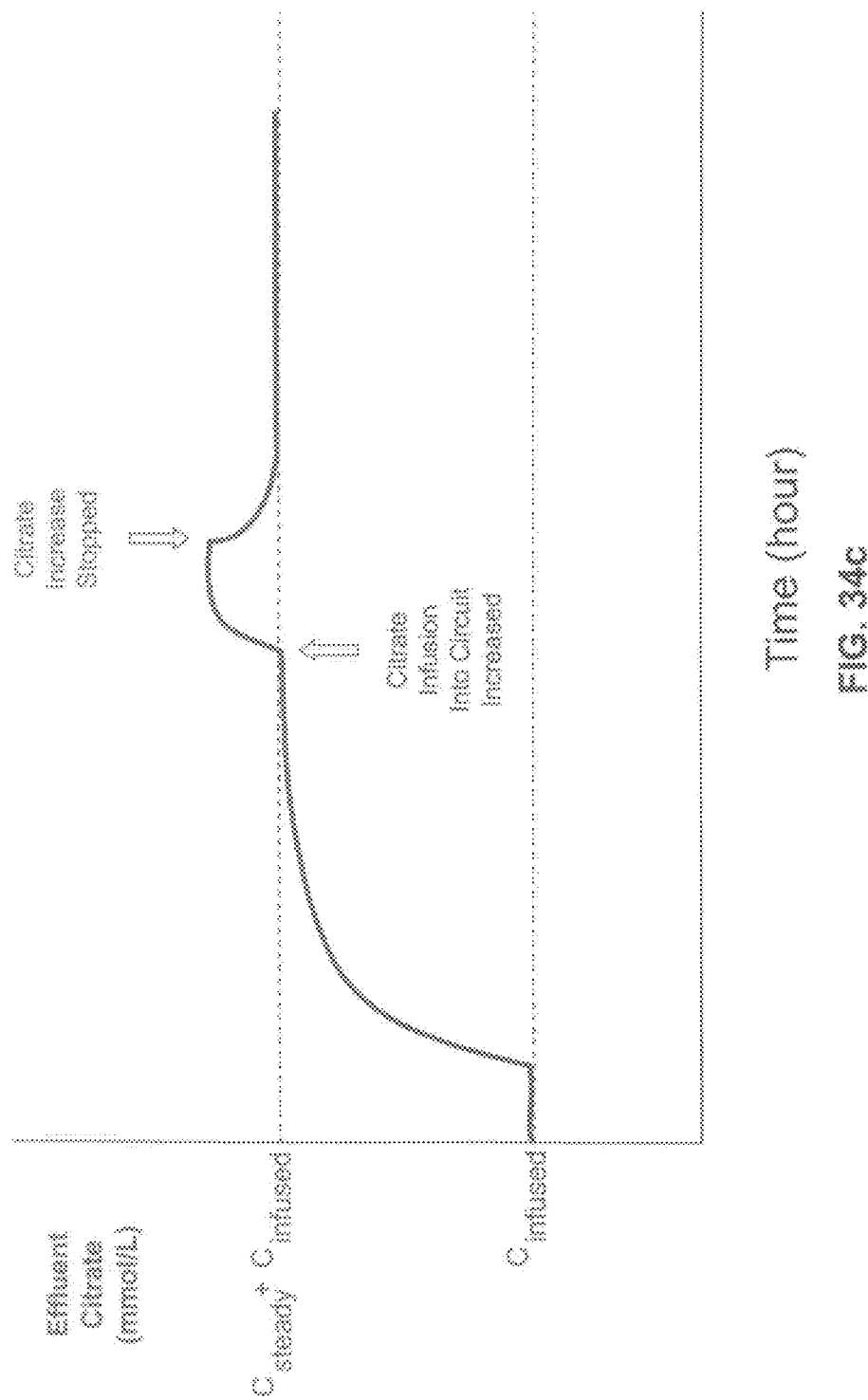
FIG. 34c is a graph depicting the effluent citrate concentration as measured by an online filter clearance and patency monitor according to the present invention.

The OSS as a citrate sensor may be designed to provide real-time, online clearance measurements (FIG. 34c) for any type of blood purification based renal replacement therapy that utilizes RCA including CVVH, CVVHDF, CVVHD, and SLED as well as IHD. FIG. 34c illustrates an online filter clearance and patency monitor according to the present invention, where the citrate concentration is measured by a citrate sensor in the drain circuit of an RRT machine utilizing RCA. Increasing the infusion of citrate into the blood entering the CRRT circuit for a short period of time produces a corresponding response in the citrate measured in the drain circuit. Data from the transient increase in citrate concentration can then be used to determine the dialyzer citrate clearance online. Accuracy may be superior to the existing online clearance monitoring technology based on conductivity measurements, depending on the resolving accuracy of the citrate sensor implementation.

The OSS as a citrate plus calcium (and magnesium) sensor may be designed to provide data that allows accurate, real-time display of the patient's systemic calcium, magnesium and citrate levels for safety and the dosing of calcium and magnesium replacement infusions appropriate for the losses of these ions through the CRRT circuit, thereby reducing and likely obviating the need for frequent calcium and magnesium monitoring during the CRRT procedure. It also allows for the mathematically exact derivation of the individual patient's rate of citrate metabolism, which in turn allows the selection of the most appropriate RCA fluid compositions for the patient to maintain acid-base balance.

The OSS according to the present invention may be designed to monitor organ function in real time with specific examples of monitoring liver function through citrate metabolism and monitoring glomerular filtration rate and renal tubular function through the detection of inulin and PAH levels in the effluent of CRRT circuits. The ability to monitor liver metabolic function in real time can be of great benefit in acute- or chronic liver failure and pre- and post-liver transplantation. The ability to monitor glomerular filtration rate and or renal tubular secretory function will be of great importance in the future, when assessing when to stop CRRT because of recovery of renal function will be a clinical challenge in non-oliguric ARF patients. These patients will all have normal serum chemistries on CRRT as a result of the high CRRT clearance goals gradually becoming the standard of practice. The OSS can monitor any organ, including the heart as long as a water-soluble, filterable compound is identified that is cleared exclusively by the target organ at a rate in excess of its clearance through the extracorporeal blood circuit.

The OSS of the present invention as a citrate, calcium and magnesium sensor will allow RCA for RRT to be delivered safely with possibly no intervention and monitoring from health care personnel. The OSS as part of the RCA home system with OCM and OSS with single needle access will represent a major safety improvement over any home RRT machine and will allow RCA (that is more powerful than heparin and has no systemic bleeding effects) to enter the home setting for nocturnal renal replacement therapies.

In one implementation of the blood bolus based online filter performance monitor, a method for online dextrose dialysance monitoring may be accomplished and optimized with the fluid compositions described herein and an optical dextrose sensor. The dextrose dialysance may then be used to calculate the citrate and calcium dialysance. These modifications may further improve the safety monitoring of automated citrate anticoagulation.

The use of the pre-filter anticoagulant citrate infusion to measure blood bolus-based filter conductivity and filter citrate dialysance has been described previously herein. Any implementation of the method that introduces a known change to the pre-filter blood composition is contemplated according to the present invention, the effect of which is subsequently measured in the post-filter dialysate and/or in the post-filter blood. Online dextrose dialysance is measurable using a dextrose-sensitive optrode. Dextrose dialysance may be a complementary as well as simpler and better indirect measure of citrate dialysance than conductivity (sodium) dialysance, as dextrose (Mw 180) is closer in size to citrate (Mw 189) than Na (Mw 23), and both dextrose and citrate distribute into the plasma flow in the circuit. The red blood cell (RBC) uptake and metabolism of dextrose should have a negligible effect in the 30-60 seconds while RBCs are exposed to higher dextrose levels during the measurement procedure in the extracorporeal circuit. The fluid designs described below are optimized for online dextrose dialysance measurements and will allow checking the accuracy of the online dextrose sensor as well.

Blood bolus-based online dextrose dialysance may be adjusted for access recirculation as described in detail herein for conductivity and citrate dialysance measurements with the methods according to the present invention. A concentrated citrate infusion with concentrated dextrose added to it may be used to measure both continuous dextrose dialysance as well as intermittent bolus-based dextrose dialysance. All replacement therapy fluids and/or the fresh dialysis fluid may be essentially dextrose-free in one implementation for better fluid biocompatibility and easier dextrose dialysance calculations. At least one dextrose sensor (such as a dextrose optrode) may be provided in the filter effluent fluid line (see FIG. 21). Sensors may be deployed in duplicate as in standard safety-engineering practice. If clinical studies prove biocompatibility and safety, dextrose sensors may also be placed into the fresh fluid line(s) and/or the blood lines (see FIG. 21). Biocompatibility is not a concern in the filter effluent (drain) line. The measured effluent dextrose level may be used and all such applications are fully contemplated herein.

For example, the present invention may confirm during priming the accuracy of the sensor by filtering the priming fluid with a known dextrose content. The present invention may confirm during priming the proper loading of the citrate pump based on the high, specific dextrose level, if a double-chamber citrate bag is used with dextrose to confirm the chamber-seal was broken, and possibly identify the specific citrate formulation (acid or basic) if these are implemented with sufficiently different dextrose content for the purposes of such identification. The present invention may also confirm during priming (with the blood circuit in a recirculation mode disconnected from the patient) the proper loading of the calcium pump based on the high, specific dextrose level, to differentiate between various formulations of the calcium infusion (e.g. Ca:Mg ratio 2:1, 2.5:1 or 3:1) if these are implemented with sufficiently different dextrose content for the purposes of such identification. (This method is also possible every time after a new calcium bag is connected, as long as the blood circuit is temporarily disconnected from the patient and is operated in a recirculation mode). The present invention may also continuously measure dextrose dialysance during treatment with good accuracy, intermittently measure bolus-based dextrose dialysance with high accuracy, and indirectly calculate and thereby monitor the patient's plasma dextrose level during treatment.

The calculations for the above applications have been described above for any ultrafilterable solute in general and for conductivity and citrate specifically. These methods and any combination thereof are fully contemplated according to the present invention, as well as the above fluids with adapted dextrose content that make these methods possible utilizing the dextrose optrode or any other technique adaptable to online dextrose level monitoring in blood or filter effluent fluid. In general, to accommodate this method, dextrose is usually introduced with the citrate-containing fluid which also has a higher than normal plasma dextrose concentration. The previously described positive blood bolus method may be used to measure the dextrose dialysance. In the event the patient is very hyperglycemic, the previously described negative blood bolus method may also be used to stay in the operational range of the effluent dextrose sensor. Finally, to simplify calculations, all fluids used to deliver dextrose dialysance (with the possible exception of the citrate/dextrose-containing pre-filter replacement fluid when this fluid is used to introduce the dextrose bolus) including the pre-filter replacement fluid, the dialysis fluid, and the post-filter replacement fluid may be essentially dextrose-free to simplify the calculations. However, more complex calculations would allow the methods to be performed with dextrose-containing versions of the above fluids and such implementations are also contemplated herein.

Clinical use of simultaneous pre- and post-dilution CVVH may be limited by the fact that a more complex CRRT device with a sufficient number of fluid pumps is needed, and also by concerns about the development of dangerously high transmembrane pressures with high ultrafiltration rates. One solution to this problem may be continuous monitoring of the transmembrane pressure and increasing the ratio of the pre-dilution fluid flow to the post-dilution fluid flow while keeping the sum of these flows constant whenever the transmembrane pressure exceeds a certain limit (see Pedrini et al., Kidney International, Vol. 64 (2003), pp. 1505-1513). Another approach is defining the fluid flow prescription in advance to limit the degree of the maximal hemoconcentration allowed during post-dilution hemofiltration to a value known to be safe, and then adding enough pre-dilution-based clearance to achieve at least 66% (or other acceptable value) single pass citrate extraction. This latter method is described here in detail. The two methods of safe prescription writing and online transmembrane pressure and circuit hematocrit level monitoring may be combined for creating the safest system and are fully contemplated according to the present invention.

The calculations below are provided as an example for the systems depicted in FIGS. 35 and 39 which may both utilize concentrated citrate and calcium infusions as well as a single replacement fluid infused pre-filter and post-filter simultaneously. For the system of FIG. 35, the replacement fluid may be pre-manufactured in bags with a fixed sodium and bicarbonate content, while for the system of FIG. 39 the replacement fluid may be generated online, with variable final sodium and bicarbonate content. Similar calculations for the various fluid flows can be developed for any of the other systems shown herein. The main purposes of these calculations may be to ensure that at least 0.66 single pass fractional extraction of citrate is achieved during the simultaneous pre-post-dilution CVVH procedure, and to ensure that excessive hemoconcentration is not induced in the post-filtration ultrafiltration phase.

Water shifts between the red blood cell space and the plasma space in the blood in the extracorporeal circuit overall should have only a negligible effect on these calculations and such shifts are therefore neglected. The present invention contemplates these calculations that incorporate the treatment goals as well as the patient's systemic hemoglobin and plasma protein level to deliver high ultrafiltrate flow rates without inducing excessive hemoconcentration and/or transmembrane pressures.

The variables used in the calculations:
QB: circuit arterial limb blood flow; L/h
QB': circuit blood flow at the point of maximum ultrafiltration; L/h
QP: circuit arterial limb plasma flow (before any fluid infusion); L/h
Hgb: circuit arterial limb hemoglobin concentration; g/dL
P: circuit arterial limb plasma total protein concentration (before any fluid infusion); g/dL
Alb: circuit arterial limb plasma albumin concentration before any fluid infusion; g/dL
Cinf: anticoagulant citrate added to 1 liter of plasma water in the arterial limb of the blood circuit; mmol/L
Csys: Targeted systemic citrate level; mmol/L
Casys: Targeted systemic (and circuit arterial limb) total Ca level; mmol/L
SCit: citrate sieving coefficient; 1
ECit: Targeted single pass citrate extraction ratio on the hemofilter; no dimension; preferably >=0.66 for the system in FIG. 35 and >=0.75 for the system in FIG. 39
ECa: Achieved single pass calcium extraction ratio on the hemofilter; no dimension; about equal to ECit
Fmax: The sum of the circuit blood 3*Hgb (red blood cell hemoglobin) and P (plasma) flow expressed as the fraction of the (post-filtration reduced) total blood flow in the circuit at the point of maximum hemoconcentration (just before the post-dilution replacement fluid infusion); no dimension, arbitrarily set by the user in the range 0.5-0.6 (the lowest value used that allows enough post-filtration to at least equal the Ca infusion rate and net ultrafiltration rate at the selected QB)
QPe: Circuit arterial limb plasma water flow; L/h
QPe': Circuit plasma water flow at the point of maximum ultrafiltration
QTufpost: total post-filtration ultrafiltrate flow; L/h
QTuf: total ultrafiltrate flow; L/h
QNetuf: Net ultrafiltration in the extracorporeal circuit (fluid removed from the patient); L/h
QCit: Anticoagulant citrate flow; L/h
CCit: Citrate concentration in the anticoagulant infusion; mmol/L
QPre: Pre-dilution replacement fluid flow; L/h
Qpost: Post-dilution replacement fluid flow; L/h
QCa: Calcium plus magnesium infusion flow; L/h
CCa: Calcium concentration in the anticoagulant; mmol/L
SUrea: urea sieving coefficient; 1
KUrea: hourly urea clearance; L/min
QPe is expressed by:

$$QPe=QB*(1-3*Hgb/100)*(1-P/100) \quad (1)$$

where QB is in the range of 50-450, preferably fixed at 75 ml/min for 24-hour continuous CVVH and can be recalculated as needed for the target uremic clearance per treatment. QPe' is expressed by:

$$QPe'=QPe-QTufpost \quad (2)$$

QB' is expressed by:

$$QB'=QB-QTufpost \quad (3)$$

where $$(1-Fmax)=QPe'/QB'=(QPe-QTufpost)/(QB-QTufpost) \quad (4)$$

and $$QTufpost=(QPe-QB*(1-Fmax))/Fmax \quad (5)$$

Depending on the values of Hgb, P, and Fmax, Equation (5) may return a negative value (when the patient systemic Hgb and P is high). To overcome this, Fmax can be increased up to 0.55-0.6 and QB can be increased as needed to be able to achieve QTufpost>=QNetuf +QCa. With the lower than normal Hgb and P values prevalent in the intensive care unit, QB values that provide the target hourly uremic clearance will almost always allow sufficient QTufpost and it is unlikely that QB would have to be increased for this purpose when Fmax is >=0.55. An optimizing computer program can be utilized to find the smallest Fmax that will allow at least the needed QTufpost=QNetuf+QCa with the highest QB and clearance acceptable to the user. Aiming for a reasonably low Fmax (Fmax=0.5, for instance, with a circuit highest Hgb=about 14 g/dL and protein equal to about 8 g/dL immediately post-filter) in general is preferred to minimize hemoconcentration due to post-filtration in the circuit as much as possible.

The flow rate of the citrate anticoagulant is determined by:

$$Qcit=(QP*Cinf)/Ccit \quad (6)$$

where Cinf is preferably fixed at 8 mmol/L
The total replacement fluid flow rate is determined by:

$$Qpre+Qpost=QB \text{ for the system in FIG. 35} \quad (7.1)$$

$$Qpre+Qpost=1.5*QB \text{ for the system in FIG. 39 (more abundant, cheap online fluid supply)} \quad (7.2)$$

The concentrated citrate anticoagulant is dosed in a fixed ratio to the circuit arterial limb plasma flow in the preferred implementation. This means that with the same QB and variable Hgb and P, variable levels of hypernatremia will be induced by the anticoagulant infusion. However, this can be completely mitigated by using a fixed amount of Qpre+Qpost as defined in (7.1) and (7.2), a fixed replacement sodium of 128 in the system of FIG. 35, and a fixed replacement sodium of 132 in the system of FIG. 39, and by distributing the total replacement fluid flows between the Qpre and Qpost so that the Fmax is about 0.5 also considering the QNetuf and QCa.

The pre-dilution replacement fluid flow rate can be determined by, for instance, a recursive algorithm.

$$QCa=0 \quad (8.1)$$

$$QNetuf=\text{defined by user} \quad (8.2)$$

$$Fmax=0.5 \text{ or lowest value as established above} \quad (8.3)$$

$$Qpost=QTufpost-QNetuf-QCa \quad (8.4)$$

$$Qpre=QB-Qpost \text{ (system in FIG. 35) or } 1.5*QB-Qpost \text{ (system in FIG. 39)} \quad (8.5)$$

$$Ecit=SCit*QTuf/(Qcit+Qpre+QPe)=Scit*(Qcit+Qpre+QTufpost)/(Qcit+Qpre+QPe) \quad (8.6)$$

Since the Scit is about =1 and Qpre plus Qpost is always >=QB, then Ecit is always >=0.66 in the system according to FIG. 35 and is always >=0.75 in the system according to FIG. 39. This is a clinically safe, high single-pass fractional extraction of citrate with an economically acceptable replacement fluid utilization rate, even if the fluid is provided as a sterile, prepackaged 1× concentration fluid.

In the systems according to these protocols:

$$ECa=0.95*Ecit \quad (8.7)$$

The target systemic Ca is calculated as follows:

$$Casys=1.25+0.25*Csys+0.2*Alb \quad (8.8)$$

Csys is targeted to be 2 mM (usually it will be about 0.5 mM). If the citrate metabolism is severely impaired (e.g., shock liver), Csys may have to be targeted in the range of 3-4 mM. The calcium infusion rate is calculated:

$$QCa=(ECa*Casys*QP-(QNetuf*(1.25+0.25*Csys)))/CCa \quad (8.9)$$

The so-calculated QCa becomes the new value for the QCa in Equation (8.1). The calculations in Equations (8.1) through (8.8) can be repeated recursively until the final fluid flow rates are approximated within 1%.

Finally, the approximate pre-dilution-adjusted hourly urea clearance is calculated:

$$Kurea=Surea*(Qcit+Qpost+QNetuf+QCa)*QB/(Qcit+Qpre+QB)$$

Depending on the target versus the calculated Kurea value, the QB may be adjusted and the entire prescription may be recalculated again.

With QB, Qcit, Qpre, Qpost, QCa, and Netuf determined, the entire prescription has been defined. During treatment, the hemoglobin and albumin levels can change requiring a recalculation of the prescription. The hemoglobin level may be monitored online with a hematocrit sensor as described previously herein. The systemic citrate level, Csys, may be monitored by an online citrate sensor. The albumin and total protein level will not change rapidly and may be measured daily and/or after albumin administration. The albumin level in the circuit blood may also be monitored online by Raman spectroscopy on the arterial or venous blood lines and this application of Raman spectroscopy is also fully contemplated.

The integration of various physical implementations of Raman scatter spectroscopy with the described RCA systems according to the present invention for special clinical applications will now be described. In general, application of Raman spectroscopy starts with the qualitative identification and/or subsequent quantitative detection of an analyte of interest with clinically sufficient precision. For many analytes, the preferred site of detection is the filter effluent fluid. For some analytes, for example, but not limited to, albumin, para-amino-hippuric acid, bilirubin, protein bound analytes (e.g., toxins or medications), the site of detection may be any optically suitable point in the blood circuit. For many analytes, a specific Raman spectroscopy spectral signature may have already been described. Even in the absence of a prior known Raman signature, such a signature can be obtained for the target analyte by comparing Raman spectrum data obtained from the filter effluent or blood fluid sample matrix not containing the target analyte with Raman spectrum data of these same fluid sample matrices supplemented with the target analyte at various concentrations. Once a specific Raman spectral signature has been identified in the specific fluid sample matrix, quantitative determination of the specific analyte can be accomplished utilizing one of several methods known in the art. For analytes in very low concentrations in the sample (e.g. antibiotics), special modifications of the Raman technology (for instance, but not limited to, surface-enhanced Raman scatter spectroscopy) may be utilized. Depending on the application, obtaining the Raman scatter spectrum may take from a few seconds to a few minutes, a time completely feasible for all the specific clinical applications of Raman spectroscopy described below.

Measurement of systemic plasma albumin levels is contemplated according to the present invention. The measurement of albumin concentration at an optically suitable point in the extracorporeal blood circuit is fully contemplated according to the present invention. When the measured albumin concentration is correlated with the overall blood flow and plasma flow as well as the degree of hemoconcentration induced by the circuit at the point of measurement, the systemic albumin concentration can be determined. This information obtained online may be used to adjust the dosing of the calcium infusion with every significant (e.g., more than 0.5 g/dL) change of systemic albumin levels, further enhancing the safe automation of RCA with the systems described herein. Monitoring of albumin levels at various points in the extracorporeal blood circuit may also be helpful in special applications of extracorporeal blood processing associated with large albumin fluxes, for instance, but not limited to, plasmapheresis and certain currently available liver support circuits.

Monitoring of systemic total citrate, total calcium and total magnesium levels is also contemplated according to the present invention. The measurement of free citrate, the calcium-citrate complex and the magnesium-citrate complex as well as all forms of phosphate (free and complex species) in the filter effluent is fully contemplated according to the present invention. The same analytes can also be measured in the blood circuit and such measurements are also contemplated. As described herein, the total calcium, magnesium and citrate concentrations in the effluent can be determined by knowing the dissociation constants of the various ionic complexes and measuring a sufficient number of the free- and complexed ionic species to allow the mathematical solution of the system of chemical equations with clinically sufficient precision. Raman spectroscopy may be used alone or to complement other sensor technologies to detect some of the above target analytes. Specifically, the level of free citrate, and at least the summary level of the calcium-citrate and magnesium citrate compounds may be easily measurable. It may also be possible to separately measure the calcium-citrate and magnesium-citrate complex levels. While filter effluent fluid is a complex sample fluid matrix, most analytes will be present in micromolar concentrations, as opposed to the citrate species which will be present in the millimolar concentrations, making Raman spectroscopic quantitative determinations for these analytes very feasible. Raman spectroscopy analysis alone may be sufficient to determine the total citrate content of the effluent with clinically sufficient accuracy. This value may then be used to determine the patient systemic plasma total citrate level as described herein. The systemic citrate level may be used to monitor liver function and to adjust the dosing of the calcium infusion, further enhancing the safe automation of the RCA procedure with the systems according to the present invention. Determination of the total calcium and total magnesium content of the effluent fluid may be performed as described herein using Raman spectroscopy data of at least the above citrate-metal complex species as well as Raman determinations of any calcium-phosphate and magnesium-phosphate species present in the ultrafiltrate. These Raman spectroscopy-based methods may further be complemented by other methods to sense the free calcium and free magnesium levels as necessary. Once the filter effluent total calcium and total magnesium levels are determined, the patient systemic total calcium and total magnesium levels may be calculated as described herein. This information can be used to adjust the operation of the system, including the rate and composition (e.g., the molar ratio of the calcium and magnesium in the fluid) of the calcium infusion to further enhance the safety of automating the RCA procedure with the systems described herein.

The present invention also contemplates measurement of filter performance in clearing a Raman target solute. Any of the online filter clearance measurement techniques described herein can be performed supplemented by the measurement of the target analyte level in the filter effluent fluid (and/or the extracorporeal circuit blood or plasma) by Raman spectroscopy and all such implementations are fully contemplated. Since the response time of Raman spectroscopy may not allow real-time imaging of the solute concentration curve in the filter effluent, for instance, in response to a bolus of the analyte, steady state levels may be captured instead before, during and after a target analyte bolus, which may be delivered by the concentrated citrate anticoagulant infusion. The target analytes may include, but are not limited to, total citrate, dextrose, B12 vitamin, and low molecular weight inulin.

Monitoring of recovery of renal function is further contemplated according to the present invention. The RCA systems according to the present invention may provide CRRT treatments to patients with acute renal failure 24-hours a day with high daily clearance goals achieved. Under such conditions, it may be clinically difficult to decide when sufficient recovery of renal function has occurred to safely discontinue renal replacement therapy. As described herein, supplementing the citrate anticoagulant solution with inulin and indirectly monitoring the systemic plasma inulin level may allow the detection of recovery of renal function. In addition, the detection of inulin levels by Raman spectroscopy either on the filter effluent line or at an optically acceptable point on the blood circuit is also contemplated for this purpose. This method has several benefits. Inulin detection can be performed online, frequently and in an automated fashion. Inulin detection can be performed on the filter effluent line, and also possibly in the blood circuit. As opposed to traditional clinical markers of glomerular filtration rate (GFR) (e.g., creatinine and cystatin C whose body production may vary greatly from patient to patient), the production rate (patient load=G) of inulin will be precisely known as determined by the RCA prescription according to the present invention and the citrate anticoagulant inulin concentration. Due to the sensitivity of the Raman detection, very low inulin concentrations can be used. If low molecular weight inulin (MW around 1500-3000) is used, significant systemic inulin accumulation can be avoided. Inulin clearance is the gold standard for measuring GFR, and inulin has a long track record of being safe for infusion into human blood.

With the typical 24-hour RCA prescription providing between 20-60 ml/minute low molecular weight inulin clearance, recovery of renal function with a glomerular filtration rate $>=20$-25 ml/min (from near 0-5 ml/min initially) may be estimated to result in a 25%-100% reduction in the steady state systemic inulin level, easily measurable by the proposed effluent inulin level Raman monitoring of the present invention. For greater sensitivity, para-amino-hippuric acid (PAH) as a target analyte may also be used as discussed herein. However, depending on the degree of plasma protein binding and sieving and/or diffusivity coefficient of PAH on the filter in the RCA systems described herein, the following items should be noted. First, if PAH is cleared only minimally on the hemofilter, then separate, intermittent bolus administration by the health care team may be preferred over introducing this agent continuously with the citrate anticoagulant to avoid accumulation of PAH in the patient. Second, if PAH is cleared only minimally on the hemofilter, Raman spectroscopy may be used at any optically acceptable point on the blood circuit as opposed to on the filter effluent line to measure PAH levels in the circuit blood.

The measurement of protein-bound toxin levels (for instance, but not limited to, bilirubin) by applying Raman spectroscopy on the blood circuit is also contemplated herein. The data so obtained can be used for diagnosis of conditions and to alter treatment parameters, for instance, but not limited to, regulating the performance of a protein-bound toxin removal secondary blood processing device (e.g., extracorporeal liver support device), and all such uses are contemplated herein.

Still further, the measurement of compounds of therapeutic use (for instance, but not limited to, all antibiotics used to treat infections in a human, or other medications) by Raman spectroscopy is fully contemplated to establish systemic patient levels and to guide medication dosing. For all ultrafilterable and dialyzable compounds, a preferred site of detection may be the filter effluent line. For compounds with very low concentrations, more sensitive Raman spectroscopic methods, for instance, but not limited to, surface-enhanced Raman scatter spectroscopy may be utilized with or without an intermittent sampling device. Such data may be important for the correct dosing of various medications, including antibiotics, for the patient treated with the RCA systems as described herein.

Monitoring the filter effluent for the diagnosis of SIRS and/or specific organ injury and the resolution of SIRS and/or specific organ injury is also contemplated according to the present invention. The RCA systems described herein may be frequently used to treat patients with the systemic inflammatory syndrome (SIRS) or the suspicion of SIRS. The filter effluent during treatment of patients with SIRS and/or a specific organ injury will contain a mixture of compounds including inflammatory cytokines. Raman spectroscopy may be successfully used to differentiate between patients at risk of a certain condition based on the complex analysis of Raman spectra obtained from a similarly complex sample, human urine. The present invention contemplates the use of computerized Raman scatter spectroscopy analysis of the filter effluent to diagnose the presence of a SIRS spectrum, in order to monitor the resolution or worsening of the clinical SIRS in the patient through monitoring changes in the ultrafiltrate SIRS Raman signature. Similarly, the present invention contemplates the diagnosis and monitoring of the clinical course of specific organ injury including, but not limited to, acute kidney injury, acute lung injury, acute myocardial injury and acute liver injury through computerized, complex Raman scatter spectroscopy analysis of the filter effluent fluid.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A system for regional citrate anticoagulation in an extracorporeal blood circuit including an arterial blood line arranged to be connected to a vascular access for withdrawing blood from a patient and a venous blood line arranged to be connected to the vascular access for returning blood to the patient, the system comprising:
    a hemofilter in fluid communication with the arterial and venous blood lines;
    a first pre-filter infusion line connected to the arterial blood line upstream from the hemofilter for infusing a first pre-filter infusion solution comprising a citrate anticoagulant-containing solution into blood in the arterial blood line;
    a second pre-filter infusion line connected to the arterial blood line upstream from the hemofilter for infusing a second pre-filter infusion solution comprising a first bicarbonate-containing solution into blood in the arterial blood line;
    an effluent fluid line in fluid communication with the hemofilter for carrying effluent fluid away from the hemofilter;
    a post-filter infusion line connected to the venous blood line downstream from the hemofilter for infusing a post-filter infusion solution comprising a second bicarbonate-containing solution into blood in the venous blood line;
    an additional infusion line connected to the venous blood line downstream from a connection of the post-filter infusion line for infusing an additional infusion solution comprising a calcium- and magnesium-containing solution into blood in the venous blood line; and
    at least one arterial hematocrit sensor operably connected to the arterial blood line upstream from the second pre-filter infusion line for providing circuit plasma flow in real time for controlling at least one of hemofilter single pass citrate extraction and an infusion rate of the additional infusion solution.

2. The system of claim 1, further comprising a second hematocrit sensor operably connected to the blood circuit downstream from the second pre-filter infusion line and upstream from the additional infusion line.

3. The system of claim 1, further comprising a second arterial hematocrit sensor operably connected to the arterial blood line downstream from the second pre-filter infusion line and upstream from the hemofilter.

4. The system of claim 3, wherein the first and second arterial hematocrit sensors determine a degree of hemodilution with the second pre-filter infusion solution infusing at a known rate, and allow calculation of delivered blood flow in the arterial blood line upstream from the hemofilter in an automated manner for at least one of continuously adjusting dosing of the first pre-filter infusion solution to achieve a desired citrate to plasma flow ratio and controlling hemofilter single pass citrate extraction and the infusion rate of the additional infusion solution.

5. The system of claim 3, further comprising a first venous hematocrit sensor operably connected to the venous blood line downstream from the hemofilter and upstream from the post-filter infusion line, and a second venous hematocrit sensor operably connected to the venous blood line downstream from the post-filter infusion line and upstream from the additional infusion line.

6. The system of claim 5, wherein the first and second venous hematocrit sensors determine a degree of hemodilution with the post-filter infusion solution infusing at a known rate, and allow calculation of delivered blood flow in the venous blood line downstream from the hemofilter in an automated manner for at least one of continuously adjusting dosing of the first pre-filter infusion solution to achieve a desired citrate to plasma flow ratio and controlling hemofilter single pass citrate extraction and the infusion rate of the additional infusion solution.

7. The system of claim 5, wherein a programmed change in a flow of at least one of the second pre-filter infusion solution, the post-filter infusion solution, and the filter effluent fluid results in a programmed change in venous blood line hematocrit, wherein the programmed change in venous blood line hematocrit is detected by at least one of the first and second venous hematocrit sensors, the subsequent change in arterial blood line hematocrit due to blood access recirculation is detected by at least one of the first and second arterial hematocrit sensors, and blood access recirculation is calculated from the detected hematocrit changes in an automated manner.

8. The system of claim 1, further comprising a secondary extracorporeal blood treatment device operably connected downstream from the first pre-filter infusion line and upstream from the additional infusion line.

9. The system of claim 1, wherein at least one of the second pre-filter infusion solution and the post-filter infusion solution has a bicarbonate concentration of about 20-60 mmol/L.

10. The system of claim 1, wherein the first pre-filter infusion solution comprises a basic citrate to acid citrate ratio of about 2:1 to 8:1.

11. The system of claim 1, wherein the second pre-filter infusion solution and the post-filter infusion solution are essentially free of calcium and magnesium.

12. The system of claim 1, further comprising a control program for coordinating and monitoring the operation of the system, the control program monitoring plasma flow online to calculate an infusion rate of the first pre-filter infusion solution and the second pre-filter and post-filter infusion solutions necessary to keep the hemofilter single pass citrate extraction above about 66%.

13. The system of claim 1, further comprising a solute sensor operably connected to the effluent fluid line for measuring a solute concentration in the filter effluent fluid.

14. A method for regional citrate anticoagulation in an extracorporeal blood circuit including an arterial blood line arranged to be connected to a vascular access for withdrawing blood from a patient and a venous blood line arranged to be connected to the vascular access for returning blood to the patient, the method comprising:
providing a hemofilter in fluid communication with the arterial and venous blood lines;
providing an effluent fluid line in communication with the hemofilter for carrying a filter effluent fluid away from the hemofilter;
infusing a first pre-filter infusion solution comprising a citrate anticoagulant-containing solution into blood in the arterial blood line upstream from the hemofilter;
infusing a second pre-filter infusion solution comprising a first bicarbonate-containing solution into blood in the arterial blood line upstream from the hemofilter;
infusing a post-filter infusion solution comprising a second bicarbonate-containing solution into blood in the venous blood line downstream from the hemofilter;
infusing an additional infusion solution comprising a calcium- and magnesium-containing solution into blood in the venous blood line downstream from a connection of the post-filter infusion solution; and
sensing hematocrit on the arterial blood line upstream from the second pre-filter infusion line to provide circuit plasma flow in real time for controlling at least one of hemofilter single pass citrate extraction and an infusion rate of the additional infusion solution.

15. The method of claim 14, further comprising sensing hematocrit on the arterial blood line downstream from the first pre-filter infusion line and both upstream and downstream from the second pre-filter infusion line to determine a degree of hemodilution with the second pre-filter infusion, and calculating delivered blood flow to the hemofilter for at least one of continuously adjusting dosing of the first pre-filter infusion solution to achieve a desired citrate to plasma flow ratio and controlling the hemofilter single pass citrate extraction and the infusion rate of the additional infusion solution.

16. The method of claim 14, further comprising sensing hematocrit on the venous blood line upstream from the additional infusion line and both upstream and downstream from the post-filter infusion line to determine a degree of hemodilution with the post-filter infusion, and calculating delivered blood flow to the hemofilter for at least one of continuously adjusting dosing of the first pre-filter infusion solution to achieve a desired citrate to plasma flow ratio and controlling the hemofilter single pass citrate extraction and the infusion rate of the additional infusion solution.

17. The method of claim 14, further comprising sensing hematocrit on the venous blood line upstream from the additional infusion line, wherein a programmed change in a flow of at least one of the second pre-filter infusion solution, the post-filter infusion solution, and the filter effluent fluid results in a programmed change in venous blood line hematocrit, further comprising detecting the programmed change in venous blood line hematocrit, detecting the subsequent change in arterial blood line hematocrit due to blood access recirculation, and calculating blood access recirculation from the detected hematocrit changes in an automated manner.

18. The method of claim 14, further comprising providing a secondary extracorporeal blood treatment device operably connected downstream from the pre-filter infusion line and upstream from the additional infusion line.

19. The method of claim 14, further comprising sensing a solute concentration in the filter effluent fluid within the effluent fluid line.

20. The method of claim 14, further comprising monitoring plasma flow online to calculate an infusion rate of the first pre-filter infusion solution and the second pre-filter and post-filter infusion solutions necessary to keep the hemofilter single pass citrate extraction above about 66%.

* * * * *